(12) United States Patent
Huntington et al.

(10) Patent No.: US 11,399,822 B2
(45) Date of Patent: Aug. 2, 2022

(54) METHOD AND APPARATUS FOR PASSING SUTURE

(71) Applicant: Maruho Medical, Inc., Reno, NV (US)

(72) Inventors: Andrew J. Huntington, Reno, NV (US); Brett A. Snyder, Reno, NV (US); Matthew Byrnes Newell, Reno, NV (US); Luke W. Clauson, Reno, NV (US); Gary S. Fanton, Portola Valley, CA (US); John F. Krumme, Bainbridge Island, WA (US); Scott H. Heneveld, Whitmore, CA (US); Bryce Peterson, Hayward, CA (US); Yasuyuki Hitomi, Kyoto (JP)

(73) Assignee: Maruho Medical, Inc., Reno, NV (US)

( * ) Notice: Subject to any disclaimer, the term of this patent is extended or adjusted under 35 U.S.C. 154(b) by 2 days.

(21) Appl. No.: 16/733,740

(22) Filed: Jan. 3, 2020

(65) Prior Publication Data

US 2021/0204934 A1    Jul. 8, 2021

(51) Int. Cl.
*A61B 17/04* (2006.01)
*A61B 17/062* (2006.01)
*A61B 17/00* (2006.01)

(52) U.S. Cl.
CPC ...... *A61B 17/0469* (2013.01); *A61B 17/0625* (2013.01); *A61B 17/0485* (2013.01); *A61B 2017/00424* (2013.01); *A61B 2017/047* (2013.01)

(58) Field of Classification Search
CPC . A61B 17/34; A61B 17/0469; A61B 17/0625; A61B 17/06114; A61B 2017/0609
See application file for complete search history.

(56) References Cited

U.S. PATENT DOCUMENTS

| | | | |
|---|---|---|---|
| 4,414,908 A | 11/1983 | Eguchi et al. | |
| 4,440,171 A | 4/1984 | Nomoto et al. | |
| 4,935,027 A | 6/1990 | Yoon | |
| 7,232,446 B1 | 6/2007 | Farris | |
| 7,615,059 B2 | 11/2009 | Watschke et al. | |
| 8,177,796 B2 | 5/2012 | Akyruz et al. | |
| 9,072,480 B2 * | 7/2015 | Hart | A61B 17/0469 |

(Continued)

FOREIGN PATENT DOCUMENTS

| | | |
|---|---|---|
| WO | WO 2008/045367 | 4/2008 |
| WO | WO 2009/005527 | 1/2009 |
| WO | WO 2019/191768 | 10/2019 |

*Primary Examiner* — Tuan V Nguyen
(74) *Attorney, Agent, or Firm* — Levine Bagade Han LLP

(57) ABSTRACT

A device that can pierce and hold tissue and then pass suture through tissue. The device can have a shuttle that can removably attach to a suture and jaws that can be rotatably opened and closed with respect to each other. The device can have a first jaw having a first jaw channel and a first jaw first stop. The shuttle can have a shuttle longitudinal axis and a shuttle first stop. The shuttle first stop can have a shuttle first stop distal end. The shuttle first stop distal end can be deflectable into the first jaw first stop. When the shuttle first stop distal end is in contact with the first jaw first stop, the shuttle can be passively retained in the first jaw. A method for using the device to repeatedly pass the suture through the tissue without removing the suture or device from the target site.

20 Claims, 79 Drawing Sheets

(56) References Cited

U.S. PATENT DOCUMENTS

| | | |
|---|---|---|
| 10,258,322 B2 | 4/2019 | Fanton et al. |
| 10,631,872 B2 | 4/2020 | Raybin et al. |
| 2009/0012538 A1 | 1/2009 | Saliman et al. |
| 2009/0312773 A1* | 12/2009 | Cabrera ............. A61B 17/0469 |
| | | 606/144 |
| 2010/0211082 A1 | 8/2010 | Sauer |
| 2011/0028998 A1 | 2/2011 | Adams et al. |
| 2012/0150197 A1* | 6/2012 | Malkowski ........ A61B 17/0625 |
| | | 606/144 |
| 2012/0239062 A1 | 9/2012 | Saliman |
| 2014/0316443 A1* | 10/2014 | Fan .................. A61B 17/06004 |
| | | 606/145 |
| 2019/0321030 A1 | 10/2019 | Fanton et al. |

\* cited by examiner

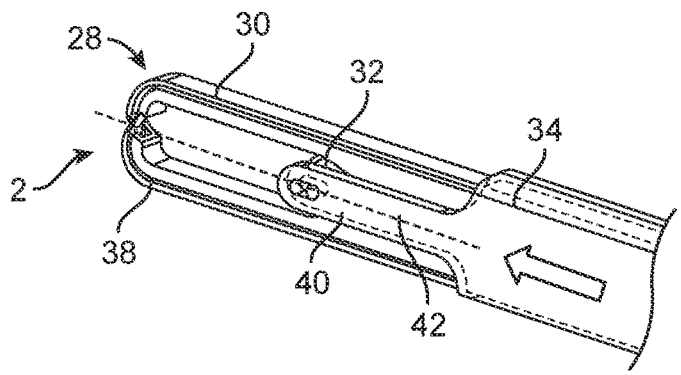
FIG. 4a
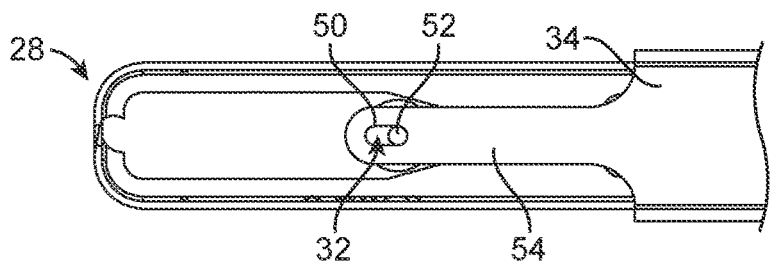
FIG. 4b
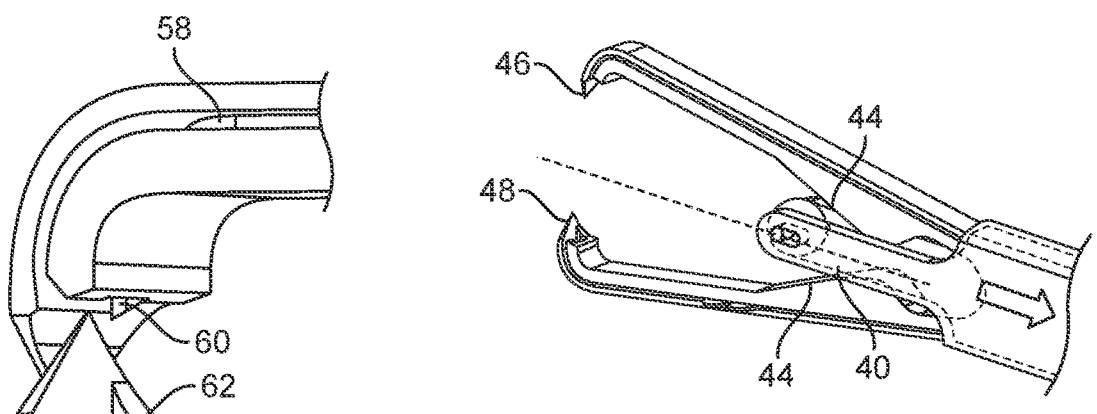
FIG. 4c
FIG. 4d
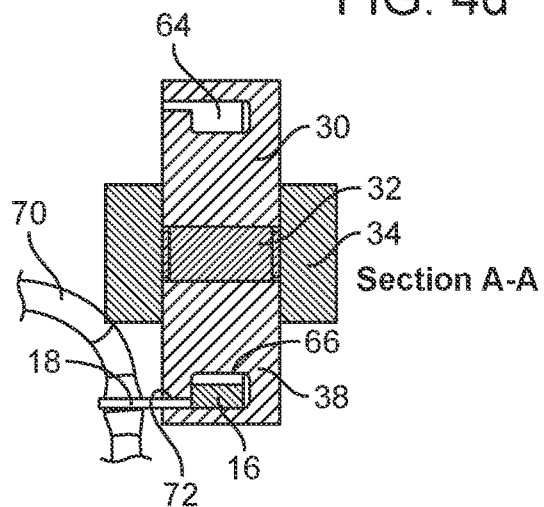
FIG. 5

Section A-A

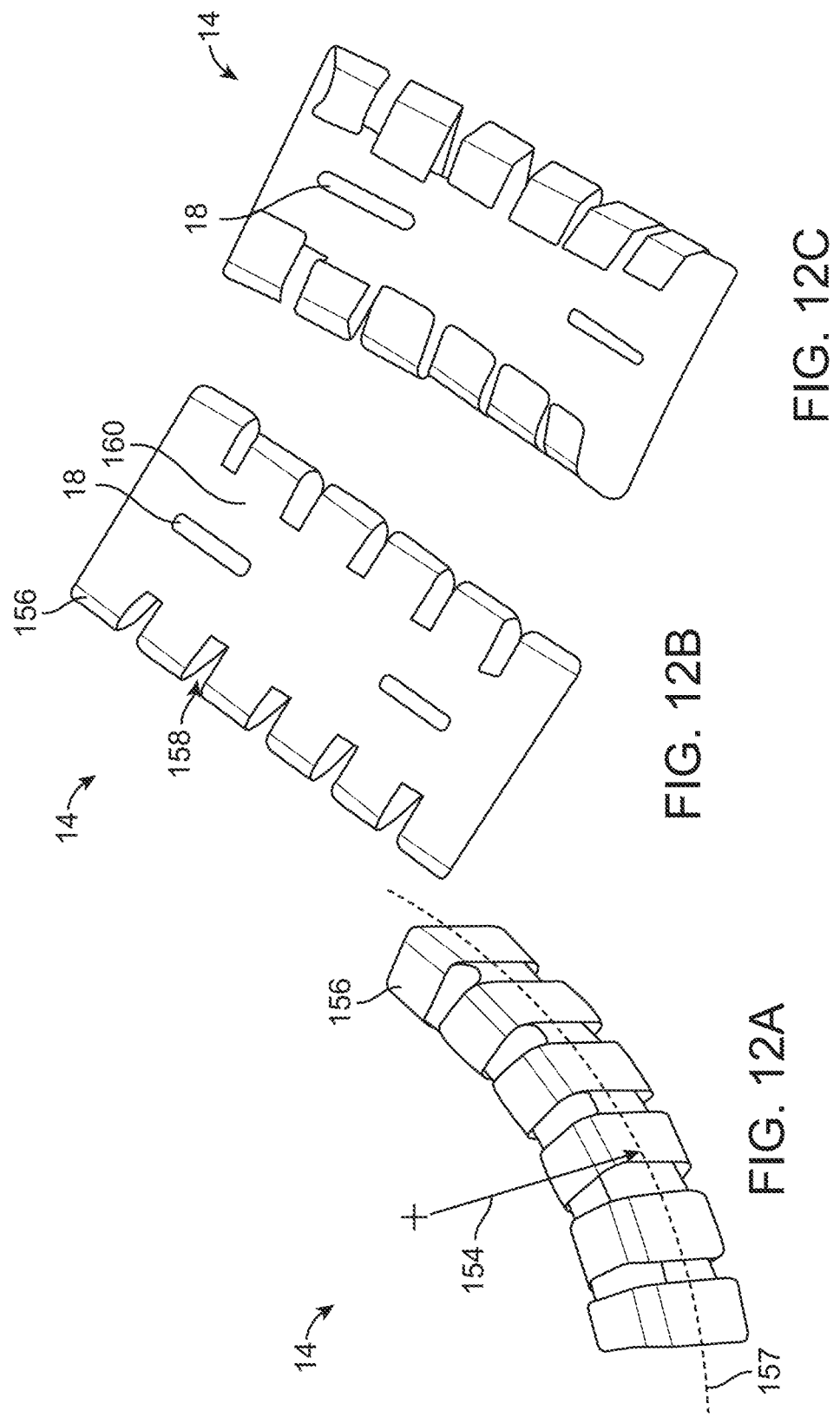

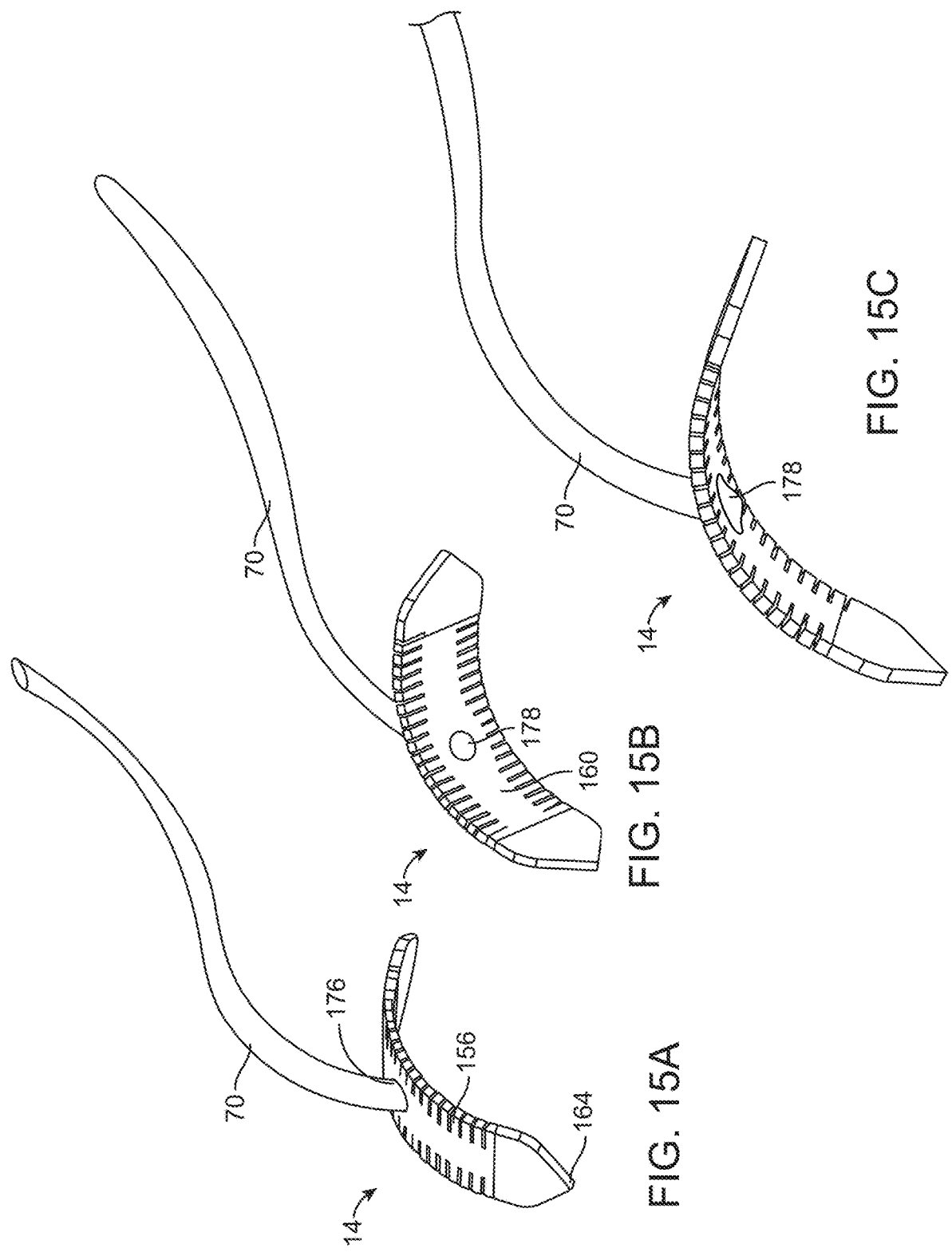

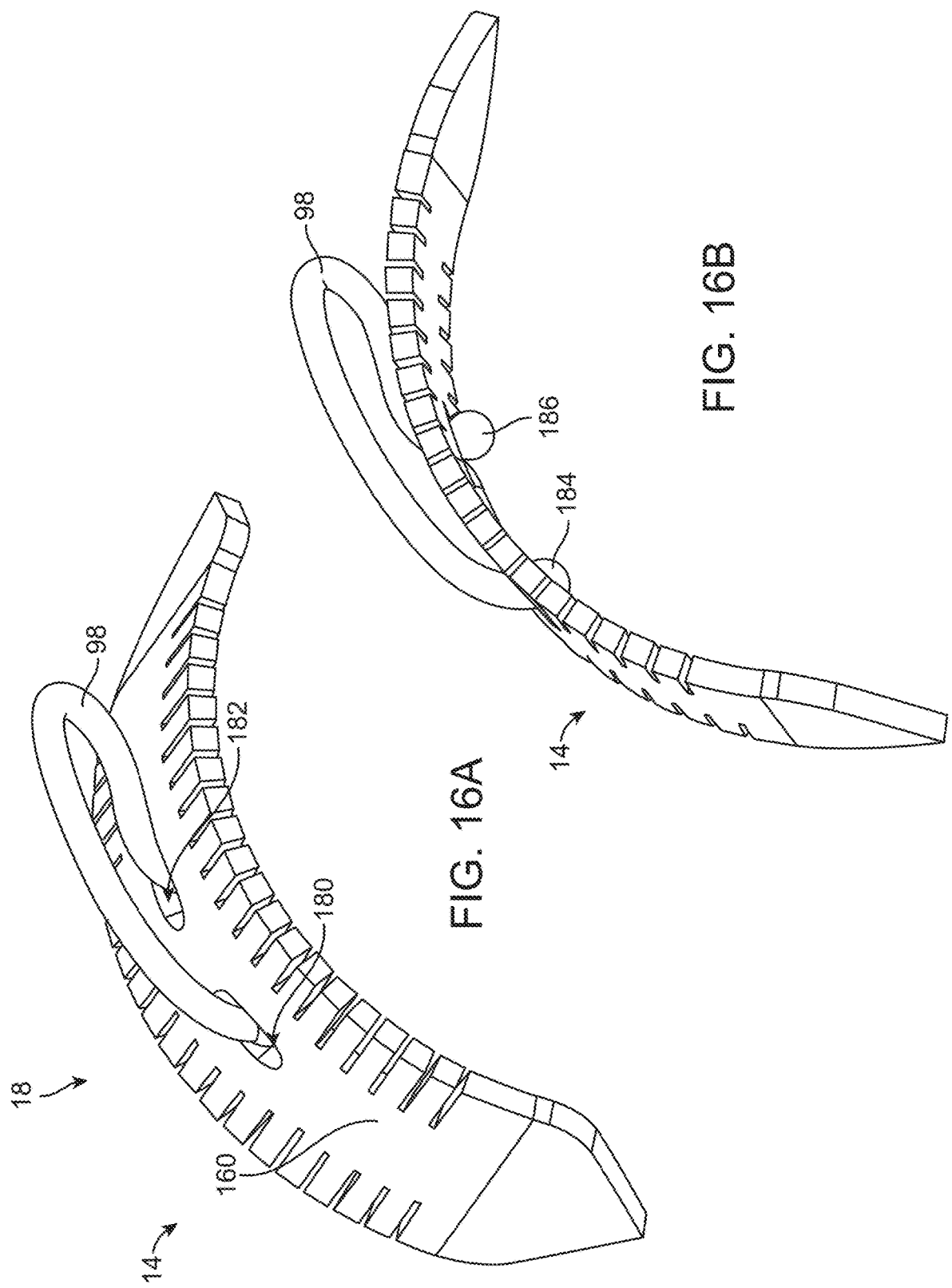

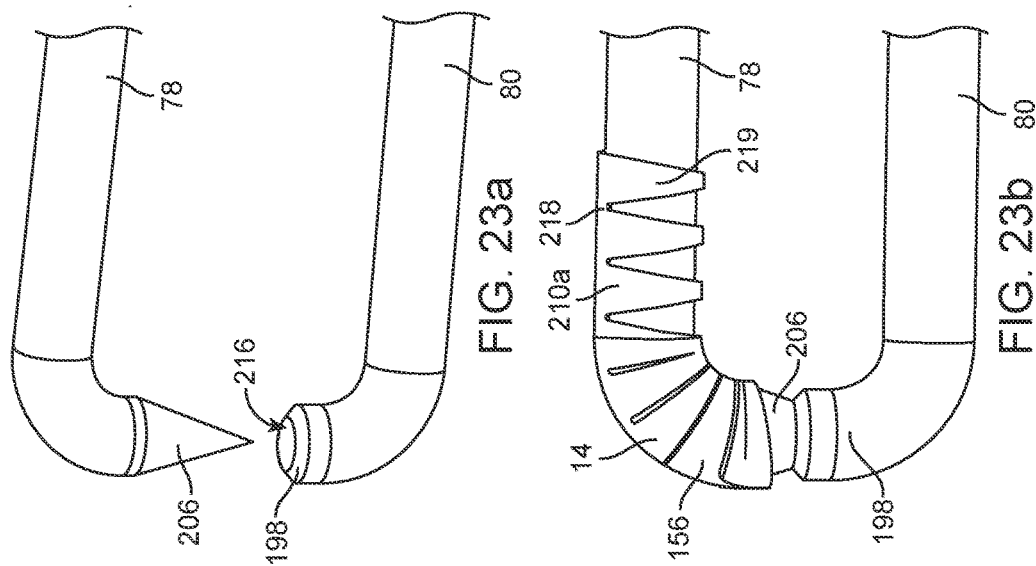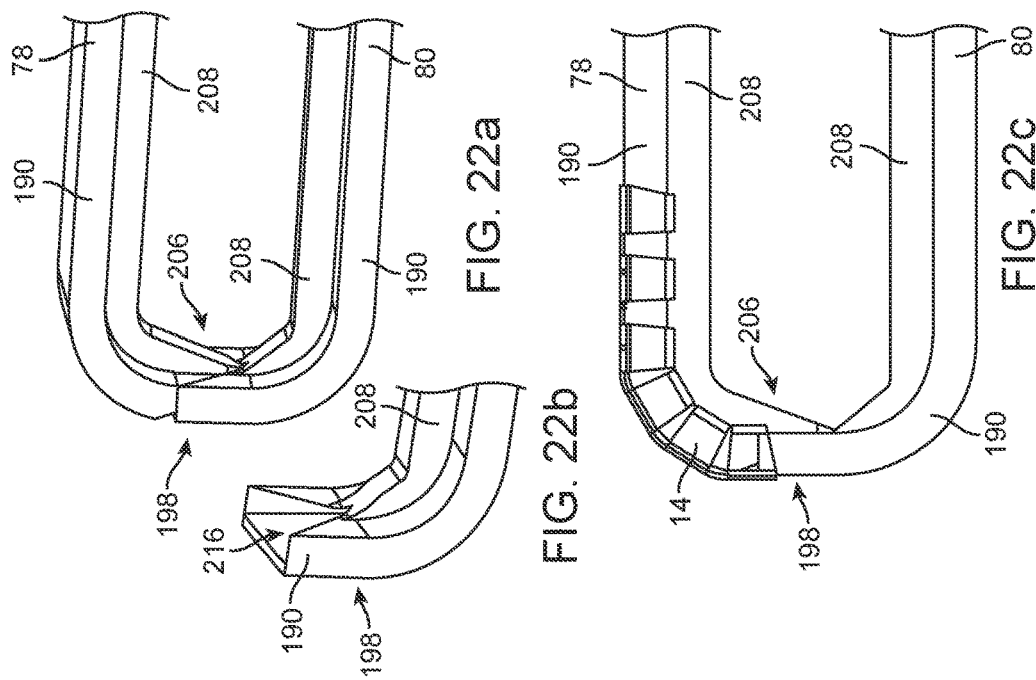

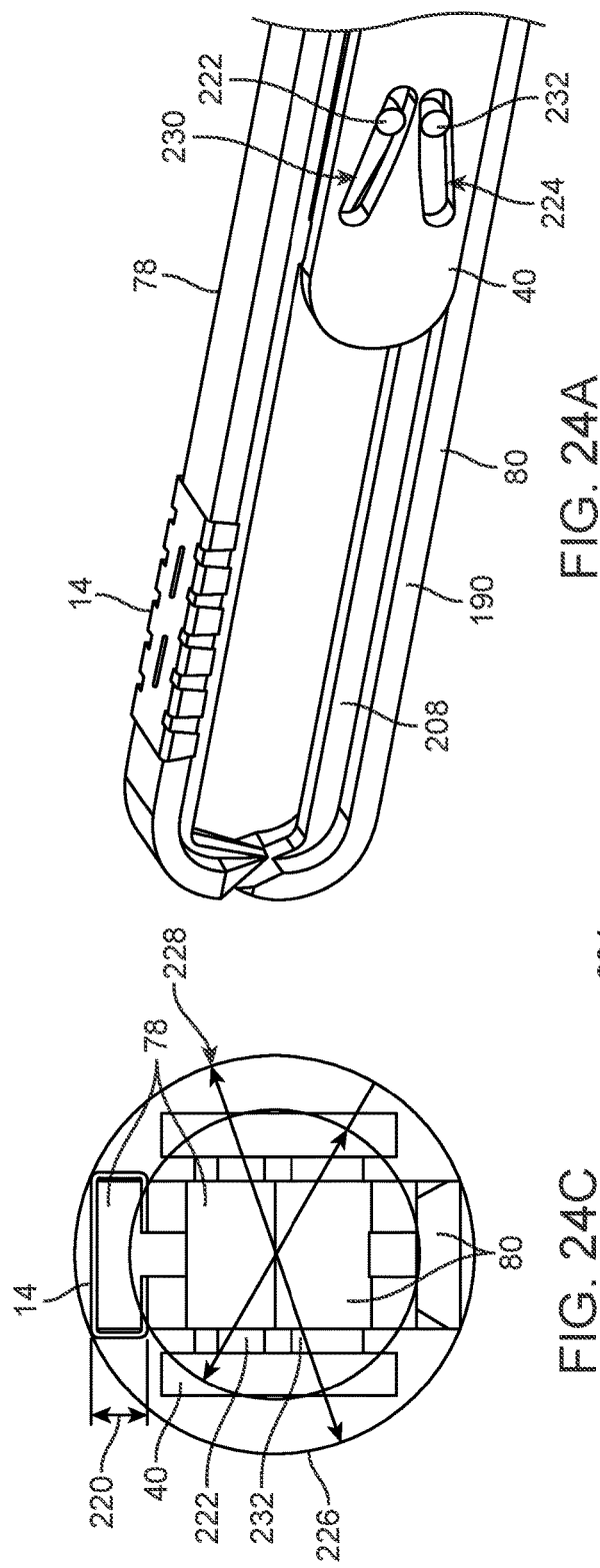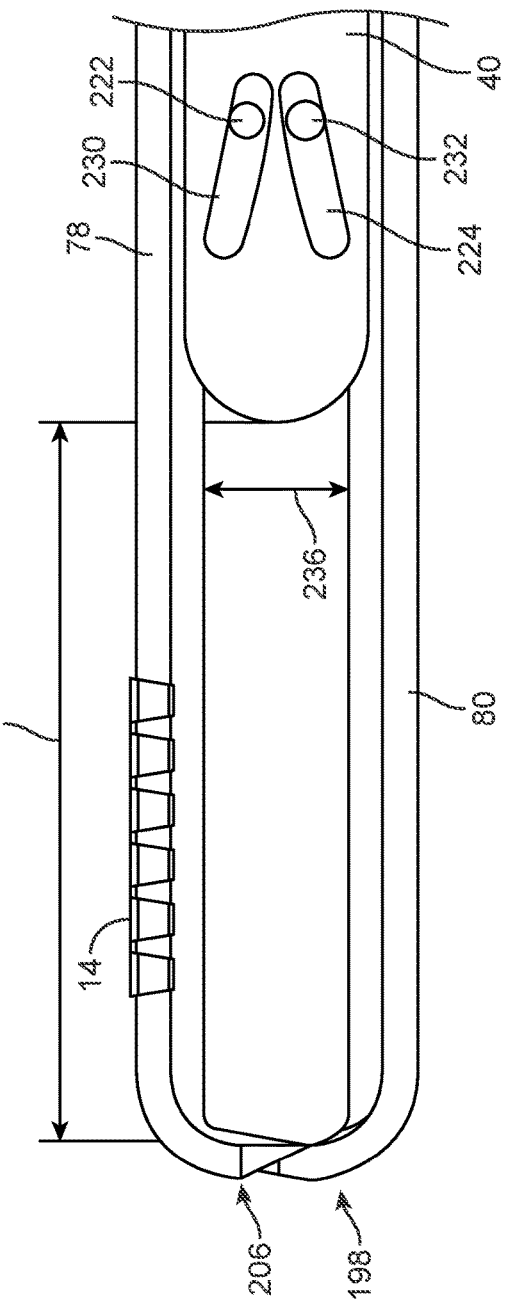

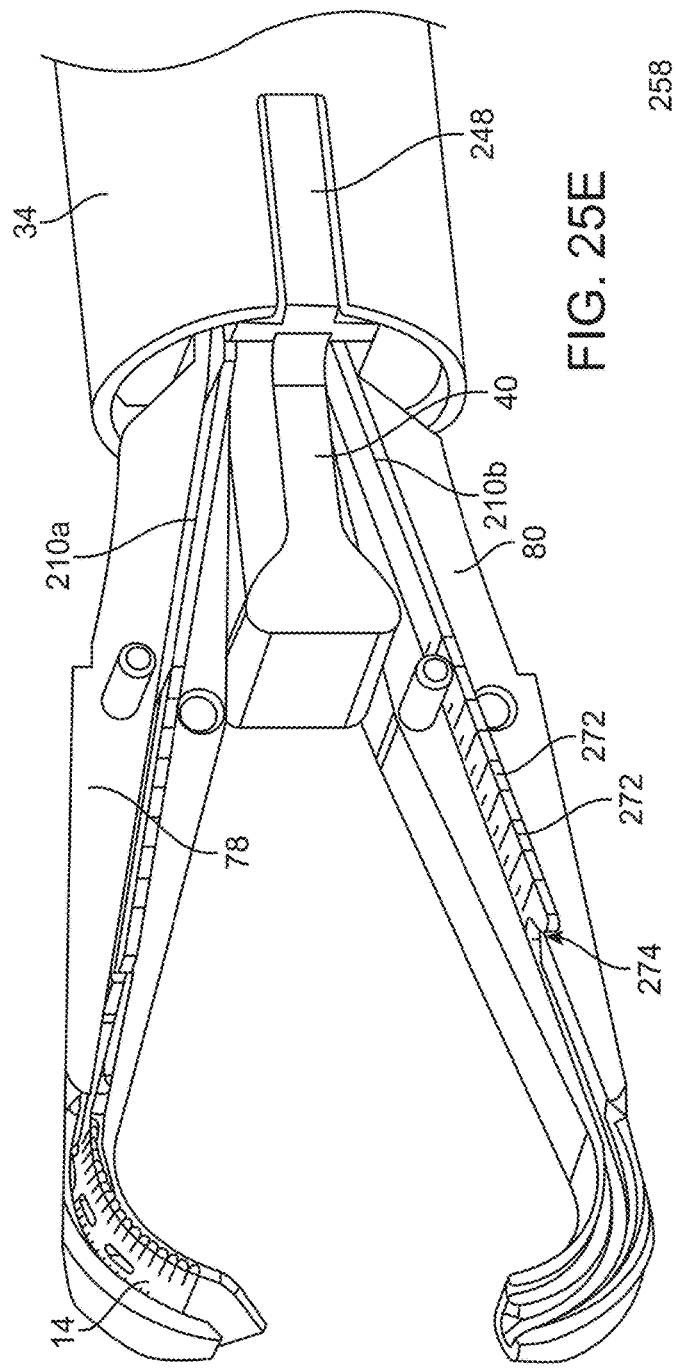
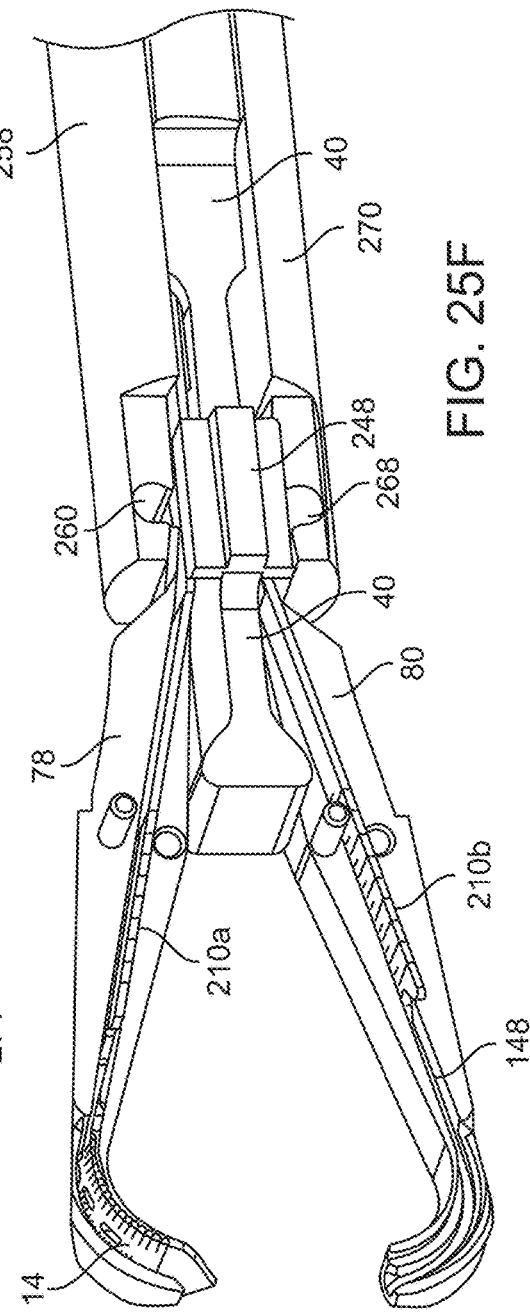

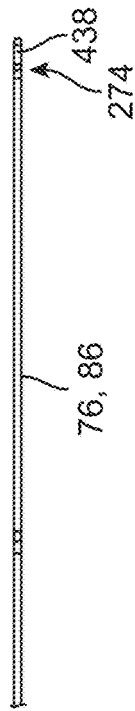
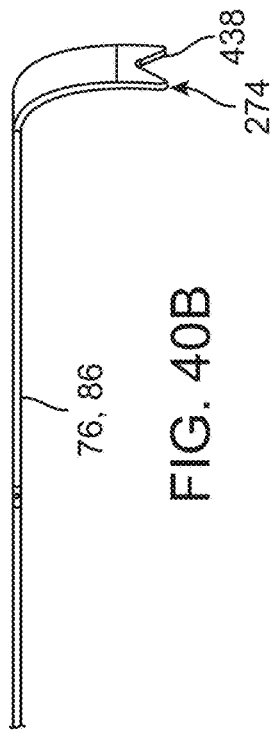
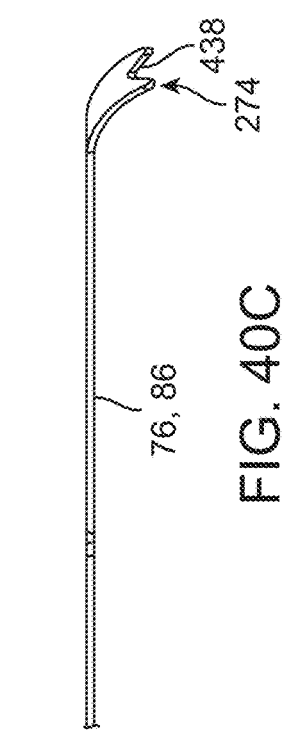
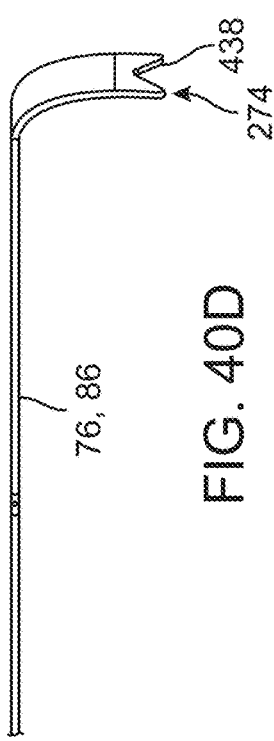
FIG. 39A  FIG. 39B  FIG. 39C  FIG. 39D
FIG. 40A  FIG. 40B  FIG. 40C  FIG. 40D

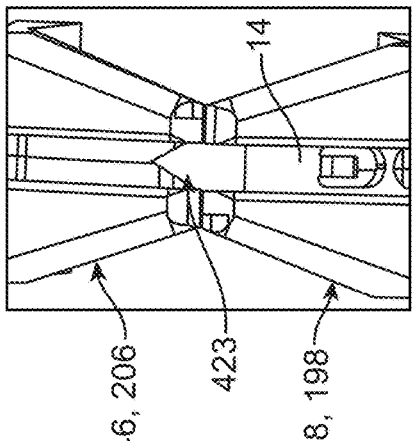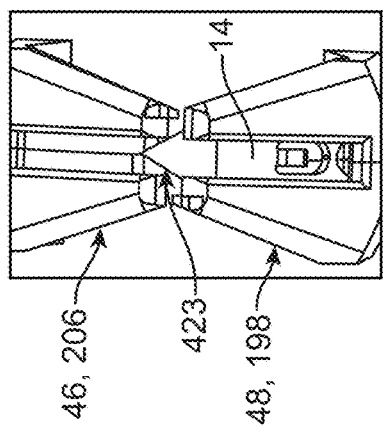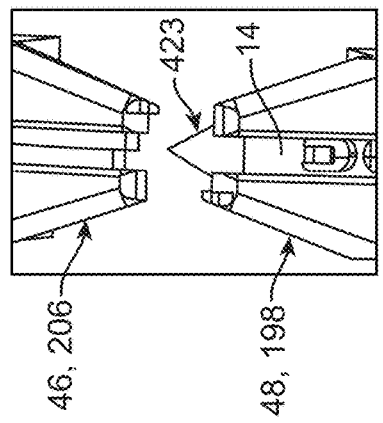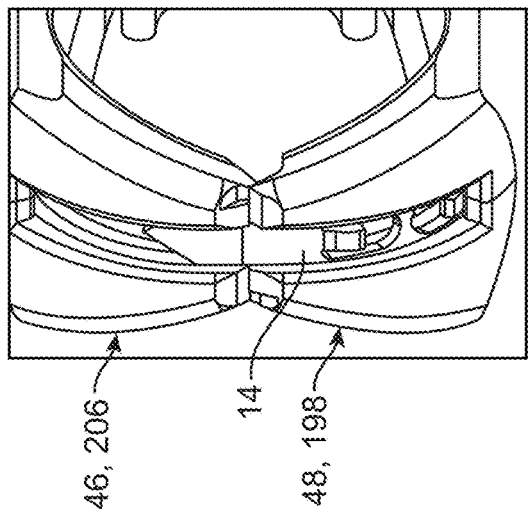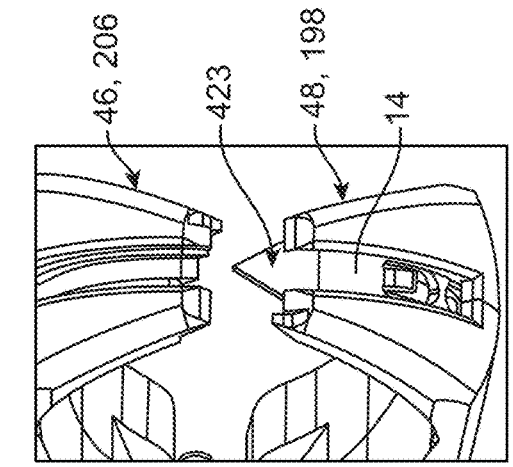
FIG. 43I
FIG. 43H
FIG. 43G
FIG. 43K
FIG. 43J

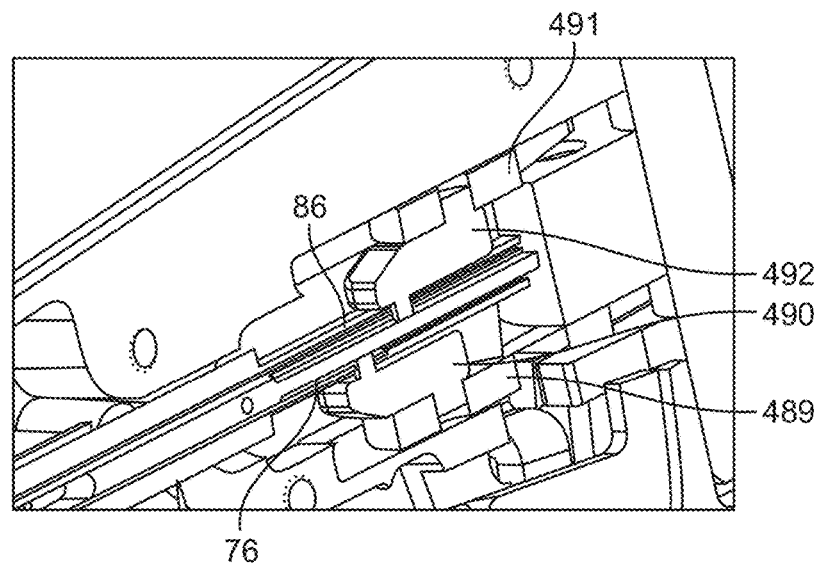
FIG. 45F
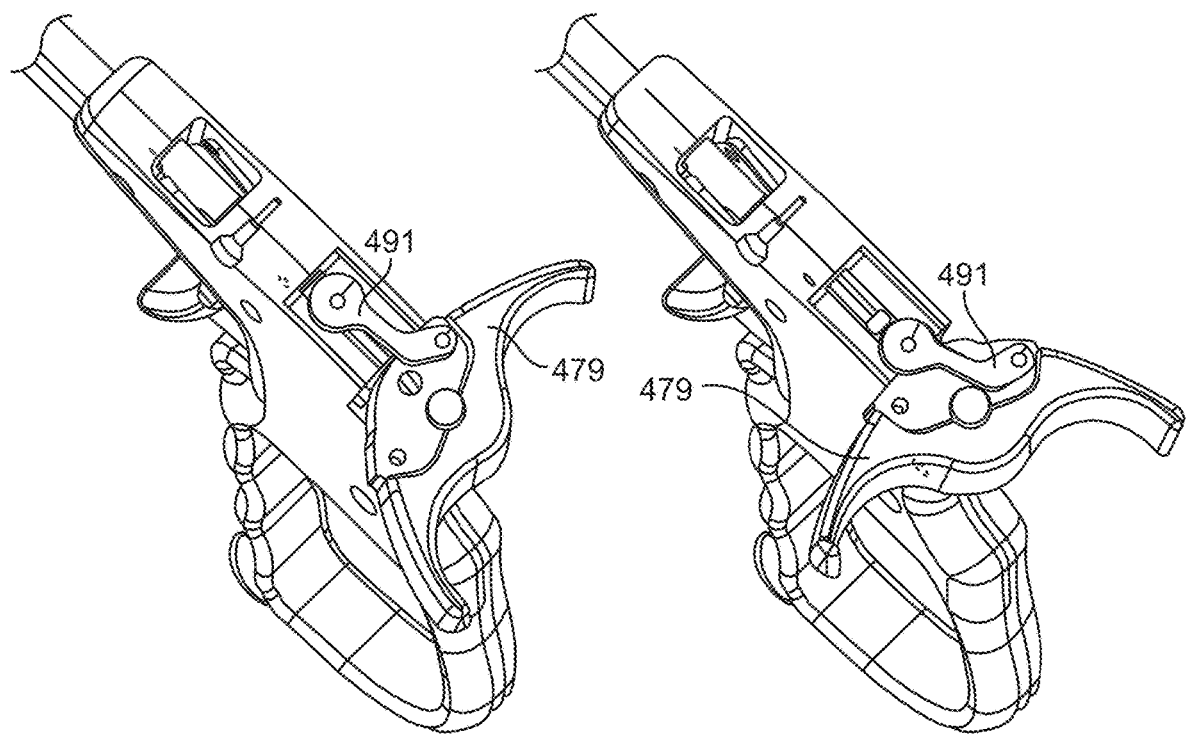
FIG. 45G
FIG. 45H

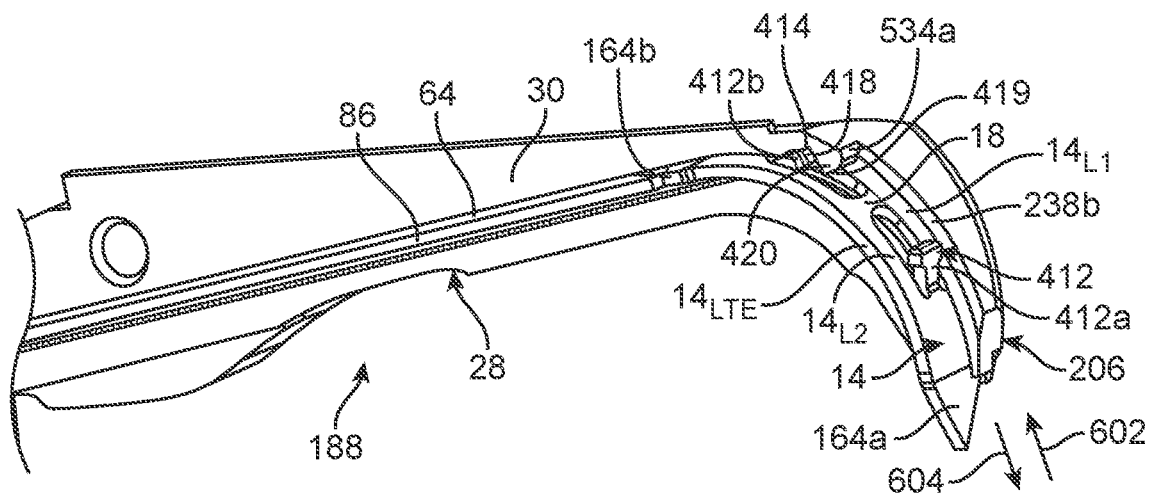
FIG. 49H$_1$
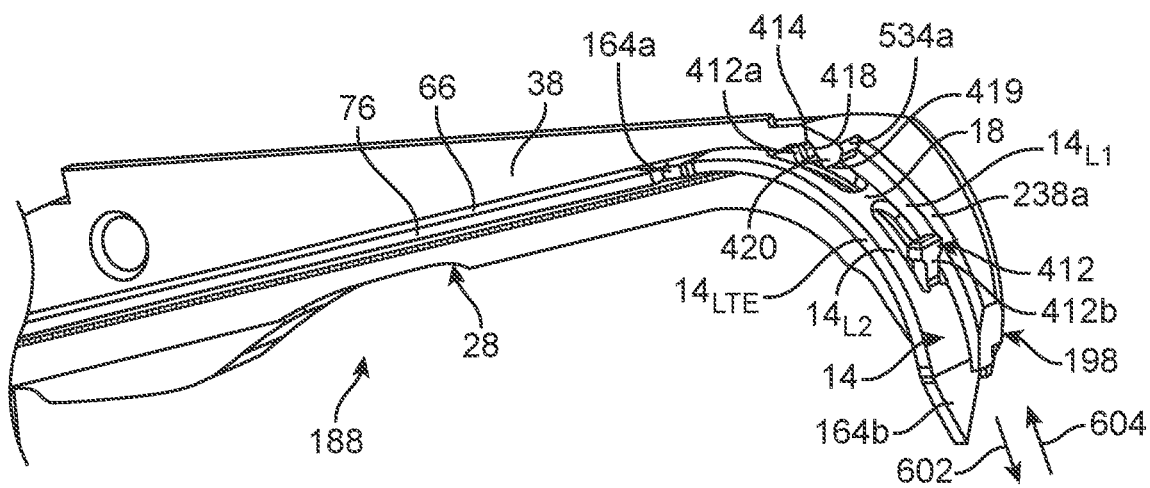
FIG. 49H$_2$

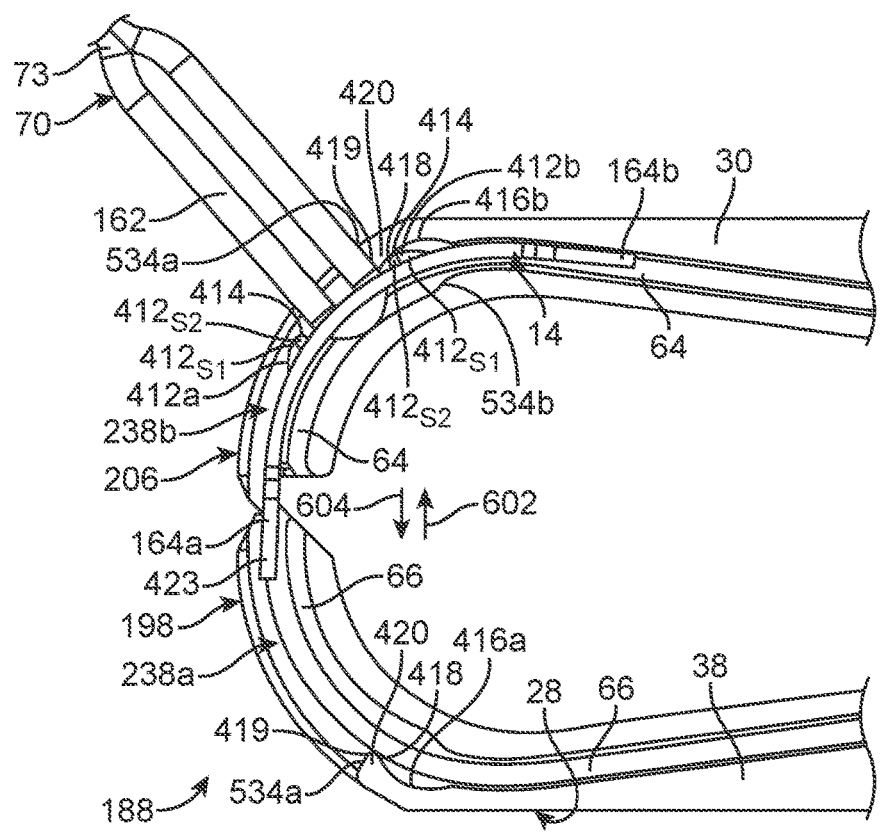
FIG. 49H₃
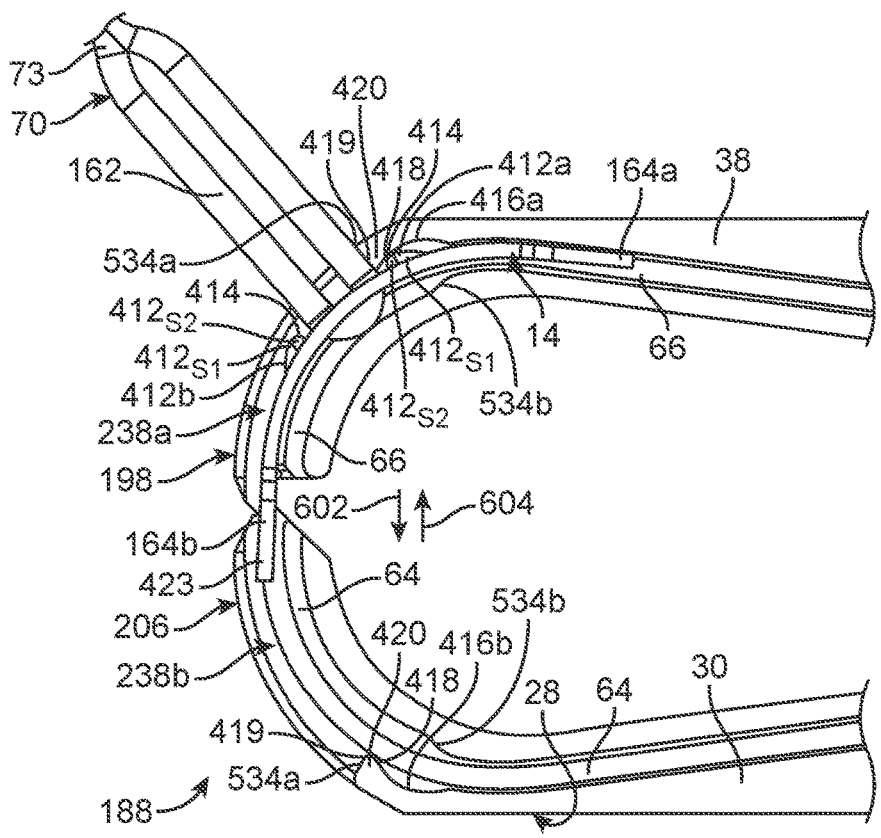
FIG. 49H₄

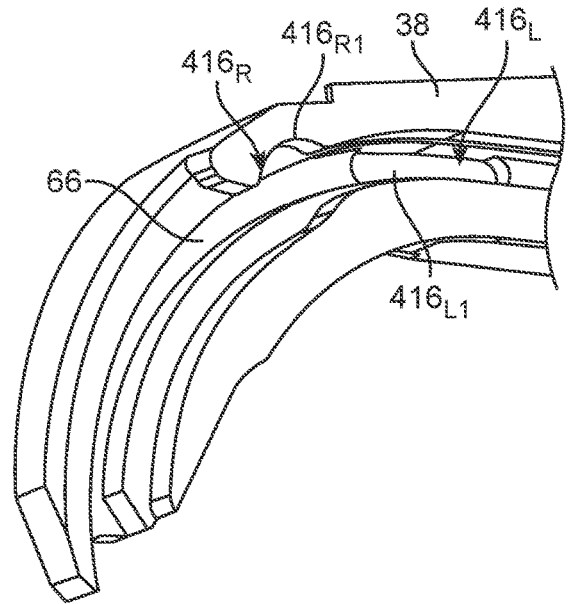
FIG. 50H₁
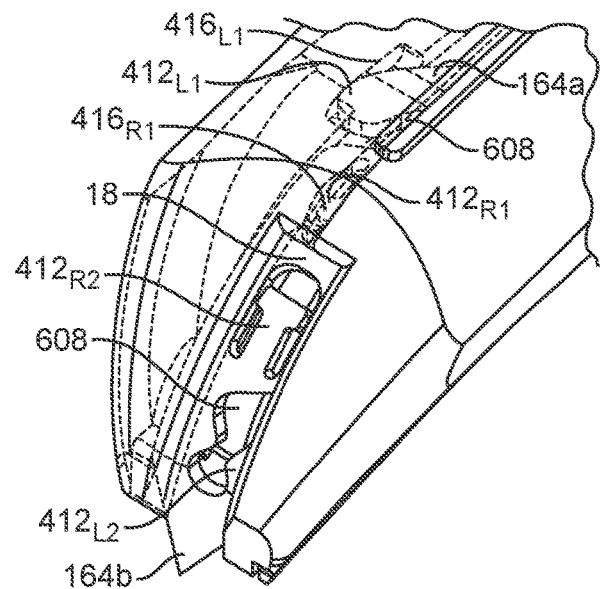
FIG. 50H₂
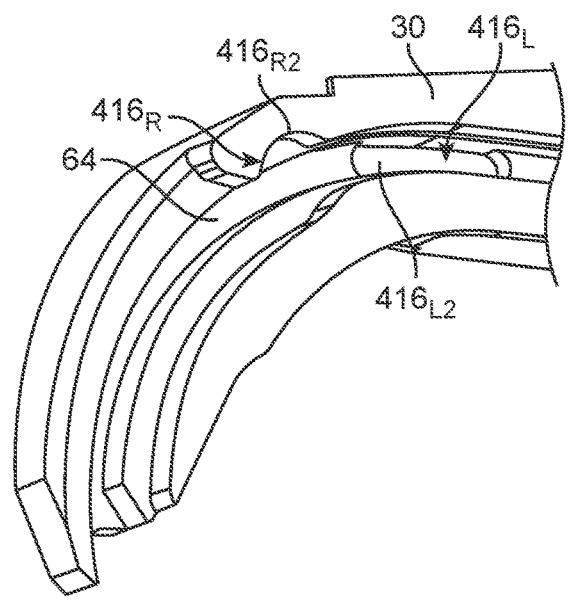
FIG. 50H₃
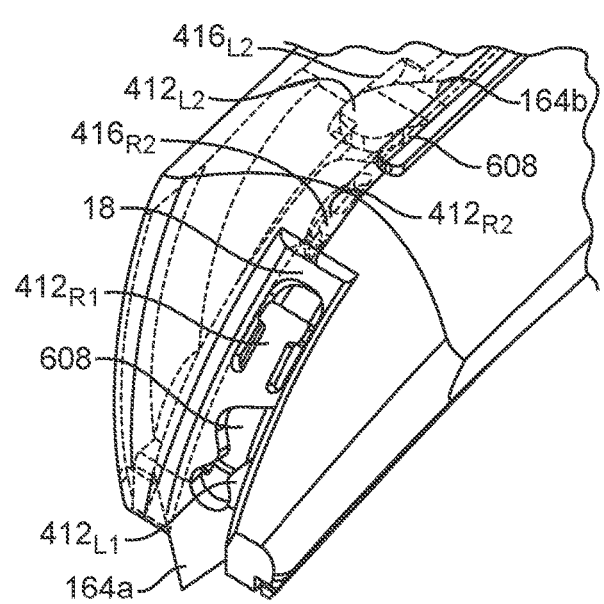
FIG. 50H₄

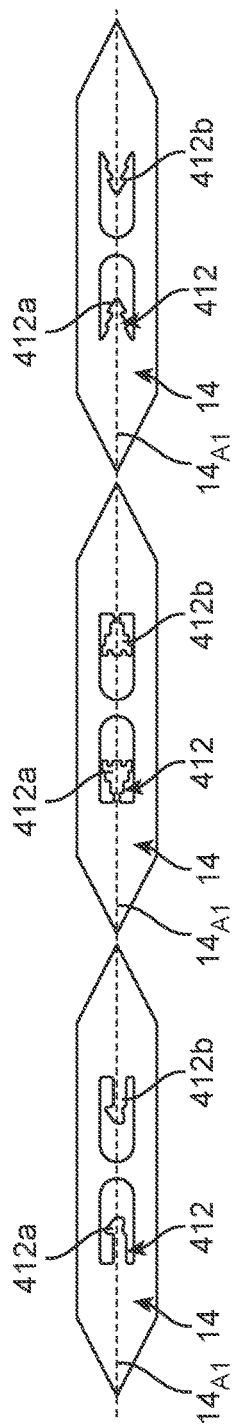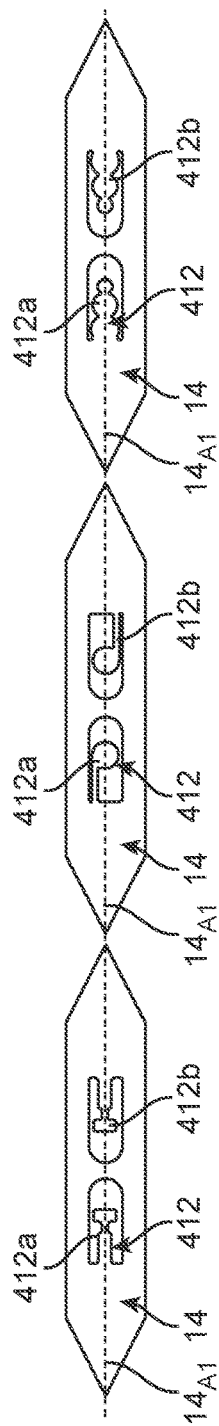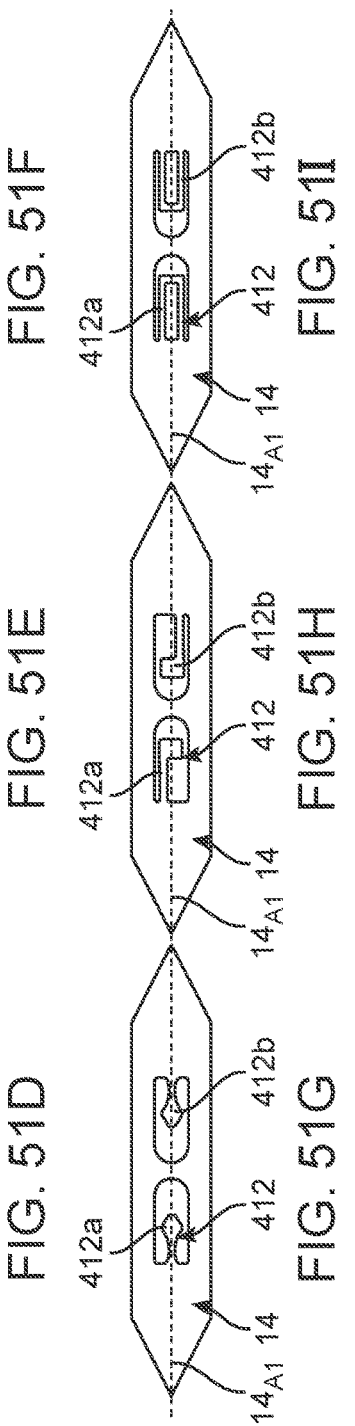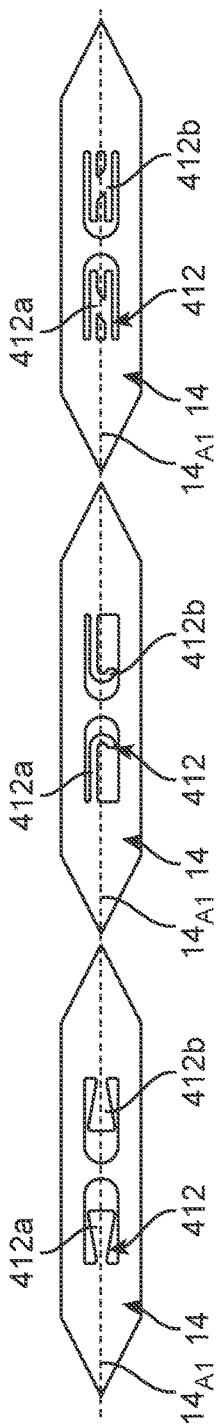

METHOD AND APPARATUS FOR PASSING SUTURE

BACKGROUND

1. Field of the Invention

The present invention relates to system, methods, and apparatus for enhancing the advancement and retention of suture through tissue.

2. Description of Related Art

Suturing apparatus in the past have had an elongate shaft and a low profile distal clamping mechanism to facilitate their use through cannulas 226 in less invasive surgery. These devices have typically included opposing jaws which clamp onto the tissue to be sutured. The end segment of the suture is pre-positioned and secured at the distal end of one jaw member. Beyond the clamping motion, the mechanism for passing a suture between the jaws and through the tissue incorporates a bendable needle. The bendable needle advances distally within the jaw member, bringing it in contact with a segment of the suture.

The needle engages and secures the suture to carry it forward. This distal advancement of the bendable needle also results in the leading end of the needle to approach and engage a ramp 44 in the jaw member, deflecting the bendable needle in a direction toward the opposing jaw. The bending of the needle requires a high force and results in excess strain on the needle component. Fracture and failure of the bendable needle is a concern.

Additionally, the bendable needle is further advanced after being deflected in a direction extending away from the jaws, and potentially into unintended anatomy. Extension of the needle in this manner is a safety concern. Even after the apparatus has completed passing the suture through the tissue, the end segment of the suture must be retrieved by retracting the entire apparatus out of the cannula.

It would be advantageous to have an apparatus that could load and unload suture without the need to remove the apparatus from the surgical site.

It would be advantageous to have an apparatus that could pass (not load and unload) suture repeatedly through tissue without the need to remove the apparatus from the surgical site. It would also be advantageous for the suture shuttling mechanism (either needle or shuttle) to be entirely contained within the apparatus during operation to improve accuracy of suture placement and improve safety of needle or shuttle position during operation.

SUMMARY OF THE INVENTION

This disclosure relates generally to suture devices and methods of suturing.

Suture manipulating devices are disclosed. For example, a suture manipulating device having a first jaw having a first jaw channel and a first jaw first stop is disclosed. The suture manipulating device can have a shuttle. The shuttle can have a shuttle longitudinal axis and a shuttle first stop. The shuttle can be slideable in the first jaw channel. The shuttle first stop can extend away from the shuttle longitudinal axis. The shuttle first stop can have a shuttle first stop proximal end and a shuttle first stop distal end. The shuttle first stop proximal end can be narrower than the shuttle first stop distal end. The shuttle first stop distal end can be deflectable into the first jaw first stop. The shuttle first stop can be engageable with the first jaw first stop. When the shuttle first stop is engaged with the first jaw first stop, the shuttle first stop distal end can be in contact with the first jaw first stop. When the shuttle first stop distal end is in contact with the first jaw first stop, the shuttle can be passively retained in the first jaw.

Suture manipulating devices are disclosed. For example, a suture manipulating device having a jaw structure having a shuttle channel having a shuttle channel first stop is disclosed. The suture manipulating device can have a shuttle. The shuttle can have a shuttle longitudinal axis and a shuttle first stop. The shuttle can be slideable in the shuttle channel. The shuttle first stop can extend away from the shuttle longitudinal axis. The shuttle first stop can have a shuttle first stop proximal end and a shuttle first stop distal end. The shuttle first stop proximal end can be narrower than the shuttle first stop distal end. The shuttle first stop can be moveable into the shuttle channel first stop. The shuttle first stop can be engageable with the shuttle channel first stop. When the shuttle first stop is not engaged with the shuttle channel first stop, the shuttle first stop can have a shuttle first stop non-deflected shape. When the shuttle first stop is engaged with the shuttle channel first stop, the shuttle first stop can have a shuttle first stop deflected shape.

Suture manipulating devices are disclosed. For example, a suture manipulating device having a jaw having a shuttle channel having a female stop is disclosed. The suture manipulating device can have a shuttle. The shuttle can have a shuttle longitudinal axis and a male stop. The shuttle can be translatable in the shuttle channel. The male stop can be engageable with the female stop. The male stop can extend away from the shuttle longitudinal axis. The male stop can have a male stop proximal end and a male stop distal end. The male stop distal end can be wider than the male stop proximal end. The male stop can be translatable into and out of the female stop. The male stop can be deflectable into and out of the female stop.

BRIEF DESCRIPTION OF THE FIGURES

The drawings shown and described are exemplary embodiments and non-limiting.

Like reference numerals indicate identical or functionally equivalent features throughout.

FIGS. 4*a* and 4*b* are close-up perspective and side views, respectively, of the distal end of a variation of the suture passing device in a closed configuration.

FIG. 4*c* is a close-up of the distal end of FIGS. 4*a* and 4*b*.

FIG. 4*d* is a close-up perspective view of the distal end of the device of FIG. 4*a* in a closed configuration.

FIG. 5 is a variation of cross-section A-A of FIG. 1*a* with the device attached to a length of a suture.

FIG. 7c is a close-up view of the variation of the shuttle in FIG. 7a.

FIG. 7d is a close-up view of the distal end of the variation of the device shown in FIG. 7a.

FIGS. 9b and 11a are side perspective and side cross-section views, respectively, of a variety of a method for closing the jaws of the device of FIG. 9a.

FIG. 10b is a close-up partial see-through view of the distal end of the lower jaw of FIG. 10a.

FIGS. 12a through 12c are side, top and bottom views, respectively, of a variation of the shuttle.

FIGS. 15a through 15c are side perspective, bottom perspective, and side-bottom perspective views of a variation of the shuttle.

FIGS. 16a and 16b are top perspective and side perspective views of a variation of the shuttle.

FIGS. 22a and 22b illustrate a variation of the distal end and distal lower jaw, respectively, of the device.

FIG. 22c is a side view of the device of FIG. 22a with a shuttle.

FIGS. 23a and 23b are a variation of the distal end of the device in open and closed configurations, respectively with the device of FIG. 23b having a shuttle.

FIGS. 24a through 24c are side perspective, side and distal end views, respectively, of a variation of the device.

FIGS. 25a through 25f are bottom and side perspective, partial see-through (the upper jaw is see-through), longitudinal cross-section, partial cut-away close-up, and partial cut-away views, respectively, of the distal end of a variation of the device with the jaws in an opened configuration with the shuttle and pushers in various positions, and with the compression cover not shown in FIG. 25f for illustrative purposes.

FIG. 26b does not show the pushers for illustrative purposes.

FIG. 39A illustrates a side view of a variation of a pusher.

FIG. 39B illustrates a side view of a variation of a pusher.

FIG. 39C illustrates a side view of a variation of a pusher.

FIG. 39D illustrates a side view of a variation of a pusher.

FIG. 40A illustrates a perspective view of the pusher of FIG. 39A having a shuttle seat.

FIG. 40B illustrates a perspective view of the pusher of FIG. 39B having a shuttle seat.

FIG. 40C illustrates a perspective view of the pusher of FIG. 39C having a shuttle seat.

FIG. 40D illustrates a perspective view of the pusher of FIG. 39D having a shuttle seat.

FIG. 43G illustrates a variation of the upper and lower jaws.
FIG. 43H illustrates a variation of the upper and lower jaws.
FIG. 43I illustrates a variation of the upper and lower jaws.
FIG. 43J illustrates a variation of the upper and lower jaws.
FIG. 43K illustrates a variation of the upper and lower jaws.
FIG. 45F illustrates a variation of a handle of the device.
FIG. 45G illustrates a variation of a handle of the device.
FIG. 45H illustrates a variation of a handle of the device.

Figure 49A:
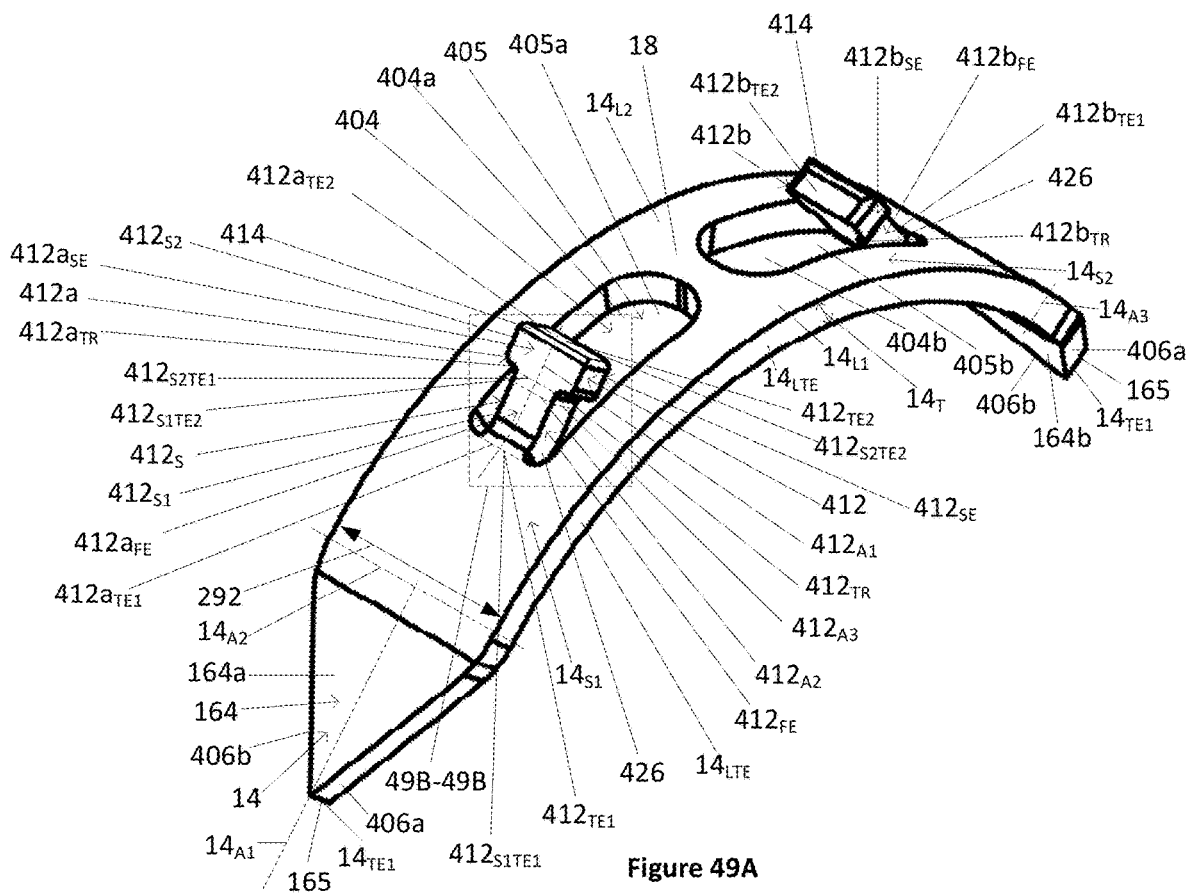
FIG. 49A illustrates a perspective view of a variation of a shuttle.

FIG. $49H_1$ illustrates the shuttle of FIG. 49A in an upper jaw with half of the upper jaw shown transparent.

FIG. $49H_2$ illustrates the shuttle of FIG. 49A in a lower jaw with half of the lower rjaw shown transparent.

FIG. $49H_3$ illustrates a variation of the device with the shuttle of FIG. 49A in the upper jaw with half of the lower and upper jaws shown transparent.

FIG. $49H_4$ illustrates a variation of the device with the shuttle of FIG. 49A in the lower jaw with half of the lower and upper jaws shown transparent.

Figure 50A:
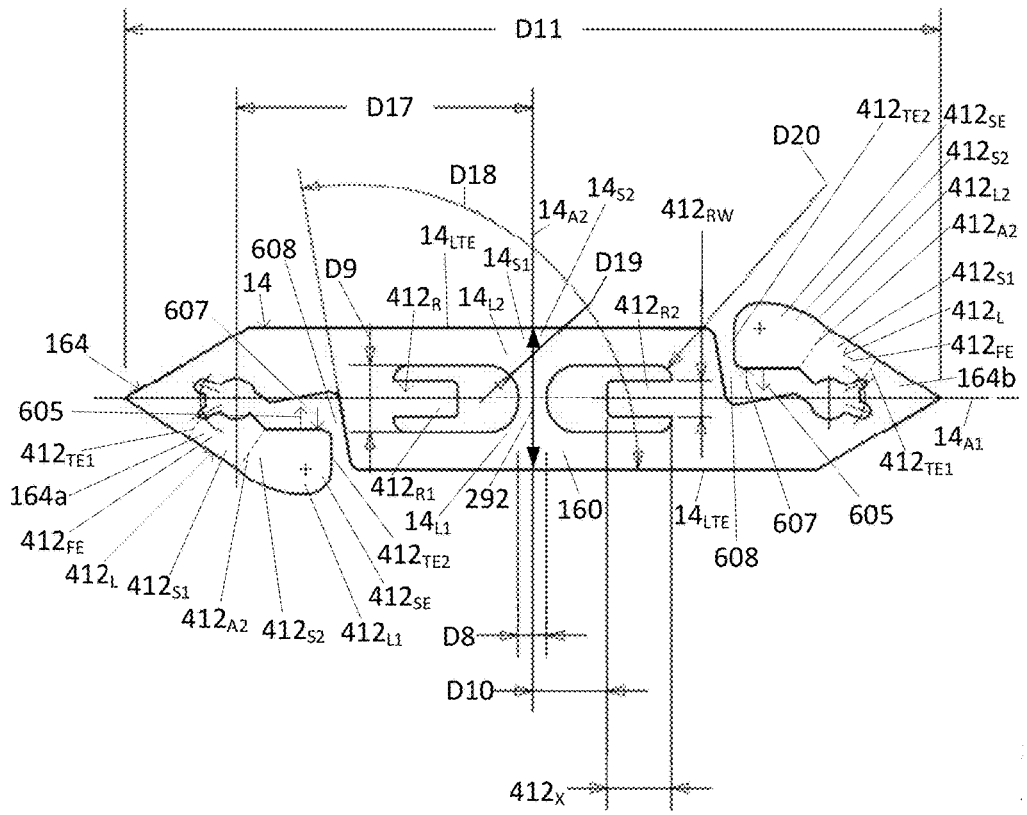

FIG. 50A illustrates a top view of a variation of a shuttle in a flat configuration.

Figure 50B:
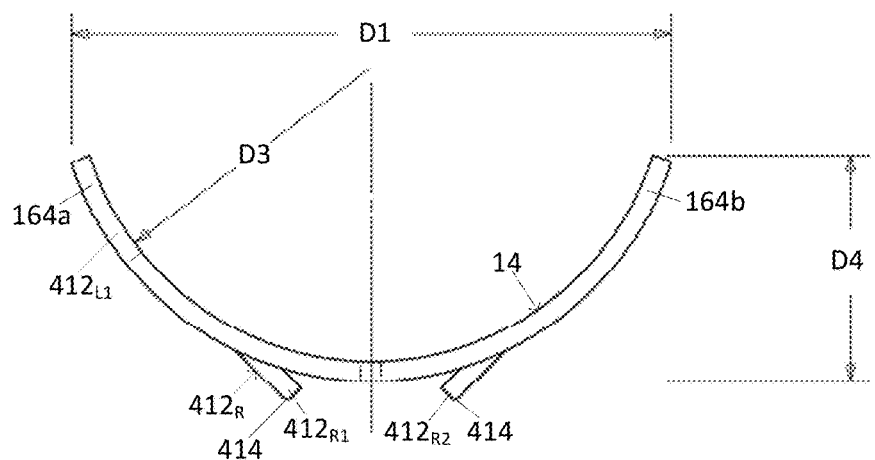

FIG. 50B illustrates a side view of the shuttle of FIG. 50A in a shape set configuration.

Figure 50C:
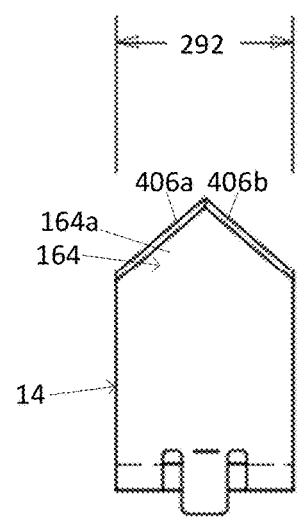

FIG. 50C illustrates an end view of the shuttle of FIG. 50B.

Figure 50D:
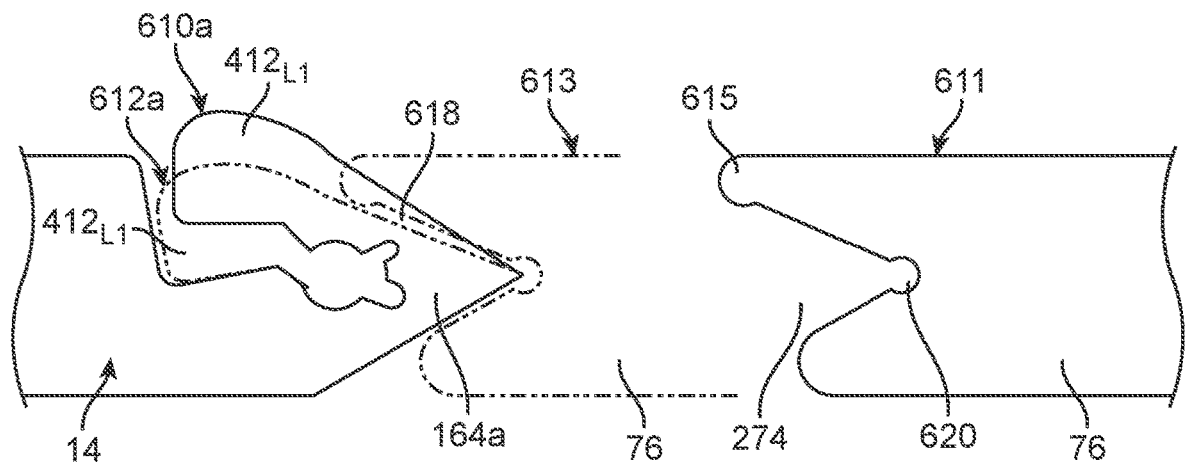
Figure 50E:
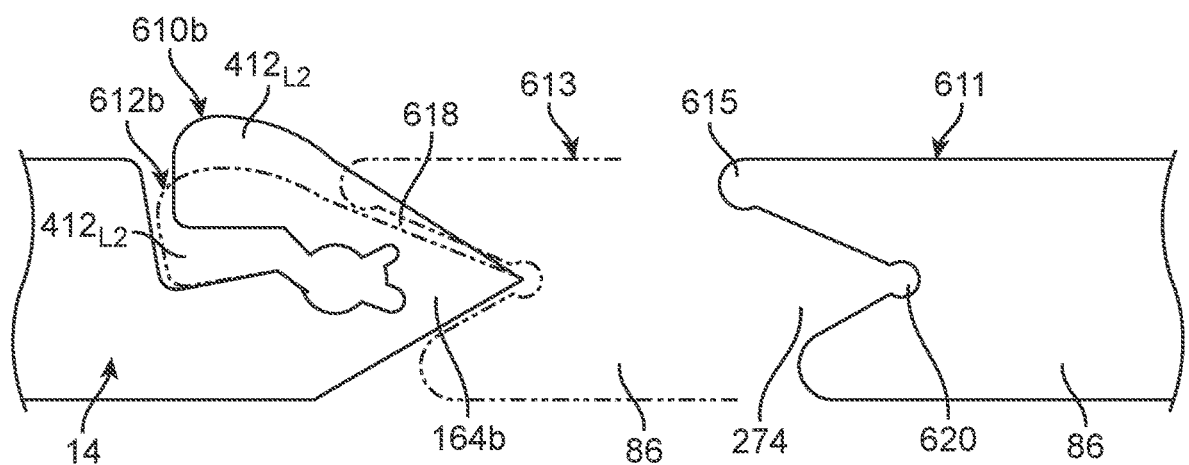

FIG. 50E illustrates a top view of a variation of the shuttle of FIG. 50B and a variation of a lower jaw pusher in a lower jaw shuttle track with the lower jaw shuttle track shown transparent.

FIG. 50D illustrates a top view of a variation of the shuttle of FIG. 50B and a variation of an upper jaw pusher in an upper jaw shuttle track with the upper jaw shuttle track shown transparent.

Figure 50F:
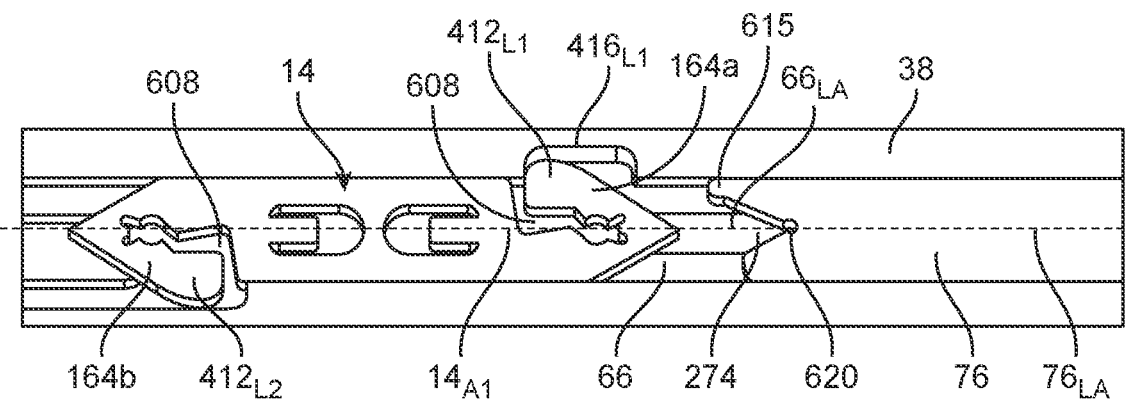

FIG. 50F illustrates a top view of a variation of the shuttle of FIG. 50B and a variation of a lower jaw pusher in a lower jaw shuttle track with a top of the lower jaw shown transparent.

Figure 50G:
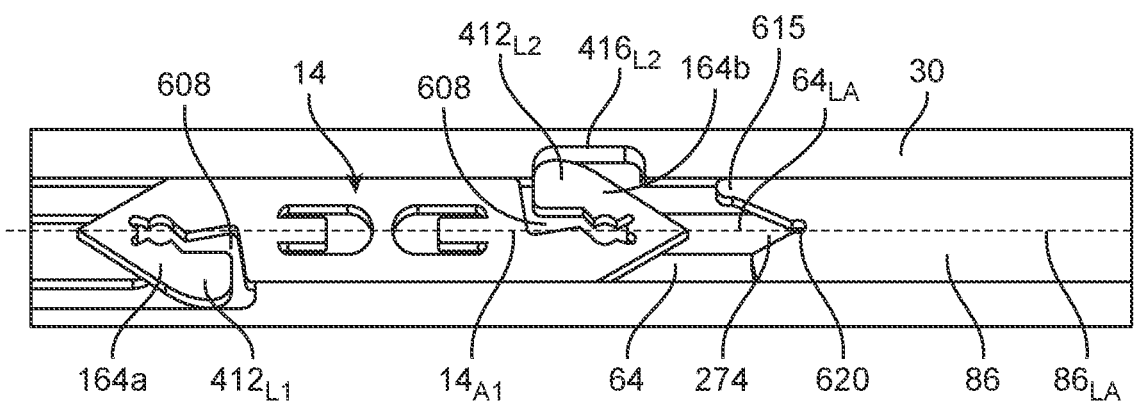

FIG. 50G illustrates a top view of a variation of the shuttle of FIG. 50B and a variation of an upper jaw pusher in an upper jaw shuttle track with a top of the upper jaw shown transparent.

FIG. $50H_1$ illustrates a perspective view of a variation of a lower jaw with half of the lower jaw shown transparent.

FIG. $50H_2$ illustrates a perspective view of the lower jaw of FIG. $50H_1$ with a variation of a shuttle and with half of the lower jaw shown transparent.

FIG. $50H_3$ illustrates a perspective view of a variation of an upper jaw with half of the upper jaw shown transparent.

FIG. $50H_4$ illustrates a perspective view of the upper jaw of FIG. $50H_4$ with a variation of a shuttle and with half of the upper jaw shown transparent.

FIGS. 51A-51L illustrate top views of variations of shuttles and variations of male stops.

Figure 52A:
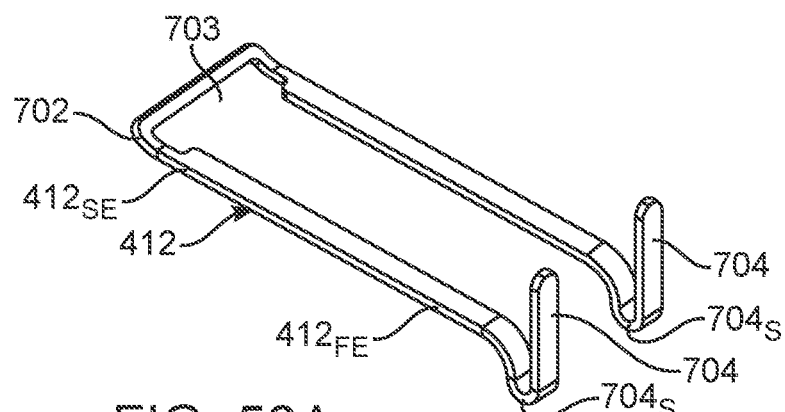

FIG. 52A is a perspective view of a variation of a male stop.

Figure 52B:
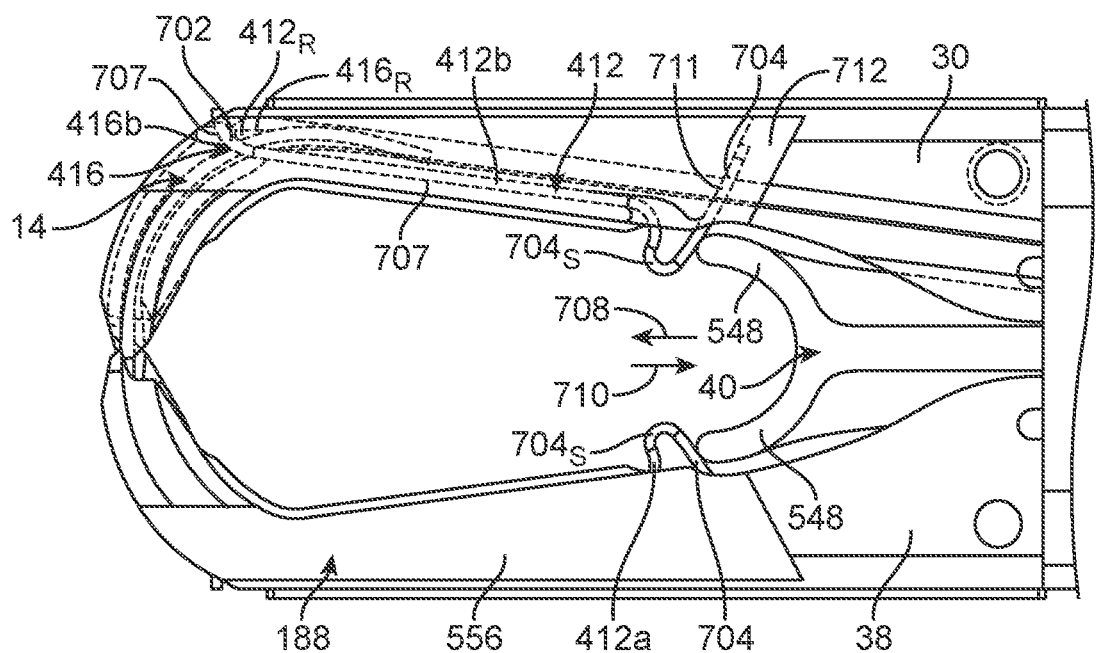

FIG. 52B is a side view of a lower jaw and a side view of an upper jaw with the male stop of FIG. 52A in a disengaged configuration, with the upper jaw shown transparent.

Figure 52C:
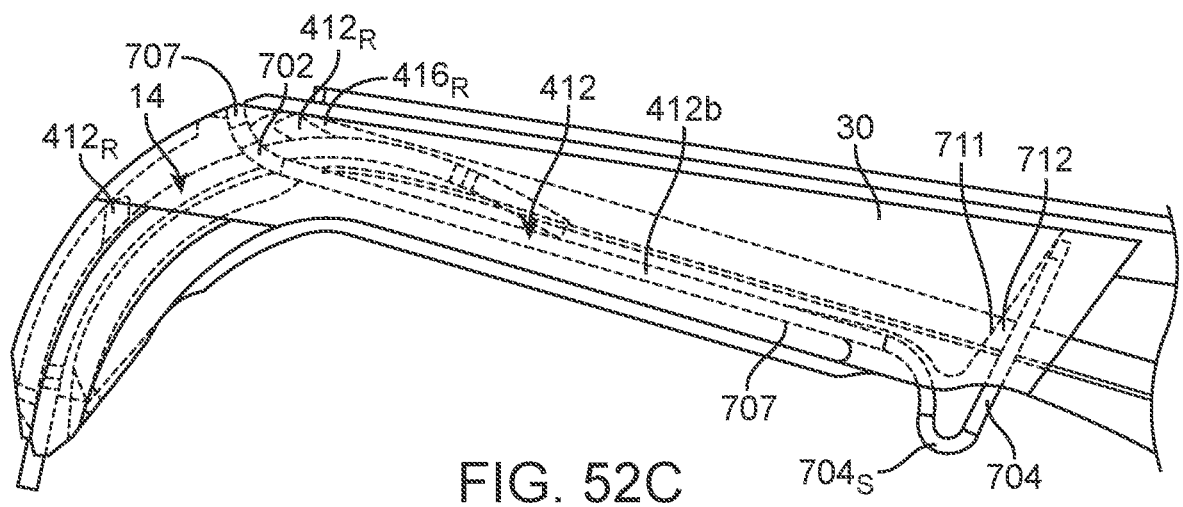

FIG. 52C is a side view of the upper jaw of FIG. 52B with the male stop in an engaged configuration.

Figure 52D:
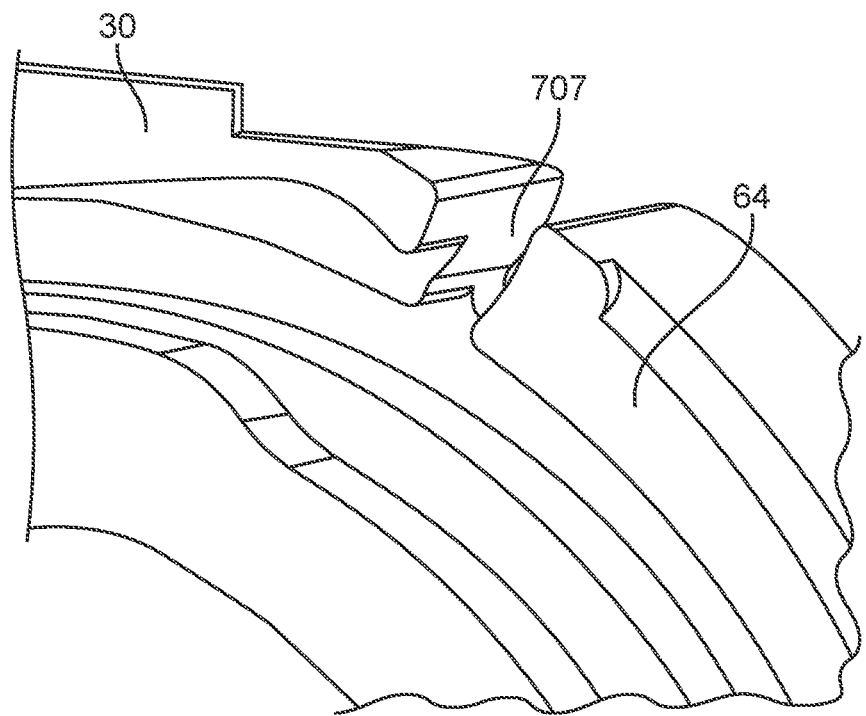

FIG. 52D is a close-up of FIG. 52C without a shuttle or a male stop.

Figure 52E:
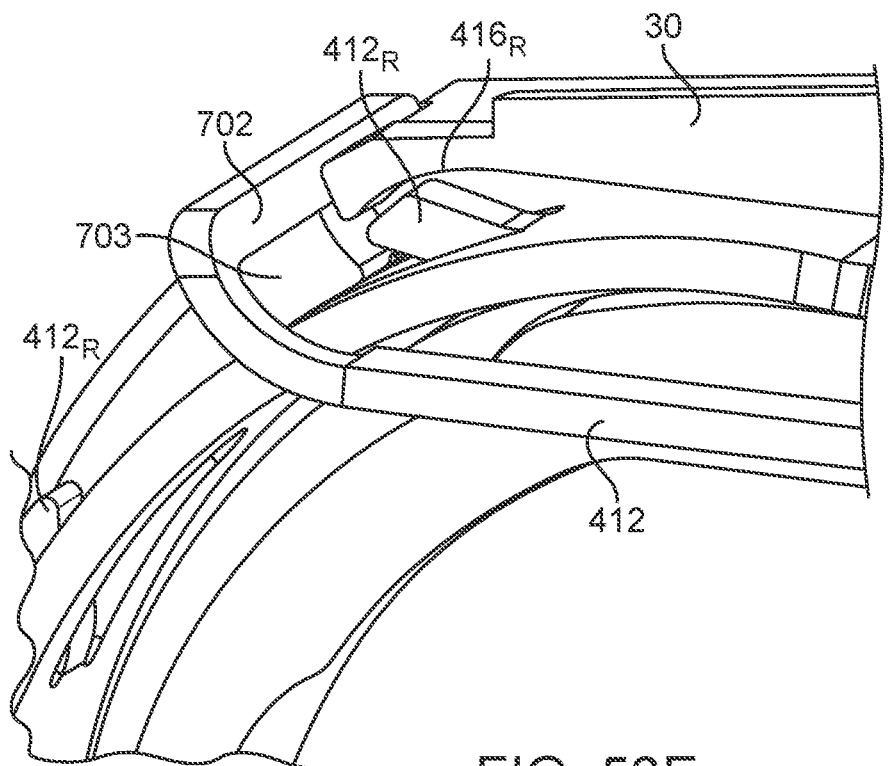

FIG. 52E is a close-up perspective view of FIG. 52B.

DETAILED DESCRIPTION

Figure 1A:
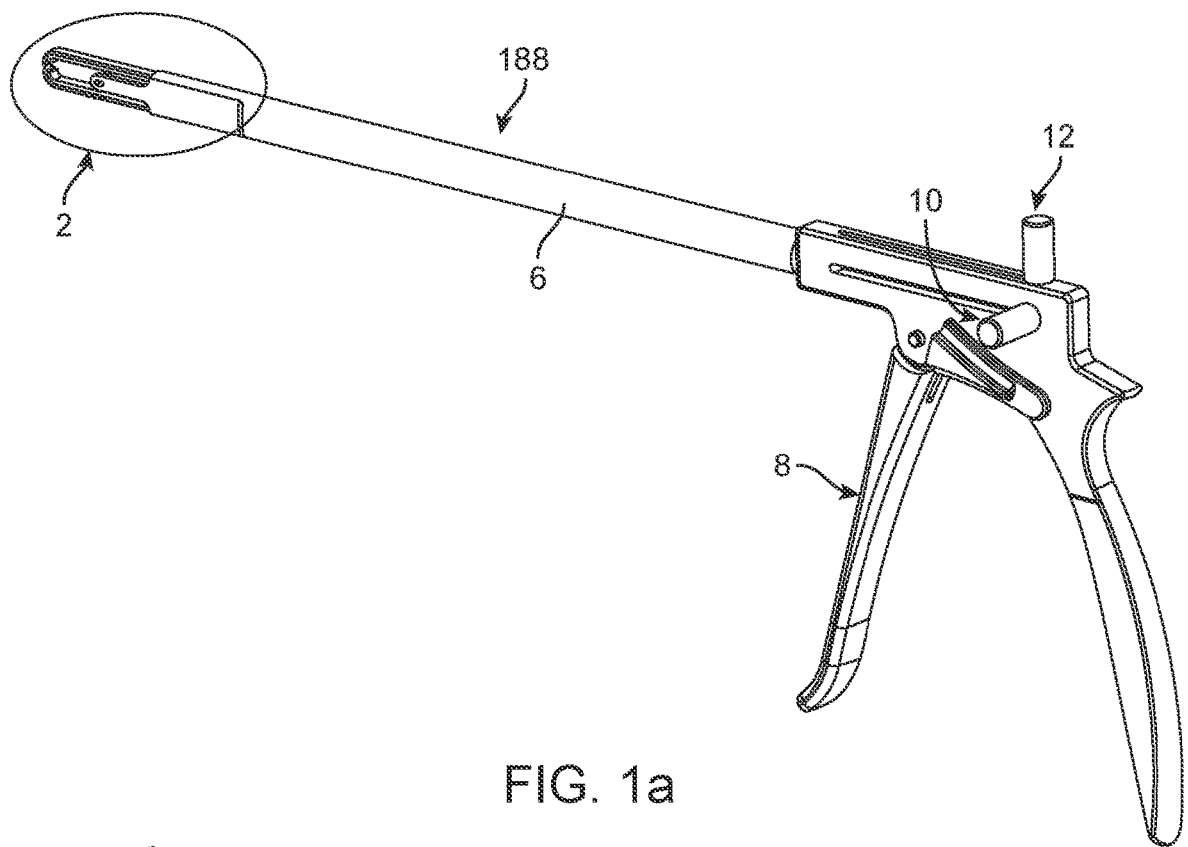
FIGS. 1*a*, 1*b* and 1*c* are perspective, top and side views, respectively, of a variation of the suture passing device.
Figure 1B:
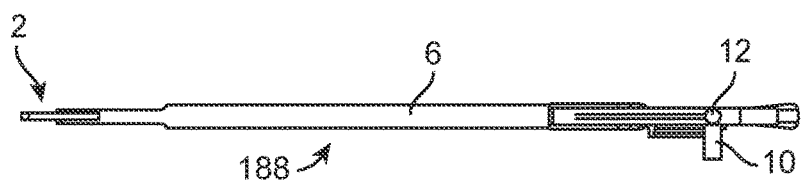
Figure 1C:
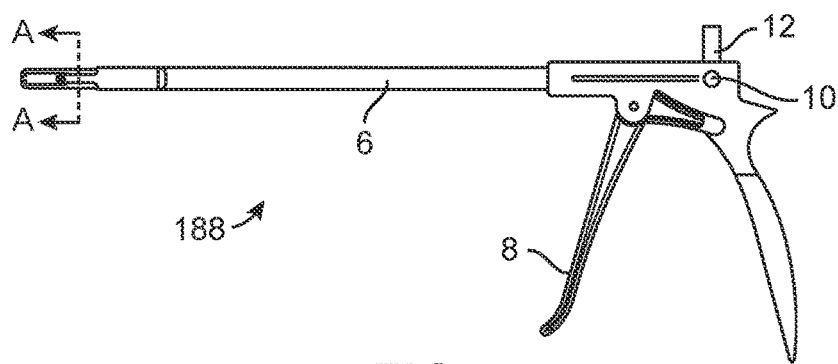

FIGS. 1a through 1c illustrate a suture passing device 188 that can be used to pass suture 70 through soft or hard tissue 74 without removing the device 188 or the suture 70 from the target site while creating one or more complete stitches.

The suture passing device 188 can have an ergonomic handle 104, a sliding tube actuator 6, and a distal end 2. The ergonomic handle 104 can be used to control the distal end 2. The ergonomic handle 104 can have a side knob 10. The ergonomic handle 104 can have a top knob 12. The top knob 12 and/or the side knob 10 can individually or in concert, advance and/or retract the upper 86 and/or lower pusher 76.

The sliding tube actuator 6 can have an outer compression cover 34 and an inner rod (not shown due to obstruction by the outer compression cover 34). The inner rod can be fixedly attached to the handle 104 and the proximal end of the jaw structure 28. The outer compression cover 34 can be radially outside of the inner rod. The outer compression cover 34 can be actuated by the handle 104, for example be distally and proximally translated with respect to the handle 104 when the trigger 8 is squeezed or released.

Figure 2A:
FIGS. 2*a* and 2*b* are a distant and close-up view, respectively, of a variation of the shuttle in a straight configuration.
Figure 2B:
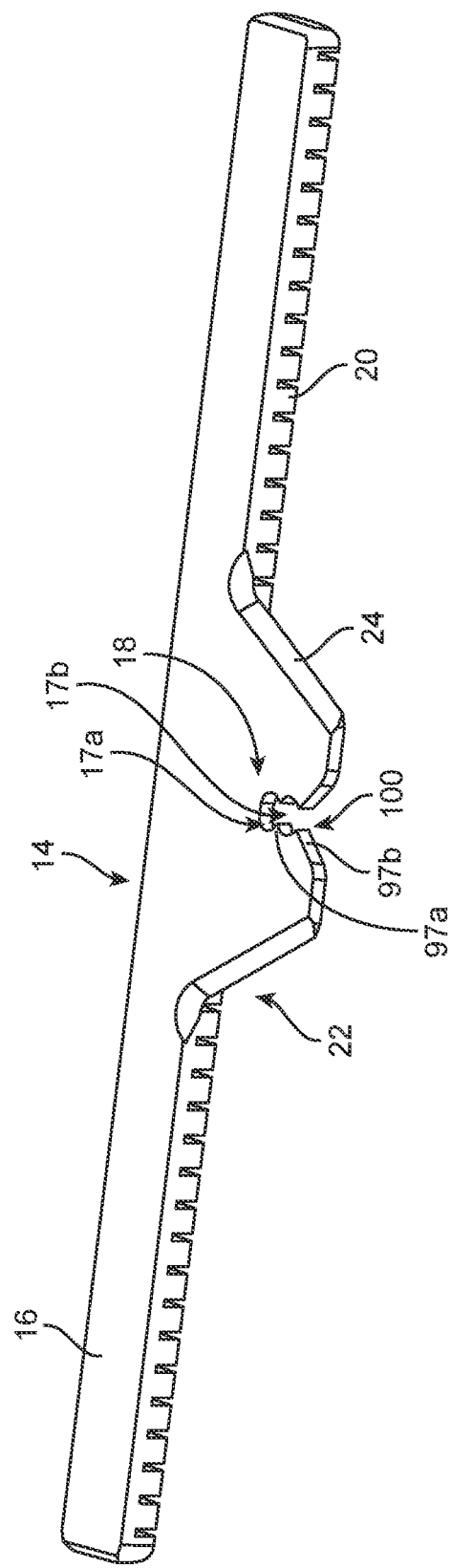

FIGS. 2a and 2b illustrate that the device 188 can have a sliding ribbon shuttle 14 or needle held within the device 188. The shuttle 14 can have an elongated shuttle rail 16. The shuttle rail 16 can have numerous slits 20 along one or both sides of the shuttle rail 16. The slits 20 can be positioned at regular or irregular length intervals along the rail 16.

The shuttle 14 can have a suture holder 18 extending laterally from the rail 16. The shuttle 14, for example the suture holder 18, can extend out of the lateral side slot 72 of the arm structure. The suture holder 18 can extend from the left and/or right side of the device 188. The distal end 2 of the device 188 can be reversible so the suture holder 18 can be switched from one side of the device 188 to the other side of the device 188. The suture holder 18 can have a generally flat, isosceles trapezoid configuration. The suture holder 18 can have a suture holding notch 100. The notch 100 can have an inner hole 17a, an outer hole 17b contiguous with the inner hole 17a, and a first cleat 97a positioned between the inner hole 17a and the outer hole 17b. The notch 100 can have a second cleat 97b on the side of the outer hole away from the inner hole. The notch 100 can be configured to secure to suture 70. For example, the suture 70 can be compressed and friction fit in the inner cleat 97a.

The suture holder 18 can have a front leading edge and a rear leading edge. The edges can be slanted at a right or non-right angle with respect to the longitudinal axis of the rail 16. One or both of the edges can be sharpened to be traumatic to tissue 74, for example to cut through soft tissue 74. The edges can cut through tissue 74, allowing the suture holder 18 to pull the suture 70 through the tissue 74 immediately behind the respective edge.

The shuttle 14 can be made from a flexible polymer, such as PEEK, a resilient metal such as Nitinol, any material disclosed herein or combinations thereof. The shuttle 14 can be made from a molded polymer. The shuttle 14 can be pre-curved, for example to reduce resistance when going around curves in the tracks.

Figure 2C:
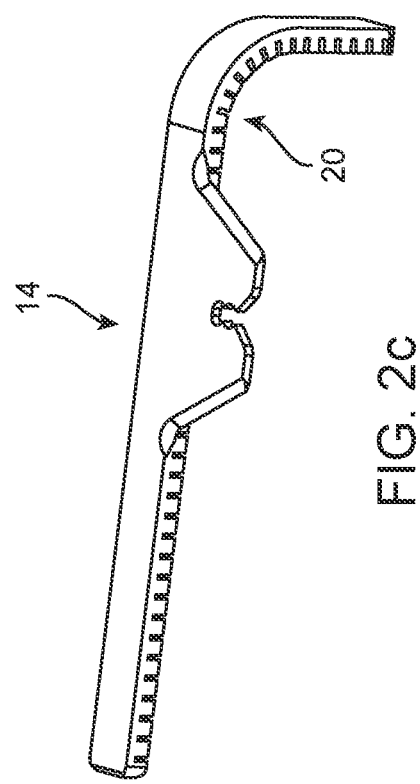
FIG. 2*c* is a close-up view of the variation of the shuttle from FIGS. 2*a* and 2*b* in a curved configuration.

FIG. 2c illustrates that the rail 16 can curve at the locations of the slits 20, and/or the rail 16 can be pre-curved.

Figure 3A:
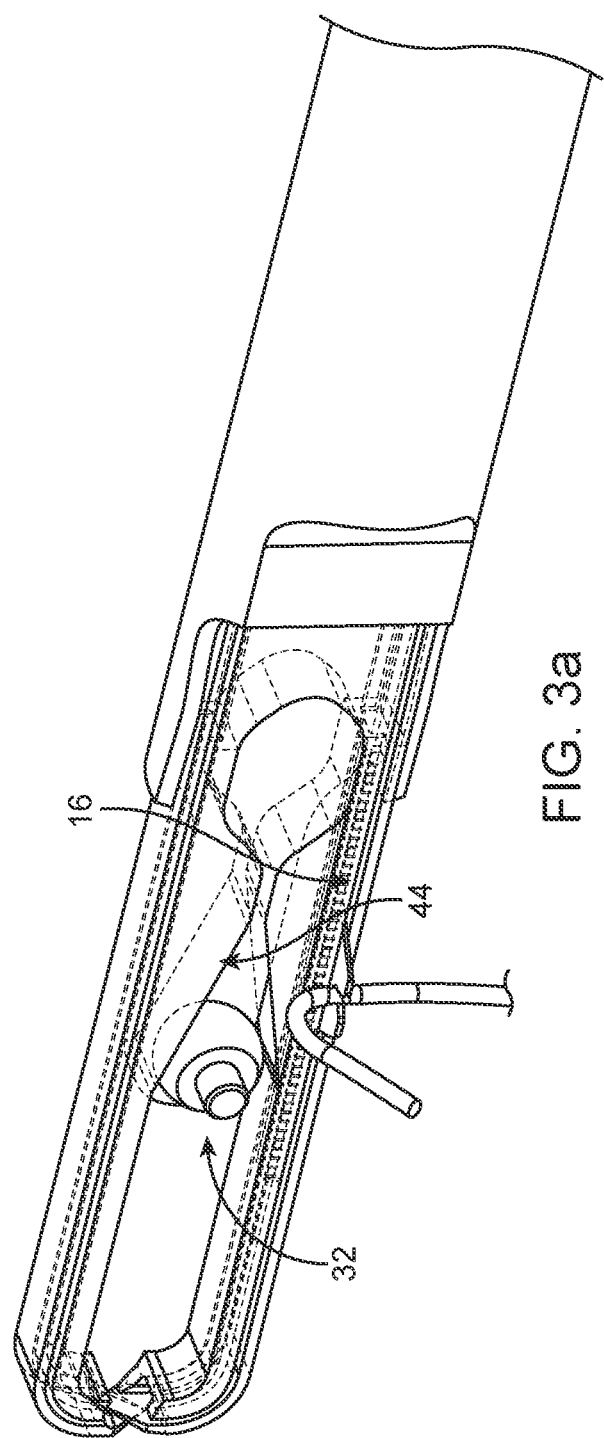
FIG. 3*a* is a close-up, perspective, partial see-through view of the distal end of a variation of the suture passing device attached to a length of a suture.
Figure 3B:
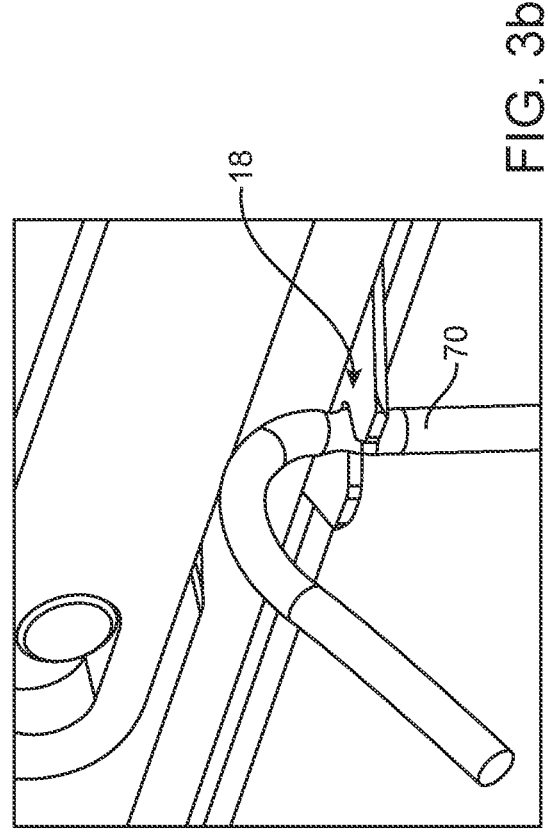
FIG. 3*b* is a close-up view of a portion of FIG. 3*a*.

FIGS. 3a and 3b illustrate that the suture passing device 188 can capture or releasably attach to the suture 70 in the inner and/or outer cleats 97a and/or 97b of the suture holder 18. The suture 70 can be loaded or held laterally of the jaw structure 28, out of plane with the rotation of the jaws. The device 188 can make multiple passes of the suture 70 through the tissue 74 without extracting or reloading the suture passing device 188. The jaw structure 28 can resiliently deform open at the proximal end of the jaw structure 28, having no hinge. The jaws can be opened and/or closed with no mechanical pivots or linkages in the jaw structure 28.

FIG. 4a illustrates that the suture passer device 188 can have a jaw structure 28 with a top jaw 30 and a bottom jaw 38. The entire jaw structure 28 can be an integral piece of material, such as a single molded, cast, or cut element of Nitinol, other resilient metal or polymer, any other material listed herein, or combinations thereof. The jaw structure 28 can be configured to be in an opened configuration (as shown in FIG. 4d) when in an unbiased configuration (i.e., when no external forces are applied).

The jaw structure 28 can have a jaw structure longitudinal axis 42. Each jaw can also have a respective jaw longitudinal axis along the jaw.

The inside channel of the compression cover 34 can be sized and shaped to fit over the jaw structure 28 with minimum clearance when the jaw structure 28 is in a closed configuration. When the compression cover is translated distally 138 with respect to the jaw structure 28, as shown by arrow, the compression cover 34 can press the top and bottom jaws 38 toward the jaw structure longitudinal axis 42. The jaw structure 28 can be fully compressed into a closed configuration, as shown in FIGS. 4a through 4c. In this way, when an actuation lever such as the trigger 8 is actuated, the channel or compression cover 34 can advance to cam closed the jaws. The jaws can pre-pierce the tissue and establish a continuous track for the shuttle to pass through the tissue.

The compression cover 34 can be attached to an opening ball 32 positioned between the first and second jaws.

FIG. 4b illustrates that the opening ball 32 can be rotatably or fixedly attached to a ball axle 52 passing laterally through the opening ball 32. The ball axle 52 can extend out from the lateral sides of the ball 32. The ball axle 52 can be slidably received by axle slots 50 formed through distal arms 54 or extensions 138 of the compression cover 34. When the jaw structure 28 is in a closed configuration, the ball axle 52 can abut and interference fit against the proximal end of the axle slot 50, for example to prevent overextension of the compression cover 34 over the jaw structure 28. When the jaw structure 28 is in an opened configuration, the ball axle 52 can abut and interference fit against the distal end 2 of the axle slot 50, for example to prevent overrotation of the jaws and/or pulling the ball 32 past the ramps 44 on the inside of the jaw structure 28.

FIG. 4c illustrates that the bottom track 66 can distally terminate in a bottom track port 62. The top track 64 can distally terminate at a top track port 60. The top track port 60 can align with and be adjacent to (as shown) or in contact with the bottom track port 62 when the jaw structure 28 is in a closed configuration with the first jaw tip 46 interdigitating with the second jaw tip 48. The tracks of the upper jaw 78 and bottom jaw 38 can form a continuous path when the jaw structure 28 is in a closed configuration. The first jaw tip 46 can interdigitate with and be adjacent or in contact with the second jaw tip 48 when the jaw structure 28 is in a closed configuration.

FIG. 4d illustrates that that compression cover 34 can be translated proximally 126, as shown by arrow, with respect to the jaw structure 28. The ball axle 52 can slide to the distal end 2 of the axle slot 50. The axle slot 50 can then pull the ball axle 52, and therefore the opening ball 32, proximally. The opening ball 32 can then press against the inside surface ramp 44 of the first jaw and/or second jaw. The first jaw tip 46 and/or second jaw tip 48 can then rotate away from the opposing jaw tip. The jaw structure 28 can then be in an opened configuration, as shown.

The proximal ends of the jaws can be rigid or flexible, for example to bend around the opening of the compression cover 34 when the jaws are in an opened configuration. The entire jaws or just the proximal ends of the jaws can be made from Nitinol, for example with the distal ends of the jaws made from stainless steel.

FIG. 5 illustrates that the side slot 72 can extend laterally from one side of the tracks. The rail 16 of the shuttle 14 can be taller than the height of the side slot 72. The rail 16 can be too large to pass through the side slot 72. The suture holder 18 can extend laterally from the rail 16 through the side slot 72. The suture holder 18 can hold the suture 70 laterally spaced away from the jaw.

Figure 6A:
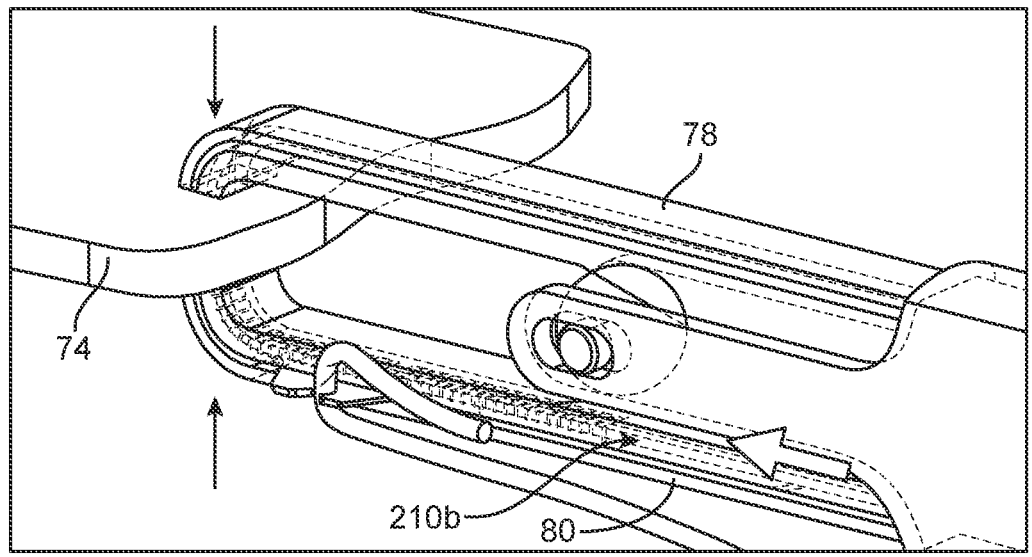
FIGS. 6*a* through 6*d* illustrate a variation of a method of using a variation of the suture passing device to create a stitch in a piece of tissue.

FIG. 6a illustrates that the upper jaw 78 and the lower jaw 80 can be closed, as shown by arrows, and compressed through tissue 74, such as soft tissue 74 in the rotator cuff or other joint. The upper jaw tip 206 and/or the lower jaw tip 198 can pierce the tissue 74. The upper jaw tip 206 and the lower jaw tip 198 can interdigitate in or adjacent to the tissue 74. The hole created by the touching or interdigitating of the upper jaw tip 206 and/or the lower jaw tip 198 can be a hole in the tissue 74 through which the shuttle 14 and/or suture 70 can pass. The compression cover can be pushed distally 138 to further compress the first jaw toward the second jaw, for example to force the jaw tips to pierce the tissue 74.

The lower pusher 76 can be advanced distally, as shown by arrow, as controlled by the handle 104. The lower pusher 76 can force or push the shuttle 14 through the track to move distally and to carry the suture 70 with the shuttle 14.

Figure 6B:
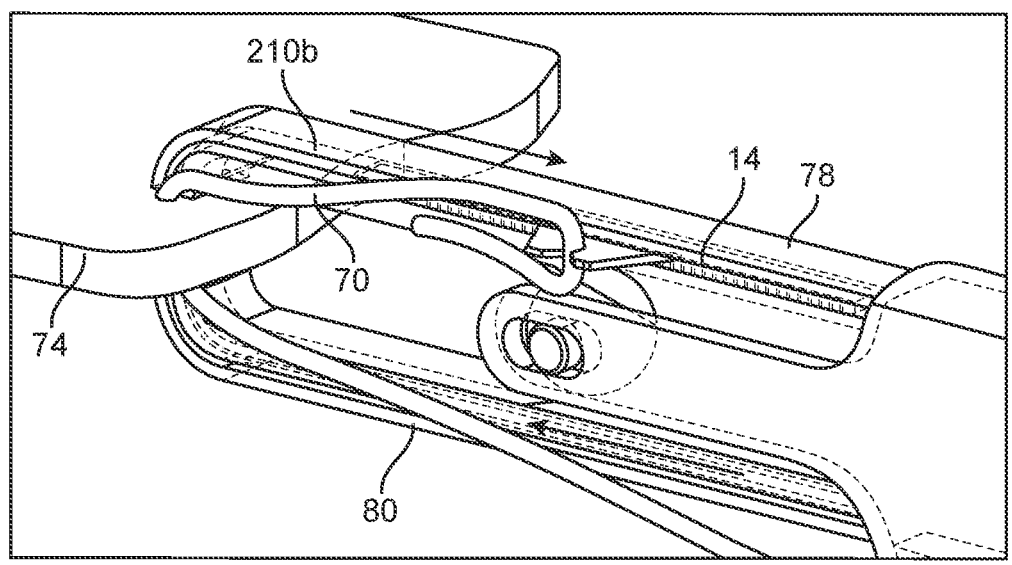

FIG. 6b illustrates that the lower pusher 76 can continue to be pushed by the handle 104. The lower pusher 76 can push the shuttle 14 through the tissue 74. The front edge 22 of the suture holder 18 can cut through the tissue 74 and the suture holder 18 can pull the suture through the cut created in the tissue 74 by the front edge 22 and/or through the piercing created in the tissue 74 by the tips of the jaw. The pusher and the shuttle 14 can move along the longitudinal axis of the jaws.

The shuttle 14 can then be positioned entirely in the track of the upper jaw 78. The lower pusher 76 can then be withdrawn from the track of the upper and/or lower jaw 80, and/or the lower pusher 76 can be left in place but the resistive force can be removed, allowing the lower pusher 76 to slide freely in the tracks.

Figure 6C:
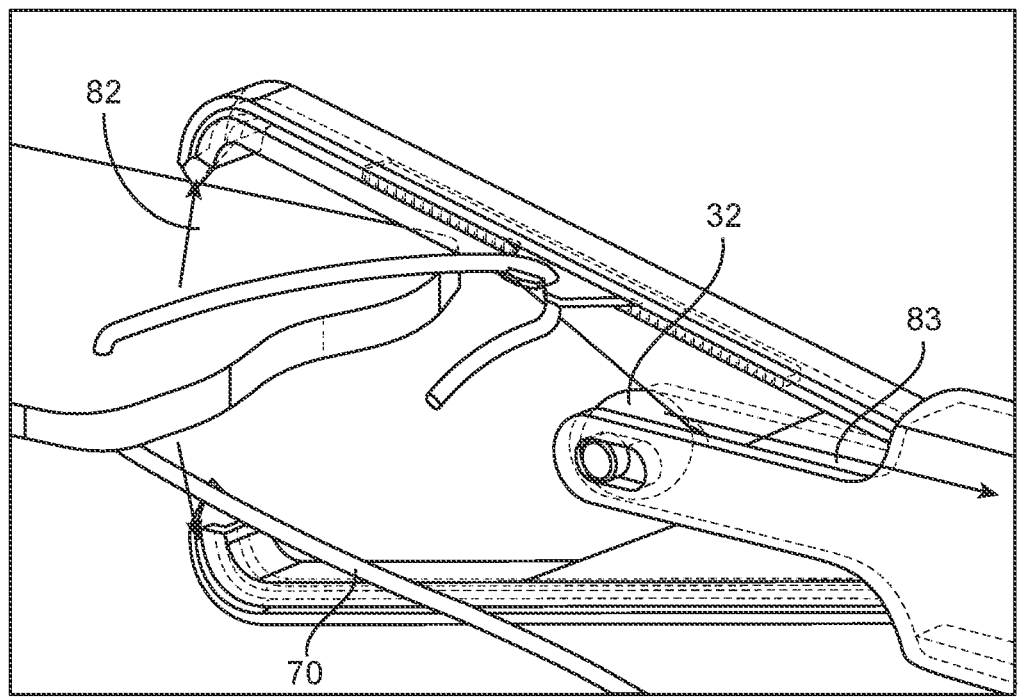

FIG. 6c illustrates that the compression cover can then be translated proximally 126 (e.g., by releasing or squeezing the trigger 8), as shown by arrow 83. The ball axle 52 can be pulled proximally, forcing the opening ball 32 against the inner surface of the top and/or bottom jaws 38. The opening ball 32 can thus resiliently force open the top and/or bottom jaw 38. The jaws can then be unclamped (i.e., rotated open, as shown by arrows 82), and be cleared from the tissue 74.

The device 188 can then be shifted to a position where the distal end 2 of the device 188 is adjacent (e.g., lateral) to where the suture initially passed through the tissue 74.

Figure 6D:
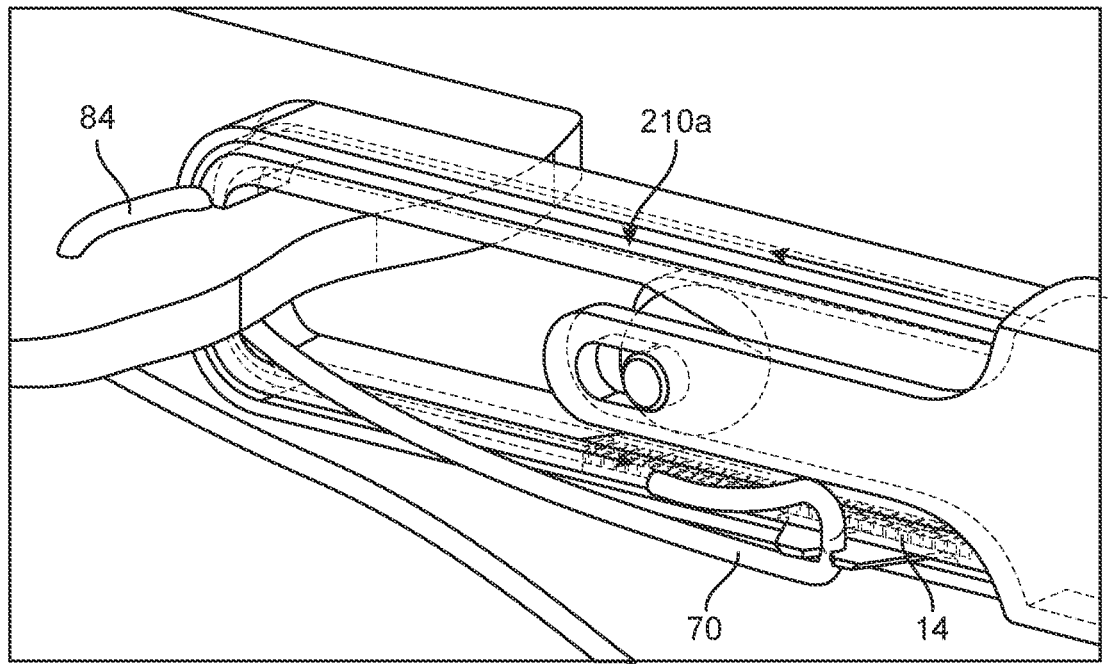

FIG. 6d illustrates that the jaw can then be closed, piercing the tissue 74 adjacent to the first passage of the suture 70 through the tissue 74. The upper pusher 86 can then be forced distally, as shown by arrow, by the handle 104. The upper pusher 86 can force or push the shuttle 14 along the track in the reverse direction from shown in FIGS. 6a and 6b. The rear edge 24 of the suture holder 18 can then cut the tissue 74 as the suture holder 18 passes through the tissue 74, carrying the suture 70 through the tissue 74. Thus a mattress stitch of the suture 70 through the tissue 74 can be created.

The shuttle 14 can then be in the home position, as shown in FIG. 6a. The upper pusher 86 can then be withdrawn from the track of the upper and/or lower jaw 80, and/or the upper pusher 86 can be left in place but the resistive force can be removed, allowing the upper pusher 86 to slide freely in the tracks. The jaws can be reopened and repositioned, and the device 188 can create another stitch repeating the method shown in FIGS. 6a through 6d. The jaws can be reopened and removed from the target site when the stitching is complete or to deliver a second stitch.

Figure 7A:
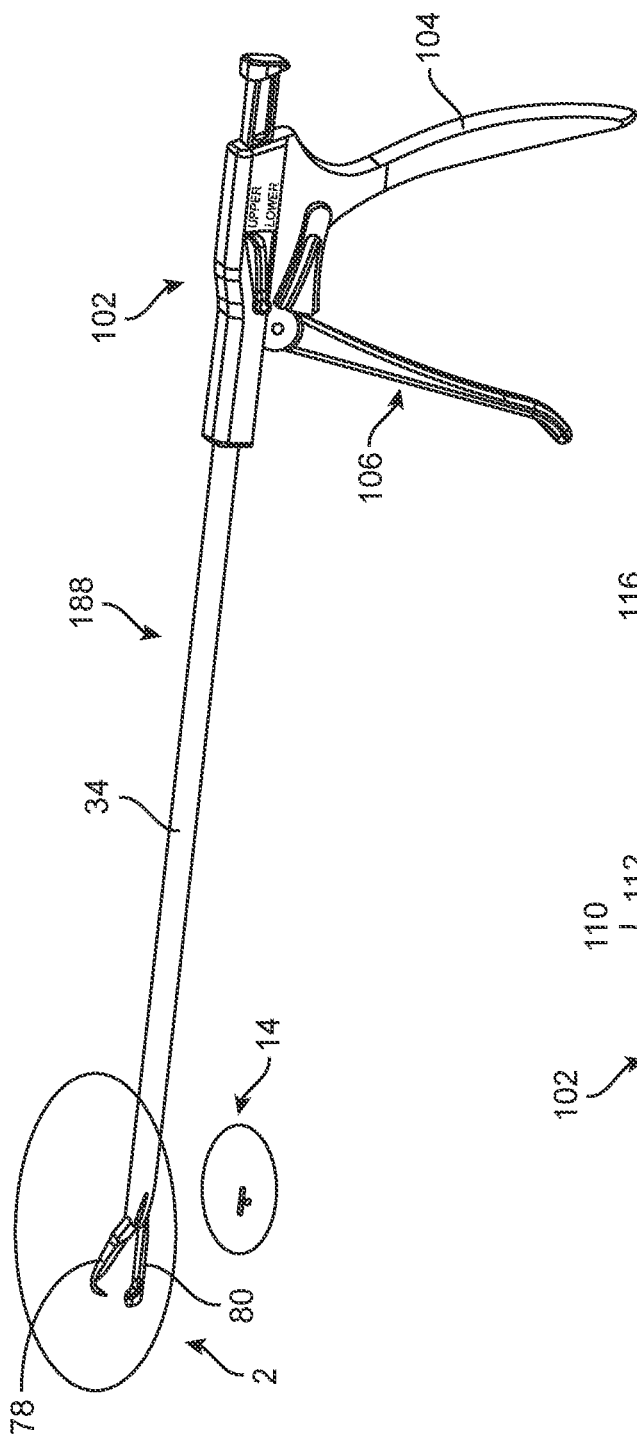
FIGS. 7a and 7b are a side perspective view and a close-up a variation of the device with an exploded view of a shuttle, and a close-up of the proximal end of the device, respectively.

FIG. 7a illustrate that the device 188 can have a base 102 and a handle 104 extending from the base 102. The device 188 can have a rotatable lever 106 rotatably attached to the base 102 or handle 104. The device 188 can have a compression cover 34 translatably attached to and extending distally from the base 102.

The distal end 2 of the device 188 can have the upper and lower jaws 80. The upper jaw 78 can be rotatable with respect to the lower jaw 80 and vice versa.

The compression cover 34 can be slidably attached to one or both jaws. The rotatable lever 106 can be attached to the compression cover 34. For example, squeezing and rotating the lever 106 toward the handle 104 can push the compression cover distally 138 with respect to the jaws. The compression cover can distally slide over the jaws, rotating the upper jaw 78 toward the lower jaw 80 and closing the jaws. The lever 106 can be spring loaded to rotate away from the handle 104, proximally retract the compression cover 126, and return the jaws to an open configuration when external pressure or squeezing is no longer applied to the lever 106.

Figure 7B:
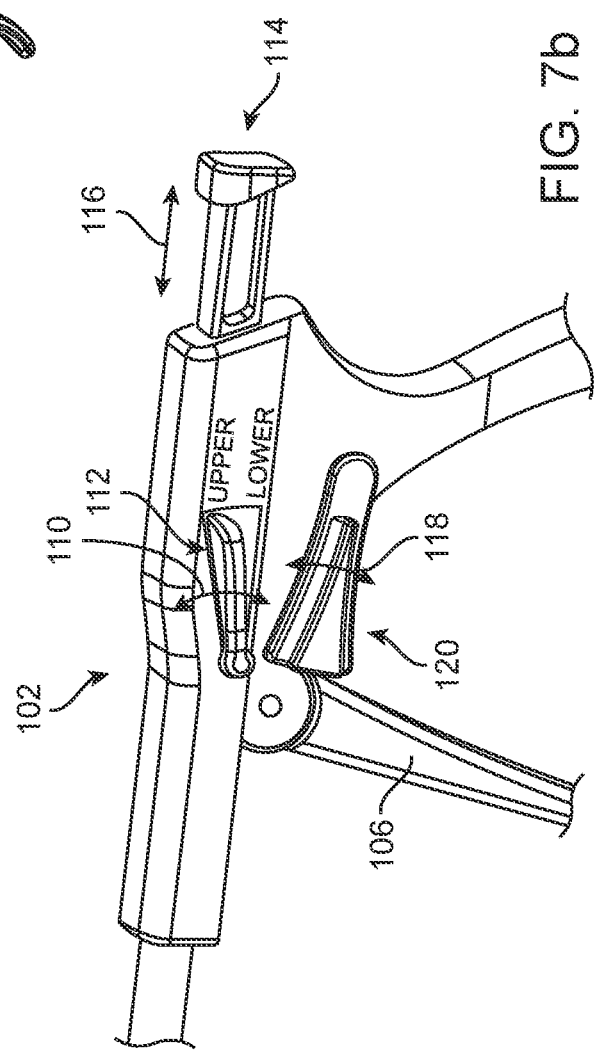

FIG. 7b illustrates that a pusher shaft or button can extend distally from the base 102 or handle 104. The pusher shaft or button can be translated with respect to the base 102 and/or handle 104, as shown by arrows. The pusher shaft can be configured to push and/or pull one or both pushers. Pressing or pulling on the pusher shaft can translate the pusher. A single pusher shaft or button can be toggled between both pushers.

A pusher toggle, such as a side paddle 112 can extend from the lateral side of the base 102. The side paddle 112 can be positioned on the top or bottom of the base 102 or the handle 104. The side paddle 112 can rotate 110 with respect to the base 102, as shown by arrow. The side paddle 112 can be configured to orient the pusher shaft or button to translate the upper pusher 86 or lower pusher 76 depending on the position of the side paddle 112.

The device 188 can have a lever 106 lock 120. The lever 106 lock 120 can extend laterally from the base 102. The lock 120 can rotate 118, as shown by arrows, with respect to the base 102. The lock 120 can be configured to fix or secure the lever 106 closed or in a particular angular position with respect to the base 102. For example, the lever 106 lock can fix the lever 106 closed, in turn fixing the jaws in a closed configuration.

Figure 7C:
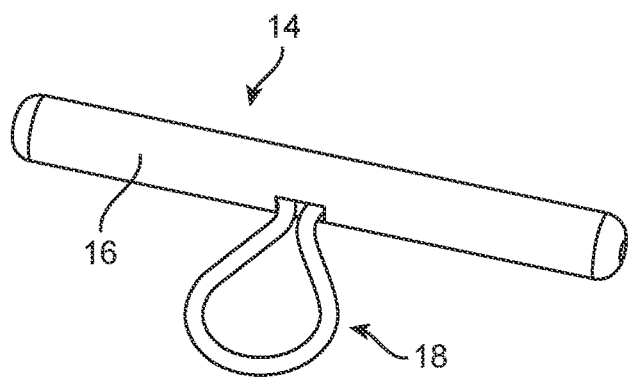

FIG. 7c illustrates that the shuttle 14 can have a rail 16 that can be a cylindrical tube or sleeve. The rail 16 can be made from Nylon, other materials disclosed herein, or combinations thereof. The rail 16 can have rounded (e.g., hemi-spherical) or flat terminal longitudinal ends.

The shuttle 14 can have a suture holder 18 that can be a wire loop 98 extending laterally from the rail 16. The wire loop 98 can have a wire. The wire loop 98 can extend in a flat plane. The terminal ends of the wire can be anchored—e.g., removably or fixedly attached to the rail 16, for example through a port or slot in the lateral side of the rail 16. The suture 70 can extend through and remain within the area defined by the perimeter of the wire loop 98 while the suture 70 is retained by the suture 70 passer.

Figure 7D:
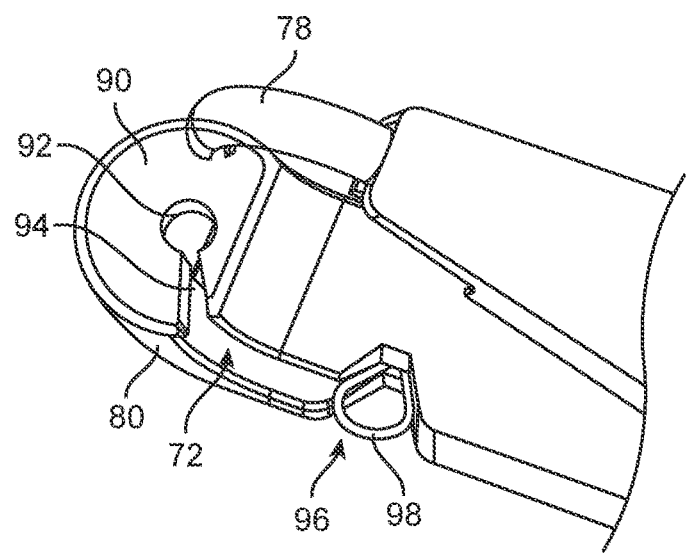

FIG. 7d illustrates that the lower jaw 80 (as shown) and/or upper jaw 78 can have one or more loading notches or docks 96. The loading dock 96 can expose the suture holder 18, such as the wire loop 98, for suture 70 loading/unloading. The suture holder 18 can extend into the loading notch. For example the wire loop 98 can extend through the side slot 72 and into the holding notch 100 with the shuttle 14 is in a position for loading and/or unloading the suture 70 to and/or from the shuttle 14. For example, the shuttle 14 can be at the proximal-most position for the shuttle 14 on the bottom track 66 when the suture holder 18 is aligned with the loading dock 96. The side slot 72 can terminate at the loading dock 96, for example, interference fitting the wall of the loading dock 96 against the shuttle 14 and/or suture holder 18 to prevent further translation of the shuttle 14 proximally along the jaw.

The lower 80 and/or upper jaws 78 can have a septum 90 can cover a medial terminal face at the distal end 2 of the lower jaw 80 (as shown) and/or upper jaw 78. The septum 90 can be a flexible material that can be configured to seal around all or part of the shuttle 14 as the shuttle 14 passes through the septum 90. For example, the septum 90 can be made from a fabric, or a solid panel of polymer such as polyurethane or polyester.

The septum 90 can have a septum rail port 92. The septum rail port 92 can be aligned with the terminal end of the bottom track 66 and/or top track 64.

The septum 90 can have a septum slot 94. The septum slot 94 can be aligned with the side slot 72 of the bottom track 66 and/or the upper track 264.

The septum 90 can be configured to wipe or squeegee debris, such as tissue 74 and biological fluids, from the shuttle 14 as the shuttle 14 passes through the septum 90, for example to prevent or minimize debris and fluids entering the top and/or bottom tracks 66.

Figure 8A:
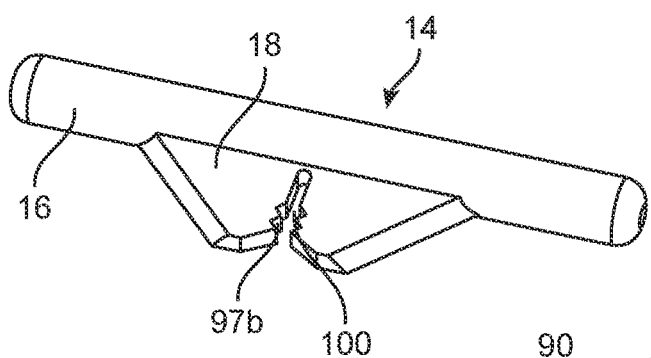
FIG. 8a illustrates a variation of the shuttle.

FIG. 8a illustrates that the shuttle 14 can have a rail 16 that can have a cylinder and suture holder 18 can be as described in FIGS. 2b and 2c. The holding notch 100 can have angular cleats 97. The holding notch 100 can extend to side of the rail 16.

Figure 8B:
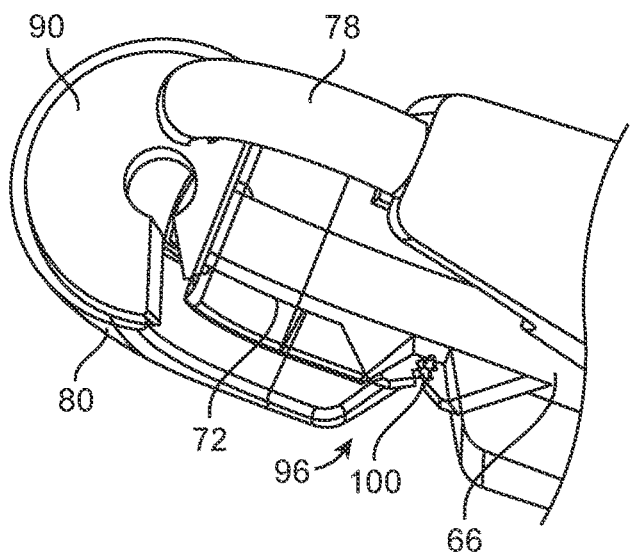
FIG. 8b illustrates a close-up view of a variation of the distal end of the device.

FIG. 8b illustrates that the shuttle 14 can be positioned so the holding notch 100 of the suture holder 18 can be in the loading dock 96 when the suture 70 is attached to or removed from the holding notch 100. The suture 70 can be pressed into (e.g., for attaching) or pulled from (e.g., for removing, detaching or repositioning) the holding notch 100. A longitudinally opposing pair of first cleats 97 can laterally friction fit or interference fit the suture 70 in the holding notch 100. A longitudinally opposing pair of second cleats 97 can medially friction fit or interference fit the suture 70 in the holding notch 100 (i.e., the suture 70 can be radially fixed between the pair of first cleats 97 on a lateral side of the suture 70 and the pair of second cleats 97 on a medial side of the suture 70).

The suture 70 can be radially fixed between a pair of longitudinally opposed cleats 97 that can dig into and compress or puncture the external surface of the suture 70.

The shuttle 14 can interference fit or otherwise be stopped by the lower jaw 80 from moving proximal to a position where the holding notch 100 is exposed in the loading dock 96.

Figure 9A:
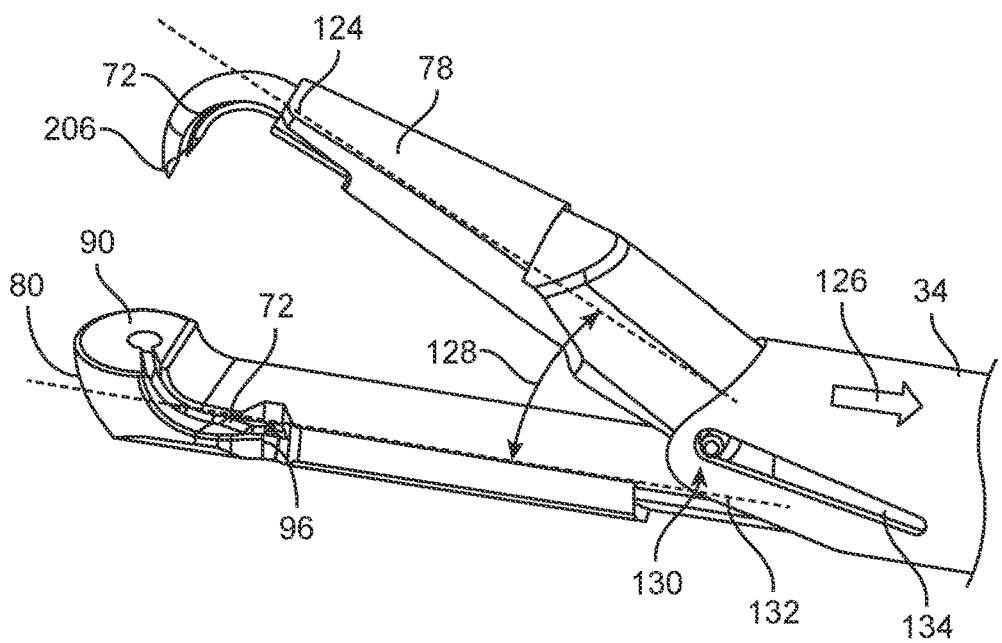
FIGS. 9a and 10a are side perspective and partial see-through side perspective views, respectively, of a variety of the device in an opened configuration.
Figure 10A:
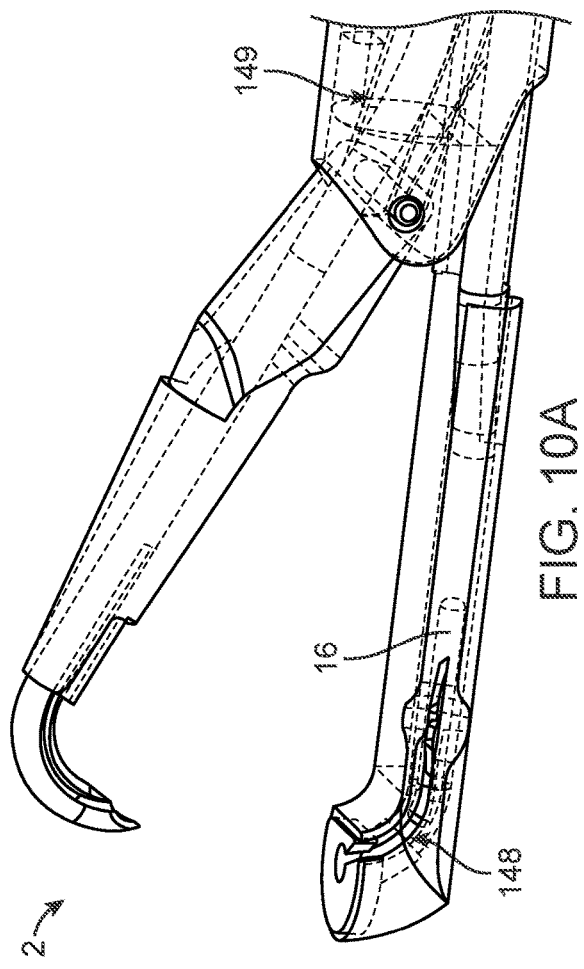
Figure 10B:
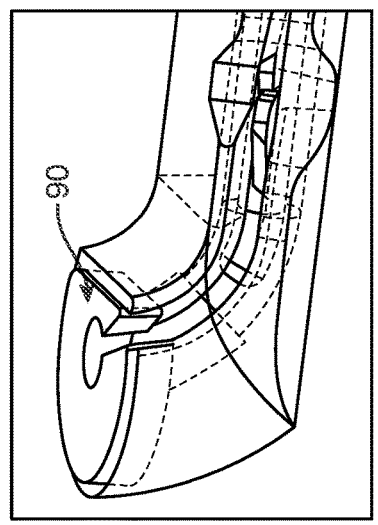

FIGS. 9a, 10a and 10b illustrate that the device 188 can be in an open configuration with the upper jaw 78 positioned rotated away from the lower jaw 80. The upper jaw 78 can have an upper jaw longitudinal axis. The lower jaw 80 can have a lower jaw longitudinal axis 132. The lower jaw longitudinal axis 132 (as shown) or the upper jaw longitudinal axis 124 can be parallel and/or collinear with the compression cover longitudinal axis. The upper law longitudinal axis 124 and the lower jaw longitudinal axis 132 can intersect at a jaw angle 128. When the jaws are in an open configuration, the jaw angle 128 can be from about 30° to about 45°, more narrowly from about 30° to about 40°.

The compression cover 34 can be translated and retracted proximally, as shown by arrow 126, away from the jaws. The upper jaw 78 can have a slot slide pin 130 that can extend laterally from one or both lateral sides of the proximal end of the upper jaw 78.

The distal end 2 of the compression cover 34 can have one or more ramp slots 134 on one or both lateral sides of the compression cover 34. The ramp slot 134 can narrow as the ramp slot 134 extends proximally (i.e., widen as the ramp slot 134 extends distally). The ramp slot 134 can be at a non-zero angle (i.e., non-aligned) to the longitudinal axis of the compression cover 34.

The slot slide pin 130 can be configured to extend through the ramp slot 134. The slot slide pin 130 can slide within the ramp slot 134. The slot slide pin 130 can friction fit into the narrower, proximal end of the ramp slot 134, for example friction-fitting the jaws in a closed configuration and providing tactile feedback to the user of the jaw angle 128.

FIG. 10a illustrates that the upper track can pass through a hinge tube 149 where is extends past the distal opening of the compression cover 34 and into the upper jaw. The hinge tube 149 can be made from nitinol, for example. The hinge tube 149 can flex when the upper jaw is rotated. The hinge tube 149 can be an integrated length of the entire upper track, or can be a separate length of tube attached on one or each end to the remainder of the upper track.

Figure 9B:
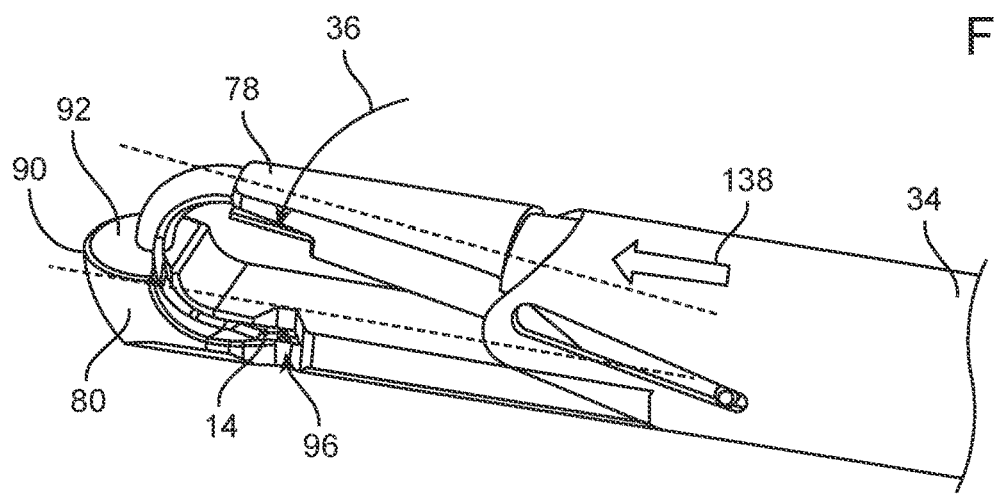
Figure 11A:
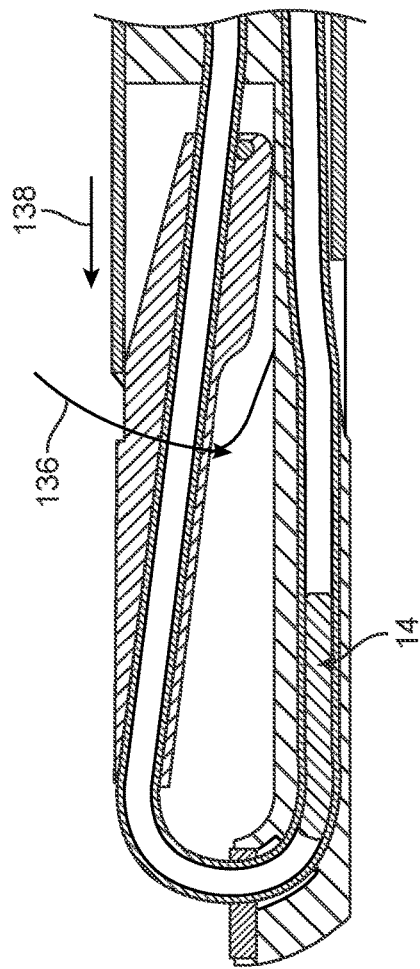

FIGS. 9b and 11a illustrate that the compression cover 34 can be distally extended or advanced, as shown by arrow 138, with respect to the jaws. The compression cover 34 can force the jaws to rotate toward each other to a closed configuration. For example, the upper jaw 78 can rotate, as shown by arrow 136, while the lower jaw 80 remains in a rotationally fixed position with respect to the compression cover 34, or vice versa, or the jaws can both rotate with respect to the compression cover 34. Thus, a lever, such as the trigger 8, can be actuated to advance the outer tube or compression cover 34 to cam closed the jaws.

When the jaws are in a closed configuration, the jaw angle 128 can be from about 0° to about 3°, more narrowly from about 0° to about 2°, for example about 0°.

Figure 9C:
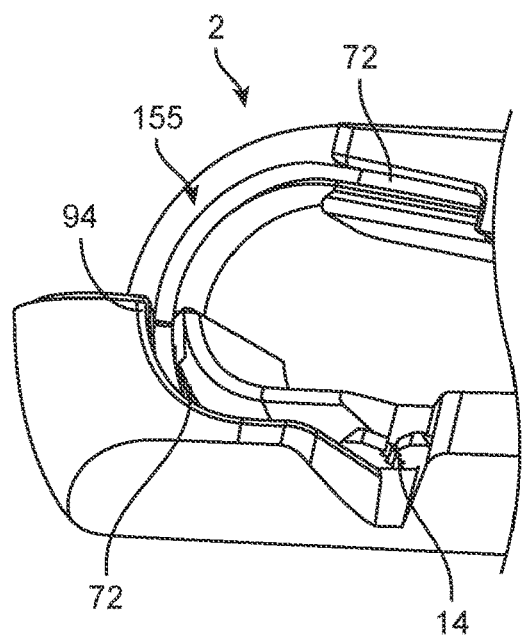
FIGS. 9c and 11b are a close-up view and a side see-through view, respectively, of the distal end of the device in FIG. 9b.
Figure 11B:
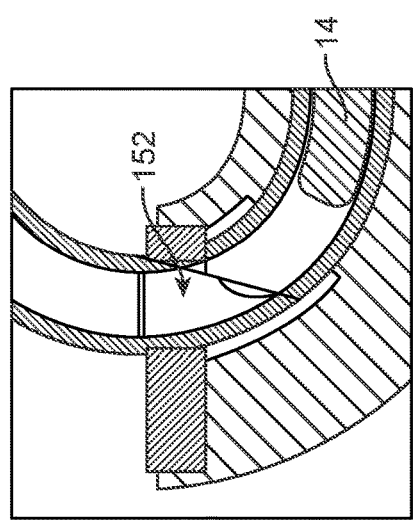

FIGS. 9c and 11b illustrate that the upper jaw tip 206 can be pressed into and through the septum rail port 92. The top or upper track 264 can form a continuous lumen 152 with the bottom or lower track 148, for example, that the shuttle 14 can slide through.

A side slot 72 of upper jaw 78 can align with a side slot 72 of lower jaw 80. The suture holder 18 can extend through the side slot 72 and hold the suture 70 in the side slot 72. The suture holder 18 can translate suture 70 back and forth between the upper 78 and lower jaws 80 in the side slot 72 as the shuttle 14 is translated back and forth between the upper 78 and lower jaws 80.

FIGS. 12a through 12c illustrate that the shuttle 14 can a rail 16, for example a shuttle spine 160, and shuttle 14 lateral arms or fingers extending laterally and/or inwardly from the shuttle spine 160. The shuttle fingers 156 can extend laterally, downwardly, and medially with respect to the shuttle spine 160, as shown. The shuttles 14 can have slits 20 or shuttle lateral slots 158 between the shuttle fingers 156. The shuttle fingers 156 can be flexible or rigid.

The shuttle 14 can have a shuttle longitudinal axis 157 (also referred to as the shuttle longitudinal axis $14_{A1}$). The shuttle longitudinal axis 157 can be flat or curved, for example have a shuttle radius of curvature 154 from about 3 mm to about 5 mm, more narrowly from about 3 mm to about 4 mm, for example about 3.5 mm.

The shuttle spine 160 can be flexible or rigid. The shuttle 14 can be made from a single panel of material (e.g., metal), for example by bending and laser cutting the panel.

The suture holders 18 can be one, two or more circular, oval, or otherwise elongated, longitudinal slots in the shuttle spine 160. For example, the suture 70 can extend through one or both suture holders 18. The suture 70 can be fused to the shuttle 14 adjacent to the suture holders 18. A detachable or fixed frame can be attached to the slots in the shuttle 14 and the suture 70 can be attached to the detachable frame. For example, the detachable frame can be an arc-shaped wire attached at a first end to a first slot in the shuttle spine 160 and at a second end to the adjacent second slot in the shuttle spine 160.

Figure 13A:
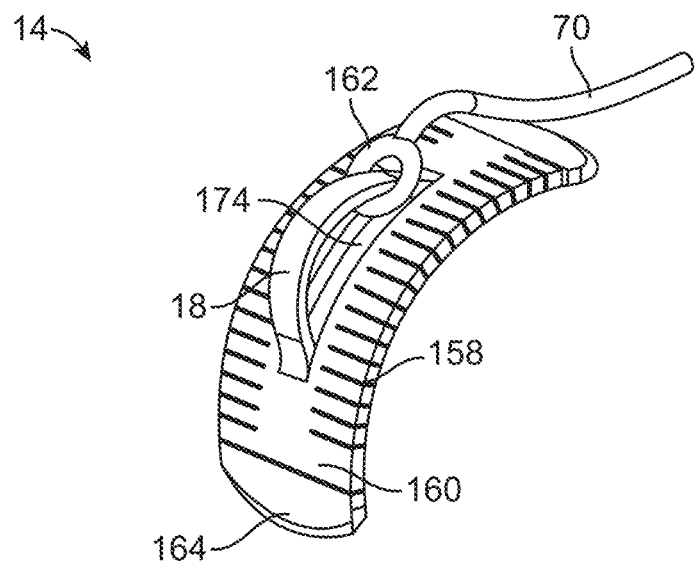
FIGS. 13a and 13b illustrate variations of the shuttle.

FIG. 13a illustrates that the suture holder 18 can be an arc integral with the shuttle spine 160. For example, the shuttle 14 can be made from a single panel of material (e.g., metal). The lateral sides of the suture holder 18 can be cut, and the longitudinal ends can remain integrated with the shuttle spine 160. The suture holder 18 can then be bent or otherwise deformed away from the plane of the shuttle spine 160, for example forming an arc away from the plane of the shuttle spine 160.

The suture 70 can have a suture loop 162 at the terminal end of the suture 70. The suture loop 162 can extend around and completely or partially circumscribe the suture holder 18. The remainder of the suture 70 can be integral with the suture loop 162, or can removably attached to the suture loop 162. The suture loop 162 can be circular or oval.

Figure 13B:
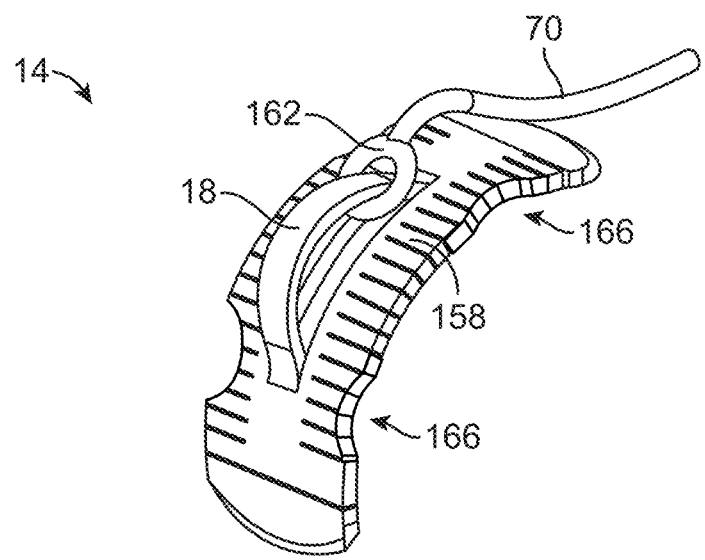

FIG. 13b illustrates that the shuttle 14 can have one or more shuttle notches 166 or cut-outs. For example, the shuttle 14 can have two shuttle notches 166 on each lateral site of the shuttle. The shuttle notches 166 can be even longitudinally spaced and distributed along the shuttle 14. The shuttle notches 166 can be curved. The sides of the shuttle 14, other than at the notches, can be straight.

A radius of curvature of the shuttle notch 166 can be from about 1 mm to about 2 mm.

Figure 14A:
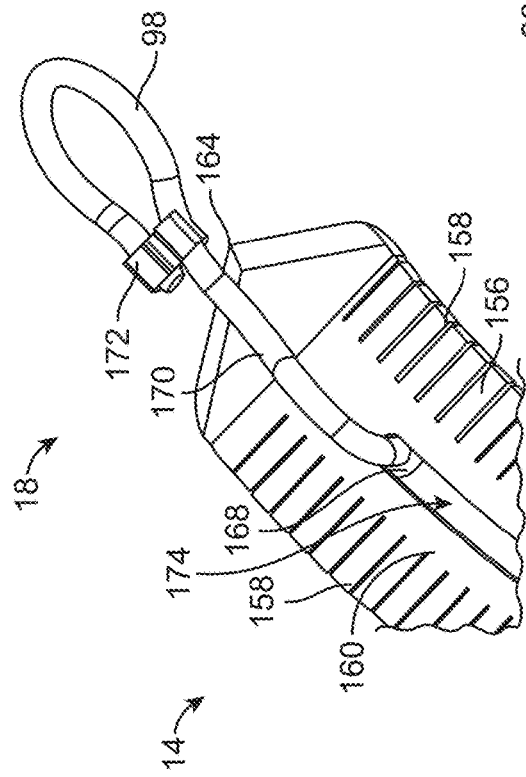
FIGS. 14a through 14c are top end, front perspective, and bottom perspective views, respectively, of a variation of the shuttle.
Figure 14C:
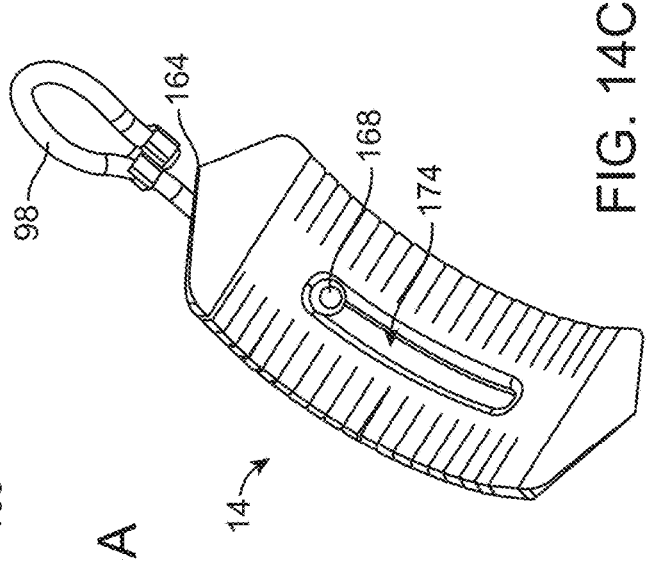
Figure 14B:
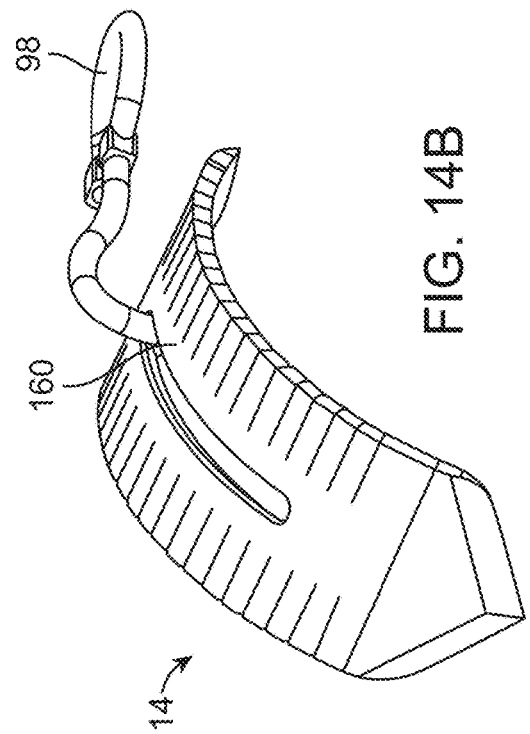

FIGS. 14a through 14c illustrate that one or both of the longitudinally terminal ends of the shuttle 14 can be curved or sharpened shuttle tips 164. For example, the shuttle tip 164 can have an angled chisel tip or needle tip.

The shuttle holder can have a holder leader 170 extending away from the shuttle spine 160. The end of the holder leader 170 away from the shuttle spine 160 can be a closed wire loop 98 configured to attach to the suture 70. A loop neck 172, such as a dual clamp, can fix a first terminal end of the leader wire to an intermediate point on the holder leader 170, as shown. A second terminal end of the holder leader 170 can extend through the shuttle longitudinal slot 174 and terminate at a leader anchor 168 such as a crimp or swaged ball or disc having a larger diameter than the width of the shuttle longitudinal slot 174, for example to slidably attach the suture holder 18 to the shuttle longitudinal slot 174. The suture holder 18 can be slidably captured in the shuttle longitudinal slot 174 by the leader anchor 168.

The holder leader 170 can be translatably and/or rotationally fixed in the shuttle longitudinal slot 174 or can slide and/or rotate in the shuttle longitudinal slot 174. For example, the wire loop 98 can extend past a first end of the shuttle spine 160 when the shuttle 14 is being translated in a first direction (e.g., toward the lower jaw 80 from the upper jaw 78), and the holder leader 170 can passively rotate and translate when the shuttle 14 is then translated in a second direction (e.g., toward the upper jaw 78 from the lower jaw 80).

The holder leader 170 can be rigid or flexible. For example, the holder leader 170 can be made from stainless steel, other material disclosed herein, or combinations thereof.

The suture 70 can be passed through and/or tied to the wire loop 98. The wire loop 98 can be at a height away from the shuttle spine 160. The wire loop 98 can extend proximally or distally past the end of the shuttle tip 164. For example, the suture 70 can be attached to the wire loop 98 away from sharp edge sharps to minimize the risk of cutting or damaging the suture 70.

FIGS. 15a and 15b illustrate that suture 70 can be directly attached or fused to the shuttle spine 160 at a suture attachment 176 in the longitudinal and lateral middle of the shuttle 14. The suture 70 can be braided.

For example, the entire shuttle 14 can be made from plastic and can be molded, overmolded, or otherwise joined to a plastic suture. The suture can be thermally formed to the shuttle 14. The suture 70 can extend through the shuttle 14, for example at a suture anchor 178. The suture anchor 178 can be the terminal end of the suture 70 extending through and attached to the shuttle 14.

FIGS. 16a and 16b illustrate that the leader or wire loop 98 can extend partially or entirely in a plane perpendicular to the plane of the shuttle spine 160. A first terminal end of the wire loop 98 can have a leader first anchor 184. A second terminal end of the wire loop 98 can have a leader second anchor 186. The shuttle spine 160 can have a shuttle longitudinal first slot 180 and a shuttle longitudinal second slot 182. The shuttle longitudinal slots 174 can be elongated or circular. The wire loop 98 can be made from Nitinol and/or steel, for example, and can be tied to the suture.

The wire loop 98 can extend through the shuttle longitudinal slots 174. The leader first and second anchors can be on the underside (e.g., the concave side or radially interior side) of the shuttle spine 160. The wire loop 98 can be on the outerside (e.g., the convex side or radially exterior side) of the shuttle spine 160. Neither, one, or both of the leader anchors 168 can be fixed or integrated (e.g., melted or welded) to the shuttle spine 160. Neither, one or both of the leader anchors 168 can be slidably attached to the longitudinal slots. The wire loop 98 can be fixed or slide longitudinally with respect to the shuttle spine 160.

The wire loop 98 can have a longitudinally symmetric or assymetric (as shown) shape. For example, the wire loop 98 can be an arc (similar to the shape shown by the suture holder 18 in FIGS. 13a and 13b) or can assymetrically overhang (as shown) toward one of the ends of the longitudinal shuttle.

Figures 17A, 17B, 17C, 17D:
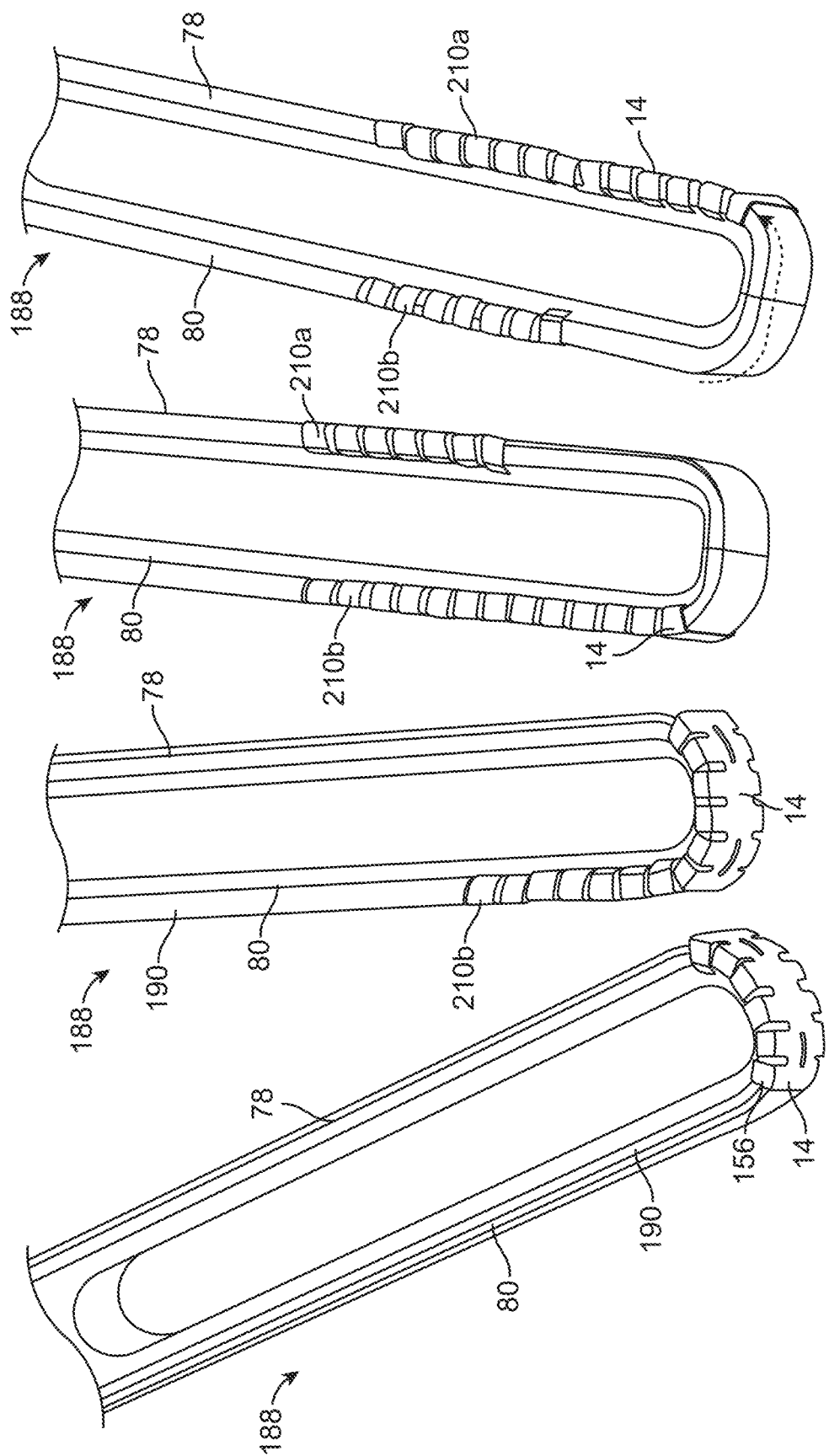
FIG. 17a illustrates a variation of the device with the shuttle of FIGS. 12a through 12c.
FIG. 17b illustrates a variation of the device of FIG. 17a with a pusher.
FIGS. 17c and 17d illustrate a variation of the device of FIG. 17a with two pushers in different configurations.

FIG. 17a illustrates that the device 188 can have the shuttle 14 in a position spanning across the upper jaw 78 and the lower jaw 80. The jaws can have jaw lateral ridges 190. The shuttle fingers 156 can wrap around the jaw lateral ridges 190, for example, slidably attaching the shuttle to the jaws. The jaw lateral ridges 190 at the terminal ends of the upper 78 or top jaw 30 and the bottom or lower jaw 80 can align when the jaws are in a closed configuration, for example so the shuttle 14 can slide along a continuous ridge between the upper 78 and lower jaws 80.

FIG. 17b illustrates that the device 188 can have a lower pusher 76 slidably attached to the jaw lateral ridge 190 on the lower jaw 80. The lower pusher 76 can abut the shuttle 14.

FIG. 17c illustrates that the device 188 can have an upper pusher 86 slidably attached to the jaw lateral ridge 190 on the upper jaw 78. The upper 86 and/or lower pushers 76 can be shaped like the shuttle 14. The shuttle 14 can be pushed onto a straight length of the lower jaw 80. The shuttle 14 can deform to a straight configuration when on a straight length of the jaws and to a curved configuration when on a curved length of the jaws.

The pushers can be generally shaped similarly to the shuttles 14, having fingers, longitudinal slots, spines and lateral slots between the fingers. More than one pusher can be used concurrently on a single device 188 (e.g., if the pushers in FIGS. 17b through 17d were shuttles 14 and if additional pushers were used), for example to deliver multiple sutures 70 to the same target site.

FIG. 17d illustrates that the shuttle 14 can be pushed, as shown, to the upper jaw 78 by the lower pusher 76. The lower pusher 76 can then retreat onto the lower jaw 80.

Figure 18A:
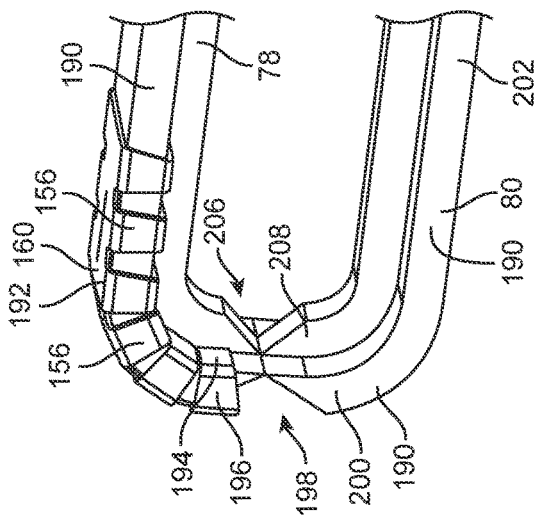
FIGS. 18a and 18b are side perspective and side views, respectively, of a variation of the distal end of the device.
Figure 18B:
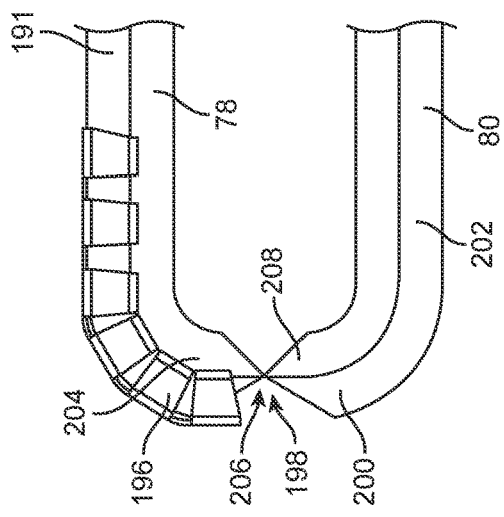

FIGS. 18a and 18b illustrate that the upper and/or lower jaws 80 can each have jaw spines 208. The jaw spines 208 can extend medially from the remainder of the jaws toward (as shown) or away from the jaw control extension longitudinal axis. For example, the jaws spines can extend from the remainder of the jaws distally until the terminal distal ends 2 of the jaws, distal to where the jaws extend into a medially-curved jaw medial extension closer to and in the respective jaw tip from a jaw longitudinal extension 191, 202.

The jaws can have jaw lateral ridges 190 or rails 16, as described elsewhere herein. The jaws can have a T-shaped cross-section.

The shuttle 14 can have shuttle fingers 156 that can each have a shuttle downward extension 196. The shuttle finger 156 can each have a shuttle lateral extensions 192 extending laterally from the respective shuttle spine 160. The shuttle fingers 156 can have shuttle downward extensions 196 that can each extend downward (e.g., toward the longitudinal axis of the jaw structure) from the laterally terminal ends of the lateral extensions. The shuttle fingers 156 can have shuttle inward extensions 194 that can extend inward from the shuttle downward extensions 196. The shuttle spines 160 and/or lateral extensions, downward extensions, and inward extensions can slidably wrap around the jaw lateral ridges 190.

The upper jaw tip 206 and/or lower jaw tip 198 can have blunt, beveled (e.g., needle-tip), chisel (e.g., beveled on opposite sides, as shown in FIGS. 18*a* and 18*b*), conical, Sprotte, diamond, Tuohy tips, or combinations thereof (e.g., the upper jaw tip 206 can have a first tip shape and the lower jaw tip 198 can have a second tip shape). The bevel on the distal side of the jaw tips can have the same angle and length, or a smaller angle and longer length than the bevel on the proximal side of the jaw tips.

The upper jaw tip 206 can have a tip gap 290 or touch the lower jaw tip 198 when the jaws are in a closed configuration.

Figure 19A:
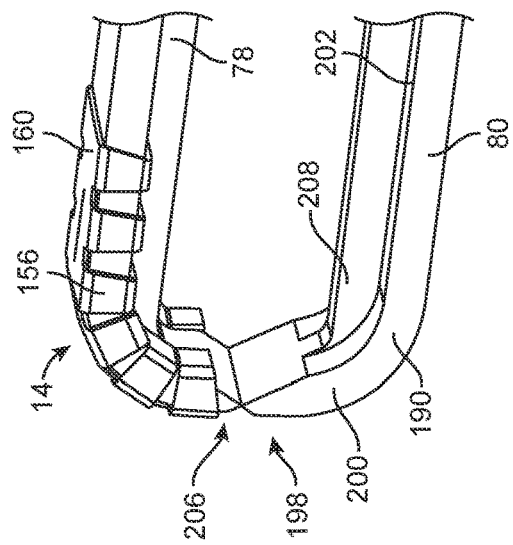
FIGS. 19a and 19b are side perspective and side views, respectively, of a variation of the distal end of the device.
Figure 19B:
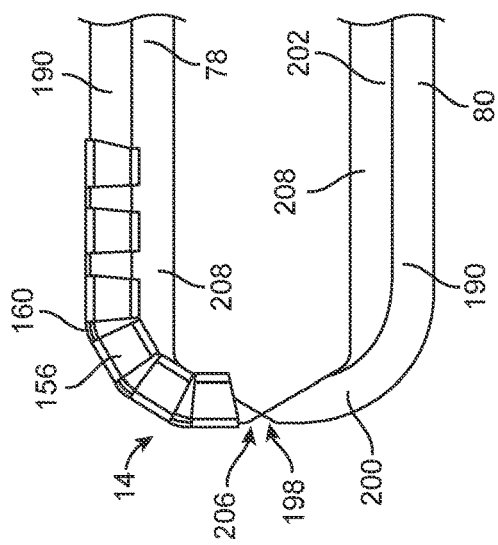

FIGS. 19*a* and 19*b* illustrate that the jaw spines 208 in one or both jaws can terminate before the respective jaw tips or jaw medial extensions.

The bevel on the proximal side of the jaw tips can have a smaller angle and longer length than the bevel on the distal side of the jaw tips.

Figure 20A:
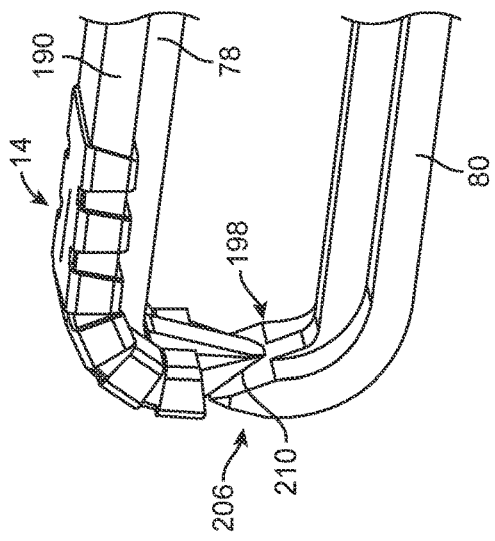
FIGS. 20a and 20b are side perspective and side views, respectively, of a variation of the distal end of the device.
Figure 20B:
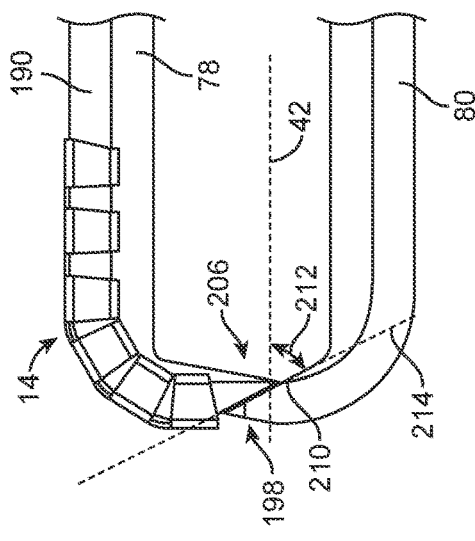

FIGS. 20*a* and 20*b* illustrate that the jaw spine 208 on the upper jaw 78 can extend along the straight length of the upper jaw 78 and can terminate at or proximal to the upper jaw medial extension 204 or upper jaw tip 206. The jaw lateral ridge 190 on the upper jaw 78 can extend to the terminal distal tip of the upper jaw 78.

The jaw spine 208 on the lower jaw 80 can extend to the terminal distal tip of the lower jaw 80.

The jaw lateral ridge 190 on the lower jaw 80 can extend along the straight length of the lower jaw 80 and can terminate at or proximal to the lower jaw medial extension 200 or lower jaw tip 198.

When the jaws are in a closed configuration, the lower jaw tip 198 can be positioned proximally to and overlap the upper jaw tip 206. The upper jaw tip 206 and lower jaw tip 198 can overlap along a tip interface 211. For example, the distal end 2 of the jaw spine 208 on the lower jaw 80 can overlap and slide against the proximal side of the upper jaw tip 206. The upper jaw tip 206 can contact the lower jaw tip 198 at the tip interface 211 or there can be a gap between the upper jaw tip 206 and the lower jaw tip 198 at the tip interface 211.

The tip interface 211 can have a tip interface axis 214 with respect to the jaw structure longitudinal axis 42. The tip interface axis 214 can intersect the jaw structure longitudinal axis 42 at a tip interface angle 212 of about 90°.

The upper jaw tip 206 can be distal to the lower jaw tip 198 at the tip interface 211.

The distal terminal end of the jaw lateral ridge 190 of the upper jaw 78 can contact or not contact the distal terminal end of the jaw lateral ridge 190 of the lower jaw 80 when the jaws are in a closed configuration.

Figure 21A:
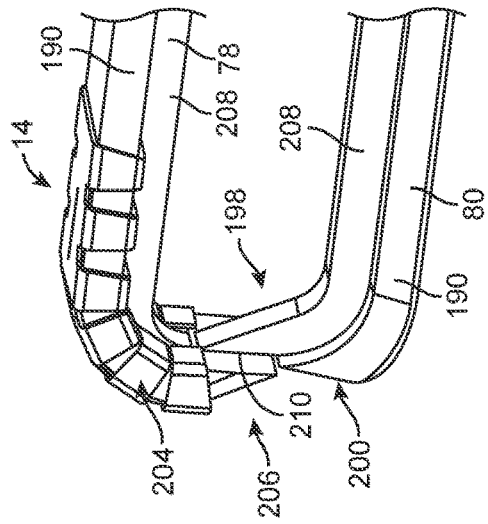
FIGS. 21a and 21b are side perspective and side views, respectively, of a variation of the distal end of the device.
Figure 21B:
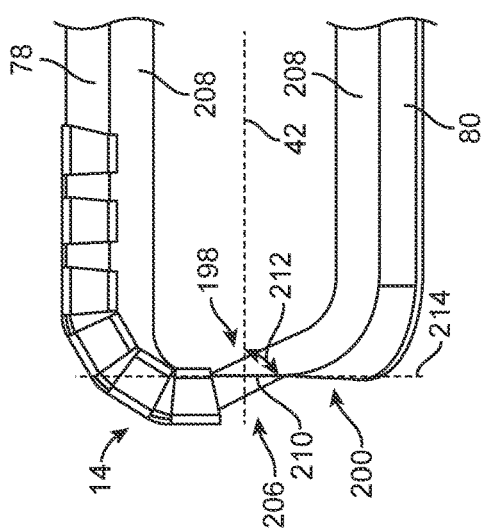
Figure 25A:
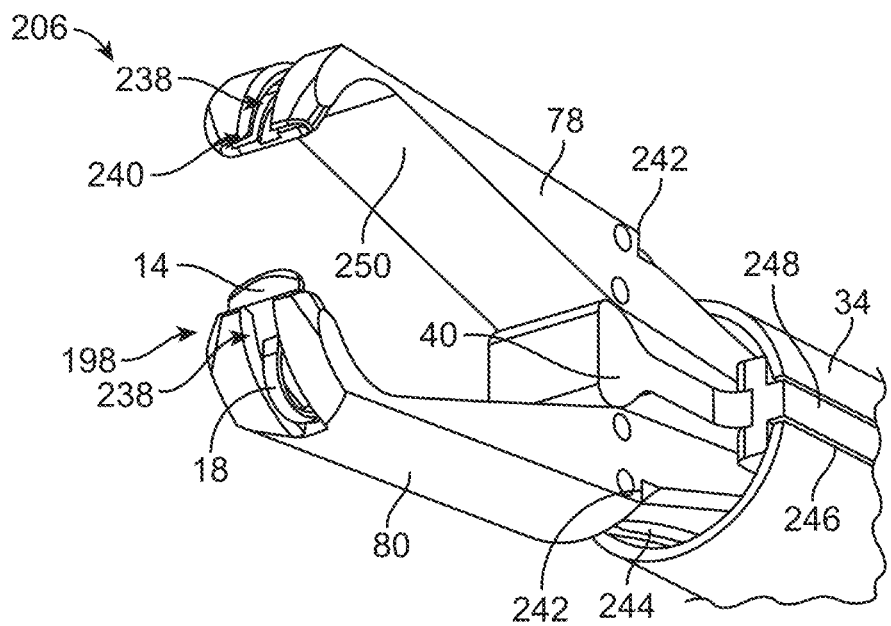
Figure 25B:
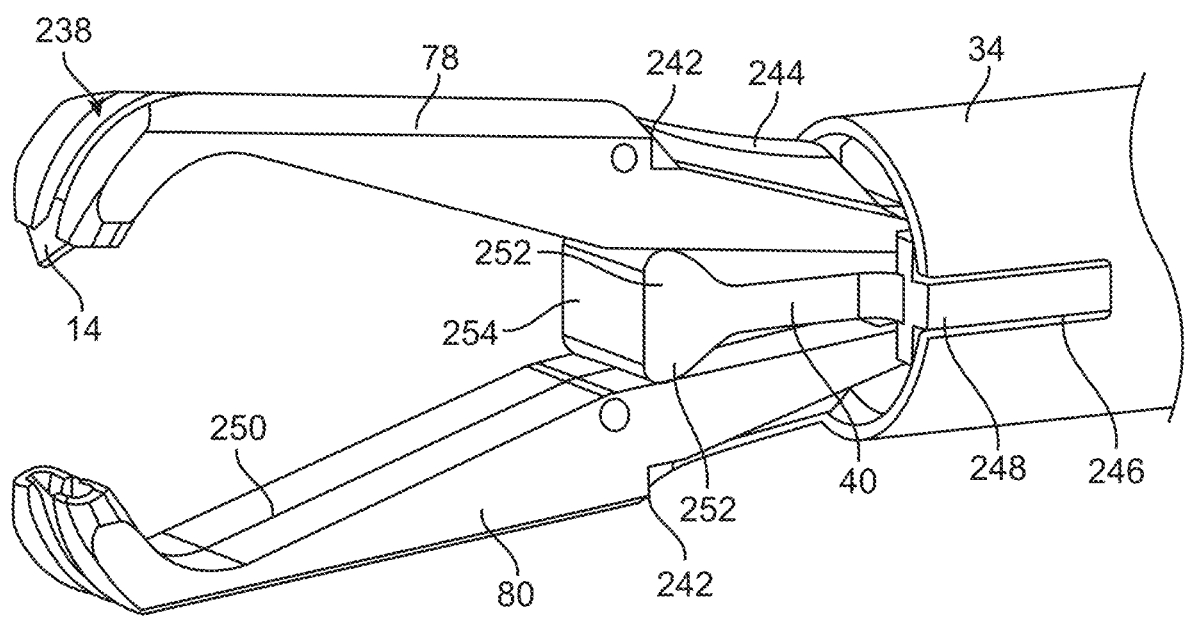
Figure 25C:
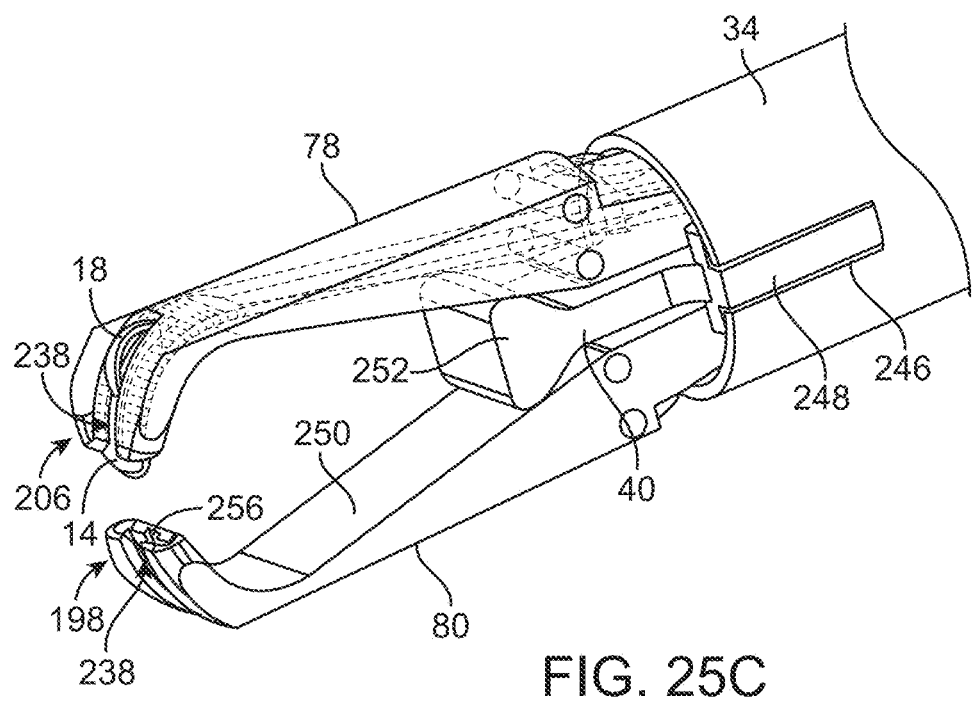
Figure 25D:
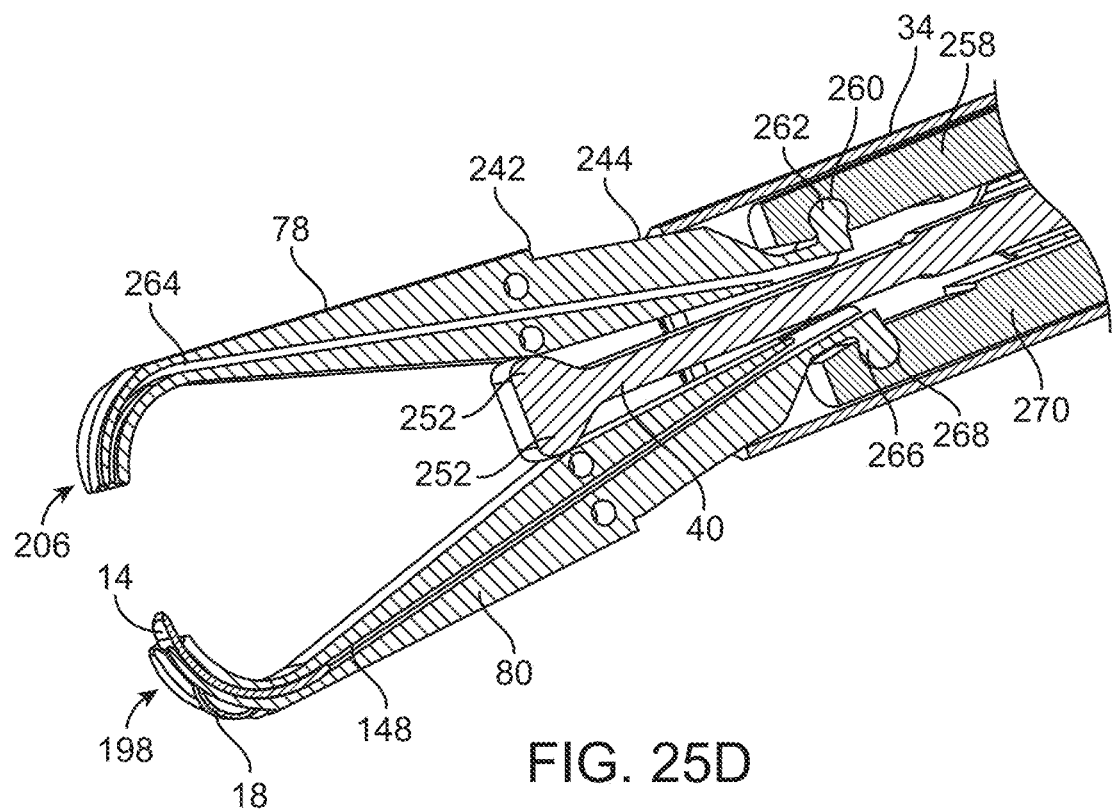
Figure 26A:
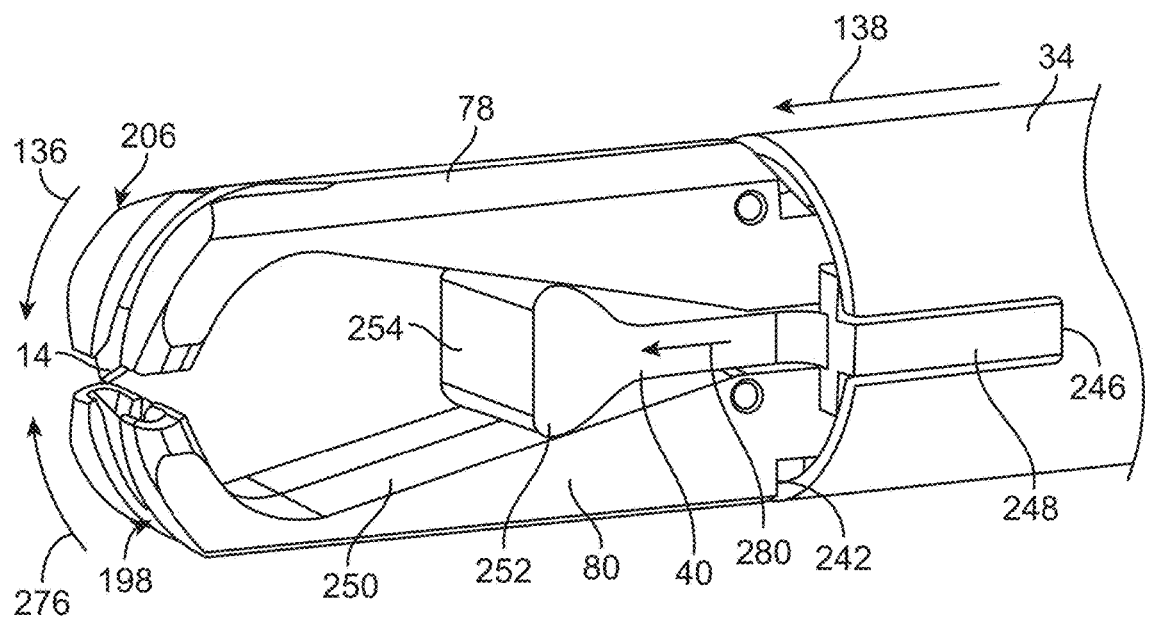
FIG. 26a is a side perspective view of a variation of the distal end of device with the jaws in a closed configuration with the shuttle in the upper jaw and not engaged in the lower jaw.
Figure 26B:
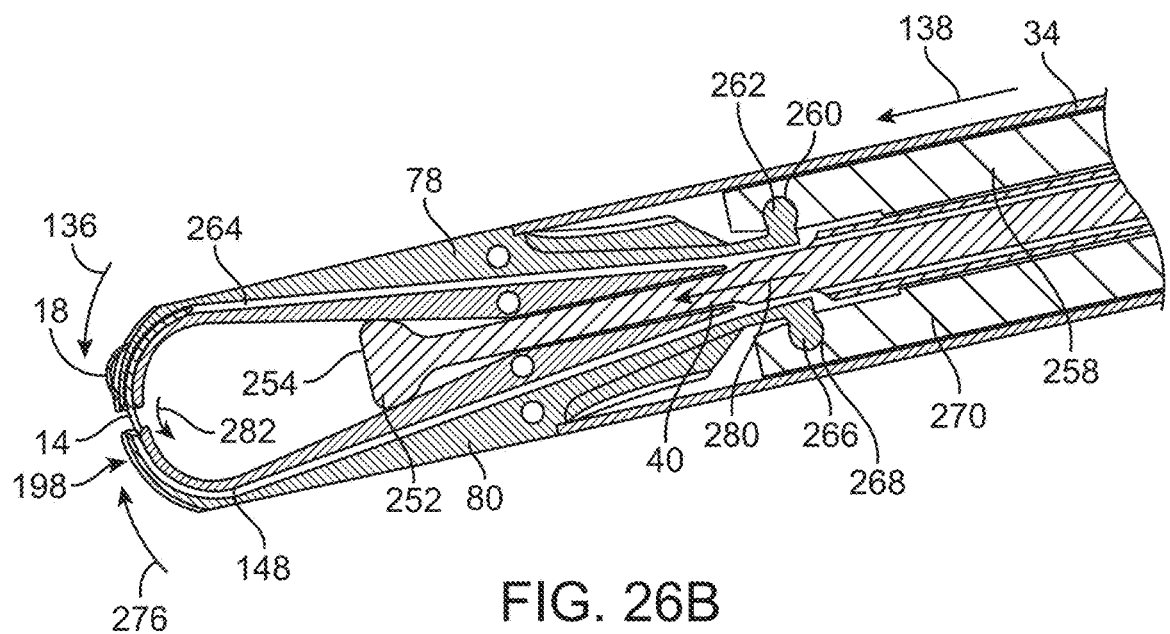
FIGS. 26b and 26c are longitudinal cross-section and side perspective views, respectively, of the device of FIG. 26a with the shuttle in the top and bottom jaws.
Figure 26C:
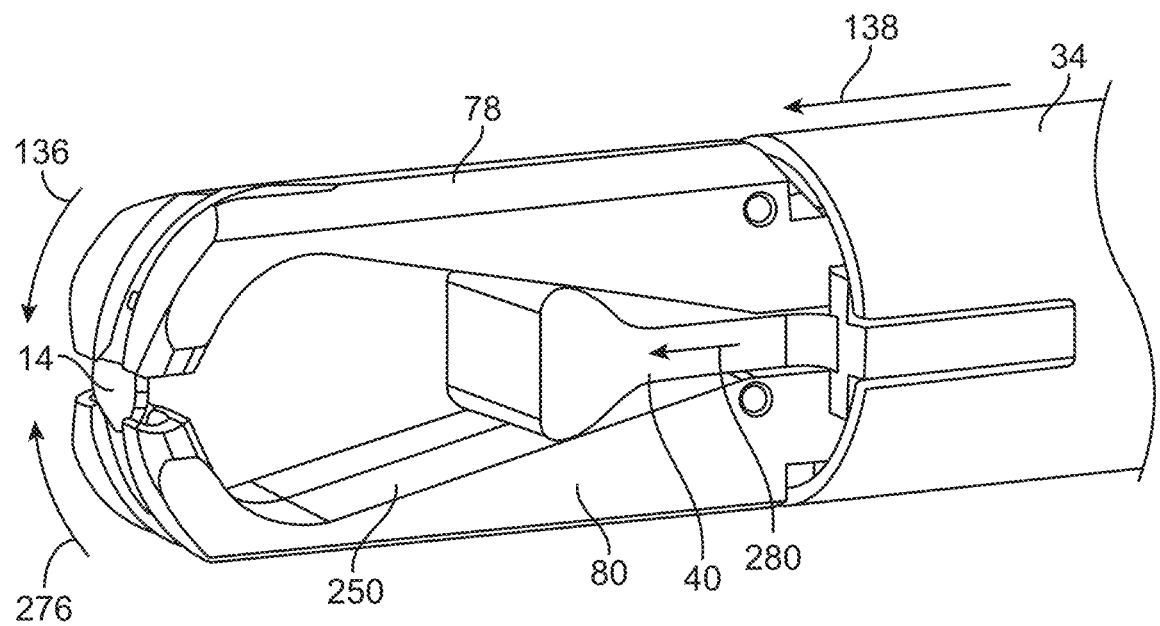
Figure 26D:
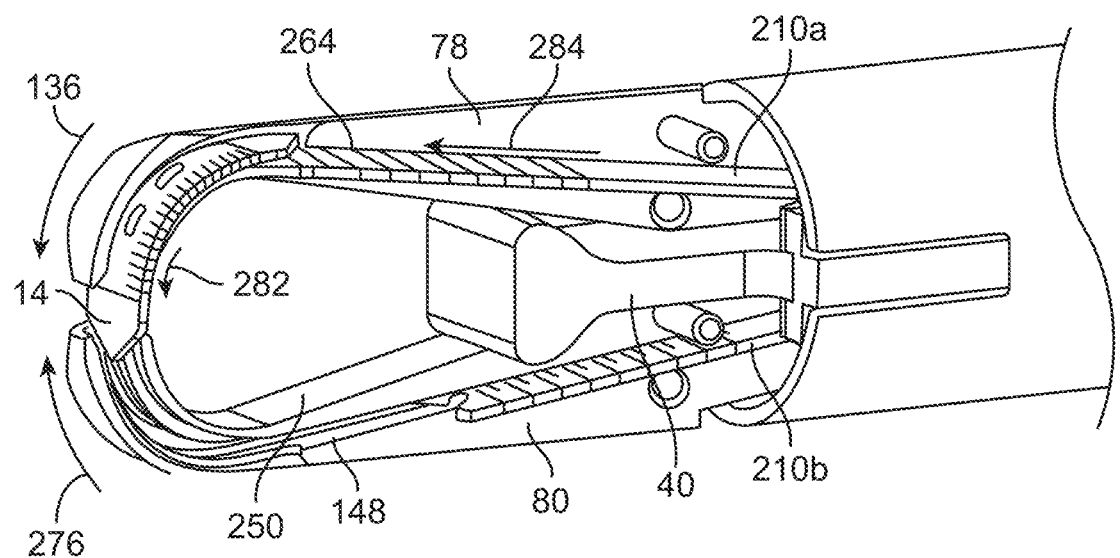
FIG. 26d is a partial cut-away view of FIG. 26c.

FIGS. 21*a* and 21*b* illustrate that the tip interface 211 can have a tip interface axis 214 with respect to the jaw structure longitudinal axis 42. The lower jaw tip 198 can be distal to the upper jaw tip 206 at the tip interface 211. The tip interface angle 212 can be from about 30° to about 60°, more narrowly 30° to about 45°, for example about 35°.

FIGS. 22*a* through 22*c* illustrate that the distal end 2 of the lower jaw tip 198 (as shown) or upper jaw tip 206 can have a tip seat 216. The tip seat 216 can be shaped to receive the shape of the opposite jaw tip. For example, the tip seat 216 can be triangular (e.g., A-shaped or V-shaped).

The tip seat 216 can surround the lateral sides and distal side of the upper jaw tip 206 when the jaws are in a closed configuration. The tip seat 216 can contact or not contact (i.e., there can be a gap) the upper jaw tip 206 when the jaws are in a closed configuration.

The jaw lateral ridge 190 of the jaw with the tip seat 216 (the bottom jaw 38, as shown) can extend to the terminal end of the lower jaw tip 198 and the tip seat 216. The jaw lateral ridge 190 of the jaw opposite of the tip seat 216 (the upper jaw 78, as shown) can narrow, for to a point at the terminal end of the respective jaw tip. The narrowed jaw lateral ridge 190 can be received within the tip seat 216.

FIGS. 23*a* and 23*b* illustrate that the upper 78 and/or lower jaws 80 can have circular or oval cross-sections. The upper 78 and/or lower jaws 80 can be made from solid or hollow rods, for example having a diameter of from about 0.030 in. to about 0.100 in., for example about 0.060 in.

The terminal end of the upper and/or lower jaw tip 198 can have a conical shape. The terminal end of the lower jaw tip 198 can have an tip seat 216 that can be inverse or negative to a conical shape, for example sized and shaped to receive the upper jaw tip 206.

The shuttle 14 can have a circular or oval cross-section.

The pushers can have pusher fingers 219 extending from the pusher spine 218, similar to the shuttle fingers 156 and shuttle spine 160. The pusher fingers 219 can be triangular.

FIGS. 24*a* through 24*c* illustrate that the distal end 2 of the device 188 can be inserted into a cannula 226, for example to be deployed percutaneously through a cannula 226 inserted in a patient at a target site. The cannula 226 can have a cannula inner diameter 228. The cannula inner diameter 228 can be from about 4 mm to about 8 mm, for example 7 mm, or 6.86 mm (0.270 in.), or 15 French gauge (5 mm (0.197 in.)).

The shuttle 14 can have a shuttle height 220. The shuttle height 220 can be from about 0.020 in. to 0.060 in., for example about 0.041 in.

The compression cover 34 can be attached to or integral with one or more jaw control extensions 40. For example the jaw control extensions 40 can extend from the lateral distal ends 2 of the compression cover 34. The jaw control extension 40 can slidably attach to or contact the jaws directly or indirectly. The jaw control extension 40 can push the jaws apart from each other when the jaw control extension 40 is translated proximally with respect to the jaws, and toward each other when the jaw control extension 40 is translated distally with respect to the jaws.

One or more upper cam pins 222 can extend laterally from the one or both lateral sides of the proximal end of the upper jaw 78. One or more lower cam pins 232 can extend laterally from the one or both lateral sides of the proximal end of the lower jaw 80 at the same or different longitudinal position as the upper cam pins 222.

The jaw control extensions 40 can have one or more upper cam slots 230 and one or more lower cam slots 224. The upper 230 and/or lower cam slots 224 can be straight, curved, angled (as shown) or a combination thereof. The cam pins can be positioned inside and through the respective cam slots. The cam pins can slide within the cam slots.

When the jaw control extension 40 is translated distally with respect to the jaws, the cam pins can slide proximally within the respective cam slots and rotate the jaws away from each other. When the jaw control extension 40 is translated proximally with respect to the jaws, the cam pins can slide distally within the cam slots and rotate the jaws toward each other.

The jaws can have a jaw extension length 234. The jaw extension length 234 can be the length from the distal end 2 of the jaw control extension 40 to the proximal side of the jaw tips. The jaw extension length 234 when the jaws are in a closed configuration can be from about 5 mm to about 30 mm, for example about 16 mm and 15.95 mm.

The jaws can have a jaw straight gap 236 along the straight length of the jaws. The jaw straight gap 236 can be from about 1 mm to about 3.5 mm, for example about 1.1 mm or about 3.2 mm. For example, the cannula inner diameter 228 can be 5 mm and the jaw straight gap 236 can be about 1.1 mm.

The jaws can be separate or can be integrated at a jaw body. Jaws integrated in a jaw body can rotatably deform away from each other when moved into an open configuration.

FIGS. 25*a* through 25*f* illustrate that the upper jaw tip 206 and/or lower jaw tip 198 can have suture holder slots 238. The suture holder slots 238 can extend medially along the outer surface of the respective jaw tip. The suture holder slot 238 can extend from the outer surface of the jaw tip to the respective track. The suture holder 18 can be accessible through or extend out of the suture holder slot 238. The suture 70 (not shown) can attach to or be integral with the suture holder 18 in or outside of the suture holder slot 238.

The upper track 264 can distally terminate at an upper jaw tip shuttle port 240. The lower track 148 can distally terminate at a lower jaw tip shuttle port 256. The shuttle 14 can extend out of or into, and pass through each of the shuttle 14 ports. During use, the sharpened shuttle tip 164 extending out of the shuttle port can pierce, cut and dissect tissue 74 when the jaws are rotated to a closed configuration.

The upper jaw 78 and/or lower jaw 80 can have a jaw stop 242. The jaw stop 242 can be a feature, shape or configuration that can abut and stop the distal translation of the compression cover 34 with respect to the jaws. For example, the distal terminal end of the compression cover 34 can abut the jaw stops 242 when the jaws are in a closed configuration.

The radially inner surface of the jaws can have radially inner slopes 250.

The upper jaw 78 and/or lower jaw 80 can have a jaw slide 244. The jaw slide 244 can be a radially outer surface of the jaws between the jaw stops 242 and the compression cover 34 when the compression cover 34 is in a proximally retracted 126 position with respect to the jaws and/or the jaws are in an opened configuration. The jaw slide 244 can increase in radius from the jaw structure longitudinal axis 42 in the distal longitudinal direction (e.g., the larger the longitudinal dimension of the jaw slide 244, the larger the radial dimension of the jaw slide 244). When the compression cover is translated distally 138 with respect to the jaws, the radially inner distal edge of the compression cover 34 can slide along the jaw slide 244, and press the jaw slide 244 toward the jaw structure longitudinal axis 42. A radially compressive force delivered from the compression cover 34 to the jaw slide 244 can create a torque in the respective jaw, rotating the respective jaw toward the jaw structure longitudinal axis 42 and the opposing jaw.

The device 188 can have a jaw control extension 40. The jaw control extension 40 can extend along the jaw structure longitudinal axis 42. The jaw control extension 40 can extend between the jaws proximal to the jaw tips. The jaw control extensions 40 can terminate in a jaw control extension head 254.

The jaw control extension head 254 can have one or two lobes or cams. Each lobe can extend from the longitudinal axis of the jaw control extension 40 toward a jaw. The lobes can act similarly to the opening roller ball shown in FIGS. 4*a*, 4*d*, and elsewhere herein. The upper jaw 78 and lower jaw 80 can have upper and inner jaw radially inner slopes 250, respectively. The inner slopes can be the radially inner surfaces of the jaws proximal to the jaw tips and distal to the jaw control extension head 254 when the jaw control extension head 254 is in a proximally retracted position with respect to the jaws. The radially inner slope 250 can increase in radius from the jaw structure longitudinal axis 42 in the distal longitudinal direction (e.g., the larger the longitudinal dimension of the radially inner slope 250, the larger the radial dimension of the radially inner slope 250). When the jaw control extension 40 is proximally translated or retracted with respect to the jaws, the lobes can slide against the radially inner slopes 250 of the jaws and press the jaws away from each other into an open configuration.

When the jaws are in an open configuration, the compression cover 34 can be positioned at or proximally past the proximal end of the jaw slides 244, and the jaw extension head can be positioned at or proximally past the proximal end of the radially inner slopes 250.

The jaw control extension 40 can be attached to or integral with a control rail 248. The control rail 248 can extend radially from one or both lateral sides of the jaw control extension 40, for example in a plane at a right angle to a plane defined by the opposing jaws or the opposing extension head lobes 252.

The compression cover 34 can have a control rail slot 246. The control rail slot 246 can extend to the distal terminal end of the compression cover 34. The control rail 248 can be fixed to or longitudinally translate within the control rail slot 246. The control rail 248 can interference fit, abut or stop against the proximal end of the control rail slot 246, for example when the control rail 248 is in a proximal or distal longitudinal position with respect to the jaws. The control rail 248 can move longitudinally in unison (i.e., coincidentally) with the compression cover 34 in the distal and/or longitudinal directions. The control rail 248 can move longitudinally in unison with the jaw control extension 40 in the distal and/or longitudinal directions.

The device 188 can have an upper socket arm 258 and a lower socket arm 270 radially inside of the compression cover 34. The upper socket arm 258 and lower socket arm 270 can be a single integrated element (e.g., a hollow cylinder) or separate elements. The upper socket arm 258 can be opposite the lower socket arm 270. The upper socket arm 258 can be translatably fixed (i.e., mechanically attached to translate in unison) to the lower socket arm 270. The jaw control extension 40 can extend longitudinally between the upper 258 and lower socket arms 270 or within a hollow channel inside a unitary socket arm (comprising the upper 258 and lower socket arms 270 as an integrated element). The distal terminal ends of the socket arms can extend to or proximal to the distal terminal end of the compression cover 34 when the jaws are in an open configuration.

The proximal terminal end of the upper jaw 78 can have a laterally elongated upper jaw bearing 262. The upper jaw bearing 262 can extend radially outward from the remainder for the proximal end of the upper jaw 78.

The distal end 2 of the upper socket arm 258 can have a laterally elongated upper jaw socket 260. The upper jaw socket 260 can open medially and have a diameter approximately equal to or slightly larger than the diameter of the upper jaw bearing 262.

An upper jaw 78 hinge can have the upper jaw bearing 262 and the upper jaw socket 260. The upper jaw 78 can rotate around the transverse axis of the upper jaw bearing 262. The upper jaw bearing 262 can rotate in the upper jaw socket 260.

The proximal terminal end of the lower jaw 80 can have a laterally elongated lower jaw bearing 266. The lower jaw bearing 266 can extend radially outward from the remainder for the proximal end of the lower jaw 80.

The distal end 2 of the lower socket arm 270 can have a laterally elongated lower jaw socket 268. The lower jaw socket 268 can open medially and have a diameter approximately equal to or slightly larger than the diameter of the lower jaw bearing 266.

A lower jaw 80 hinge can have the lower jaw bearing 266 and the lower jaw socket 268. The lower jaw 80 can rotate around the transverse axis of the lower jaw bearing 266. The lower jaw bearing 266 can rotate in the lower jaw socket 268.

The upper 86 and/or lower pushers 76 can have entire lengths or only distal ends 2 that can have articulated segmentations 286. The articulated segments 286 can rotate with respect to each other around an axis perpendicular to the longitudinal axis of the respective pusher. The articulated segmentations 286 can be connected by a discrete hinge (e.g., a pin or snap connection) or can be longitudinally coincidental or longitudinally alternating lateral slots cut into the sides of the pusher, similar to the shape of the shuttle lateral slots 158. The proximal end of either or both upper 86 and lower pushers 76 can have a continuous, non-segmented, flat, uniform ribbon of material.

Each of the upper 86 and/or lower pushers 76 can have distal terminal ends that can have a shuttle seat 274. The shuttle seat 274 can be an inverse shape to the shape of the shuttle tip 164. For example, if the shuttle tip 164 has an angled end, the shuttle seat 274 can have the opposite angle. If the shuttle tip 164 has a convex curved end, the shuttle seat 274 can have a concave curved end with the same radius of curvature as the shuttle tip 164.

FIGS. 26a through 26d illustrate that the compression cover 34 can be distally translated, as shown by arrow, with respect to the jaws. The compression cover 34 can deliver translational force through the edges of the control rail slot 246 to the control rail 248. The control rail 248 can deliver the translational force to the jaw control extension 40. The jaw control extension 40 can translate distally, as shown by arrow, concurrently with the compression cover 34. The compression cover 34 can translate 138 over the jaw slides 244, pressing radially inward on the jaw slides 244. The jaw control extension head 254 can move distally with respect to the jaws, as shown by arrow 280, for example, allowing the closure of the jaws without interference fitting or abutting against the jaw control extension head 254. The upper jaw 78 and/or lower jaw 80 can rotate radially inward, as shown by arrows.

When the jaws are in a closed configuration, the compression cover 34 can be positioned at or adjacent to the jaw stop 242, and the jaw extension head can be positioned at or proximally past the proximal end of the radially inner slopes 250.

When the jaws are in a closed configuration, if the shuttle 14 is in the upper track 264, the upper pusher 86 can translate distally through the upper track 264. The distal terminal end of the upper pusher 86 can abut the shuttle 14. The upper pusher 86 can then push the shuttle 14 through the upper track 264, out the upper jaw tip shuttle port 240 and into the lower jaw tip shuttle port 256.

When the jaws are in a closed configuration, if the shuttle 14 is in the lower track 148, the lower pusher 76 can translate distally through the lower track 148. The distal terminal end of the lower pusher 76 can abut the shuttle 14. The lower pusher 76 can then push the shuttle 14 through the lower track 148, out the lower jaw tip shuttle port 256 and into the upper jaw tip shuttle port 240.

When the shuttle 14 is pushed from the upper track 264 to the lower track 148 or vice versa, the shuttle 14 can be curvilinearly translated 282, as shown by arrow, following the paths of the upper track 264 and the lower track 148.

When the jaws are in a closed configuration, the shuttle 14 can move from the upper jaw 78 to the lower jaw 80, as shown by arrow, back to the upper jaw 78, and can repeat the motion from the upper jaw 78 to the lower jaw 80, and optionally from the lower jaw 80 to the upper jaw 78 one, two or more times.

The device 188 can have a pusher lockout that can prevent translation of the pushers and the shuttle 14 when the jaws are in an open configuration.

The device 188 can have a jaw lockout preventing opening of the jaws when either of the pushers is extended out of the respective jaw tip shuttle port and/or when the shuttle 14 is concurrently in the upper jaw 78 and the lower jaw 80.

Figure 27:
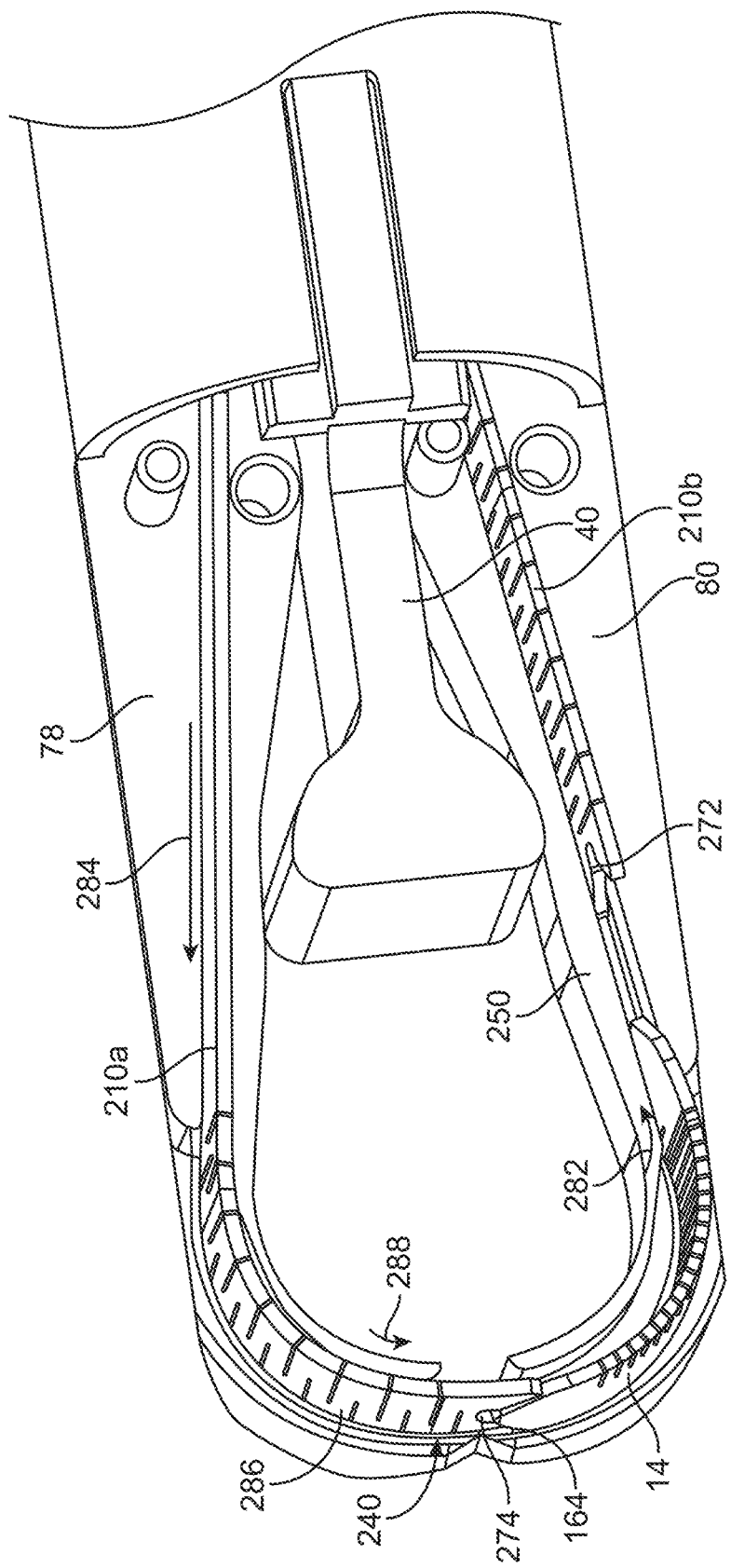
FIG. 27 is a close-up, partial cut-away view of the distal end of a variation of the device with the shuttle in the lower jaw and the upper pusher extending out of the upper jaw and partially entering the lower jaw.

FIG. 27 illustrates that the upper pusher 86 can be distally translated with respect to the jaws. The upper pusher 86 can curvilinearly translate, as shown by arrows 284 and 288, along the upper track 264. The distal terminal end of the upper pusher 86 can exit out of and extend from the upper jaw tip shuttle port 240. The V-shaped (or A-shaped), or curved (e.g., U-shaped) shuttle seat 274 at the distal terminal end of the upper pusher 86 can abut the V-shaped (or A-shaped), or curved (e.g., U-shaped) shuttle tip 164 at the terminal end of the shuttle. The upper pusher 86 can push the shuttle 14 through the upper track 264, across the gap between the upper jaw tip shuttle port 240 and the lower jaw tip shuttle port 256, and into the lower track 148. The shuttle 14 can have a curvilinear translation 282, as shown by arrow, along the tracks.

The lower pusher 76 can have no or one lower pusher articulating segment (as shown), or can have a number of articulating segments, similar to the upper pusher 86 in FIG. 27.

Figure 28:
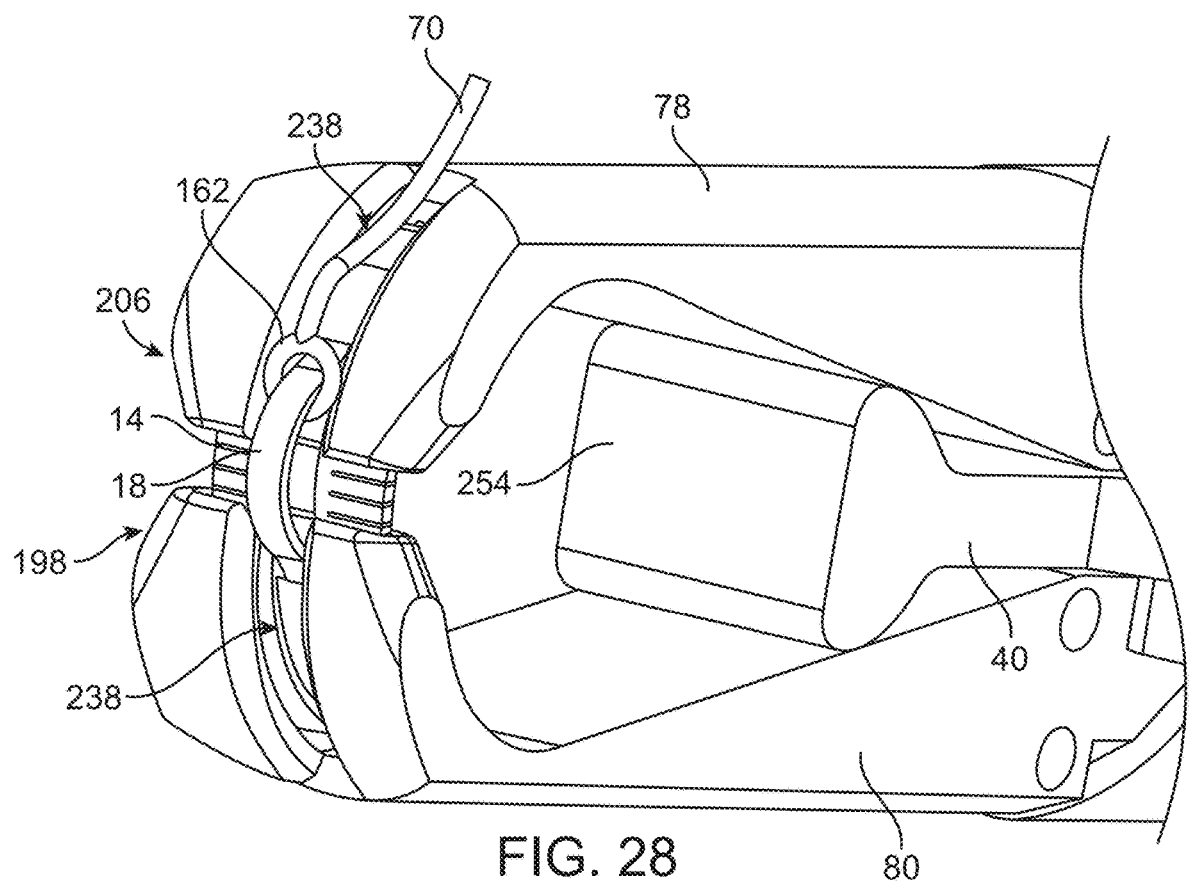
FIG. 28 is a close-up end perspective view of a variation of the device with the shuttle and suture of FIG. 13a or 13b.

FIG. 28 illustrates that the suture 70 can be tied or adhered directly to suture holder 18, for example as shown in FIGS. 13a and 13b. The suture 70 can have a suture loop 162. The suture loop 162 can circumscribe the suture holder 18.

Figure 29:
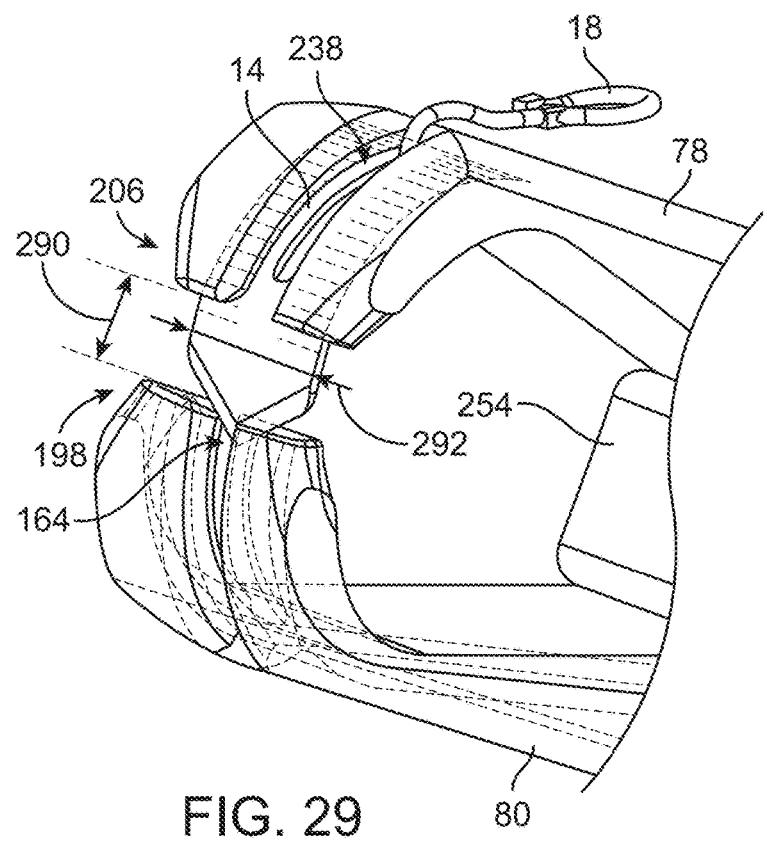
FIG. 29 is a close-up end perspective view of a variation of the device with the shuttle and suture of FIGS. 14a through 14c.

FIG. 29 illustrates that when the jaws are in a closed configuration, the terminal end of the upper jaw tip 206 can be in contact with or have a tip gap 290 to the terminal end of the lower tip jaw. The tip gap 290 can be from about 0 in. to about 0.020 in., for example about 0.008 in.

The shuttle 14 can have a shuttle width 292. The shuttle width 292 can be from about 0.030 in. to about 0.100 in., for example about 0.060 in, or, as another example, about 0.055 in. As another example, the shuttle width 292 can be about 0.053 in. to about 0.057 in., or more broadly, from about 0.35 in. to about 0.075 in., including every 0.001 in. increment within these ranges (e.g., 0.055 in.).

The shuttle 14 can be made from nickel titanium alloys (e.g., Nitinol), stainless steel, other materials disclosed herein, or combinations thereof.

Figure 30A:
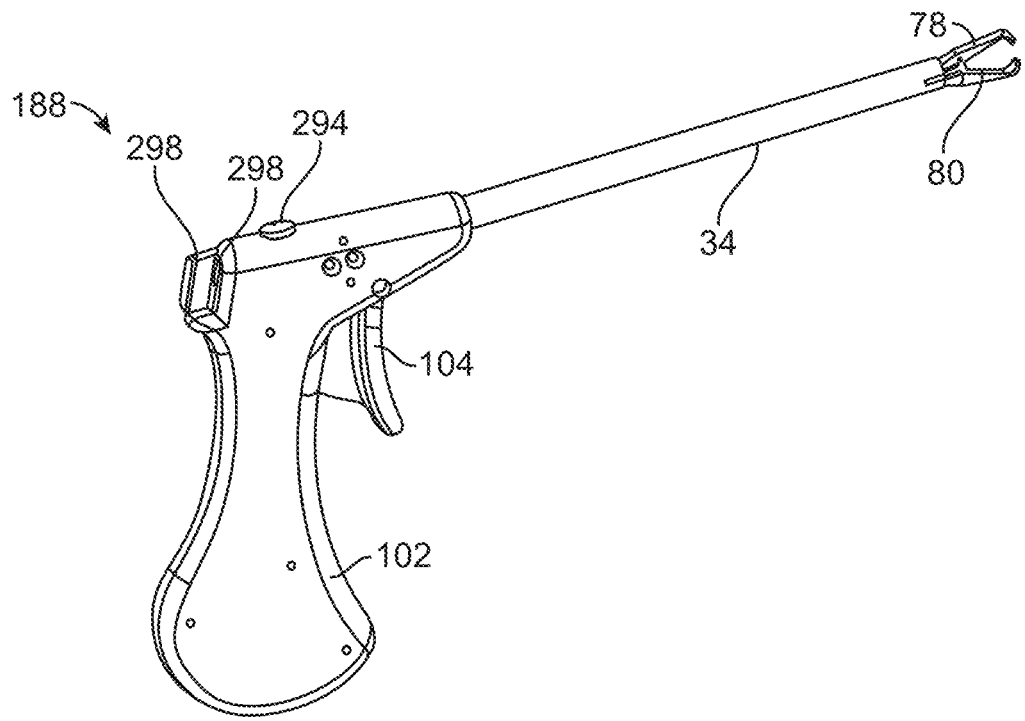
FIGS. 30a and 30b are right rear, and left cut-away views, respectively, of a variation of the device.
Figure 30B:
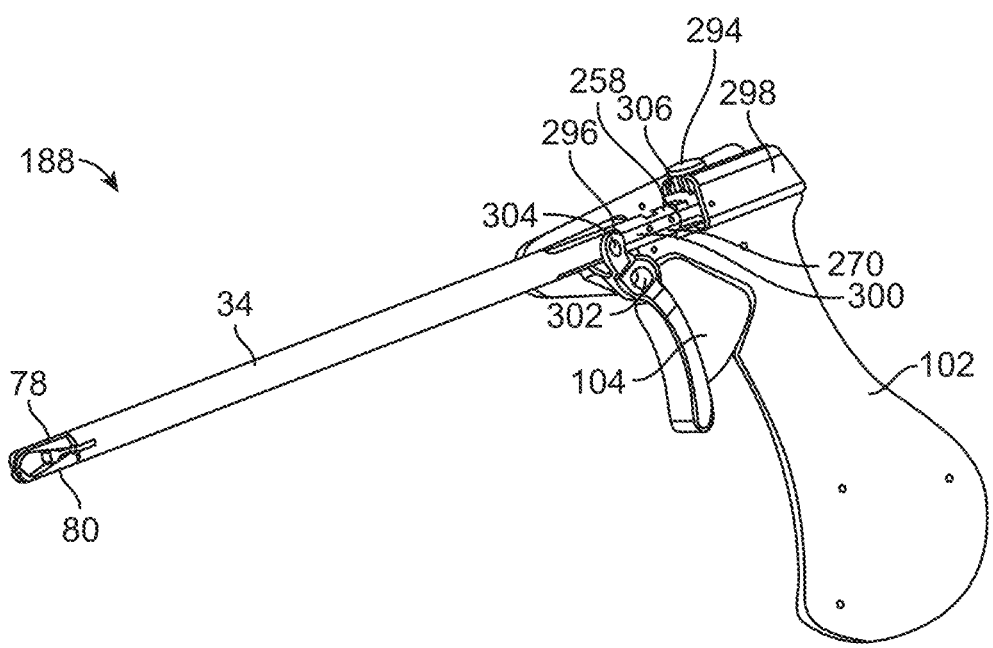
Figure 31:
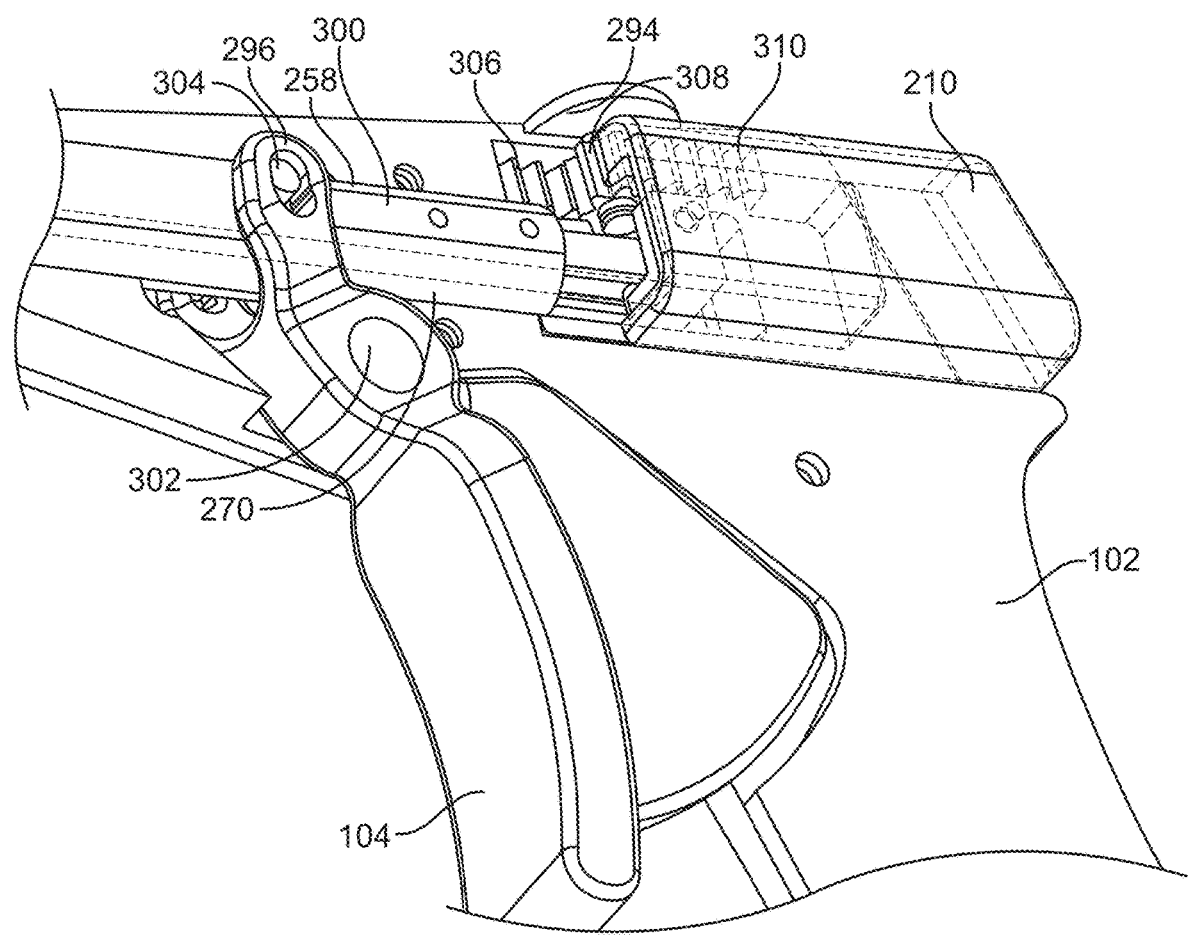
FIG. 31 is a partially cut-away and partially see-through view of the proximal end of a variation of the device.

FIGS. 30a, 30b and 31 illustrate that the lever 106 or handle 104 can control the rotation, and opening and closing of the jaws.

The handle 104 can have a handle pivot 302. The handle pivot 302 can be a rotatable pin joint where the handle 104 can rotatably attach to the base 102. The handle 104 can rotate around the handle pivot 302 with respect to the base 102.

The handle 104 can be attached to the socket arms and/or the compression cover 34 (as shown). For example, the compression cover 34 can have radially and/or laterally extending cover pins 304. The cover pins 304 can attach to the jaw control extension 40. The handle 104 can have one or two transmission ports 314 or loops 296 on opposing lateral sides of the compression cover 34. The cover pins 304 can extend through the transmission loops 296.

The other of the socket arms (as shown) and compression cover 34 not attached to the handle 104 can be attached to the base 102.

Squeezing and rotating the handle 104 toward the base 102 can distally extend 138 the compression cover 34 and jaw control extension 40 with respect to the jaws, or proximally retract 126 the jaws with respect to the compression cover 34 and jaw control extension 40. When the handle 104 is rotated, the jaws can move to an open configuration. For example, when the bottom of the handle 104 is rotated proximally toward the base 102, the transmission loop 296 can rotate distally toward the jaws, pushing the cover pin 304 and the compression cover 34 distally. The transmission loop 296 can force the compression cover 34 and/or jaw control extension 40 to translate distally, for example, closing the jaws.

The proximal end of the upper socket arm 258 and the proximal end of the lower socket arm 270 can be an integral element or can be fixedly attached by a socket arm brace 300.

The terminal proximal end of the upper pusher 86 can attach to or be integrated with an upper pusher 86 shaft and/or upper pusher button 210a. The terminal proximal end of the lower pusher 76 can attach to or be integrated with a lower pusher shaft and/or lower pusher button 210b. The proximal distal ends 2 of the upper pusher button 210a and lower pusher button 210b can be above and below each other or side-by-side (e.g., left and right, as shown). The device 188 can be configured so that pressing (e.g., distally translating) the upper pusher button 210a can distally advance the upper pusher 86, and pressing (e.g., distally translating) the lower pusher button 210b can distally advance the upper pusher 86. Pressing the upper pusher button 210 can proximally retract the lower pusher 76 and/or lower pusher button 210b. Pressing the lower pusher button 210b can proximally retract the upper pusher 86 and/or upper pusher button 210.

The medial sides of the distal ends 2 of the upper and lower pusher buttons 210b can have upper pusher button gears 310 and lower pusher button gears 306, respectively. The upper pusher button gears 310 can face the lower pusher button gears 306.

The pusher toggle knob 294 can be rotatably attached to the base 102. The pusher toggle knob 294 can be integrated or rotationally fixed to a pusher toggle knob gear 308. The pusher toggle knob gear 308 can rotatably interface and interdigitate with the upper pusher button gear 310 on a first side and with the lower pusher button gear 306 on the opposite side of the upper pusher button gear 310.

When the upper pusher button translates distally 284, the upper pusher button gear 310 can rotate the pusher toggle gear, for example also rotating the top of the pusher toggle knob 294 to a position indicating that the upper pusher button 210a has been translated distally 284. The top surface or circumference of the top of the pusher toggle knob 294 can have an indicator, such as an arrow, that can indicate whether the upper pusher 86 or the lower pusher 76 has been translated and by how far, for example indicating the position of the shuttle 14 in the upper track 264, lower track 148, extending out of one track, or extending across both tracks simultaneously. The pusher toggle gear can simultaneously proximally translate the lower pusher button gear 306. For example, when the upper pusher 86 is distally translated, the lower pusher 76 can be simultaneously proximally translated at the same speed.

When the lower pusher button 210b translates distally, the lower pusher button gear 306 can rotate the pusher toggle gear, for example also rotating the top of the pusher toggle knob 294 to a position indicating that the upper pusher button 210a has been translated distally 284. The pusher toggle gear can simultaneously proximally translate the upper pusher button gear 310. For example, when the lower pusher 76 is distally translated, the upper pusher 86 can be simultaneously proximally translated at the same speed.

The pusher toggle knob 294 can be rotated to translate the upper pusher 86 and the lower pusher 76 by transmitting the torque applied to pusher toggle knob 294 through the pusher toggle knob gear 308 and to the upper pusher button gear 310 and/or lower pusher button gear 306 with or without pressing on the proximal terminal ends of the pusher buttons.

Figure 32A:
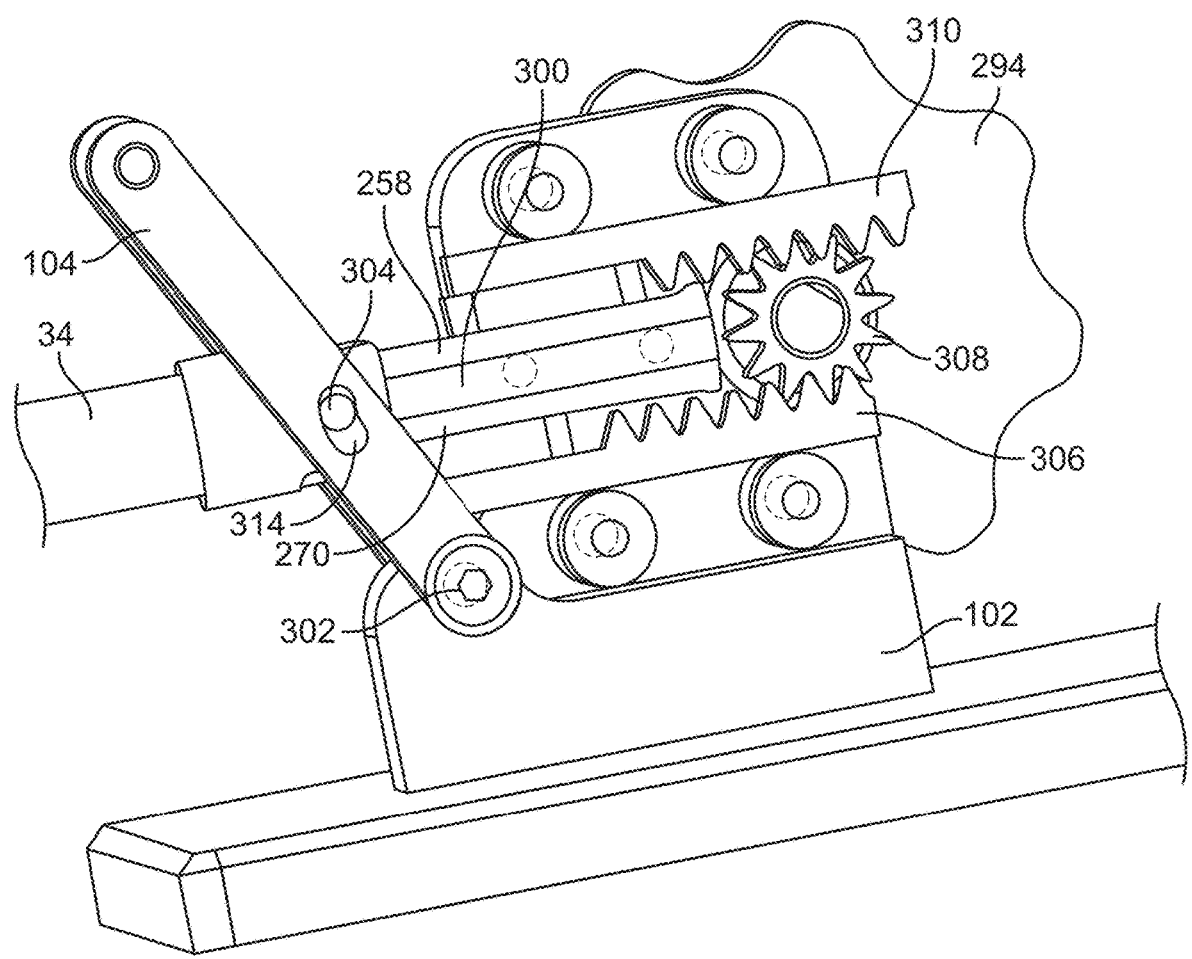
FIGS. 32a and 32b are left and right perspective views of a variation of the pusher drive gears of the device.
Figure 32B:
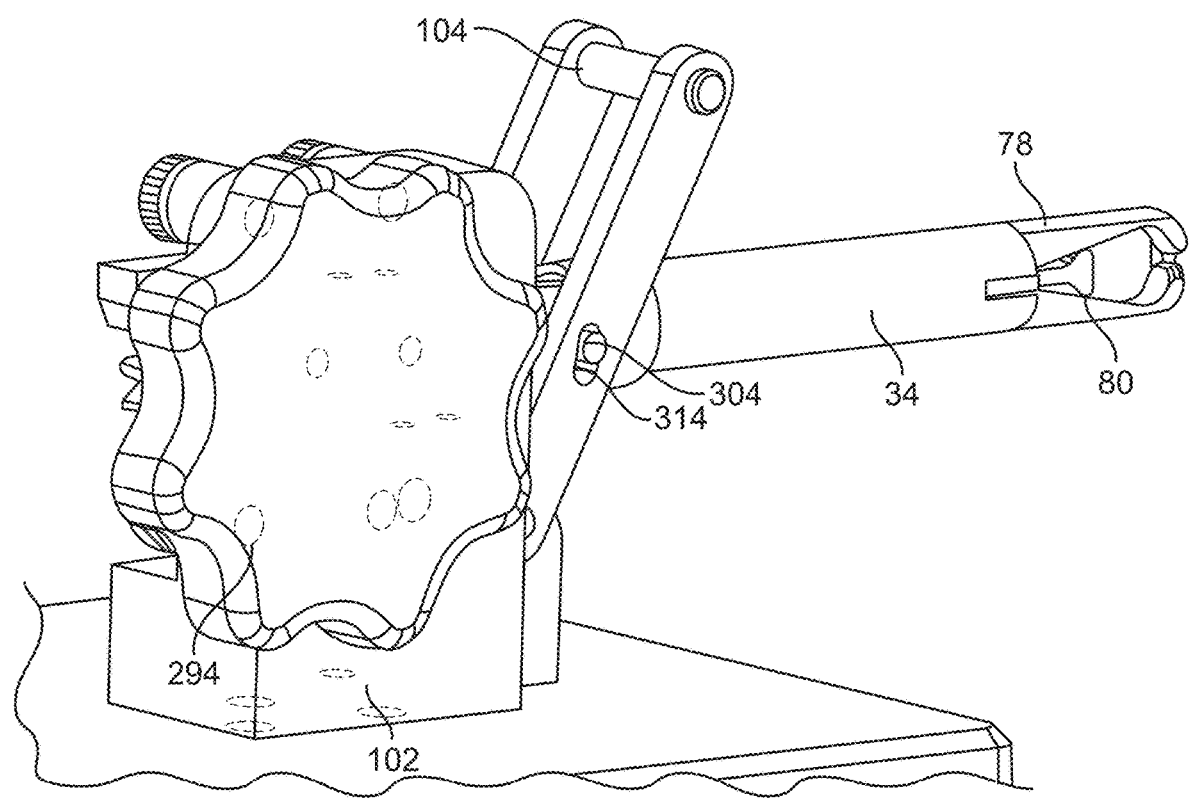

FIGS. 32a and 32b illustrates that the pusher toggle knob 294 can be rotated to translate the upper pusher 86 and the lower pusher 76 by transmitting the torque applied to pusher toggle knob 294 through the pusher toggle knob gear 308 and to the upper pusher button gear 310 and/or lower pusher button gear 306 with or without pressing on the proximal terminal ends of the pusher buttons.

The diameter of the pusher toggle knob 294 can be smaller than the width of the base 102, as shown in FIGS. 30a, 30b and 31, or larger than the width and height of the base 102, and the same size or larger than the handle 104, and the compression cover 34, as shown in FIGS. 32a and 32b.

In a variation of a method of use, the distal end 2 of the device 188 including the jaws can be inserted through a percutaneous cannula 226 when the jaws are in a closed configuration. When the distal end 2 of the device 188 exits the distal end 2 of the cannula 226 at the target site, the handle 104 can be released to rotate away from the base 102. The handle rotation away from the base 102 can move the jaws to an open configuration. The distal end 2 of the device 188 can then be further positioned so the target site is between the upper jaw distal tip 206 and the lower jaw distal tip 198. The handle 104 can then be squeezed to rotate the handle 104 toward the base 102. The handle rotation toward the base 102 can move the jaws into a closed configuration, pinching together tissue 74 at the target site. The shuttle 14 can be completely recessed in the jaw into which the shuttle 14 is loaded, or the shuttle tip 164 can extend out of whichever jaw the shuttle is currently loaded into. The shuttle tip 164 can pierce the tissue 74 as the jaws are closed or after the jaws are closed when the shuttle 14 is translated.

After the jaws are closed, the upper 210a or lower pusher button 210b (e.g., respective to whichever track the shuttle 14 is currently in) can be pressed, distally advancing the respective pusher. The respective pusher can press the shuttle 14 distally, through the gap between the upper 78 and lower jaws 80, if such a gap exists, or directly from one jaw to the other jaw. The shuttle 14 can pull the suture 70 to follow the path of the shuttle 14 or follow a path adjacent to the shuttle 14. When the respective pusher button is fully depressed, the device 188 can emit a sound and/or tactile response (e.g., from a snap or detent in the button or pusher and track) and the pusher toggle knob 294 can have an indicator (e.g., a line or arrow) indicating that the shuttle 14 has been fully translated across the jaws.

The handle 104 can then be rotated away from the base 102. For example, the handle 104 can be released and spring loaded to return to a position rotated away from the base 102. The rotating handle can proximally translate the transmission loop 296. The transmission loop 296 can proximally pull and translate the compression cover 34 and jaw control extension 40, opening the jaws.

The device 188 can then be repositioned so the jaw tips are removed entirely, for example if stitching is complete, or moved adjacent to their previous position in order to place a new stitch. The handle 104 can then be squeezed, closing the jaws. The pusher button of the track in which the shuttle 14 is positioned can then be pressed. The shuttle 14 can then move to the opposite jaw, as described above, pulling the suture 70 through the tissue 74 and forming a stitch.

The above method can be repeated as needed to create a length and position of desired stitches.

Any or all elements of the device 188 and/or other devices 188 or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CON-ICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example), tungsten-rhenium alloys, polymers such as polyethylene teraphathalate (PET)/polyester (e.g., DACRON® from E. I. Du Pont de Nemours and Company, Wilmington, Del.), polypropylene, (PET), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue 74, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

The shuttle 14 throughout the disclosure herein can be attached to a suture 70. Accordingly, the suture 70 can be attached to the shuttle 14 and can follow the movement of the shuttle 14. Similarly, the suture 70 can be attached to and detached from the shuttle 14, for example, attached before and detached after the desired stitching or suturing is complete.

The shuttle 14 can be translatable (e.g., slideable) in the jaw structure 28, for example, in the jaw tracks (e.g., jaw tracks 66 and 64). The shuttle can be configured to translate (e.g., slide) in the jaw structure 28, for example, the jaw tracks (e.g., jaw tracks 66 and 64).

Figure 33A:
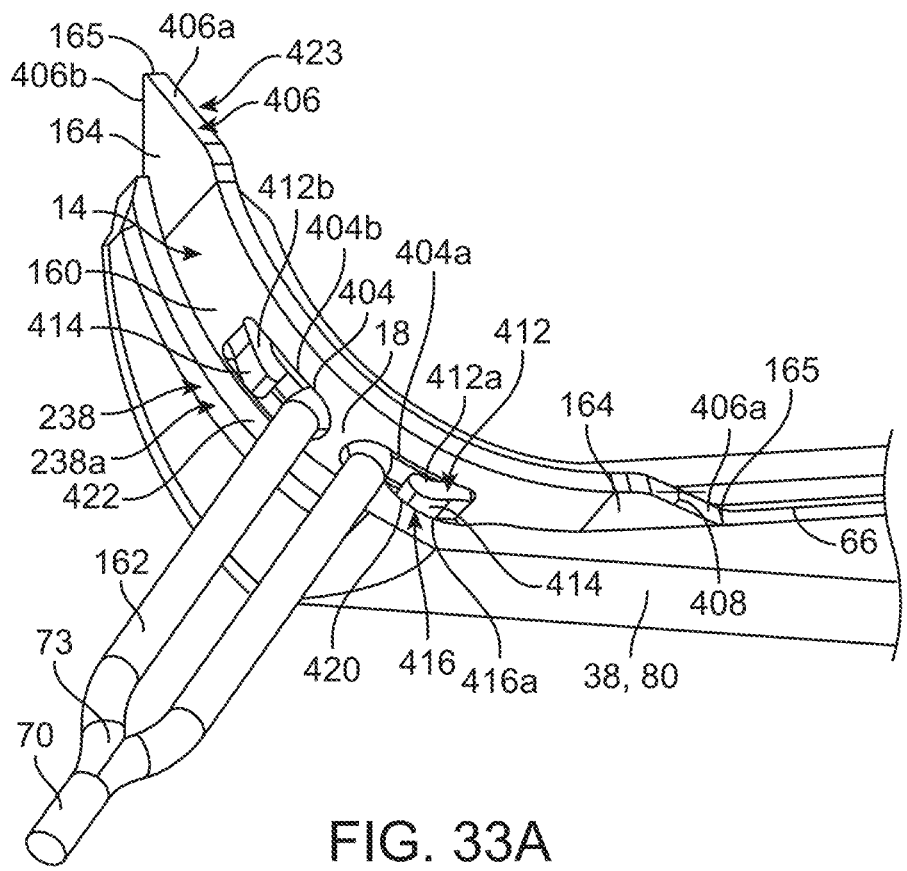
FIG. 33A illustrates a variation of the shuttle in a lower jaw with half the lower jaw shown transparent.

FIG. 33A illustrates that the suture holder 18 can be attached to or integrated with the shuttle 14. For example, the suture holder 18 can be a bridge integrated with the shuttle spine 160. A portion of the shuttle spine 160 can define the suture holder 18. As another example, the suture holder 18 can be removably attached to the shuttle 14. The suture holder 18 can extend between a shuttle first lateral side and a shuttle second lateral side. The suture holder 18 can extend between a shuttle first longitudinal side and a shuttle second longitudinal side. The suture holder 18 can be in the longitudinal center of the shuttle 14, on a proximal end of the shuttle 14, or on a distal end of the shuttle 14. A center of the suture holder 18 can be in the transverse center of the shuttle 14, on a first lateral side of the shuttle, or on a second lateral side of the shuttle. The suture holder 18 can be in the plane of the shuttle spine 160, extend away from the plane of the shuttle spine 160, or both. For example, FIG. 33A illustrates that the suture holder 18 does not extend away from the plane of the shuttle spine 160. The plane of the suture holder 18 can be flush with or coincident with the plane of the shuttle spine 160. This can advantageously allow the shuttle and suture holder 14, 18 to take up less space, thereby minimizing the trauma to surrounding tissue as the shuttle 14 is passed between the upper and lower jaws 30, 38 since it brings the base of the suture 70 closer to the shuttle 14. With the suture 70 closer to the shuttle 14, the force of the suture 70 against surrounding tissue is reduced as compared to when the suture 70 is connected to a structure out of the plane of the shuttle spine 160 (e.g., the suture holder 18 of FIGS. 13a and 13b). The shuttle and suture holder 18 can be a monolithic structure. The suture loop 162 can extend around and completely or partially circumscribe the suture holder 18. The remainder of the suture 70 can be integral with the suture loop 162, or can removably attached to the suture loop 162. The suture loop 162 can be attached to or integrated with the suture 70 at a suture junction 73. The suture junction 73 can be a knot, a braid, or both. The suture loop 162 can be circular, oval, or stadium-shaped.

The shuttle 14 can have zero, one, or multiple suture holes 404, for example, 0 to 4 or more suture holes 404, including every 1 suture hole increment within this range. For example, FIG. 33A illustrates that the shuttle 14 can have a first suture hole 404a and a second suture hole 404b. The shuttle holes 404 (e.g., first and second suture holes 404a, 404b) can have a regular or irregular shape, for example, curved, polygonal, or both. The suture holes 404 can be defined by one or more curved surfaces or curved edges, for example, one or more curved surfaces or curved edges of the shuttle 14. The suture holes 404 can be defined by one or more flat surfaces or straight edges, for example, one or more flat surfaces or straight edges of the shuttle 14. The suture holes 404 can have a cross-sectional shape of a circle, ellipse, rectangle, stadium, horseshoe, star, slot, or any combination thereof. The suture holes 404 can have such cross sectional shapes when the shuttle is curved or flat. The suture holes 404 can have a constant cross-sectional area or a tapered cross-sectional area.

The shuttle tips 164 can be beveled, non-beveled, or both. For example, FIG. 33A illustrates that the shuttle tips 164 can be non-beveled. The shuttle tips 164 can have one or multiple tip surfaces 406, for example, 1 to 4 or more tip surfaces 406, including every 1 tip surface increment within this range (e.g., 1 tip surface, 2 tip surfaces). For example, FIG. 33A illustrates that the shuttle tips 164 can have a first tip surface 406a (e.g., a first non-beveled tip surface as shown in FIG. 33A) and a second tip surface 406b (e.g., a second non-beveled tip surface as shown in FIG. 33A). The non-beveled portion of the shuttle tips 164 can advantageously improve the force transfer from the upper and lower pushers 86, 76, thereby making it easier for the pushers 86 and 76 to push against the shuttle 14. A larger component of the force from the pushers (e.g., pushers 86 and 76) can be transferred along the longitudinal axis of the shuttle 14 when the shuttle tip 164 has a non-beveled surface 406 as compared to a beveled surface (e.g., the beveled surfaces shown in FIGS. 14a-14c). For beveled surfaces, a portion of the force applied to the shuttle 14 is directed against the surfaces that define the lower and upper tracks 66, 64 perpendicularly away from the beveled surface. When a pusher applies a longitudinal force against a beveled surface, a portion of the longitudinal force applied to the shuttle 14 by the pusher is transformed into a transverse component away from the longitudinal axis of the shuttle 14.

FIG. 33A further illustrates that the shuttle tips 164 can be tapered to form a terminal tip 165. The terminal tip 165 can be an edge or part of a rounded or flat surface. The tapered portion of the shuttle tip 164 can be a first bevel, for example, a first transverse bevel toward a longitudinal axis (e.g., center longitudinal axis) of the shuttle 14. The non-beveled surfaces 406 can thereby form first tissue cutting surfaces that are beveled in a first direction. The bevel referred to in the preceding paragraph can refer to a second bevel, for example, a second transverse bevel angled relative to a transverse axis perpendicular to the transverse axis of the first bevel and toward a longitudinal axis (e.g., center longitudinal axis) of the shuttle 14. Such a second bevel is shown in FIGS. 14a-14c. The second bevels can define second beveled surfaces along the taper that face a second direction different from the first direction. The second bevels can form second tissue cutting surfaces. The shuttle tips 164 can pierce or cut tissue. The tapered portion of the shuttle tips 164 can pierce or cut tissue. The tip surfaces 406 (e.g., tip surfaces 406a and 406b) can pierce or cut tissue. When the shuttle tips 164 have first and second bevels, the first and second bevels can pierce tissue or cut tissue. FIG. 33A illustrates that the shuttle tips 164 can be non-sharpened, meaning that while the edges are tapered to form a first cutting surface, the cutting surfaces 406 themselves can be chamfered or non-chamfered. The shuttle tips 164 can be non-sharpened and still cut or pierce tissue, where sharpened or non-sharpened can refer to the presence or non-presence of a second bevel (e.g., as shown in FIGS. 14a-14c), respectively.

FIG. 33A further illustrates that the device 188 can have one or multiple male stops 412 (also referred to as male catches, male detents, stops, catchers, detents) and one or multiple female stops 416 (also referred to as female catches, female detents, stops, catchers, detents). The device 188 can have, for example, 1-10 or more male stops 412, including every 1 male stop increment within this range (e.g., 1, 2, 3, 4 or more male stops). The device 188 can have, for example, 1-10 or more female stops 416, including every 1 female stop increment within this range (e.g., 1, 2, 3, 4 or more female stops).

The male stops 412 can be attached to or integrated with the device 188. For example, the male stops 412 can be part of, attached to, or integrated with the shuttle 14. As another example, the male stops 412 can be part of, attached to, or integrated with the jaws (e.g., jaws 30, 38, 78, 80). As yet another example, the device 188 can have some male stops 412 that are part of, attached to, or integrated with the shuttle 14 and can have some male stops 412 that are part of, attached to, or integrated with the jaws (e.g., jaws 330, 38, 78, 80). As yet still another example, the male stops 412 can be part of, attached to, or integrated with the pushers (e.g., the lower and upper pushers 76, 86).

The female stops 416 can be attached to or integrated with the device 188. For example, the female stops 416 can be part of, attached to, or integrated with the shuttle 14. As another example, the female stops 416 can be part of, attached to, or integrated with the jaws (e.g., jaws 330, 38, 78, 80). As yet another example, the device 188 can have some female stops 416 that are part of, attached to, or integrated with the shuttle 14 and can have some female stops 416 that are part of, attached to, or integrated with the jaws (e.g., jaws 330, 38, 78, 80). As yet still another example, the female stops 416 can be part of, attached to, or integrated with the pushers (e.g., the lower and upper pushers 76, 86).

FIGS. 33A-34B illustrate, for example, that the shuttle 14 can have the male stops 412 and that the jaws (e.g., jaws 330, 38, 78, 80) can have the female stops 416. For example, FIGS. 33A-34B illustrate that the shuttle 14 can have a first male stop 412a and a second male stop 412b, that the lower jaw (e.g., jaw 38, 80) can have a first female stop 416a (also referred to as the lower jaw first female stop 416a and other similar terms) configured to releasably engage with or releasably attach to the first male stop 412a, and that the upper jaw (e.g., jaw 30, jaw 78) can have a second female stop 416b (also referred to as the upper jaw first female stop 416b and other similar terms) configured to releasably engage with or releasably attach to the second male stop 412b. Half of the lower and upper jaws are shown transparent in FIGS. 33A-34B so that the shuttle 14 can be more easily seen in the jaw tracks (e.g., lower and upper tracks 66, 64), and so that the male and female stops 412, 416 can be more easily seen.

Each male stop 412 can releasably fit into, attach to, or engage with a corresponding female stop 416, for example, via a friction fit, snap fit, magnetic fit, ratchet fit, or any combination thereof. For example, the first male stop 412a can be configured to releasably attach to the first female stop 416a and the second male stop 412b can be configured to releasably attach to the second female stop 416b. When two stops (e.g., male and female stops 412, 416) are releasably attached to one another, a threshold release force can be required to release the stops from one another. The threshold release force can be from about 1.0 Newton to about 10.0 Newtons or more, including every 0.5 Newton increment within this range (e.g., 4.0 Newtons, 4.5 Newtons, 5.0 Newtons). As another example, the release force can be from about 0.5 lbs to about 1.5 lbs, including every 0.1 lb increment within this range (e.g., 1.0 lb).

The male stops 412 can be a positive feature such as a protrusion, bump, ridge, arm, extension, flexure, detent flexure, or any combination thereof. The male stops 412 can be straight and/or curved. The male stops 412 can be flexible, rigid, or both (e.g., a first portion can be flexible and a second portion can be rigid). The male stops 412 can be one or more springs. The female stops 416 can be a negative feature such as a void, space, pocket, notch, hole, through hole, recess, detent recess, or any combination thereof. The female stops 416 can be flexible, rigid, or both (e.g., a first portion can be flexible and a second portion can be rigid). The male and female stops 412, 416 can include magnets that attract one another to keep the male and female stops releasably attached together.

The male stops 412 can have a male surface 414 and the female stops 416 can have a female surface 418. The male and female surfaces 414, 418 can be configured to engage with one another, slidably engage with one another, contact one another other, or any combination thereof. The female stops 416 can have a lip 420 configured to engage with, slidably engage with, or contact the male stop 412, or any combination thereof. The male stops 412 can be configured to engage with, slidably engage with, or contact the lip 420, or any combination thereof.

For each male-female stop pair, the male and female surfaces 414,418 can engage with one another and/or the male stop 412 can engage with the lip 420, for example, when the male stop 412 is being forced into the female stop 416, when the male stop 412 is being withdrawn from the female stop 416, when the female stop 416 is being forced over or onto the male stop 412, when the female stop 416 is being withdrawn from the male stop 412, when the male and female stops 412, 416 are attached to one another (also referred to as the stopped position, caught position, fixed position), or any combination thereof. As another example, two female stops 416 can engage with one another, for example, where the two female stops 416 include a magnet. As yet another example, two male stops 412 can engage with one another, for example, where the two male stops include a magnet. The male and/or female stops 412, 416 can form a hook or hook-like feature to releasably catch the other stop.

Figure 34A:
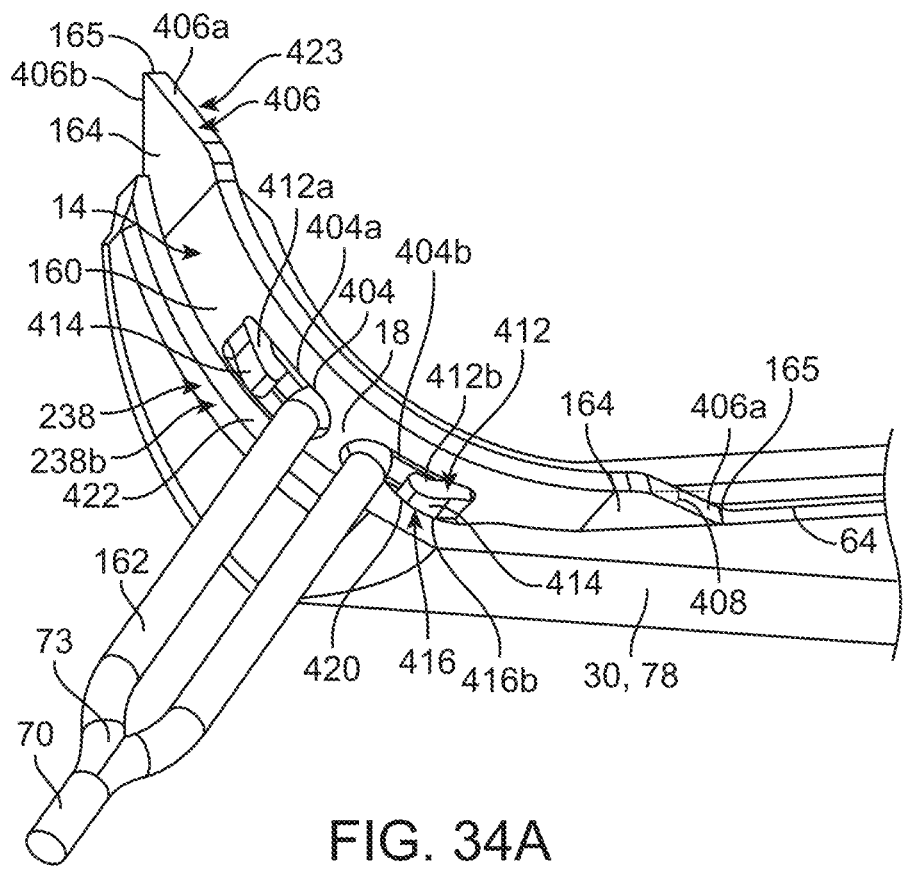
FIG. 34A illustrates a variation of the shuttle in an upper jaw with half the upper jaw shown transparent.

The male stops 412 can move relative to the female stops 416, vice versa, or both. The female stops 416 can move relative to the male stops 412, vice versa, or both. For example, FIG. 33A illustrates that the male stops 412 can be translatable (e.g., slidably translatable) in the lower jaw track, for example, in a first direction toward the first female stop 416a and in a second direction away from the first female stop 416a, or vice versa such that the first female stop 416a is translatable toward and away from a male stops 412 (e.g., for arrangements where the female stop 416 is integrated with or attached to the shuttle 14 and the male stop 412 is integrated with or attached to the lower jaw). As another example, FIG. 34A illustrates that the male stops 412 can be translatable (e.g., slidably translatable) in the upper jaw track, for example, in a first direction toward the second female stop 416b and in a second direction away from the second female stop 416b, or vice versa such that the second female stop 416b is translatable toward and away from a male stop 412 (e.g., for arrangements where the female stop 416 is integrated with or attached to the shuttle 14 and the male stop 412 is integrated with or attached to the upper jaw). The first and second directions can be opposite from one another.

Figure 33B:
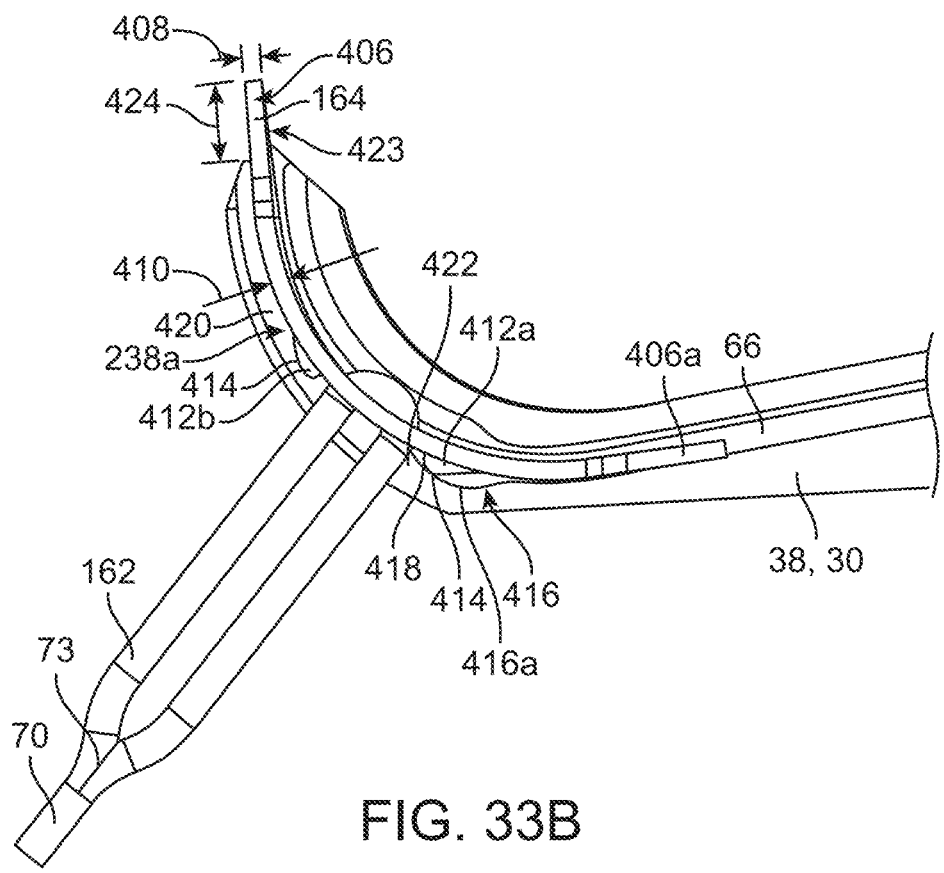
FIG. 33B illustrates a variation of the shuttle in a lower jaw with half the lower jaw shown transparent.

FIGS. 33A and 33B illustrate that when the shuttle 14 is being translated (e.g., pushed by the upper jaw pusher 86, pulled by the lower jaw pusher 76, or both) in a first direction in the lower jaw track toward the first female stop 416a, the lip 420 can exert a force against the first male stop 412a that causes the first male stop 412a to flex toward a longitudinal axis of the shuttle 14. This flexure can allow the first male stop 412a to fit into the first female stop 416a. Upon passing by the lip 420, the first male stop 412a can rebound to its neutral position or to a less flexed position and releasably lock the shuttle 14 to the lower jaw via the releasable attachment between the first male stop 412a and the first female stop 416a. FIGS. 33A and 33B further illustrate that when the shuttle 14 is being translated (e.g., pulled by the upper jaw pusher 86, pushed by the lower jaw pusher 76, or both) in a second direction (e.g., opposite the first direction) in the lower jaw track away from the first female stop 416a, the female surface 418 can exert a force against the first male stop 412a that causes the first male stop 412a to flex toward a longitudinal axis of the shuttle 14. This flexure can allow the first male stop 412a to slide under and past the lip 420. Upon passing by the lip 420 in the second direction, the first male stop 412a can rebound to its neutral position (also referred to as a non-flexed position). When the first male stop 412a flexes, it can deflect into the first suture hole 404a.

Figure 34B:
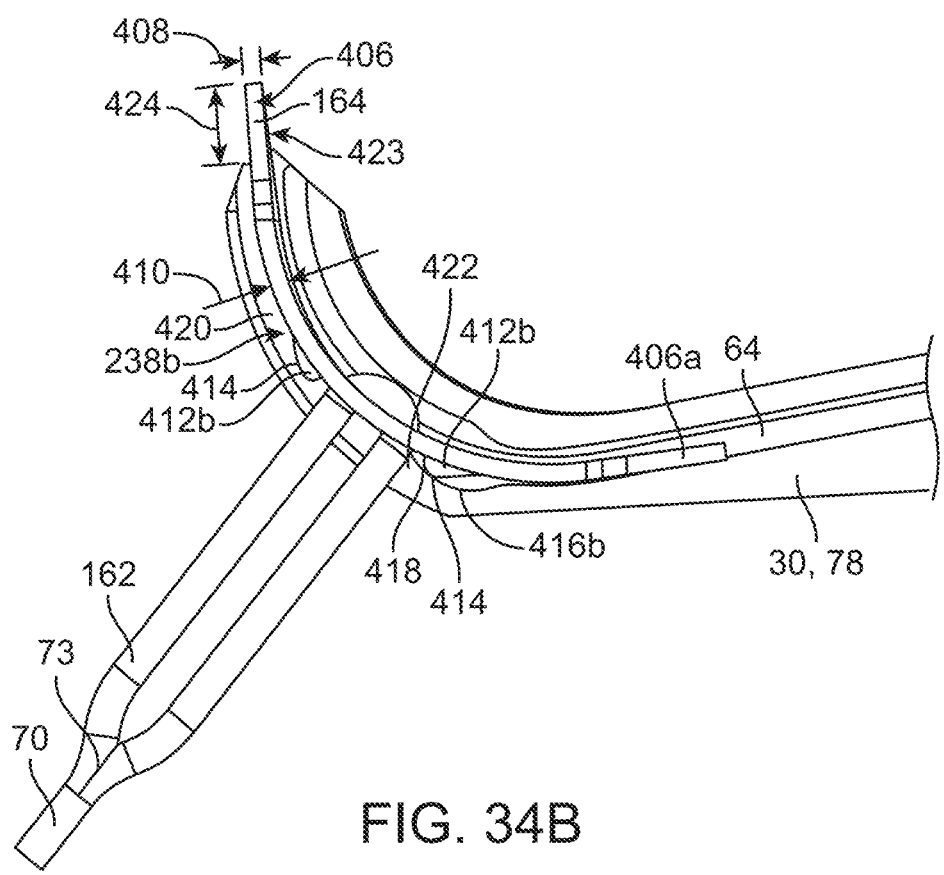
FIG. 34B illustrates a variation of the shuttle in an upper jaw with half the upper jaw shown transparent.

FIGS. 34A and 34B illustrate that when the shuttle 14 is being translated (e.g., pushed by the lower jaw pusher 76, pulled by the upper jaw pusher 76, or both) in a first direction in the upper jaw track toward the second female stop 416b, the lip 420 can exert a force against the second male stop 412b that causes the second male stop 412b to flex toward a longitudinal axis of the shuttle 14. This flexure can allow the second male stop 412b to fit into the second female stop 416b. Upon passing by the lip 420, the second male stop 412b can rebound to its neutral position or to a less flexed position and releasably lock the shuttle 14 to the upper jaw via the releasable attachment between the second male stop 412b and the second female stop 416b. FIGS. 34A and 34B further illustrate that when the shuttle 14 is being translated (e.g., pushed by the upper jaw pusher 86, pulled by the lower jaw pusher 76, or both) in a second direction (e.g., opposite the first direction) in the upper jaw track away from the second female stop 416b, the female surface 418 can exert a force against the second male stop 412b that causes the second male stop 412b to flex toward a longitudinal axis of the shuttle 14. This flexure can allow the second male stop 412b to slide under and past the lip 420. Upon passing by the lip 420 in the second direction, the second male stop 412b can rebound to its neutral position (also referred to as a non-flexed position). When the first male stop 412a flexes, it can deflect into the second suture hole 404b.

The lip 420 can resist passage of the first and second male stops 412a, 412b along the second direction out of the first and second female stops 416a, 416b with the threshold release force. The female surface 418 can be an inner surface of the lip 420. The lip 420 can resist passage of the first and second male stops 412a, 412b along the first direction into the first and second female stops 416a, 416b with the threshold release force or a lesser force (e.g., a force 10% to 75% of the threshold release force).

The device 188 can have zero, one, or multiple male stops 412 and zero, one, or multiple female stops 416 on the device distal end 2 (e.g., closer to the jaws than to the handle 104) and/or on the device proximal end (e.g., closer to the handle 104 than to the jaws). For example, the upper jaw (e.g., upper jaw 78) can have one or multiple male stops 412, one or multiple female stops 416, or any combination thereof. The lower jaw (e.g., lower jaw 80) can have one or multiple male stops 412, one or multiple female stops 416, or any combination thereof. The male and/or female stops 412 and/or 416 can be attached to or integrated with the jaw, the jaw track, or both. The shuttle 14 can have one or multiple male stops 412, one or multiple female stops 416, or any combination thereof. The male stops 412 can extend away from and/or toward a longitudinal axis of the shuttle 14. The male stops 412 can extend away from and/or toward a longitudinal axis of a jaw track (e.g., tracks 66 and 64). The female stops 416 can extend away from and/or toward a longitudinal axis of the shuttle 14. The female stops 416 can extend away from and/or toward a longitudinal axis of a jaw track (e.g., tracks 66 and 64).

For example, FIG. 33A illustrates that the shuttle 14 can have a first male stop 412a and a second male stop 412b, and that the lower and upper jaw tracks (e.g., tracks 66 and 64) can each define a female stop 416 (e.g., a first female stop 416a in the lower jaw and a second female stop 416b in the upper jaw). The lower and upper jaws can each define one or multiple female stops 416. For example, the first male stop 412a can releasably attach to the first female stop 416a and the second male stop 412b can releasably attach to a second female stop 416b. FIG. 33A illustrates that the first and second male stops 412a, 412b can extend away from a longitudinal axis (e.g., center longitudinal axis) of the shuttle toward a longitudinal center of the shuttle 14. The first and second male stops 412a, 412b can be the same or a different dimension away from the longitudinal center of the shuttle 14 as the other detent.

FIGS. 33A-34B further illustrate a surface 422 of jaw suture slots 238, for example, lower jaw suture slot 238a and upper jaw suture slot 238b.

FIGS. 33B and 34B illustrate that the shuttle tips 164 can have a shuttle tip thickness 408 of about 0.05 mm to about 0.75 mm, including every 0.05 mm increment within this range (e.g., 0.15 mm, 0.20 mm, 0.25 mm). The shuttle tip thickness 408 can be the width of the non-beveled surfaces 406. As another example, the shuttle tip thickness 408 can be from about 0.0080 in. to about 0.0090 in. (e.g., 0.0085 in.).

FIGS. 33B and 34B further illustrate that the shuttle 14 can have a shuttle thickness 410 (also referred to as the shuttle thickness $14_T$) of about 0.05 mm to about 0.75 mm, including every 0.05 mm increment within this range (e.g., 0.15 mm, 0.20 mm, 0.25 mm). The shuttle tip thickness 408 can be the same or different from the shuttle thickness 410. The shuttle tip thickness 408 can be less than, equal to, or greater than the shuttle thickness 410. For example, the shuttle tip thickness 408 can be about 0.15 mm and the shuttle thickness 410 can be about 0.25 mm, or vice versa.

The shuttle 14 can be made from a single panel of material (e.g., metal). The suture holes 404 can be cut, leaving the shuttle 14 and the male stops 412. The shuttle 14 can then be bent, which can result in the male stops 412 extending out of the plane of the shuttle spine 160.

FIGS. 33A-34B further illustrate that a portion 423 of the shuttle tips 164 can remain exposed outside of the jaws when the shuttle 14 is fully translated into the jaws. The exposed portion 423 can have an exposed length 424, for example, from about 0.25 mm to about 5.00 mm or more, including every 0.25 mm increment within this range (e.g., 0.50 mm, 1.00 mm, 1.50 mm). The exposed portion 423 can align the lower and upper jaws when they close. The exposed portion 423 can pierce tissue when the lower and upper jaws are closed against each other and before the shuttle 14 is translated to the other jaw. This can advantageously leverage the clamping force of the jaws to cut tissue with the shuttle 14. A portion of the exposed portion 423 can pierce tissue when the shuttle 14 is translated from the lower jaw to the upper jaw, or vice versa.

Figure 35:
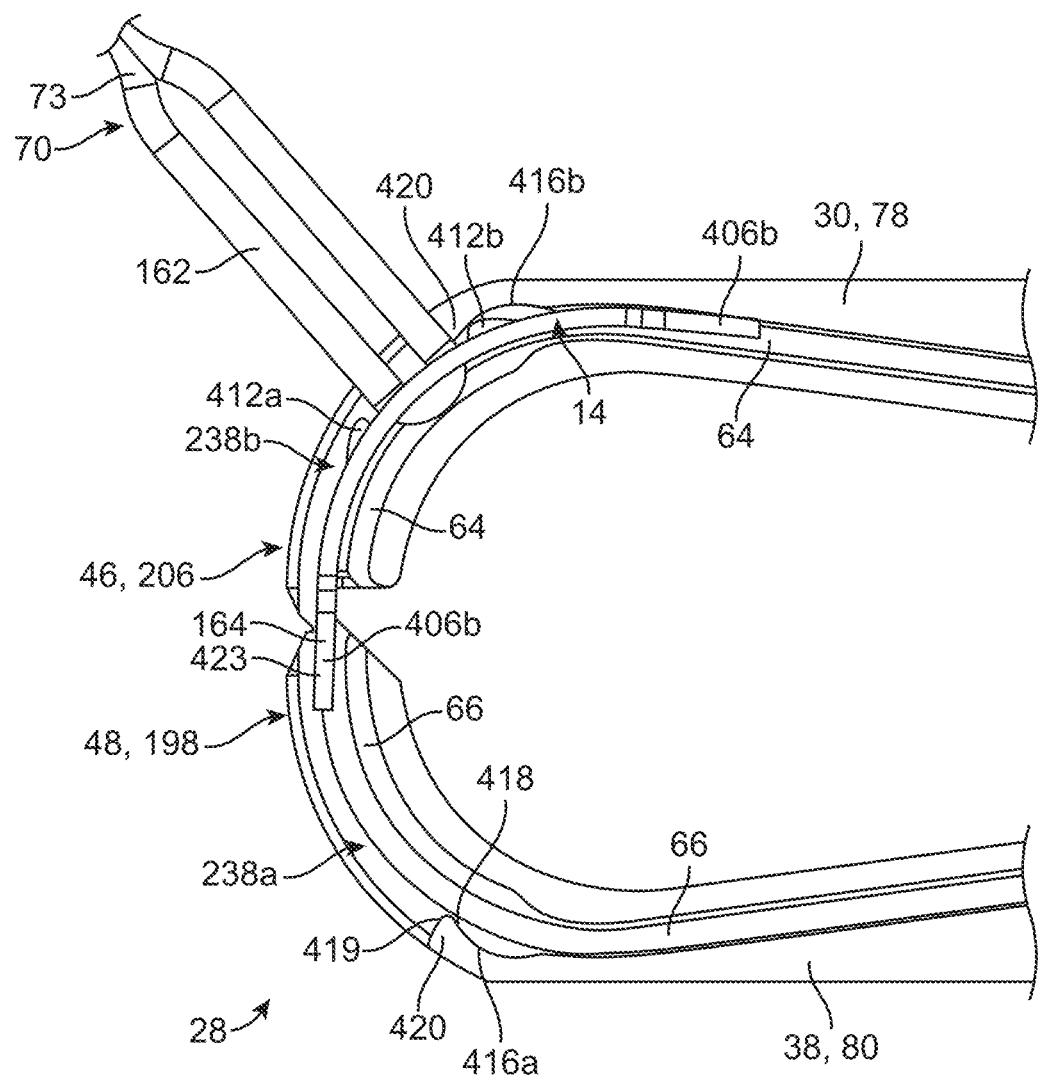
FIG. 35 illustrates a variation of the device with half the lower and upper jaws shown transparent.

FIG. 35 illustrates that all or a portion of the exposed portion 423 can be in the other jaw when the lower and upper jaws are closed and before the shuttle 14 is translated to the other jaw via the lower or upper pusher 76, 86. For example, when the jaws are moved from an open configuration to a closed configuration with the exposed portion 423 extending from the upper jaw (e.g., jaw 30, jaw 78) as shown in FIGS. 33A and 33B, the exposed portion 423 can be moved into the lower jaw (e.g., jaw 38, jaw 80) via the jaws closing with or without translation (e.g., simultaneous translation) of the shuttle 14 into the lower jaw via an upper and/or lower pusher while the jaws are being closed.

FIG. 35 further illustrates that the female stops 416 can have an outer surface 419 and an inner surface 418 (also referred to as a female surface). The outer surface 419 can be flat or curved. The outer surface 419 can define a ramp surface for the male stops 412 to flex against. The outer surface 419 can define a plane at an angle to a longitudinal axis of the shuttle. For example, the plane of the outer surface 419 can be perpendicular or substantially perpendicular to the center longitudinal axis of the shuttle. The inner surface can be flat or curved. The inner surface 418 can define a ramp surface for the male stops 412 to flex against.

FIG. 35 further illustrates that when the lower and upper jaws are closed the jaws can define a continuous track for the shuttle 14 such the lower jaw track 66 and the upper jaw track 64 are continuous with one another. The tracks of the upper jaw and bottom jaw can form a continuous path when the jaw structure 28 is in a closed configuration.

FIG. 35 further illustrates that the first jaw tip (e.g., jaw tip 46, jaw tip 206) can be configured to interdigitate with the second jaw tip (e.g., jaw tip 48, jaw tip 198). For example, the first jaw tip can interdigitate with and be adjacent or in contact with the second jaw tip when the jaw structure 28 is in a closed configuration. The jaw tips can be sharpened. The jaw tips can be tapered. The jaw tips can be sharp and seat into each other to form a continuous track when the jaw structure 28 is in a closed configuration. The jaw tips can seat into each other to connect the lower and upper jaw tracks 66, 64 to each other.

Figure 36A:
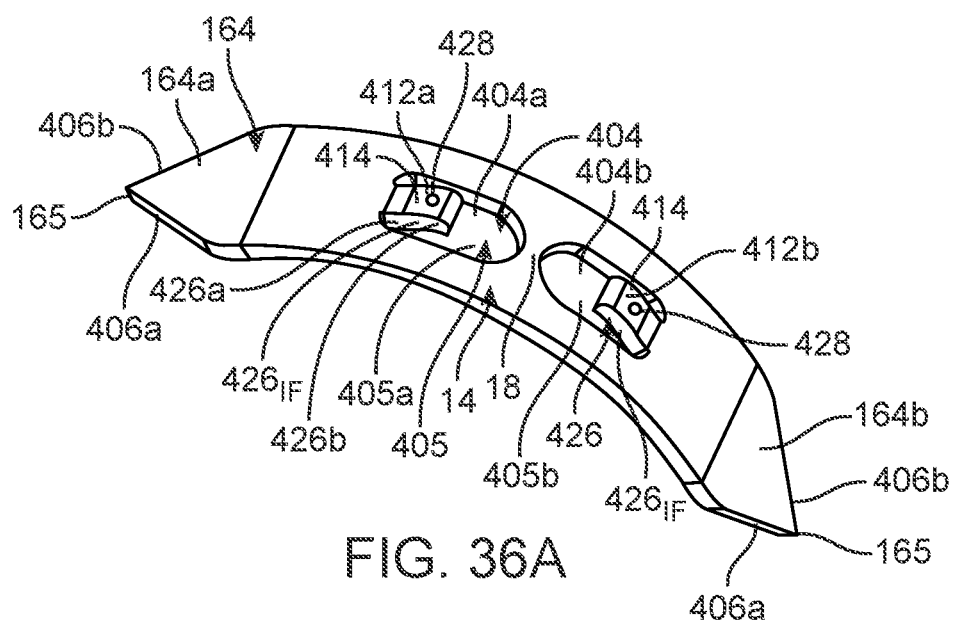
FIG. 36A illustrates a perspective view of a variation of a shuttle.

FIG. 36A illustrates that the shuttle 14 can have a shuttle first tip 164a and a shuttle second tip 164b.

FIG. 36A further illustrates that the shuttle 14 can have zero, one, or multiple shuttle holes 405, for example, 1 to 6 or more shuttle holes 405, including every 1 shuttle hole increment within this range (e.g., 2 shuttle holes, 4 shuttle holes). The shuttle 14 can have a first shuttle hole 405a and a second shuttle hole 405b. The shuttle holes 405 (e.g., holes 405a and 405b) can be the same as or different from the suture holes 404 (e.g., holes 404a and 404b). The male and/or female stops 412, 416 can move into and out of the shuttle holes 405, the suture holes 404, or any combination thereof, for example, via flexing, bending, translating, and/or rotating into and out of the holes 405 and/or 404.

FIG. 36A further illustrates that the male stops 412 can have one or multiple bends 426. For example, FIG. 36A illustrates that the male stops 412 can have a first bend 426a and a second bend 426b. The male stops 412 can have inflection points $426_{IF}$ where the curvature of the male stop 412 changes direction or its concavity. For example, FIG. 36A illustrates that the male stops 412 can have an inflection point 426w between two bends 426 (e.g., between the first and second bends 426a, 426b) where the male stops 412 change concavity (e.g., from concave up for the first bend 426a to concave down for the second bend 426b as shown in FIG. 36A).

FIG. 36A further illustrates that one or more magnets 428 can be attached to or integrated with the male stops 412 on a first side of the detents, for example, on or under the first surface 414 (also referred to as a male surface). The magnets 428 can be configured to be magnetically attracted to a magnet attached to or integrated with the upper or lower jaw having an opposite dipole as the magnets 428.

Figure 36B:
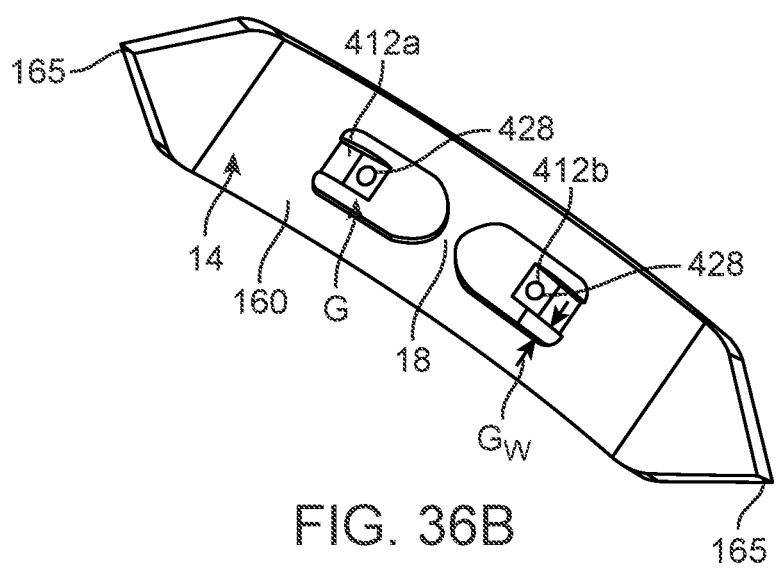
FIG. 36B illustrates a bottom view of the shuttle of FIG. 36A.

FIG. 36B illustrates that the one or more magnets 428 can be attached to or integrated with a second surface 415 of the male stops 412, for example, to an underside of the male stops 412.

FIG. 36B further illustrates that there can be a gap G on each side of the male stop 412 between the male stop 412 and the shuttle body 160. The gap G can advantageously inhibit or prevent pressure from forming in the jaws by allowing gas, liquid, or solids to flow or pass through the gap G as the shuttle 14 is advanced into the jaws. There can be a gap on each lateral side of the male stop 412 as shown in FIG. 36B. As another example, there may not be any gaps G between the male stops 412 and the shuttle body 160, or the gap G can be on only one side of the male stop 412 instead of both sides as shown in FIG. 36B. The gaps G can have a gap width $G_W$ that can be, for example, constant (e.g., as shown in FIG. 36B) or tapered. As another example, the gaps G can have multiple gap widths $G_W$. For example, FIG. 36B further illustrates that the gap G can have a constant width, for example, as measured between the lateral edge or surface of the male stop 412 and the lateral edge or surface of the shuttle body 160.

FIG. 36B further illustrates that the terminal tips 165 can have a sharpened edge. The sharpened edge can be configured to pierce tissue.

Figure 36C:
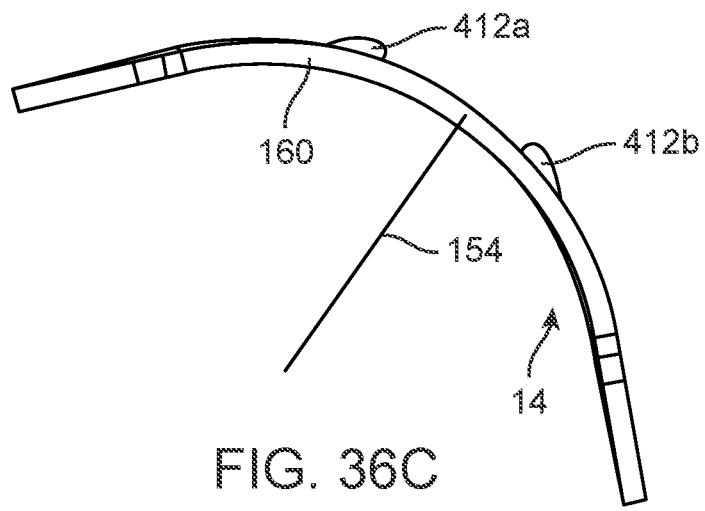
FIG. 36C illustrates a side view of the shuttle of FIG. 36A.

FIG. 36C illustrates that the male stops 412 (e.g., first and second male stops 412*a*, 412*b*) can extend away from a longitudinal axis of the shuttle 14 out of the plane of the shuttle spine 160.

The shuttle longitudinal axis (e.g., longitudinal axis 157) can be flat or curved. FIG. 36C illustrates that the shuttle radius of curvature 154 can be from about 2.00 mm to about 5.00 mm or more, including every 0.01 mm increment within this range (e.g., 2.84 mm).

The shuttle 14 can be straight or have a preformed bend or curve (e.g., having the radius of curvature 154). The shuttle 14 can have a preformed bend having a radius of curvature of about 40% to about 200% of the radius of curvature 154, including every 1% increment within this range (e.g., 50%).

The curvature of the shuttle 14 can be constant. The curvature of the shuttle 14 can be fixed. The shuttle 14 can be flexible. The shuttle 14 can be rigid. The shuttle 14 can transition between curved and straight configurations. Having a preformed bend within this range can reduce the strain on the shuttle 14. For example, the strain can be reduced for variations where the shuttle 14 shifts between straight and curved configurations when moving within and/or between the jaws.

Figure 37C:
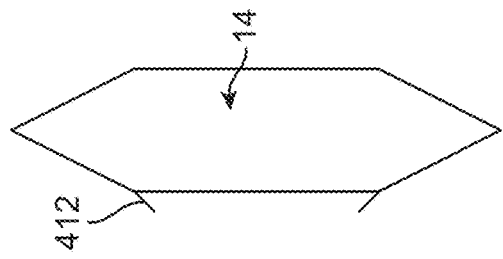
FIG. 37C illustrates a top or bottom view of a variation of a shuttle.
Figure 37E:
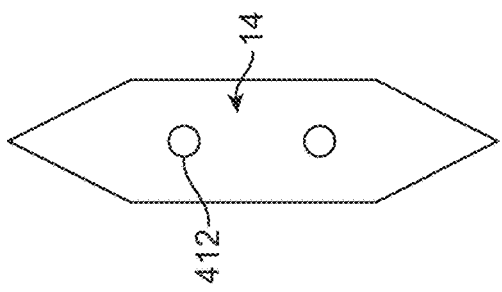
FIG. 37E illustrates a top or bottom view of a variation of a shuttle.
Figure 37B:
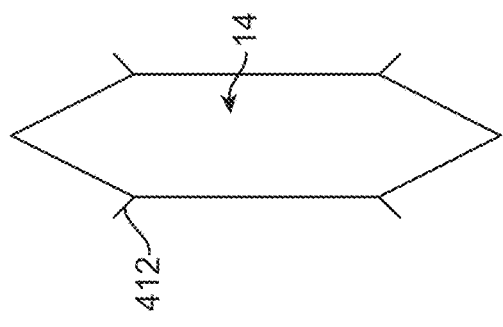
FIG. 37B illustrates a top or bottom view of a variation of a shuttle.
Figure 37D:
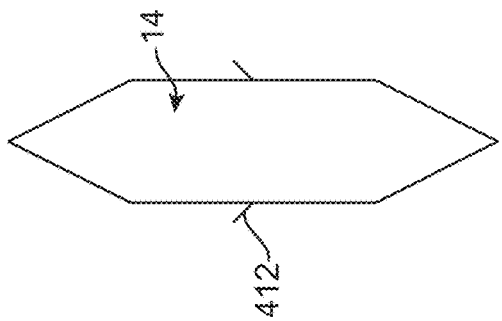
FIG. 37D illustrates a top or bottom view of a variation of a shuttle.
Figure 37A:
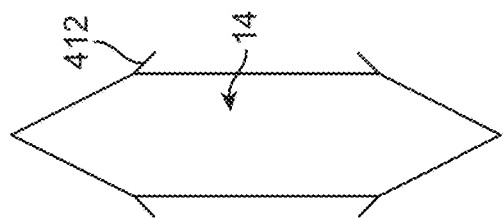
FIG. 37A illustrates a top or bottom view of a variation of a shuttle.

FIGS. 37A-37E illustrate that the shuttle 14 can have the male stops 412 arranged as shown. FIGS. 37A-37D illustrate that the male stops 412 can be arms that extend away from the body of the shuttle 14. FIG. 37E illustrates that the male stops 412 can be bumps on a surface of the shuttle 14.

Figure 38A:
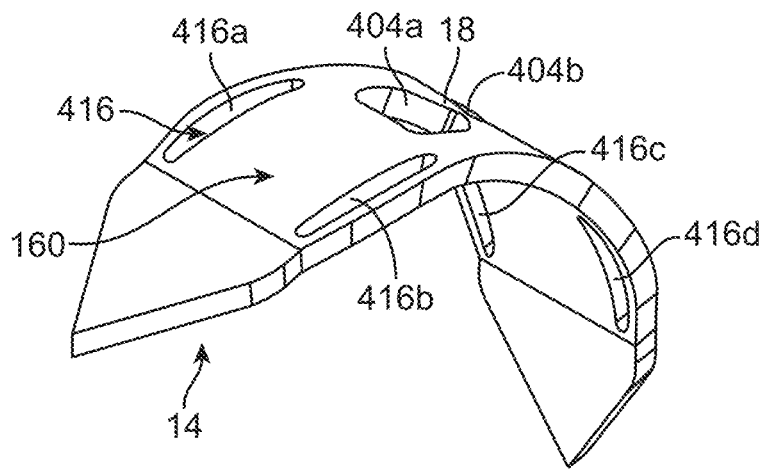
FIG. 38A illustrates a perspective view of a variation of a shuttle.
Figure 38B:
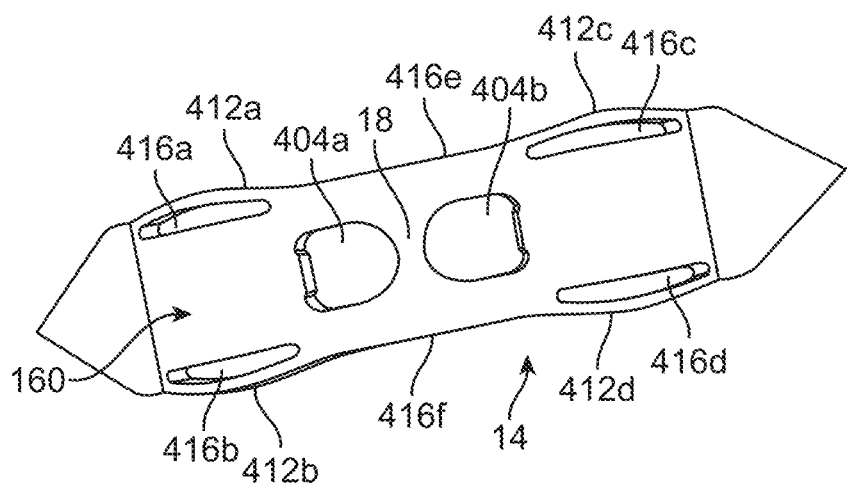
FIG. 38B illustrates a bottom view of the shuttle of FIG. 38A.

FIGS. 38A and 38B illustrate that the shuttle 14 can have one or multiple female stops 416, for example, first, second, third, and fourth female stops 416*a*, 416*b*, 416*c*, and 416*d*. The female stops 416 can be slots that extend partially (e.g., a recess) or fully (e.g., a through hole) through the shuttle spine 160. A male stop 412 can be attached to or integrated with the jaws and can be configured to releasably attach to the female detents shown in FIGS. 38A and 38B.

FIG. 38B further illustrates that the shuttle 14 can have one or multiple male and female stops 412, 416. For example, the shuttle 14 can have the first, second, third, and fourth female stops 416*a*, 416*b*, 416*c*, and 416*d* and can have first, second, third, and fourth male stops 412*a*, 412*b*, 412*c*, and 412*d*. The male stops 412 (e.g., 412*a*, 412*b*, 412*c*, and 412*d*) can be configured to releasably attach to female stops 416 integrated with or attached to the jaw structure 28, for example, that are in or define a shuttle track (e.g., 64 and 66). The female stops 416 (e.g., 416*a*, 416*b*, 416*c*, and 416*d*) can be configured to releasably attach to male stops 412 integrated with or attached to the jaw structure 28, for example, that are in or define a shuttle track (e.g., 64 and 66). FIG. 38B further illustrates that the shuttle 14 can define one or more female stops 416 along the perimeter of the shuttle 14. For example, a fifth female stop 416*e* can be defined between the first and third male stops 412*a*, 412*c*. As another example, a sixth female stop 416*f* can be defined between the second and fourth male stops 412*b*, 412*d*. The shuttle 14 can have any combination of male and/or female stops (e.g., 412*a*, 412*b*, 412*c*, 412*d*, 416*a*, 416*b*, 416*c*, 416*d*, 416*e* and/or 416*f*).

Figure 38C:
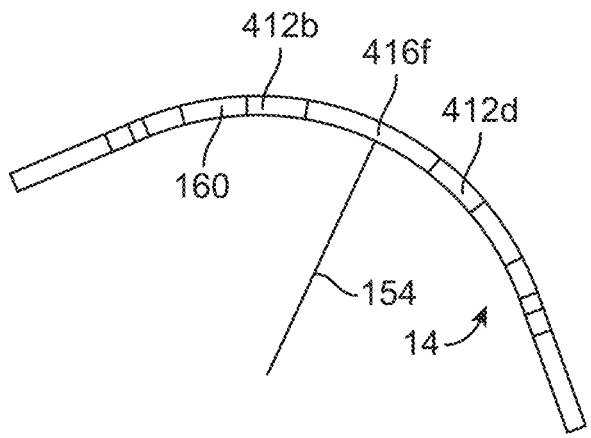
FIG. 38C illustrates a side view of the shuttle of FIG. 38A.

FIGS. 38B and 38C illustrates that the shuttle 14 can have male and/or female stops (e.g., male and/or female stops 412, 416) that extend away from a longitudinal axis of the shuttle 14 along a first transverse axis parallel to the plane of the shuttle spine 160. FIG. 38C illustrates that the male and/or female stops (e.g., male and/or female stops 412, 416) can stay within the plane of the shuttle spine 160 along a second transverse axis perpendicular to the first transverse axis.

FIG. 39A illustrates that the lower jaw and upper jaw pushers 76, 86 can have a straight configuration.

FIG. 39B illustrates that the lower jaw and upper jaw pushers 76, 86 can be bendable and take on a curved configuration, for example, when in one or both of the jaw tracks (66 and 64). The lower and upper jaw pushers 76, 86 can change to and from the straight configuration and the curved configuration as the pusher is translated through one or both of the jaw tracks (e.g., 66 and 64). A proximal portion can remain straight and a distal portion can change from the straight and curved configurations. The pushers can have a pusher radius of curvature 432 of about 1.00 mm to about 5.00 mm, including every 0.01 mm increment within this range (e.g., 2.84 mm). The pusher radius of curvature 432 can be a maximum pusher radius of curvature.

FIG. 39C illustrates that the lower jaw and upper jaw pushers 76, 86 can have a preformed curve 434. The preformed curve 434 can have a preformed pusher radius of curvature 436 of about 2.00 mm to about 10.00 mm, including every 0.01 mm increment within this range (e.g., 5.84 mm). The shuttle 14 can have a preformed bend having a radius of curvature of about 40% to about 200% of the radius of curvature 154, including every 1% increment within this range (e.g., 50%). Preforming the pushers with a curve can advantageously reduce the strain on the pushers when they transition from a straight to a curved configuration or when the transition from a less curved configuration to a more curved configuration and vice versa. For example, a pusher manufactured with a preformed curve having a radius of curvature 50% of the maximum pusher radius of curvature can reduce the strain on the pushers by 50%.

FIG. 39D illustrates that the preformed lower jaw and upper jaw pushers 76, 86 can be bendable and take on more and less curved configurations, for example, when in one or both of the jaw tracks (66 and 64). They can change to and from a straight configuration shown in FIG. 39A and the curved configuration shown in FIG. 39D. The lower and upper jaw pushers 76, 86 can change to and from the straight configuration and the curved configuration as the pusher is translated through one or both of the jaw tracks (e.g., 66 and 64). A proximal portion can remain straight and a distal portion can change from the straight and curved configurations.

FIGS. 40A-40D are perspective views of the pushers illustrated in FIGS. 39A-39D, respectively. FIGS. 40B-40D illustrate that the pushers 76 and 86 can have the shuttle seats 274 as shown. The shuttle seats 274 can be a male or female shape and inverse to the shape of the shuttle tips 164. For example, FIGS. 40B-40D illustrate that the shuttle seats 274 can have a notch shape configured to receive a shuttle tip 164. The shuttle seat 274 can have a beveled or non-beveled surface 438 configured to push against the terminal distal surface of the shuttle tips 164, for example, against the non-beveled surfaces 406, against beveled surfaces, or both.

The preformed pushers 76 and 86 can be formed with or without slots. For example, the slots can be longitudinally coincidental or longitudinally alternating lateral slots cut into the sides of the pusher, similar to the shape of the shuttle lateral slots 158.

FIGS. 41A-41E illustrate that the non-preformed and preformed pushers 76 and 86 can have one or more slots 440 and/or one or more fenestrations 442. The slots 440 can be similar to the shape of the shuttle lateral slots 158 or they can be different. The slots 440 can extend partially (e.g., a recess) or fully (e.g., a through slot) through the pushers. The fenestrations 442 can extend partially (e.g., a recess) or fully (e.g., a though hole) through the pushers. The slots 440 can have a longitudinal component and/or a transverse component relative to a pusher longitudinal axis 444. The fenestrations 442 can have a constant cross sectional area, a tapered cross-sectional area, or both. The fenestrations 442 can have a regular or irregular shape, for example, curved, polygonal, or both. The fenestrations 442 can be defined by one or more curved surfaces or curved edges, for example, one or more curved surfaces or curved edges of the pusher. The fenestrations 442 can have a cross-sectional shape of a circle, ellipse, rectangle, stadium, horseshoe, star, slot, or any combination thereof. The pushers 76 and 86 can have any combination of features illustrated in FIGS. 41A-41E.

Figure 41A:
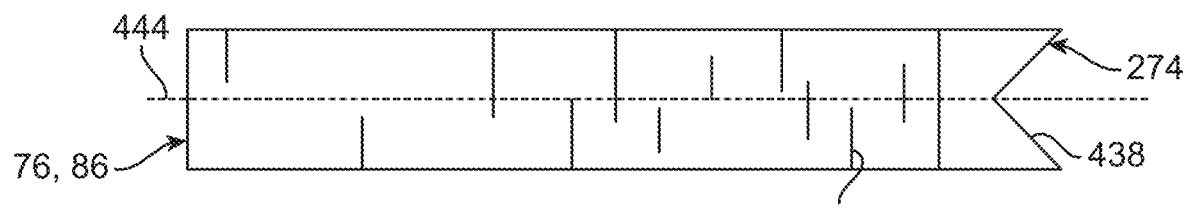
FIG. 41A illustrates a top or bottom view of a variation of a pusher.

FIG. 41A illustrates that the slots 440 can be lateral slots.

Figure 41B:
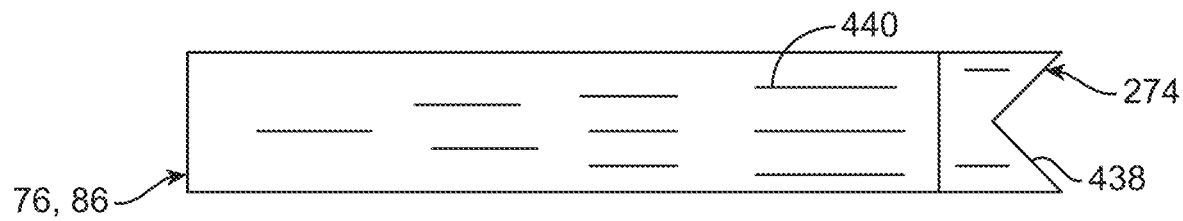
FIG. 41B illustrates a top or bottom view of a variation of a pusher.

FIG. 41B illustrates that the slots 440 can be longitudinal slots.

Figure 41C:
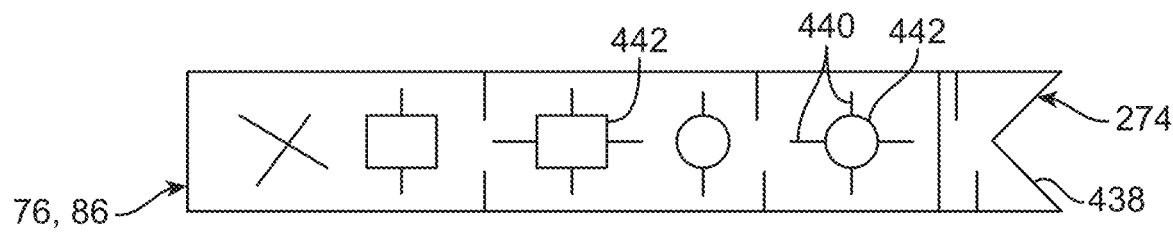
FIG. 41C illustrates a top or bottom view of a variation of a pusher.

FIG. 41C illustrates that the slots 440 can be lateral slots, longitudinal slots, and/or extend in a longitudinal and transverse direction relative to the pusher longitudinal axis 444. FIG. 41C further illustrates that the pushers can have curved and polygonal fenestrations 442 (e.g., circular and/or rectangular fenestrations 442).

Figure 41D:
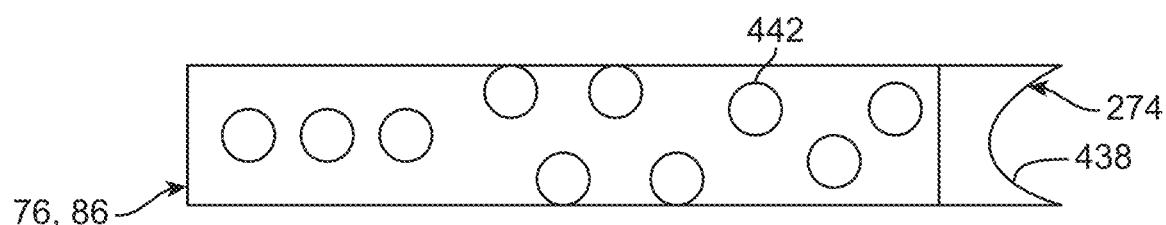
FIG. 41D illustrates a top or bottom view of a variation of a pusher.
Figure 41E:
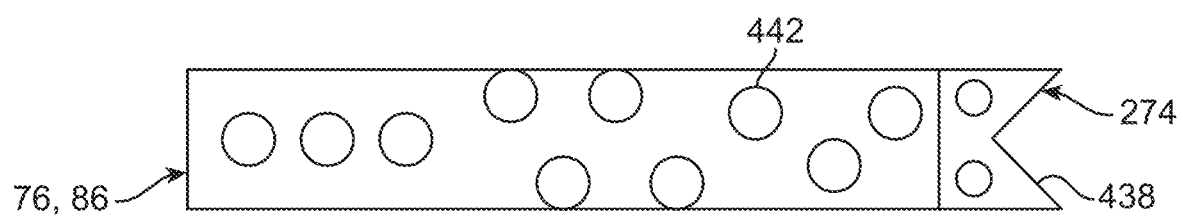
FIG. 41E illustrates a top or bottom view of a variation of a pusher.

FIG. 41D illustrates that the fenestrations 442 can be in the longitudinal center of the pushers, on the edge of the pushers, in between the center and edge of the pushers, or any combination thereof. FIG. 41D further illustrates that the shuttle seat 274 can have a curved surface or edge.

FIGS. 41A, 41B, 41E and 41F illustrate that the distal tip of the pushers 76 and 86 can have slots 440 and/or fenestrations 442.

Figure 41F:
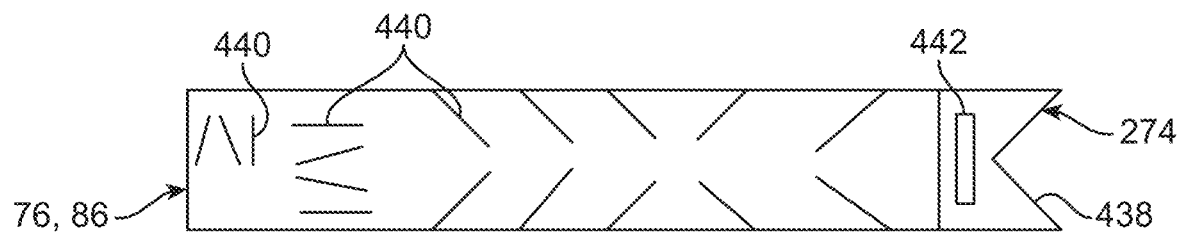
FIG. 41F illustrates a top or bottom view of a variation of a pusher.

FIG. 41F illustrates various oriented slots 440 and a fenestration 442 through the distal tip of the pushers 76 and 86.

Figure 42A:
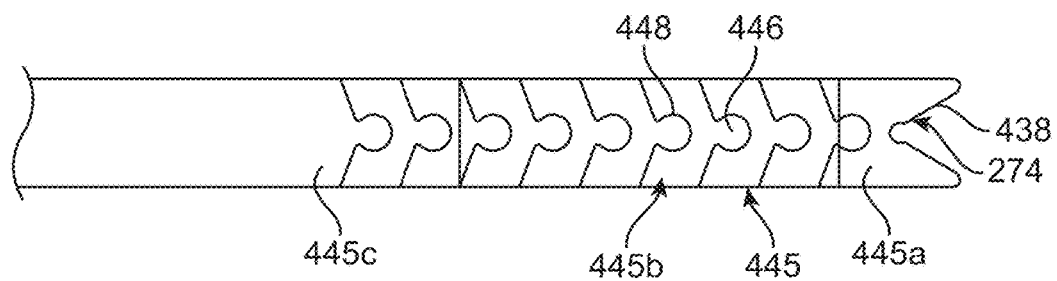
FIG. 42A illustrates a variation of a pusher.

FIGS. 42A-42D illustrate that the pushers 76 and 86 can include multiple links 445 connected together, for example, 2 to 50 or more links 445, including every 1 link increment within this range (e.g., 10 links). The links 445 can include a distal terminal link 445*a*, multiple intermediate links 445*b* and a proximal terminal link 445*c*. The links 445 can have a male connector 446 (e.g., a ball) and/or a female connector 448 (e.g., a socket). For example, FIG. 42A illustrates that the distal terminal link 445*a* can have a male or female connector 446, 448 (e.g., a female connector 448), that the intermediate links can have one or multiple (e.g., two) male connectors 446 and one or multiple (e.g., two) female connectors 448, and that the proximal terminal link 445*c* can have a male or female connector 446, 448 (e.g., a male connector 446). The links 445 can allow the pushers 76 and 86 to be bendable. For example, the links 445 can allow the pushers 76 and 86 to assume the curves shown in FIGS. 39B-39C. As another example, the links 445 can be the same or different from the articulated segmentations 286.

Figure 42B:
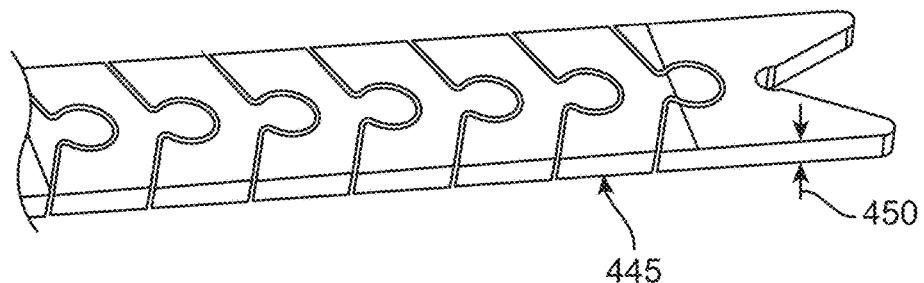
FIG. 42B illustrates a variation of a pusher.

FIG. 42B illustrates that the links 445 can have a link thickness 450 of about 0.05 mm to about 0.75 mm, including every 0.05 mm increment within this range (e.g., 0.15 mm, 0.20 mm, 0.25 mm). The link thickness 450 can be the same or different from the shuttle tip thickness 408 and/or the shuttle thickness 410. The link thickness 450 can be less than, equal to, or greater than the shuttle tip thickness 408 and/or can be less than, equal to, or greater than the shuttle thickness 410. For example, the link thickness 450 can be about 0.30 mm and the shuttle tip thickness 408 and/or the shuttle thickness 410 can be about 0.15 mm, or vice versa.

Figure 42C:
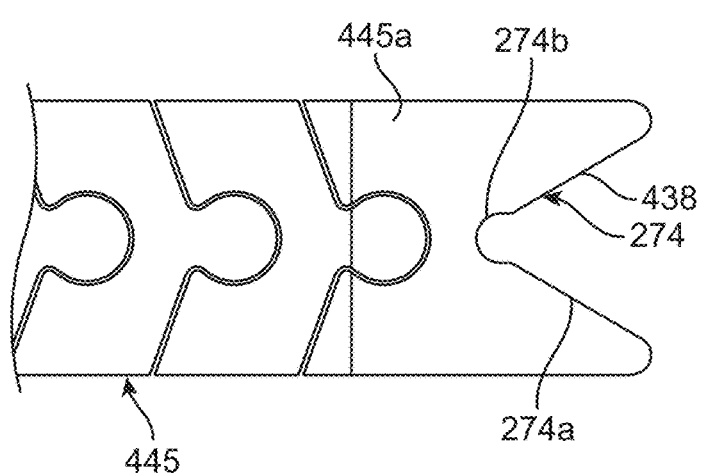
FIG. 42C illustrates a variation of a pusher.

FIG. 42C illustrates that the distal terminal link 445*a* can have a shuttle seat 274 with the shape shown. The shuttle seat can have a first seat 274*a* and a second seat 274*b*. The second seat can further prevent unwanted movement between the shuttle 14 and the pushers 76 and 86. The second seat 274*b* can provide space around distal end of the shuttle tips 154 to help prevent or inhibit the pushers and shuttles from getting stuck together, for example, due to suction created by the compression between the two components and the wet tissue environment.

Figure 42D:
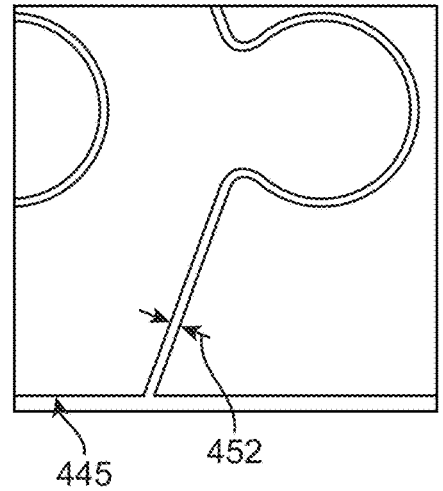
FIG. 42D illustrates a variation of a pusher component.

FIG. 42D illustrates that the links can be cut (e.g., laser cut) with a cut width 452 of about 0.01 mm to about 0.10 mm, including every 0.01 mm increment within this range (e.g., 0.02 mm). As another example, the links 445 can be separately cut and then permanently or removably attached together, for example, with a snap fit, friction fit, magnetic fit, or any combination thereof.

The shuttle 14, the first pusher 76 (also referred to as the lower jaw pusher), the second pusher 86 (also referred to as the upper jaw pusher) can be made from a flexible polymer, such as PEEK, a resilient metal such as Nitinol, any material disclosed herein or combinations thereof. The shuttle and pushers 14, 76, 86 can be coated with a strain reducing coating.

Figure 43A:
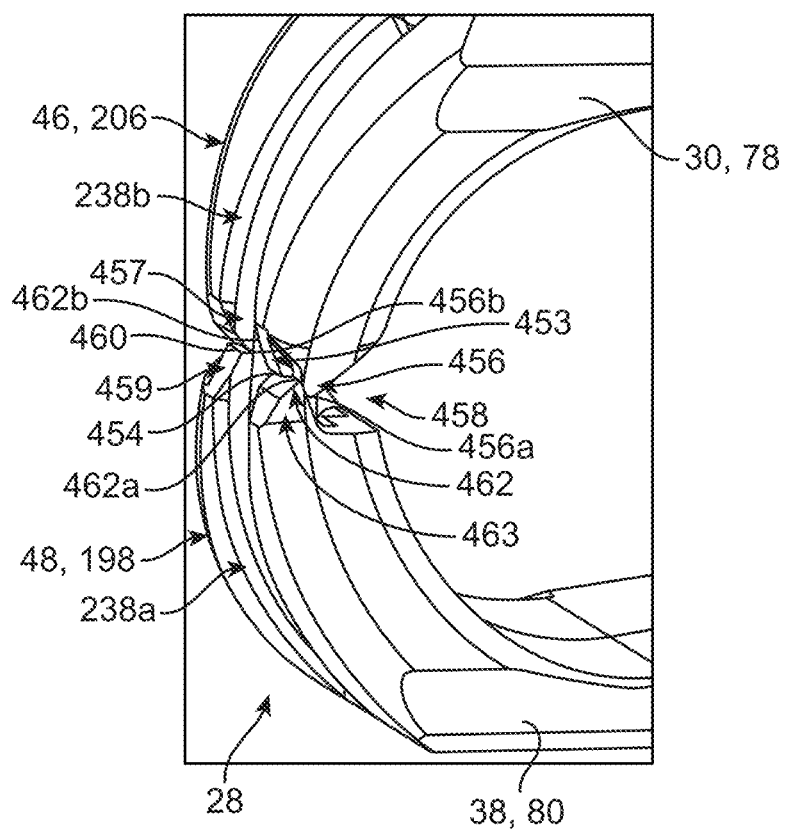
FIG. 43A illustrates a variation of the upper and lower jaws.

FIG. 43A illustrates that the first jaw tip (e.g., jaw tip 46, jaw tip 206) can interdigitate with the second jaw tip (e.g., jaw tip 48, jaw tip 198). For example, the first jaw tip can interdigitate with and be adjacent or in contact with the second jaw tip when the jaw structure 28 is in a closed configuration. The jaw tips can be sharpened. The jaw tips can be tapered. The jaw tips can be sharp and seat into each other to form a continuous track when the jaw structure 28 is in a closed configuration. The jaw tips can seat into each other to connect the lower and upper jaw tracks 66, 64 to each other.

The interdigitatable jaws can align the shuttle tracks 66 and 64, for example, to form a single continuous track. As another example, the interdigitatable jaws can align the shuttle tracks 66 and 64 such that a space is between the shuttle tracks 66 and 64. The interdigitatable jaws can inhibit or prevent the first and second jaws from moving relative to one another when the jaw structure 28 is in a closed configuration, for example, as shown in FIG. 43A. The movement that can be inhibited or prevented can include any transverse movement away from the longitudinal axis (e.g., a center longitudinal axis) of the opposing jaw. The interdigitatable jaws can pre-pierce tissue. In this way the jaws can act as a track aligner and tissue cutter.

The first jaw tip (e.g., jaw tip 46, jaw tip 206) can have a first jaw motion control 453 having a first jaw seat 454 configured to abut the second jaw when the jaw structure 28 is in a closed configuration, tissue cutting surfaces 456 and a tissue relief pocket 458. For example, the first jaw can have first and second cutting surfaces 456*a* and 456*b*. The second jaw tip (e.g., jaw tip 48, jaw tip 198) can have a second jaw motion control 459 having a second jaw seat 460 configured to abut the first jaw when the jaw structure 28 is in a closed configuration, tissue cutting surfaces 462 and a tissue relief pocket 464 (not shown). For example, the second jaw can have first and second cutting surfaces 462a and 462b.

When the jaws moved from an open configuration to a closed configuration, the first and second jaw first cutting surfaces 456a, 462a can slide past one another and cut tissue. When the jaws are closed, the first and second jaw second cutting surfaces 456b, 462b can slide past one another and cut tissue. When the jaws are in a closed configuration, a jaw tooth 463 of the second jaw defining the second jaw first cutting surface 462a can abut the first jaw seat 454. When the jaws are in a closed configuration, a jaw tooth 457 of the first jaw defining the first jaw second cutting surface 456b can abut the first jaw seat 454. As tissue is cut by the cutting surfaces the tissue relief pockets 458 and 464 can provide space for cut tissue to move into. The pockets 458 and 464 can decrease the hole that the jaws create in the tissue (e.g., tissue 74). The tissue relief pockets 458 and 464 allow the jaws to compress less tissue when the jaws are moved from an open configuration to a closed configuration.

Figure 43B:
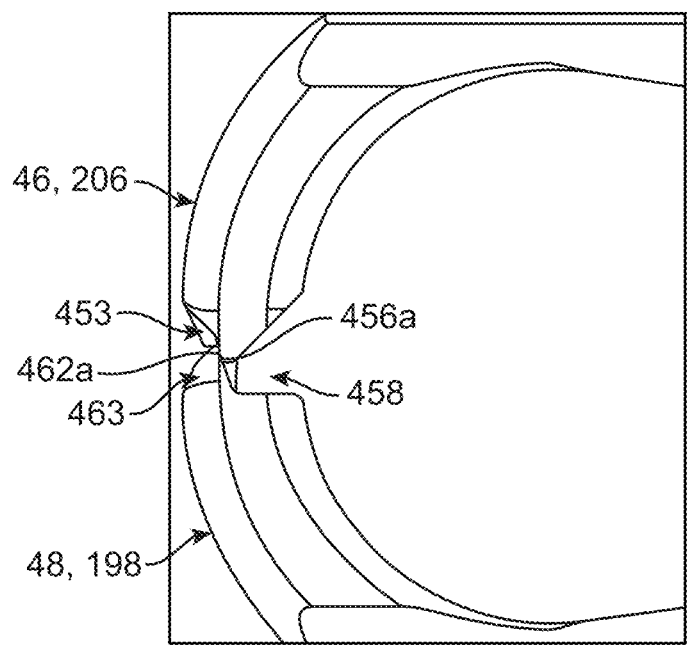
FIG. 43B illustrates a variation of the upper and lower jaws.

FIG. 43B illustrates the jaw tooth 463 of the second jaw seated against the motion control 453 of the first jaw. FIG. 43B further illustrates that the first and second jaw first cutting surfaces 456a, 462a can contact one another when the jaws are in a closed configuration.

Figure 43C:
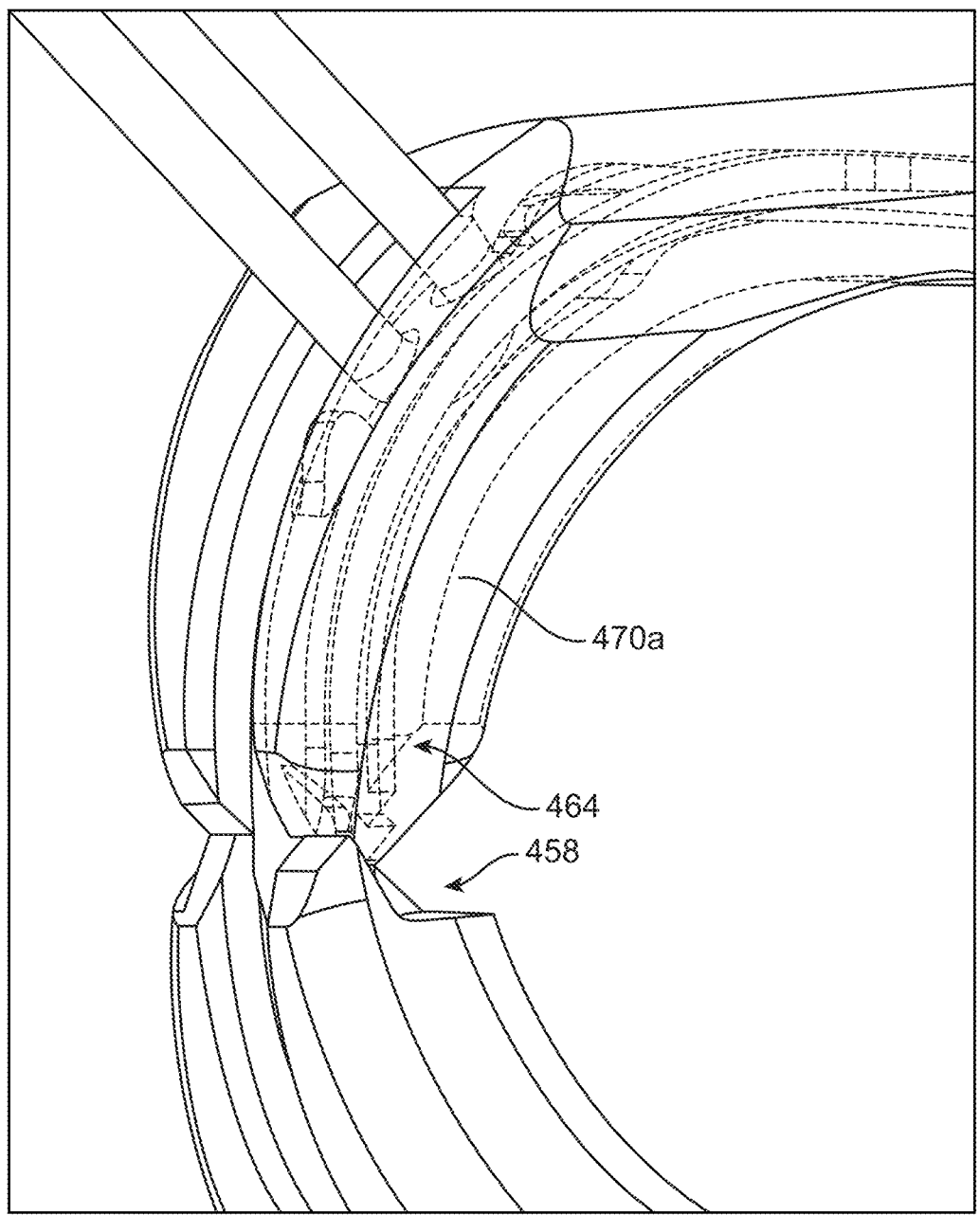
FIG. 43C illustrates a variation of the upper and lower jaws.

FIG. 43C illustrates the tissue relief pocket 464 which can be seen through the lateral half 470a of the first jaw shown as transparent. The other lateral half 470b of the first jaw is not transparent and defines the tissue relief pocket 464.

Figure 43D:
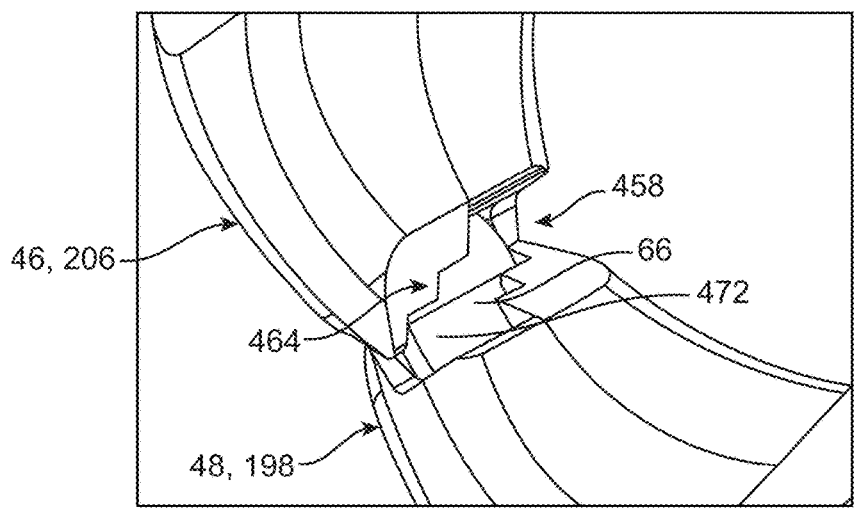
FIG. 43D illustrates a variation of the upper and lower jaws.

FIG. 43D illustrates a variation of the tissue relief pockets 458 and 464. FIG. 43D further illustrates an opening 472 to the second jaw track 66.

Figure 43E:
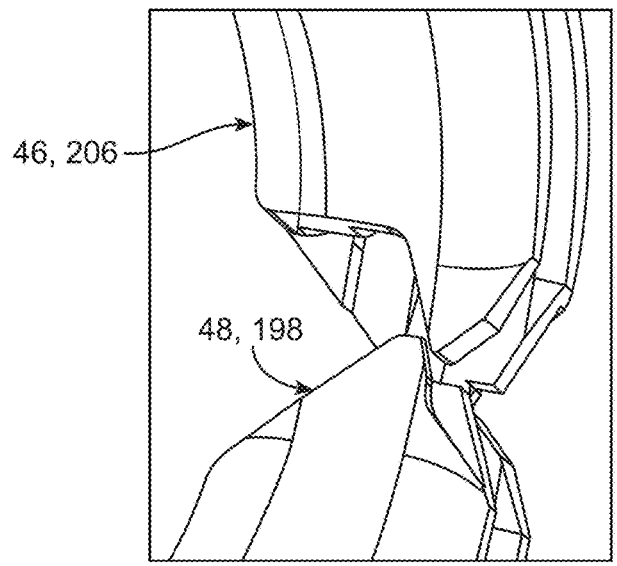
FIG. 43E illustrates a variation of the upper and lower jaws.
Figure 43F:
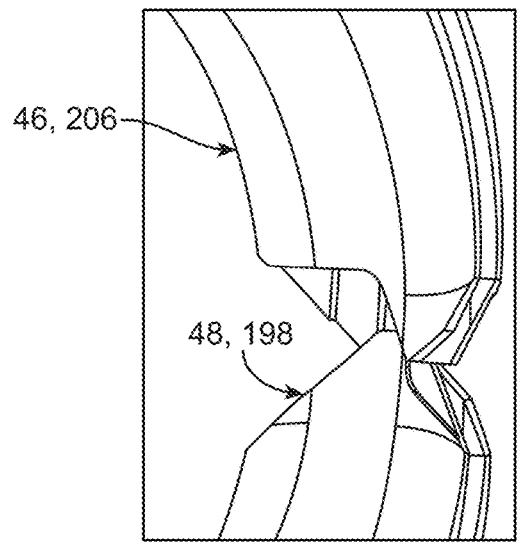
FIG. 43F illustrates a variation of the upper and lower jaws.

FIGS. 43E and 43F illustrate the first and second jaws moving from partially closed configuration to a fully closed configuration.

FIGS. 43G-43I illustrate the first and second jaws sequentially moving from partially closed configuration to a fully closed configuration with a shuttle in the lower jaw such that the jaw teeth and the shuttle exposed portion 423 pierce the tissue when the jaws are moved from the configuration illustrated in FIG. 43G to the configuration illustrated in FIG. 43I. The shuttle 14 can be any of the shuttles described and/or illustrated herein.

FIG. 43J illustrates a variation of the jaw structure 28 with the shuttle seated in the lower jaw tip.

FIG. 43K illustrates the shuttle 14 in mid-movement between the first and second jaws as the shuttle is translating in the continuous track (e.g., defined by tracks 66 and 64) from the lower jaw to the upper jaw, or vice versa.

Figure 43L:
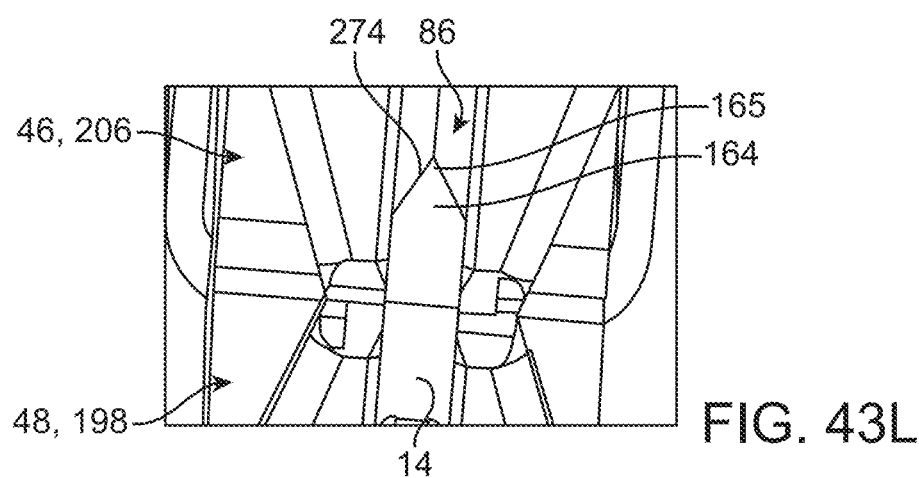
FIG. 43L illustrates a variation of the upper and lower jaws.

FIG. 43L illustrates the shuttle 14 seated in the lower jaw with the shuttle tip 164 in contact with the shuttle seat 274 of the upper jaw pusher 86. This can be the maximum extent that the upper jaw pusher 86 can extend such that it remains within the upper jaw track at full extension, or it can continue to push the shuttle 14 such that the upper jaw pusher 86 extends out of the upper jaw track at full extension. At full extension, the upper jaw pusher 86 can extend into the lower jaw track. For example, the shuttle seat 274 of the upper jaw can extend out of the upper jaw and into the lower jaw track (e.g., track 66).

Figure 43M:
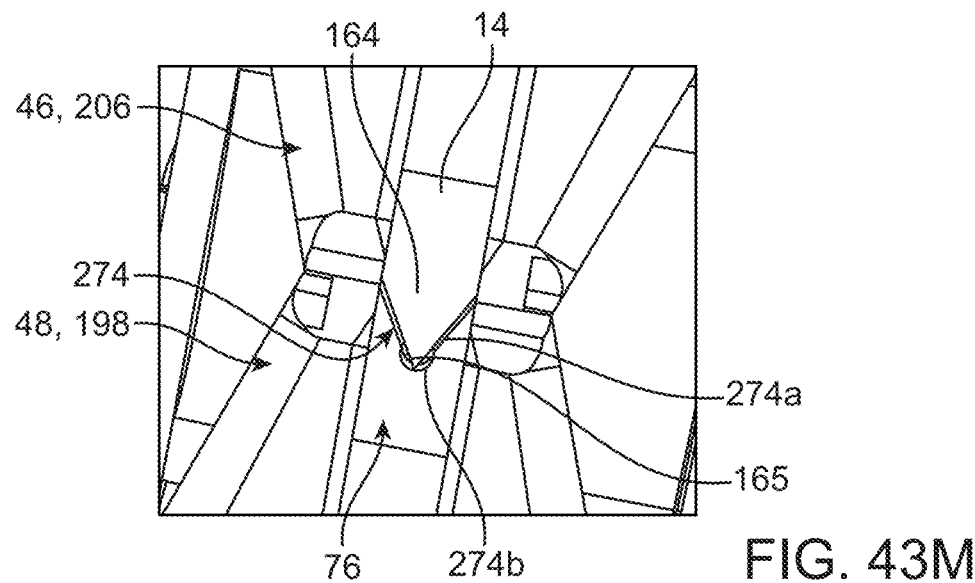
FIG. 43M illustrates a variation of the upper and lower jaws.

FIG. 43M illustrates the shuttle 14 seated in the upper jaw with the shuttle tip 164 in contact with the shuttle seat 274 of the lower jaw pusher 76. This can be the maximum extent that the lower jaw pusher 76 can extend such that it remains within the lower jaw track at full extension, or it can continue to push the shuttle 14 such that the lower jaw pusher 76 extends out of the lower jaw track at full extension. At full extension, the lower jaw pusher 76 can extend into the upper jaw track. For example, the shuttle seat 274 of the lower jaw can extend out of the lower jaw and into the upper jaw track (e.g., track 64).

FIGS. 43L and 43M further illustrate that the planes of the of the shuttle and pushers 14, 76, 86 can be flush or substantially flush with one another and/or can be parallel or substantially parallel with one another when the shuttle 14 is in contact with the pushers 76 and 86.

Figure 43N:
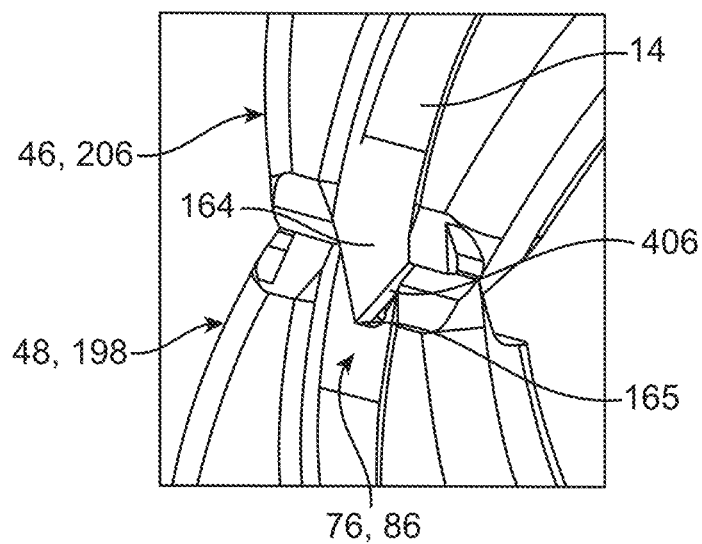
FIG. 43N illustrates a variation of the upper and lower jaws.

FIG. 43N illustrates that shuttle 14 and the pushers 76 and 86 can contact each other out of plane with one another such that the shuttle and pushers 14, 76, 86 are at an angle with one another when the shuttle 14 is in contact with the pushers 76 and 86.

Figure 44A:
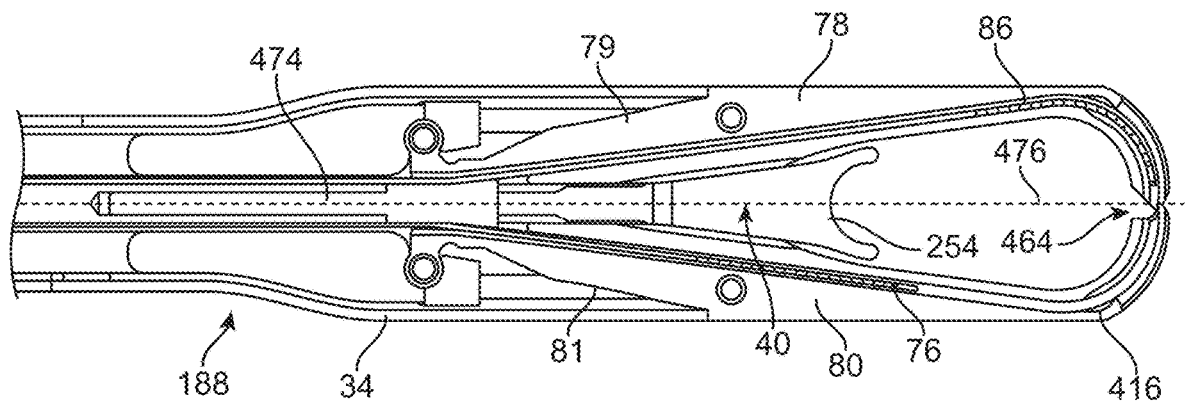
FIG. 44A illustrates a side view of a variation of the device with half the device shown transparent.
Figure 44B:
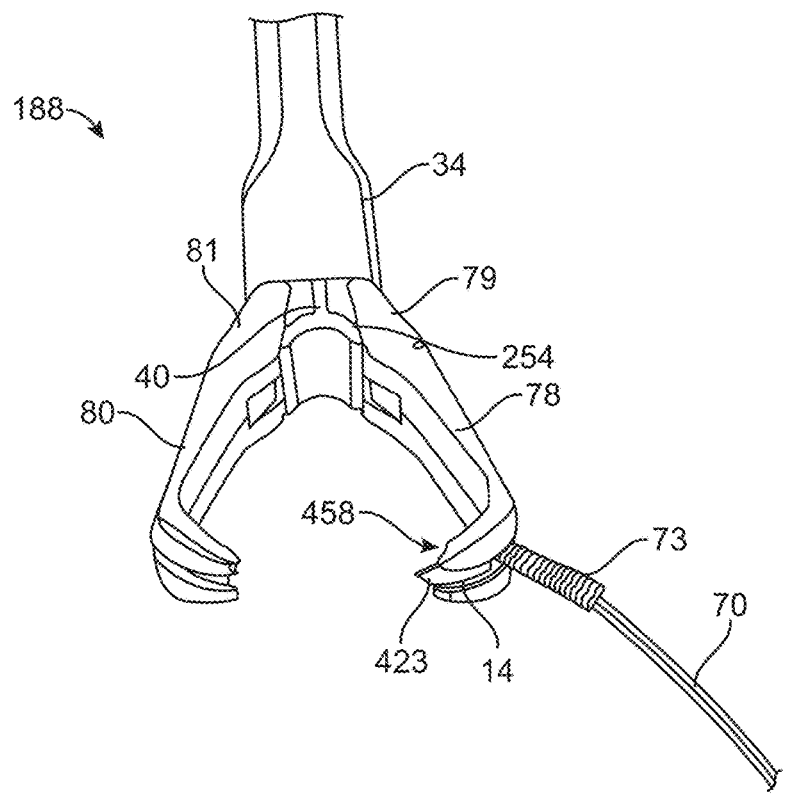
FIG. 44B illustrates a perspective view of the device of FIG. 44A.

FIGS. 44A and 44B illustrate a variation of the device 188 in a fully closed and fully open configuration, respectively.

FIGS. 44A and 44B illustrate that the jaw control extension 40 can be fixed and that the jaws 78 and 80 can move relative to the jaw control extension 40. For example, the jaws 78 and 80 can move distally and proximally against the jaw control extension 40 to open and close, respectively. The jaws 78 and 80 can move longitudinally along a device longitudinal axis 476. The jaws 78 and 80 can move into and out of the compression cover 34. The jaws 78 and 80 can be attached to a tube 474 connected to the handle controls that can translate (e.g., slidably translate) the jaws 78 and 80 into and out of the compression cover 34. FIGS. 44A and 44B illustrate that the compression cover 34 can engage with an upper jaw surface 79 and a lower jaw surface 81 to force the jaws closed when the jaws 78 and 80 are translated proximally toward the handle and into the compression cover 34. Movement of the jaws 78 and 80 in a first direction (e.g., distal movement) against the jaw control extension 40 can cause the jaws to open and move from the closed configuration shown in FIG. 44A to the open configuration shown in FIG. 44B. Movement of the jaws 78 and 80 in a second direction (e.g., proximal movement) against the compression cover 34 can cause the jaws to close and move from the open configuration shown in FIG. 44B to the closed configuration shown in FIG. 44A. The first and second directions can be opposite from one another. As another example, the jaws can be fixed and the jaw control extension can move relative to the jaws. The compression cover 34 can be longitudinally fixed or longitudinally movable.

The extension head 254 can have the shape shown such that the jaws open relative to each other when the jaws are moved out of the compression cover 34 over the extension head 254.

FIG. 44A illustrates the device 188 without a shuttle 14 for illustrative purposes and FIG. 44B illustrates the device 188 of FIG. 44A with a shuttle 14.

Figure 45A:
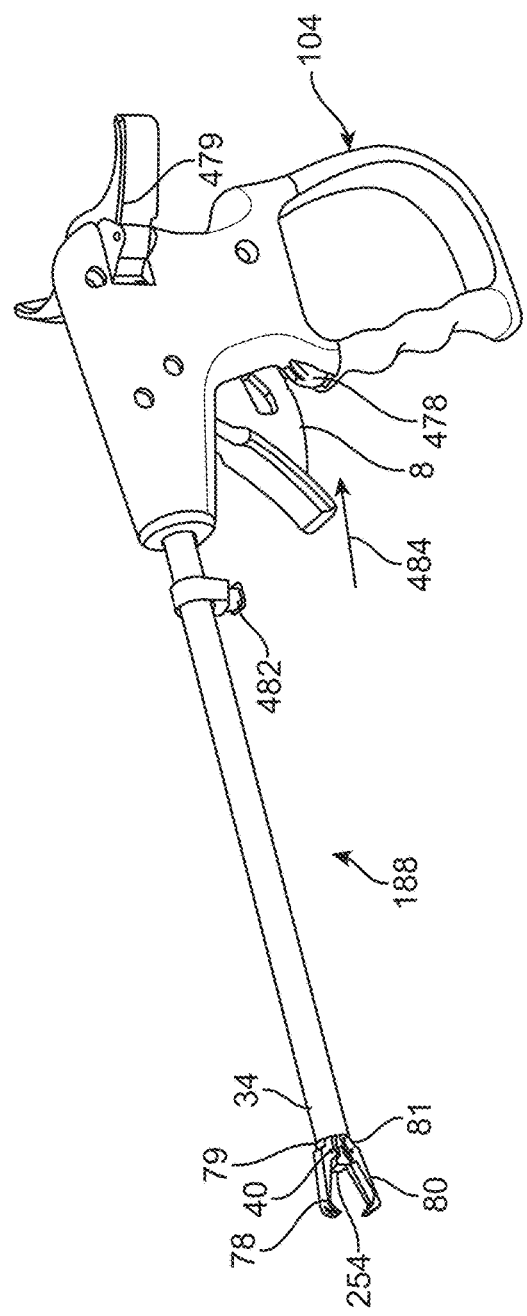
FIG. 45A illustrates a variation of the device.
Figure 45B:
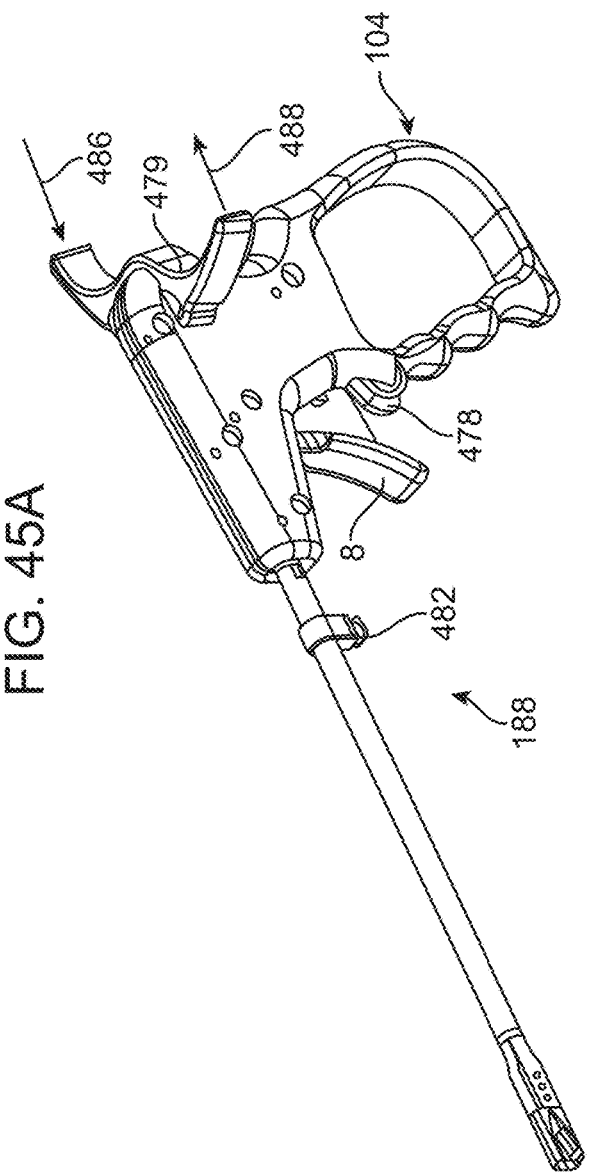
FIG. 45B illustrates a variation of the device.

FIGS. 45A and 45B illustrate a variation of the device 188 in a fully opened and fully closed configuration, respectively.

FIGS. 45A and 45B illustrate that the handle 104 can have a jaw control 8 (also referred to as a trigger), a jaw control release 478 and a shuttle control 479. The jaw control 8 can be pulled with one or more fingers in direction 484 to move the jaw control 8 to the configuration shown in FIG. 45B. The jaw control 8 can translate and/or rotate. When the jaw control 8 is moved in direction 484, the jaws 78 and 80 can move from an open configuration to a less open configuration (e.g., to the closed configuration shown in FIG. 45B). When the jaw control 8 is moved in a direction opposite to direction 484, the jaws 78 and 80 can move from a closed configuration to an open configuration (e.g., from the closed configuration in FIG. 45B to the fully open configuration illustrated in FIG. 45A).

As another example, the handle 104 can have a first press button configured to close the jaws when pressed and a second press button configured to open the jaws when pressed.

The jaw control release 478 can be a press button, a switch, a knob, or any combination thereof. The jaw control 8 can lock when the jaws 78 and 80 are in the fully closed configuration. Activating the jaw control release 478 can release the jaw control 8 from the lock position. The jaw control release 478 can be activated, for example, by pressing it. Upon pressing the jaw control release 478, the jaw control 8 can be manually returned to the position shown in FIG. 45A to fully open the jaws, or the jaw control 8 can automatically return to the position shown in FIG. 45A.

The shuttle control 479 can be a button, switch, knob, or any combination thereof. For example, FIGS. 45A and 45B illustrate that the shuttle control 479 can be a switch that can pivot. The shuttle control 479 can be locked when the jaws 78 and 80 are in the open configuration of FIG. 45A. When the jaws are closed, the shuttle control can be rotated in direction 486 and direction 488. Directions 486 and 488 can be directed opposite from one another. When the shuttle control 479 is moved in (e.g., rotated) in direction 486, the upper pusher 86 can move the shuttle 14 to the lower jaw 80. When the shuttle control 479 is moved in (e.g., rotated) in direction 488, the lower pusher 76 can move the shuttle 14 to the upper jaw 78. The shuttle control 479 can have a batwing shape, which can provide ergonomic benefits.

As another example, the handle 104 can have a first press button configured to move the upper pusher 86 when pressed and a second press button configured to move the lower pusher 76 when pressed.

FIGS. 45A and 45B further illustrate that the device 188 can have a flush port 482 having a luer connection. A cleaning fluid (e.g., enzyme cleaner) can be flushed through the device through the flush port 482 to clean it.

Figures 45C, 45D, 45E:
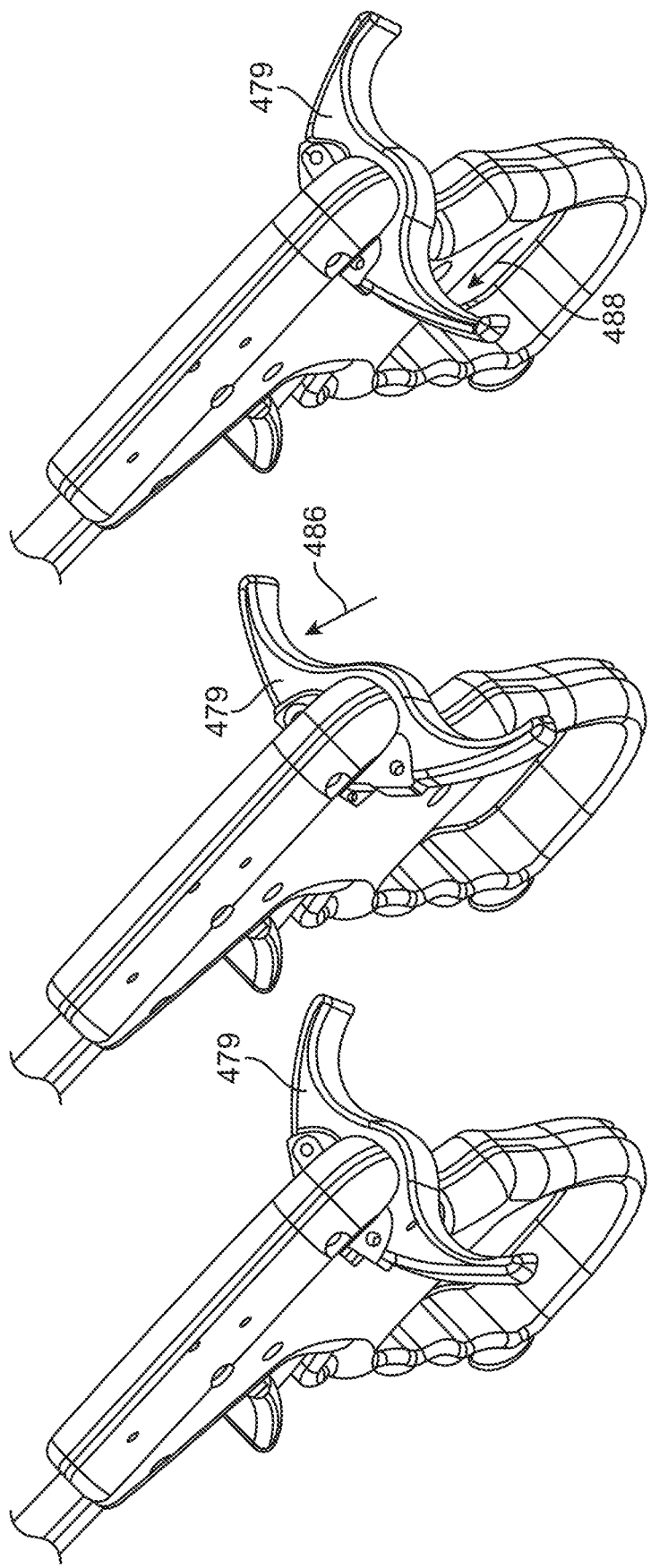
FIG. 45C illustrates a variation of a handle of the device.
FIG. 45D illustrates a variation of a handle of the device.
FIG. 45E illustrates a variation of a handle of the device.

FIG. 45C illustrates that the shuttle control 479 can have a neutral position. When the shuttle control 479 is in the neutral position, one or neither of the pushers 76 and 86 can be in contact with the shuttle 14. When the shuttle control 479 is in the neutral position, the shuttle 14 can be ejected from the jaws.

FIG. 45D illustrates the shuttle control 479 in a fully advanced position when moved in direction 486. When in the shuttle control 479 is in the fully advanced position in direction 486, the upper pusher 86 can be in a fully advanced position and the lower pusher 76 can be in a fully retracted position. For example, the upper pusher 86 can be fully advanced toward the lower jaw 80, thereby pushing the shuttle 14 into the lower jaw 80. The upper pusher 86 can push the shuttle 14 into the lower jaw 80 to the point where detents on the shuttle 14 (male and/or female stops 412, 416) releasably engage with detents on the lower jaw 80 (male and/or female stops 412, 416).

FIG. 45E illustrates the shuttle control 479 in a fully advanced position when moved in direction 488. When in the shuttle control 479 is in the fully advanced position in direction 488, the lower pusher 76 can be in a fully advanced position and the upper pusher 86 can be in a fully retracted position. For example, the lower pusher 76 can be fully advanced toward the upper jaw 78, thereby pushing the shuttle 14 into the upper jaw 78. The lower pusher 76 can push the shuttle 14 into the upper jaw 78 to the point where detents on the shuttle 14 (male and/or female stops 412, 416) releasably engage with detents on the upper jaw 78 (male and/or female stops 412, 416).

FIG. 45F illustrates that the shuttle control 479 can be coupled to an upper pusher slider 492 via linkage 491. The upper pusher slider 492 can be coupled to the upper pusher 86. FIG. 45F further illustrates that the shuttle control 479 can be coupled to a lower pusher slider 490 via linkage 489. The lower pusher slider 490 can be coupled to the lower pusher 76. The upper pusher slider 492 can be moved toward the jaws when the shuttle control 479 is moved in direction 486, and can thereby push the upper pusher distal end toward and/or into the lower jaw 80. The lower pusher slider 490 can be moved toward the jaws when the shuttle control 479 is moved in direction 488, and can thereby push the lower pusher distal end toward and/or into the upper jaw 78.

FIGS. 45G and 45H illustrate the position of the linkage 491 when the shuttle control 479 is in the positions shown in FIGS. 45D and 45E, respectively.

Figure 45J:
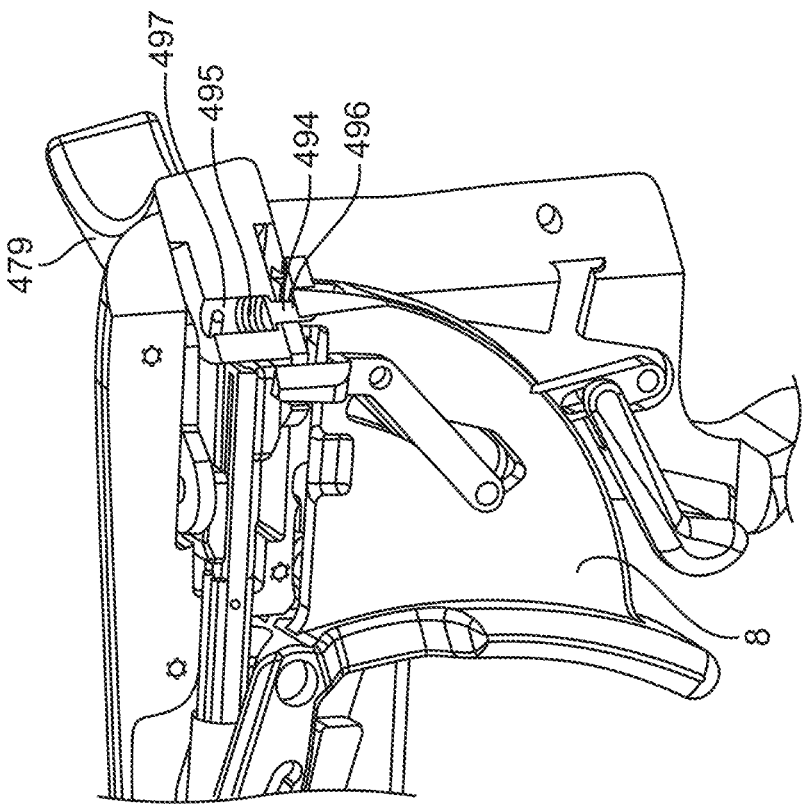
FIG. 45J illustrates a variation of a handle of the device.
Figure 45I:
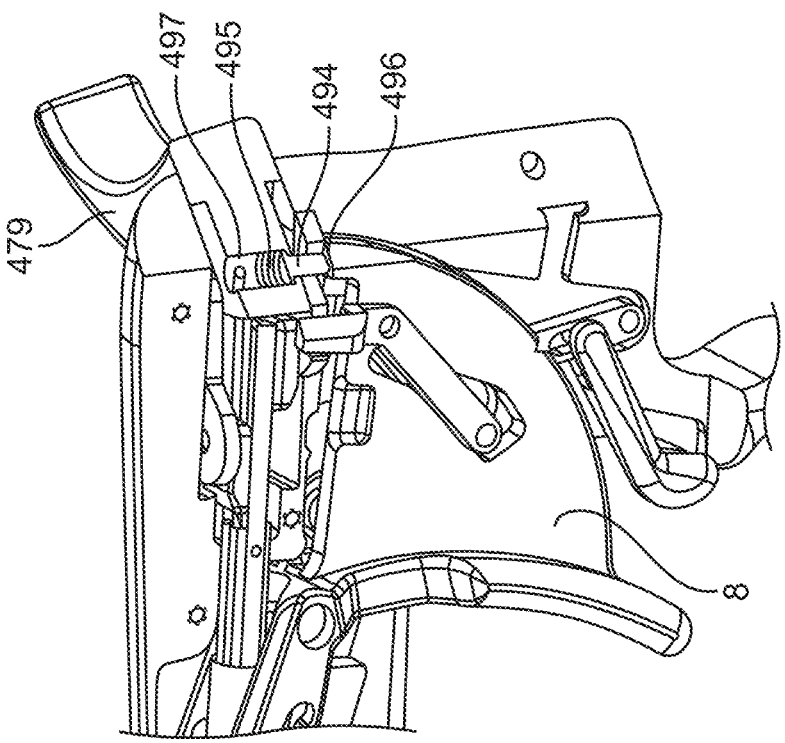
FIG. 45I illustrates a variation of a handle of the device.

FIGS. 45I and 45J illustrate a variation of a shuttle control locking pin 494. The locking pin 494 can lock the shuttle control 494 in place with the shuttle 14 in the upper or lower jaw when the jaws (e.g., jaws 78 and 80) are in the open configuration, for example, as shown in FIG. 45A. The jaw control 8 can have a locking pin controller 496 configured to rotate and/or translate to engage the locking pin 494 and push the locking pin 494 into a locking pin channel 497 to unlock the shuttle control 479 when the jaw control 8 is pulled and the jaws are in a fully closed configuration. The locking pin 494 can be biased into a locked position with a biasing element 495 such as a spring.

Figure 45K:
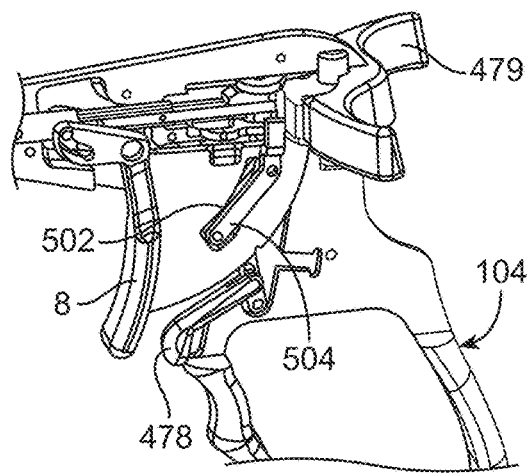
FIG. 45K illustrates a variation of a handle of the device.
Figure 45L:
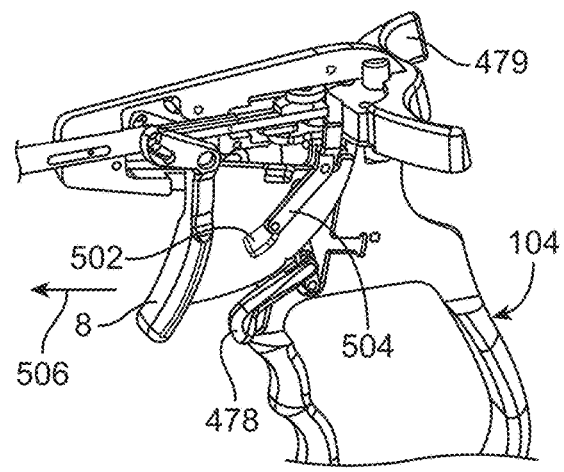
FIG. 45L illustrates a variation of a handle of the device.

FIGS. 45K and 45L illustrate that the device 188 can have an overstroke correction cam path 502 and an overstroke correction cam 504. When the jaw control release 478 is activated, the jaw control 8 can move in direction 506, which can cause the pusher slider in the fully advanced position to retract the fully advanced pusher by about 0.2 mm to about 1.0 mm to compensate and correct for overstroke caused by the tensile and compressive forces in the various structures between the handle 104 and the distal end of the device 188.

Figure 45M:
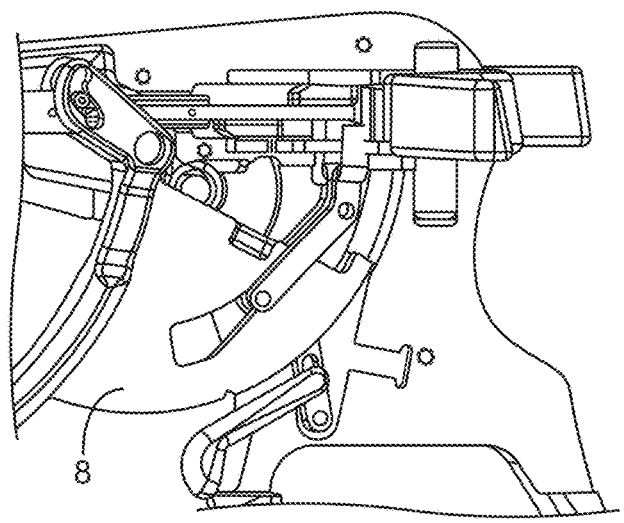
FIG. 45M illustrates a variation of a handle of the device.

FIG. 45M illustrates the jaw control 8 when the jaws are in a fully open configuration.

FIGS. 46A-46K illustrate an exploded variation of some of the components of the device 188.

Figure 46A:
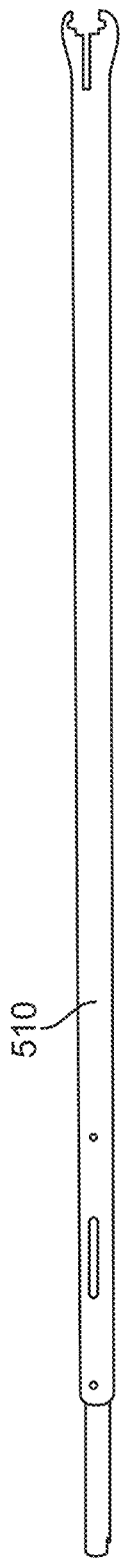
FIG. 46A illustrates a variation of a tube of the device.

FIG. 46A illustrates a variation of a tube 510 of the device 188.

Figure 46B:
FIG. 46B illustrates a variation of an upper pusher.

FIG. 46B illustrates a variation of an upper pusher 86.

Figure 46C:
FIG. 46C illustrates a variation of a lower pusher.

FIG. 46C illustrates a variation of a lower pusher 76.

Figure 46D:
FIG. 46D illustrates a variation of a tube of the device.

FIG. 46D illustrates a variation of a tube 512 of the device 188. The tube 512 can fit over the tube 510.

Figure 46E:
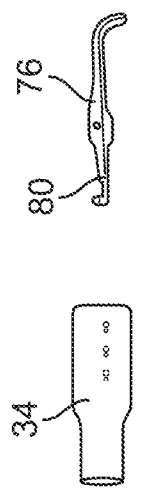
FIG. 46E illustrates a variation of a compression cover.

FIG. 46E illustrates a variation of a compression cover 34.

Figure 46F:
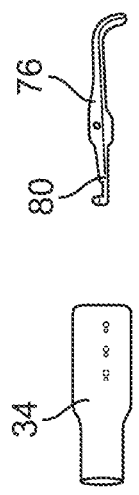
FIG. 46F illustrates a variation of a first side of the lower jaw.
Figure 46K:
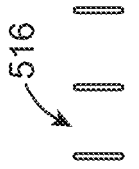
FIG. 46K illustrates pins for the connector of FIG. 46J.
Figure 46G:
FIG. 46G illustrates a variation of a second side of the lower jaw.

FIGS. 46F and 46G illustrate a variation of first and second sides of the lower jaw 80.

Figure 46H:
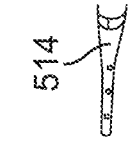
FIG. 46H illustrates a variation of a first side of the upper jaw.
Figure 46I:
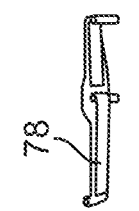
FIG. 46I illustrates a variation of a second side of the upper jaw.

FIGS. 46H and 46I illustrate a variation of first and second sides of the upper jaw 78.

Figure 46J:
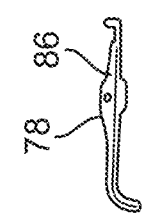
FIG. 46J illustrates a variation of a connector.

FIG. 46J illustrates a connector 514.

FIG. 46K illustrates pins 516 for the connector 514.

Throughout this application, the upper jaw and the lower jaw can also be referred to as the first jaw and the second jaw, respectively. Throughout this application, the upper jaw and the lower jaw can also be referred to as the second jaw and the first jaw, respectively.

Figure 47A:
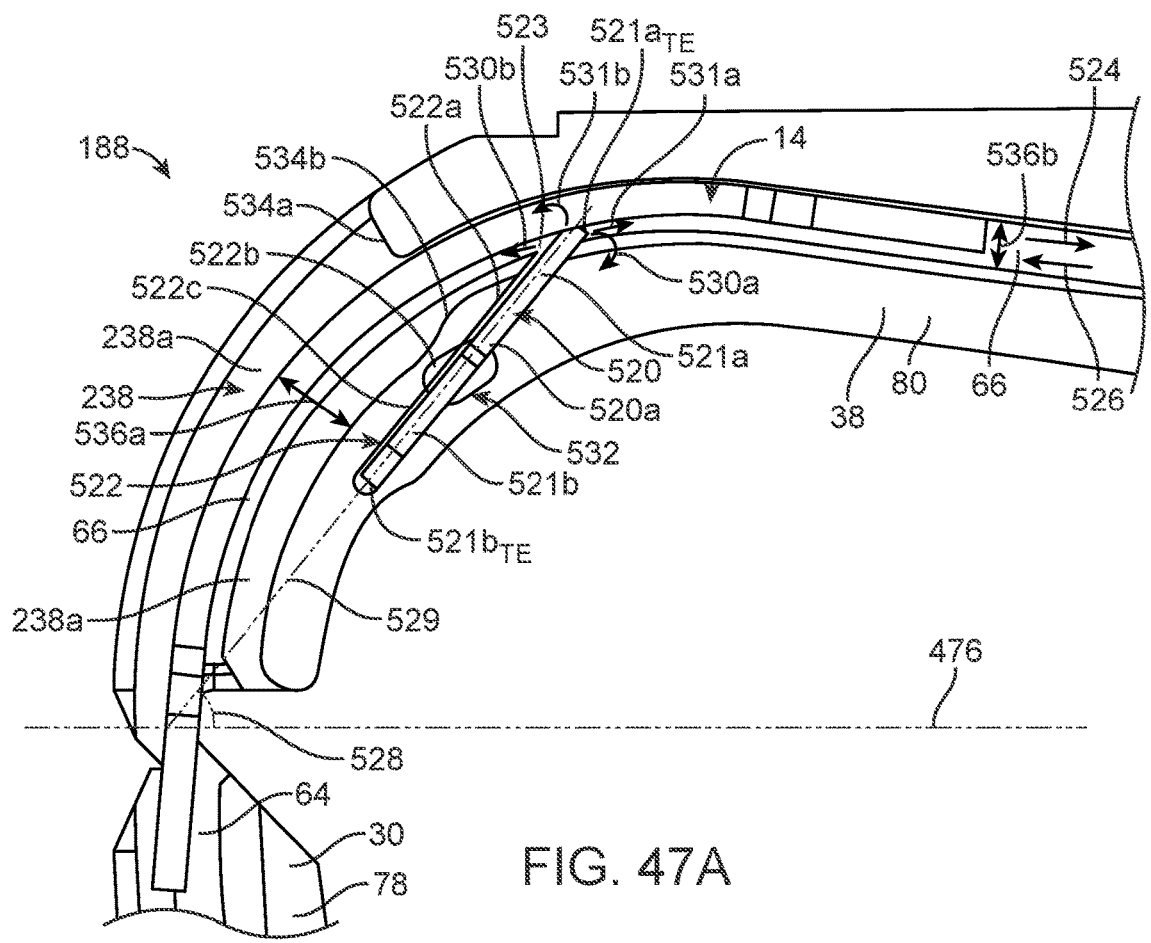
FIG. 47A illustrates a variation of the lower jaw and various components in the lower jaw with half of the lower jaw shown transparent.
Figure 47B:
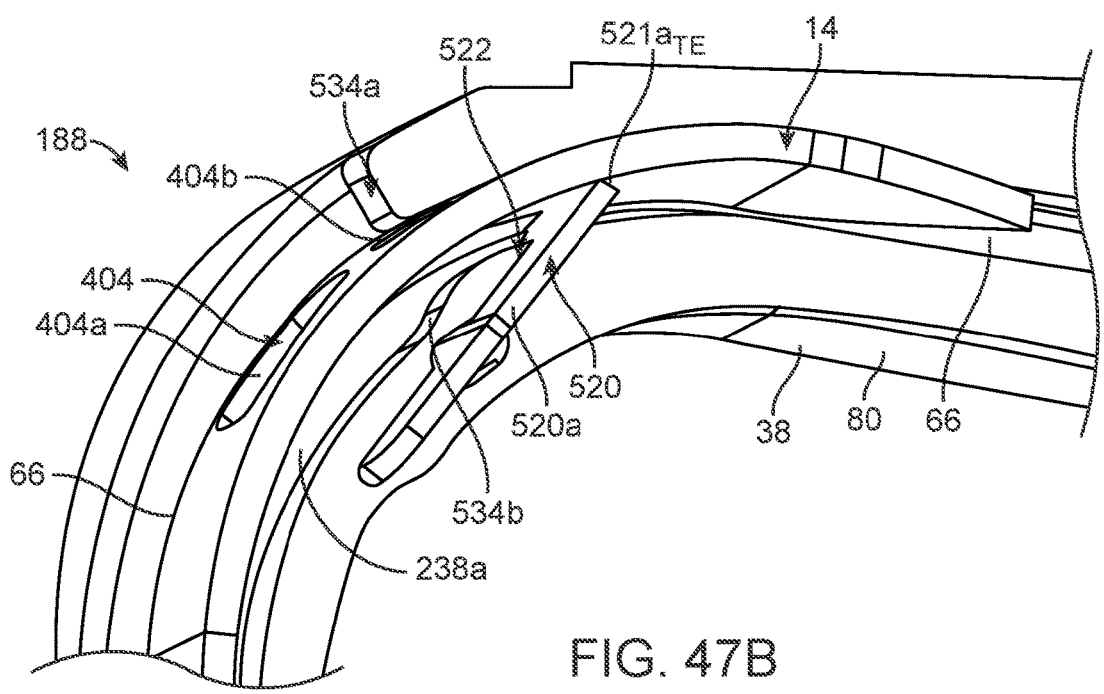
FIG. 47B illustrates a variation of the lower jaw and various components in the lower jaw with half of the lower jaw shown transparent.
Figure 47C:
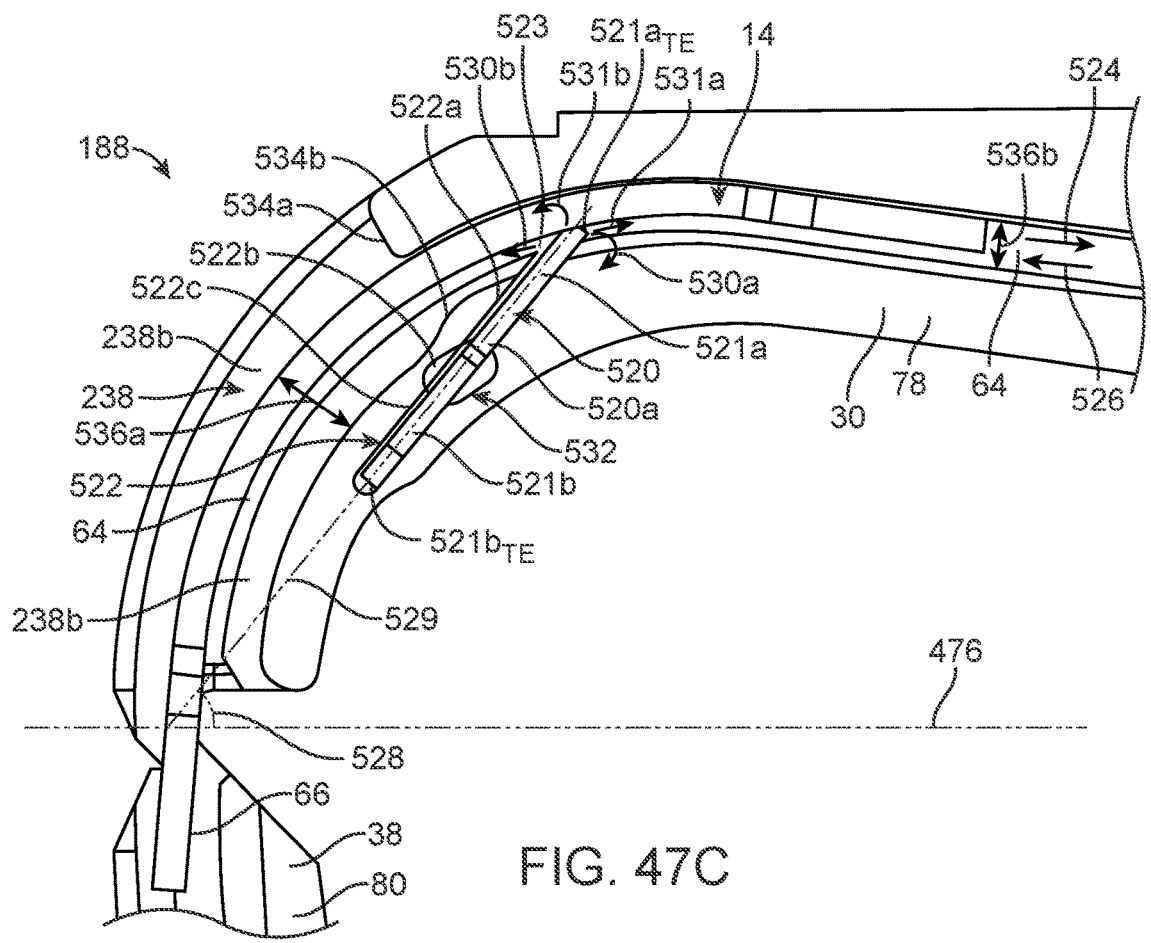
FIG. 47C illustrates a variation of the upper jaw and various components in the upper jaw with half of the upper jaw shown transparent.
Figure 47D:
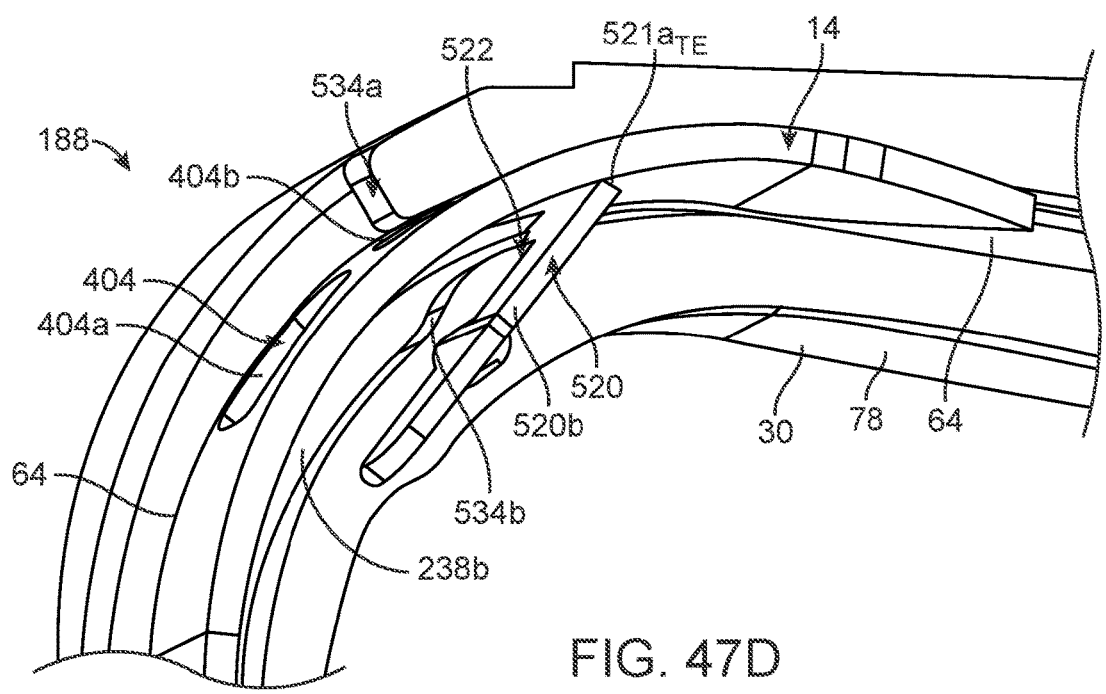
FIG. 47D illustrates a variation of the upper jaw and various components in the upper jaw with half of the upper jaw shown transparent.

FIGS. 47A-47D illustrate that the device 188 can have one or multiple shuttle stops 520. The device 188 can have, for example, 1-10 or more shuttle stops 520, including every 1 shuttle stop 520 increment within this range (e.g., 1, 2, 3, 4 or more shuttle stops 520). The upper jaw (e.g., jaw 30, jaw 78) and/or the lower jaw (e.g., jaw 38, 80) can each have one or multiple shuttle stops 520. The upper jaw can have, for example, 1-5 or more shuttle stops 520 (e.g., 1, 2, 3, 4, 5, or more shuttle stops 520). The lower jaw can have, for example, 1-5 or more shuttle stops 520 (e.g., 1, 2, 3, 4, 5, or more shuttle stops 520). The upper and lower jaws can have the same number or a different number of shuttle stops as each other. For example, the lower and upper jaws can each have 1, 2, 3, or more shuttle stops. FIGS. 47A and 47B illustrate that the lower jaw (e.g., jaw 38, 80) can have a lower jaw shuttle stop 520a configured to releasably engage with the shuttle 14, and FIGS. 47C and 47D illustrate that the upper jaw (e.g., jaw 30, jaw 78) can have an upper jaw shuttle stop 520b configured to releasably engage with the shuttle 14. Half of the lower and upper jaws (e.g., a transverse half of the lower and upper jaws on one side of the device of the device longitudinal axis) in FIGS. 47A-47D is shown transparent so that the shuttle 14 can be more easily seen in the jaw tracks (e.g., lower and upper tracks 66, 64), and so that the shuttle stops 520 (e.g., shuttle stops 520a and 520b) can be more easily seen.

The shuttle stops 520 (e.g., the lower jaw shuttle stops 520a and the upper jaw shuttle stops 520b) can be a prong, an arm, a protrusion, an extension, a flexure, a detent, a detent flexure, a male detent, or any combination thereof. The shuttle stops 520 can be straight and/or curved. The shuttle stops can be open shapes (e.g., bars, arcs, plates) or closed shapes (e.g., ring-shaped). The shuttle stops 520 can be flexible, rigid, or both (e.g., a first portion can be flexible and a second portion can be rigid). The shuttle stops 520 can be one or more springs. The shuttle stops 520 can be made from nickel titanium alloys (e.g., Nitinol), stainless steel, composite materials, or any combination thereof. The shuttle stops 520 can have a shuttle stop first longitudinal end 521a and a shuttle stop second longitudinal end 521b. The shuttle stop first longitudinal end 521a can have a shuttle stop first longitudinal end terminal end $521a_{TE}$ The shuttle stop second longitudinal end 521b can have a shuttle stop second longitudinal end terminal end $521b_{TE}$.

FIGS. 47A-47D further illustrate that each shuttle stop 520 (e.g., shuttle stops 520a, 520b) can be in a shuttle stop groove 522. Each shuttle stop groove 522 can be in a jaw (e.g., first jaw, second jaw, lower jaw, upper jaw). For example, each lower jaw shuttle stop 520a can be in a lower jaw shuttle stop groove 522a and each upper jaw shuttle stop 520b can be in an upper jaw shuttle stop groove 522b. The lower jaw shuttle stop 520a can be housed in the lower jaw shuttle stop groove 522a and the upper jaw shuttle stop 520b can be housed in the upper jaw shuttle stop groove 522b. The shuttle stop grooves 522 can have a shuttle stop groove opening 523 that opens into the shuttle tracks (e.g., lower and upper jaw shuttle tracks 66, 64) such that the shuttle stop grooves 522 intersect with the shuttle tracks. The shuttle stops 520 (e.g., shuttle stops 520a, 520b) can extend from the shuttle stop grooves 522 into the shuttle tracks. For example, the shuttle stop groove opening can be at a longitudinal terminal end of the shuttle stop groove such that a longitudinal end of the shuttle stop 520 (e.g., 521a, 521b) can extend out of the shuttle stop grove and into the shuttle track. In such cases, a longitudinal terminal end of the shuttle stop (e.g., $521a_{TE}$, $521b_{TE}$) can be in the shuttle track. As another example, the shuttle stop groove opening can be between a shuttle stop first longitudinal terminal end and a shuttle stop second longitudinal terminal end such that a longitudinal medial portion of the shuttle stop 520 between the shuttle stop first and second longitudinal terminal ends extends into (e.g., arcs into) the shuttle track. For example, FIGS. 47A-47D illustrate that the shuttle stop first longitudinal end 521a can extend into the shuttle track (e.g., shuttle tracks 66, 64) such that the shuttle stop first longitudinal end terminal end $521a_{TE}$ can be in the shuttle track. The shuttle stop first longitudinal end 521a can be further from the device longitudinal axis 476 than the shuttle stop second longitudinal end 521b. The shuttle stop first longitudinal terminal end 521a can be configured to contact the shuttle 14 when the shuttle is over the shuttle stop 520, for example, when the shuttle 14 passes over the shuttle stop 520 and when the shuttle is stationary over the shuttle stop 520.

The shuttle stop grooves 522 (e.g., grooves 522a, 522b) can open into a curved portion of the shuttle track. The shuttle stop grooves 522 (e.g., grooves 522a, 522b) can open into a straight portion of the shuttle track. For example, FIGS. 47A and 47B illustrate that the lower jaw shuttle groove 522a can intersect the lower jaw shuttle track at a curved portion of the lower jaw shuttle track). FIGS. 47C and 47D illustrate that the upper jaw shuttle groove 522b can intersect the upper jaw shuttle track at a curved portion of the upper jaw shuttle track). As another example, a first shuttle stop groove can open into a straight portion of the first jaw shuttle track and a second shuttle stop groove can open into a curved portion of the first jaw shuttle track. As yet another example, a first shuttle stop groove can open into a straight portion of the second jaw shuttle track and a second shuttle stop groove can open into a curved portion of the second jaw shuttle track.

The shuttle stops 520 (e.g., stops 520a, 520b) can be at an angle 528 relative to the device longitudinal axis 476. The shuttle stop grooves 522 (e.g., grooves 522a, 522b) can be at an angle 528 relative to the device longitudinal axis 476. An axis 529 through the shuttle stops 520 and/or the shuttle stop grooves 522 can intersect with the device longitudinal axis at the angle 528. The axis 529 can be a longitudinal axis (e.g., center longitudinal axis) through the shuttle stops 520, through the shuttle stop grooves 522, or through both. The angle 528 can be from about 10 degrees to about 170 degrees, or more narrowly, from about 10 degrees to about 80 degrees, or yet more narrowly, from about 30 degrees to about 60 degrees, including every 1 degree increment within these ranges (e.g., 10 degrees, 30 degrees, 40 degrees, 45 degrees, 50 degrees, 60 degrees, 80 degrees).

The angle 528 of the shuttle stops 520 can allow all or a portion of the shuttle 14 to pass the shuttle stops 520 when the shuttle 14 is moved into the jaws (e.g., along the shuttle tracks), including, for example, distal to proximal along the device longitudinal axis 476. When the shuttle 14 is driven (e.g., pushed, pulled, or both) into the jaws, the shuttle stops 520 can flex, catch the shuttle 14, and hold the shuttle 14 in place. The shuttle stops 520 can passively hold the shuttle 14 in place when an outward force (e.g., a force having a direction opposite to the direction of the force which drove the shuttle 14 into the jaws) is applied to the shuttle 14. FIGS. 47A and 47B illustrate the inward direction 524 and the outward direction 526 for the lower jaw. FIGS. 47C and 47D illustrate the inward direction 524 and the outward direction 526 for the upper jaw. The inward and outward directions 524, 526 can be opposite one another along, for example, the longitudinal axis of the shuttle tracks. The shuttle 14 can be passively retained by the shuttle stop 520, for example, by virtue of the arrangement of the of the shuttle stop 520 relative to the jaw and the shuttle 14. For example, the shuttle stop 520 can passively engage with the shuttle 14 as the shuttle 14 is advanced into the jaw and can be actively disengaged with the shuttle 14 so that the shuttle 14 can be advanced out of the jaw.

FIGS. 47b and 47D further illustrate that the shuttle 14 can have one or multiple suture holes 404, for example, first and second suture holes 404a, 404b. FIGS. 47B and 47D further illustrate that when the shuttle 14 is fully advanced into the lower and upper jaws, the shuttle stops 520 do not interface with or engage with the suture holes 404 (e.g., first and second suture holes 404a, 404b) or the suture. As another example, when the shuttle 14 is fully advanced into the lower and upper jaws, the shuttle stops 520 can interface with one or more of the suture holes 404, the suture, or any combination. For example, the shuttle stops 520 can interface with one or more of the suture holes 404 by extending into one or more of the suture holes 404.

FIGS. 47A-47D illustrate that when the shuttle 14 is engaged with the shuttle stop 520 (e.g., stops 520a, 520b), a threshold release force can be required to release the shuttle 14 from the shuttle stop 520 so that the shuttle 14 can be moved to the other jaw. The threshold release force can be reached and/or exceed by applying an outward force to the shuttle 14. The outward force can be applied to the shuttle 14 to reach the release force and to move the shuttle 14 into the other jaw. When the threshold release force is achieved or exceeded, the shuttle 14 can move (e.g., slide) against the shuttle stop 520 so that the shuttle 14 can move out of one jaw and into the other jaw (e.g., from the first jaw to the second jaw, and vice versa). When the threshold release force is achieved or exceeded, the static friction between the shuttle stop surface and the shuttle surface can be overcome with or without the shuttle stop 520 deflecting. Deflection of the shuttle stop 520 can include buckling, bending, flexing, compression (e.g., longitudinal compression, transverse compression, shortening), tension (e.g., stretching, lengthening) or any combination thereof of the shuttle stop 520. When the threshold release force is achieved or exceeded, the static friction between the shuttle stop surface and the shuttle surface can be overcome with or without one or multiple walls of the shuttle stop groove 522 deflecting. Deflection of the shuttle stop groove 522 can include buckling, bending, flexing, lengthening, or any combination thereof of the shuttle stop groove 522, as well as in any combination with or without deformation of one or more of the walls that define the shuttle stop groove 522 due to the shuttle stop 520 being forced against the one or more walls when an outward force is applied to the shuttle 14. The threshold release force can be from about 1.0 Newton to about 10.0 Newtons or more, including every 0.5 Newton increment within this range (e.g., 4.0 Newtons, 4.5 Newtons, 5.0 Newtons). As another example, the release force can be from about 0.5 lbs to about 1.5 lbs, including every 0.1 lb increment within this range (e.g., 1.0 lb). When the shuttle 14 is in the first jaw, the outward force (e.g., threshold release force) can be toward the second jaw. When the shuttle 14 is in the second jaw, the outward force (e.g., threshold release force) can be toward the first jaw. When the shuttle 14 is in the first jaw, the outward force (e.g., threshold release force) can be applied to the shuttle 14 so that the shuttle 14 can move in the shuttle track toward the second jaw. When the shuttle 14 is in the second jaw, the outward force (e.g., threshold release force) can be applied to the shuttle 14 so that the shuttle 14 can move in the shuttle track toward the first jaw.

The device 188 can have a shuttle stop releaser (also referred to as shuttle stop controller). The shuttle stop releaser can push on the shuttle stop 520, allowing the shuttle 14 to release from the shuttle stop 520. The shuttle stop releaser can be the shuttle 14. For example, the release force can be applied to the shuttle 14 (e.g., via a pusher) to release the shuttle 14 from the shuttle stop 520 such that the shuttle 14 can be the shuttle stop releaser. The release force can be applied to the shuttle 14 (e.g., from a pusher) to release the shuttle 14 from the shuttle stop 520 such that the shuttle 14 functions both as the shuttle 14 (e.g., carrying the suture back and forth between the jaws) and as the shuttle stop releaser. As another example, the shuttle stop releaser may not be the shuttle 14, whereby the shuttle stop releaser can selectively engage and disengage with the shuttle stop 520. In such cases, the shuttle stop releaser can reduce or eliminate the threshold release force that can be required to release the shuttle 14 from the shuttle stop 520 so that the shuttle 14 can be moved to the other jaw. The shuttle stop releaser can selectively engage and disengage with the shuttle stop 520 when the shuttle 14 is in contact with the shuttle stop 520. The shuttle stop releaser can selectively engage and disengage with the shuttle stop 520 when the shuttle 14 is not in contact with the shuttle stop 520. The shuttle stop releaser can selectively engage and disengage with the shuttle stop 520 before an outward force is applied to the shuttle 14 (e.g., via the pusher), while an outward force is applied to the shuttle 14 (e.g., via the pusher), after an outward force is applied to the shuttle 14 (e.g., via the pusher), or any combination thereof. The shuttle stop releaser can selectively engage and disengage with the shuttle stop 520 before an inward force is applied to the shuttle 14 (e.g., via the pusher), while an inward force is applied to the shuttle 14 (e.g., via the pusher), after an inward force is applied to the shuttle 14 (e.g., via the pusher), or any combination thereof. For example, when the shuttle 14 is fully advanced into the first jaw and the shuttle 14 is engaged with the shuttle stop 520, the shuttle stop releaser can push on the shuttle stop 520 to release the shuttle 14 from the grip of the shuttle stop 520.

FIG. 47A further illustrates that when the shuttle 14 is moved into a jaw (e.g., the lower jaw 38, 80), the shuttle 14 can contact and slide over the shuttle stop 520. When the shuttle 14 contacts and slides over the shuttle stop 520 as the shuttle can move in direction 524, the shuttle stop 520 can deflect, or both. For example, the shuttle stop first longitudinal end 521a can deflect in a deflection first direction. The deflection first direction can have a translation component, a rotation component, or both. For example, FIG. 47A illustrates the deflection first direction can include rotation 530a, translation 531a, or both rotation 530a and translation 531a. The rotation 530a can be clockwise rotation in the orientation shown in FIG. 47A, and the translation 531a can be translation to the right in the orientation shown in FIG. 47A. FIG. 47A further illustrates that when the shuttle is in a fully advanced position in the jaw (e.g., the lower jaw 38, 80), the shuttle stop 520 can be deflected in the first direction. When the shuttle 14 slides against the shuttle stop 520 in direction 524, the shuttle stop 520 can have a shuttle stop first deflected position. When the shuttle 14 is fully advanced into the jaw and is in contact with the shuttle stop 520, the shuttle stop can have the shuttle stop first deflected position.

FIG. 47A further illustrates that when the shuttle 14 is moved out of a jaw (e.g., the lower jaw 38, 80), the shuttle 14 can contact and slide over the shuttle stop 520. The shuttle 14 can translate over and past the shuttle stop 520 when the shuttle 14 overcomes the threshold release force and/or when the shuttle stop releaser disengages the shuttle stop 520 from the shuttle 14. When the shuttle 14 contacts and slides over the shuttle stop 520 as the shuttle moves in direction 526, the shuttle stop 520 can deflect. For example, the shuttle stop first longitudinal end 521a can deflect in a deflection second direction. The deflection second direction can have a translation component, a rotation component, or both. For example, FIG. 47A illustrates the deflection second direction can include rotation 530b, translation 531b, or both rotation 530b and translation 531b. The rotation 530b can be counterclockwise rotation in the orientation shown in FIG. 47A, and the translation 531b can be translation to the left in the orientation shown in FIG. 47A. When the shuttle 14 slides against the shuttle stop 520 in direction 526, the shuttle stop 520 can have a shuttle stop second deflected position. When the shuttle is fully retracted or advanced past the shuttle stop 520, the shuttle stop 520 can be in a shuttle stop neutral position. The shuttle stop neutral position can be a position between the shuttle stop first deflected position and the shuttle stop second deflected position.

FIG. 47A further illustrates that when the shuttle stop first longitudinal end 521a deflects, the shuttle stop second longitudinal end 521b can be fixed. When the shuttle stop first longitudinal end 521a deflects, the shuttle stop second longitudinal end 521b can deflect.

FIG. 47C further illustrates that when the shuttle 14 is moved into a jaw (e.g., the upper jaw 30, 78), the shuttle 14 can contact and slide over the shuttle stop 520. When the shuttle 14 contacts and slides over the shuttle stop 520 as the shuttle can move in direction 524, the shuttle stop 520 can deflect, or both. For example, the shuttle stop first longitudinal end 521a can deflect in a deflection first direction. The deflection first direction can have a translation component, a rotation component, or both. For example, FIG. 47C illustrates the deflection first direction can include rotation 530a, translation 531a, or both rotation 530a and translation 531a. The rotation 530a can be clockwise rotation in the orientation shown in FIG. 47C, and the translation 531a can be translation to the right in the orientation shown in FIG. 47C. FIG. 47C further illustrates that when the shuttle is in a fully advanced position in the jaw (e.g., the upper jaw 30, 78), the shuttle stop 520 can be deflected in the first direction. When the shuttle 14 slides against the shuttle stop 520 in direction 524, the shuttle stop 520 can have a shuttle stop first deflected position. When the shuttle 14 is fully advanced into the jaw and is in contact with the shuttle stop 520, the shuttle stop can have the shuttle stop first deflected position.

FIG. 47C further illustrates that when the shuttle 14 is moved out of a jaw (e.g., the upper jaw 30, 78), the shuttle 14 can contact and slide over the shuttle stop 520. The shuttle 14 can translate over and past the shuttle stop 520 when the shuttle 14 overcomes the threshold release force and/or when the shuttle stop releaser disengages the shuttle stop 520 from the shuttle 14. When the shuttle 14 contacts and slides over the shuttle stop 520 as the shuttle moves in direction 526, the shuttle stop 520 can deflect. For example, the shuttle stop first longitudinal end 521a can deflect in a deflection second direction. The deflection second direction can have a translation component, a rotation component, or both. For example, FIG. 47C illustrates the deflection second direction can include rotation 530b, translation 531b, or both rotation 530b and translation 531b. The rotation 530b can be counterclockwise rotation in the orientation shown in FIG. 47A, and the translation 531b can be translation to the left in the orientation shown in FIG. 47A. When the shuttle 14 slides against the shuttle stop 520 in direction 526, the shuttle stop 520 can have a shuttle stop second deflected position. When the shuttle is fully retracted or advanced past the shuttle stop 520, the shuttle stop 520 can be in a shuttle stop neutral position. The shuttle stop neutral position can be a position between the shuttle stop first deflected position and the shuttle stop second deflected position.

FIG. 47C further illustrates that when the shuttle stop first longitudinal end 521a deflects, the shuttle stop second longitudinal end 521b can be fixed. When the shuttle stop first longitudinal end 521a deflects, the shuttle stop second longitudinal end 521b can deflect.

The shuttle stop groove 522 can have a constant width or a tapered width. A tapered width can accommodate deflection of the shuttle stop first longitudinal end 521a. As another example, the shuttle stop groove can have a constant width portion and a tapered width portion. For example, the portion of the shuttle stop groove 522 that houses the shuttle stop first longitudinal end 521a can have a tapered width that gets wider toward the opening 523, and the portion of the shuttle stop groove 522 that houses the shuttle stop second longitudinal end 521b can have a constant width to prevent or minimize deflection of the shuttle stop second longitudinal end 521b.

FIGS. 47A-47D further illustrate that the shuttle groove 522 can have a chamber 532. The chamber 532 can be a shuttle stop deflection chamber, a shuttle stop releaser chamber, or both. When the shuttle stop first longitudinal end 521a deflects, the portion of the shuttle stop 520 that is in the chamber 532 can deflect to accommodate deflection of the shuttle stop first longitudinal end terminal end $521a_{TE}$ relative to the rest of the shuttle stop 520 (e.g., shuttle stop 520a). As another example, the shuttle stop groove 522 can extend across the chamber 532. As yet another example, the upper jaw, the lower jaw, or both, can have a groove first portion 522a, a groove second portion 522b, and a groove third portion 522c. The groove second portion 522b can include all or a portion of the chamber 532. As still yet another example, the chamber 532 can be a through-hole. The through-hole can be the terminal end of a shuttle stop releaser track inside the jaws.

FIGS. 47A-47D further illustrate that the lower and upper jaws can have a first suture stop 534a, a second suture stop 534b, or both. The first suture stop 534a can be configured to contact the suture 70. The first suture stop 534a can be configured to contact the suture loop 162. The first suture stop 534a can function as a primary or secondary shuttle stop by catching the suture 70 or the suture loop 162. When the suture 70 or suture loop 162 is in contact the first suture stop 534a, further movement of the shuttle 14 into the jaw can be inhibited or prevented. The second suture stop 534b can be configured to contact the suture 70. The second suture stop 534b can be configured to contact the suture loop 162. The second suture stop 534b can function as a primary or secondary shuttle stop by catching the suture 70 or the suture loop 162. When the suture 70 or suture loop 162 is in contact the second suture stop 534b, further movement of the shuttle 14 into the jaw can be inhibited or prevented. The first and second suture stops 534a, 534b can inhibit or prevent the suture 70 from entering the shuttle track beyond the suture holder slot. The shuttle tracks (e.g., tracks 64 and 66) can have a first height 536a and a second height 536b. The first height 536a can be greater than the second height 536b. The first height 536a can decrease to the second height 536b at the second suture stop 534b, which can be a tapered surface (e.g., smooth ramp) or a vertical surface (e.g., a step). The second height 536b can be less than the first height 536a, for example, to inhibit or prevent the suture 70 from be pulled or pushed into the shuttle track beyond the suture holder slots 238.

FIGS. 47B and 47D further illustrate that that that the shuttle holes 404 may not extend over or engage with the shuttle stop 520. As another example, the shuttle holes can extend over and/or engage with the shuttle stop 520.

FIGS. 47B and 47D further illustrate that the shuttle stop first longitudinal end terminal end $521a_{TE}$ can extend across a width of the shuttle 14.

The device 188 can have zero, one, or multiple stops. For example, the shuttle can have zero, one, or multiple stops (e.g., stops 412, 413, 416), the upper jaw can have, zero, one, or multiple stops (e.g., stops 520), the lower jaw can have zero, one, or multiple stops (e.g., stops 520), or any combination thereof.

Figure 47E:
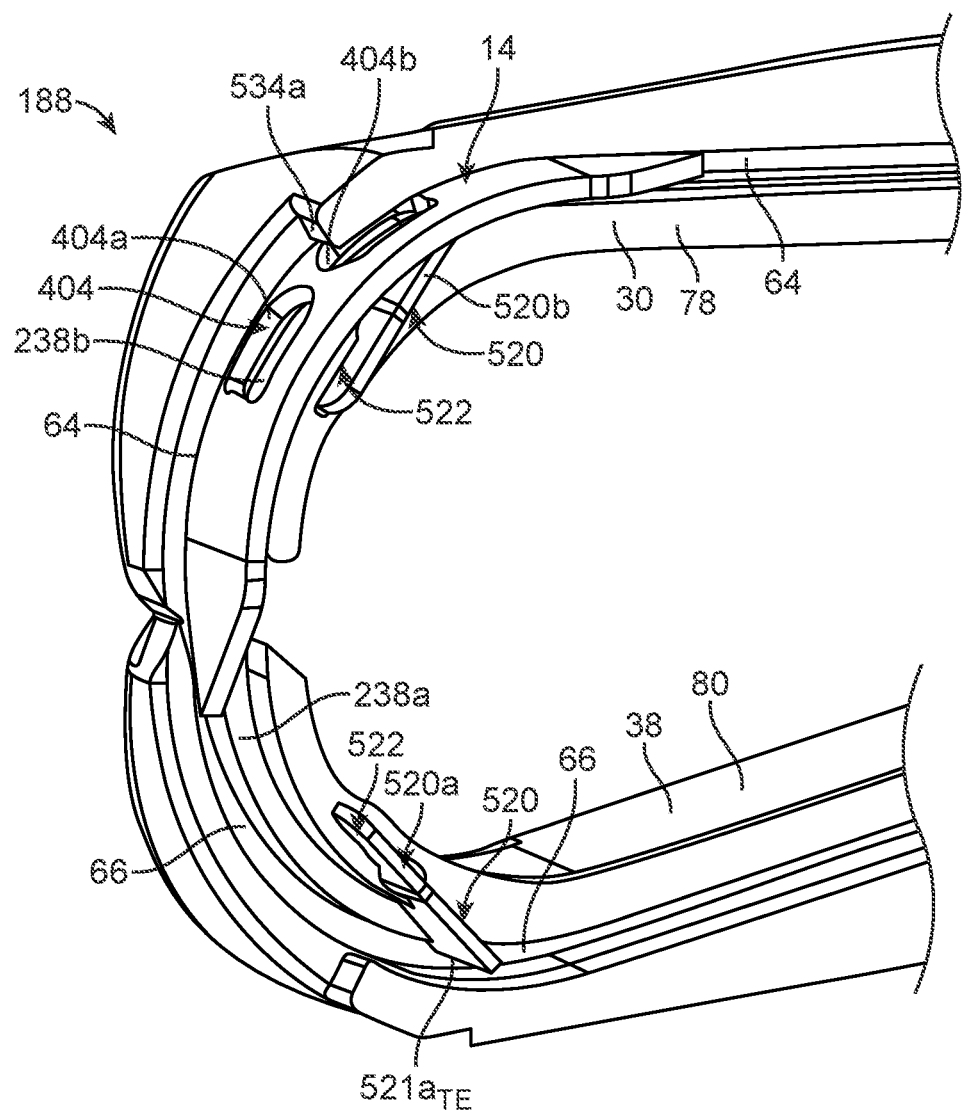
FIG. 47E illustrates a variation of the device with half the lower and upper jaws shown transparent.

FIG. 47E illustrates the lower and upper jaws together with half of the upper and lower jaws shown transparent so that the shuttle 14 and shuttle stop 520 can be seen.

FIGS. 47A-47E illustrate the pushers as transparent and/or in a retracted position.

Figure 47F:
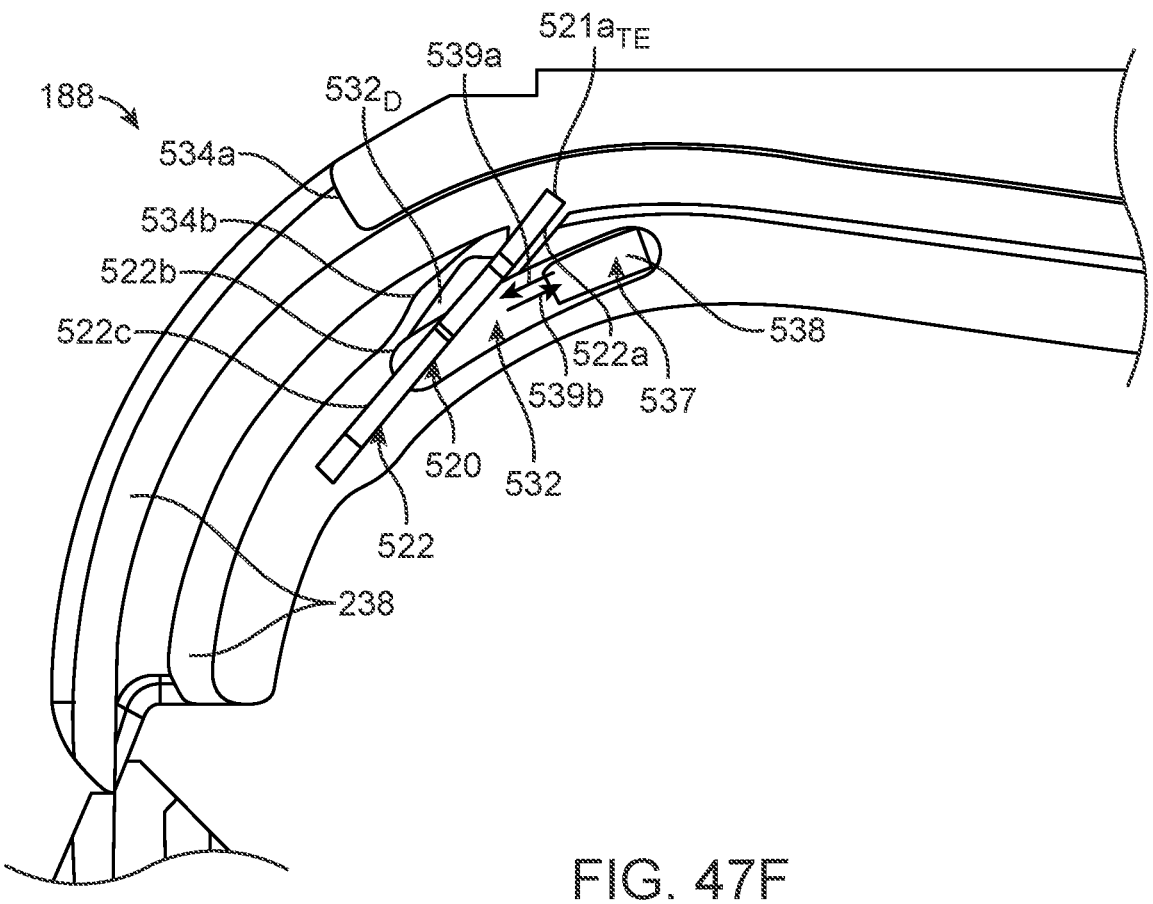
FIG. 47F illustrates a variation of the upper and/or lower jaw with various components in the upper and/or lower jaw with half of the upper and/or lower jaw shown transparent.

FIG. 47F illustrates that the device 188 can have a shuttle stop controller 537 (also referred to as a shuttle stop articulator and a shuttle stop releaser). The shuttle stop controller 537 can have a shuttle stop engager 538. The shuttle stop engager 538 can interact with the shuttle stop 520, for example, engage and disengage with the shuttle stop 520. The shuttle stop controller 537 can be in the chamber 532. A portion of the shuttle stop groove 522 can overlap with the chamber 532. For example, the second portion 522b of the shuttle stop groove 522 can overlap with the chamber 532. The shuttle stop engager 538 can be moveable into and out of the shuttle stop groove 522. The shuttle stop engager 538 can be moveable from a first end of the chamber 532 to a second end of the chamber 532 and vice versa. The shuttle stop engager 538 can be moveable from a first end of the chamber 532 toward a second end of the chamber 532 and vice versa.

Figure 47G:
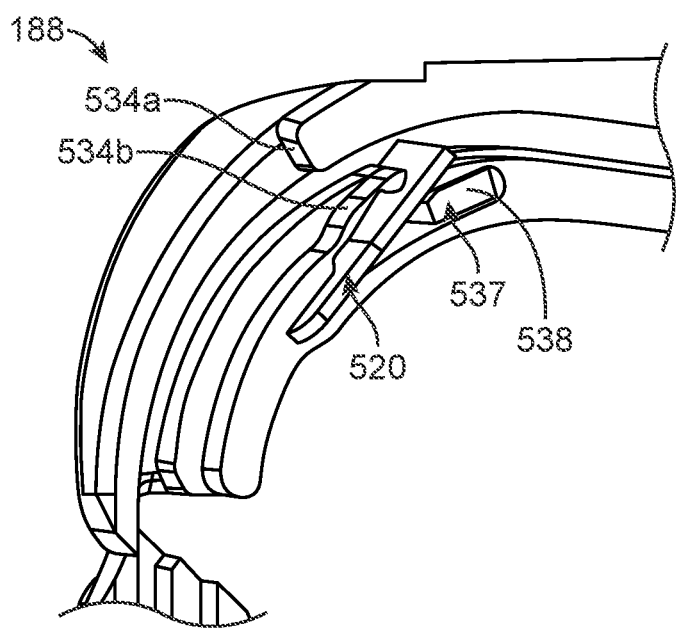
FIG. 47G illustrates a variation of the upper and/or lower jaw with various components in the upper and/or lower jaw with half of the upper and/or lower jaw shown transparent.

FIG. 47G illustrates that the shuttle stop engager 538 can extend across a width of the shuttle stop 520.

FIGS. 47F and 47G further illustrate the shuttle stop 520 in a neutral position in the chamber 532 and the shuttle stop engager 538 in a disengaged position in the shuttle stop groove 522. When the shuttle stop engager 538 is in the disengaged position, for example, as shown in FIGS. 47F and 47G, the shuttle stop engager 538 may or may not contact the shuttle stop 520. For example, FIGS. 47F and 47G illustrate that when the shuttle stop engager 538 is in the disengaged position, the shuttle stop engager 538 does not contact the shuttle stop 520. When the shuttle stop 520 is in the neutral position, for example, as shown in FIGS. 47F and 47G, the shuttle stop 520 can be partially deflected or have zero deflection. For example, FIGS. 47F and 47G illustrate that when the shuttle stop 520 is in the neutral position, the shuttle stop 520 can have a non-deflected configuration (also referred to as a relaxed configuration).

When the shuttle stop engager 538 is in a disengaged position, FIG. 47F illustrates that the shuttle stop engager 538 can be moved in direction 539a (e.g., toward the shuttle stop 520) to interface with or engage the shuttle stop 520. When the shuttle stop engager 538 engages (e.g., pushes against) the shuttle stop 520, the shuttle stop 520 can deflect (e.g., flex), allowing the shuttle 14 to release. When the shuttle stop engager 538 is in an engaged position, FIG. 47F illustrates that the shuttle stop engager 538 can be moved in direction 539b (e.g., away from the shuttle stop 520) to disengage with the shuttle stop 520.

FIGS. 47F and 47G further illustrate that the chamber 532 can have a deflection space $532_D$. A portion of the shuttle stop 520 (e.g., a middle portion of the shuttle stop 520 between the shuttle stop first and second end terminal ends $521a_{TE}$, $521b_{TE}$) can be deflectable into the deflection space $532_D$, for example, via the shuttle stop engager 538, via the shuttle 14, or via both.

FIGS. 47F and 47G further illustrate that the shuttle 14 can be in the other jaw. As another example, FIGS. 47F and 47G further illustrate that the shuttle 14 is in the jaw shown but is transparent.

FIGS. 47F and 47G further illustrate that half of the jaw (e.g., a transverse half on one side of the device longitudinal axis 476) is shown transparent.

FIGS. 47F and 47G illustrate the pushers as transparent and/or in a retracted position.

The jaw shown in FIGS. 47F and 47G can be the upper jaw. The jaw shown in FIGS. 47F and 47G can be the lower jaw.

Figure 47H:
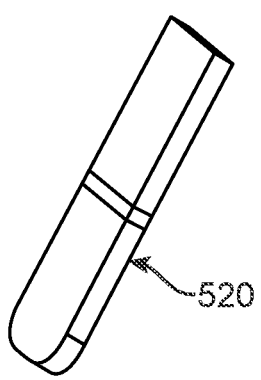
FIG. 47H illustrates a perspective view of a variation of a shuttle stop.

FIG. 47H illustrates an exemplary shuttle stop 520 having the shape and features shown. The shuttle stop can be, for example, a rod or a plate. For example, FIG. 47H illustrates that het shuttle stop 520 can be a flexible plate.

Figure 47I:
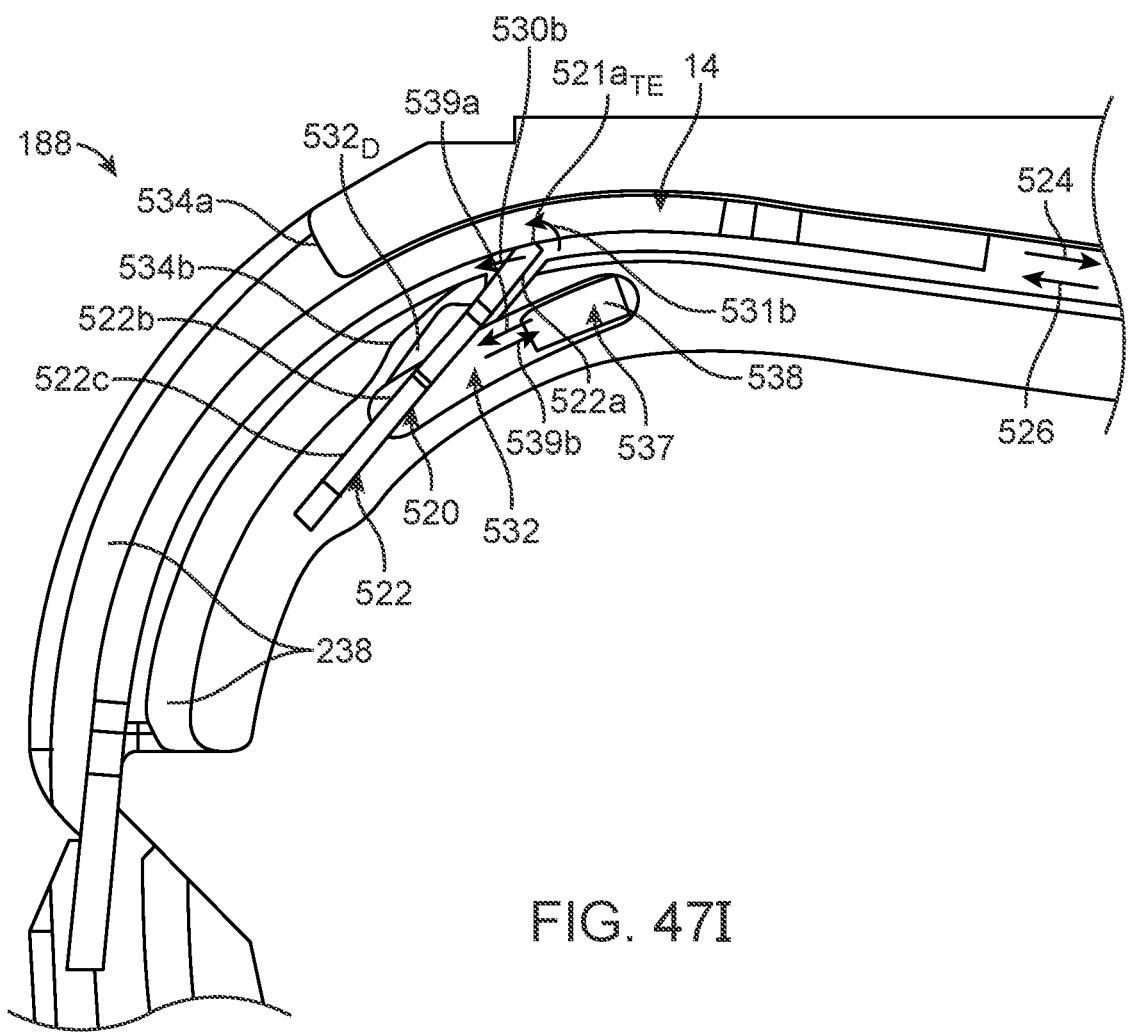
FIG. 47I illustrates a variation of the upper and/or lower jaw with various components in the upper and/or lower jaw with half of the upper and/or lower jaw shown transparent.
Figure 47J:
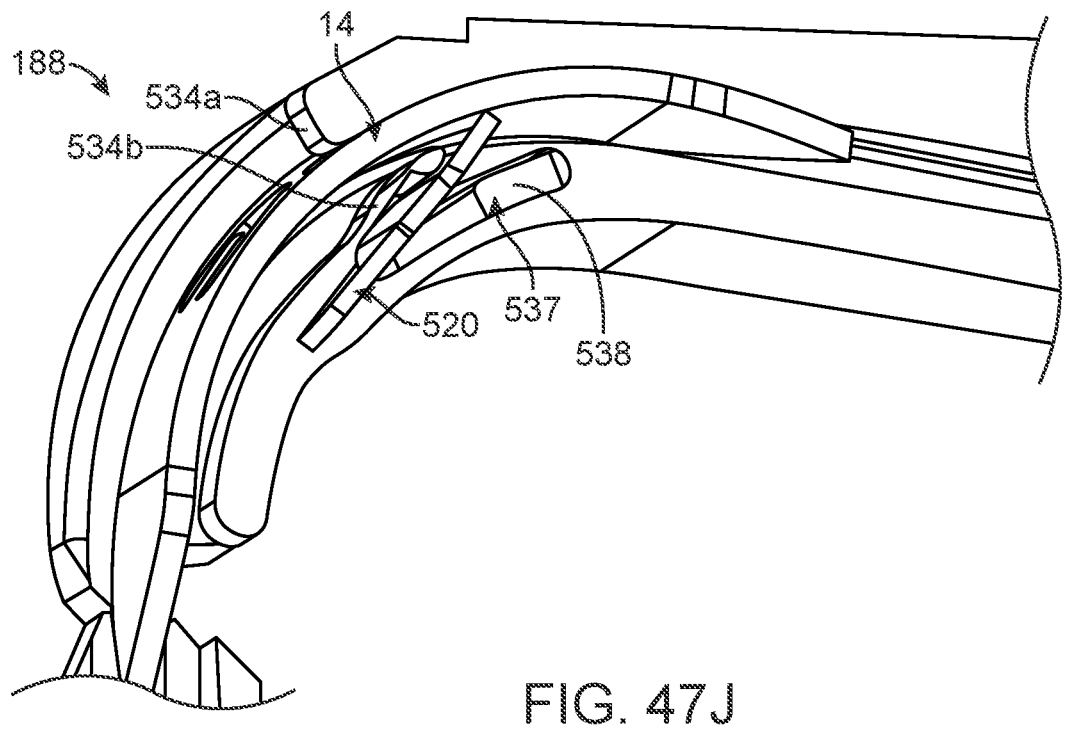
FIG. 47J illustrates a variation of the upper and/or lower jaw with various components in the upper and/or lower jaw with half of the upper and/or lower jaw shown transparent.

FIGS. 47I and 47J illustrate the shuttle stop 520 and the shuttle 14 engaged with one another. The shuttle stop 520 can become engaged with the shuttle 14 when the shuttle 14 is moved or attempted to be moved (e.g., pushed, pulled) out of the jaws in direction 526 from an advanced position in the jaw, similar to how a speed nut functions. The advanced position in the jaw shown in FIGS. 47I and 47J can be a partially advanced position of the shuttle 14 in the shuttle track or a fully advanced position of the shuttle 14 in the shuttle track. When the shuttle stop 520 is engaged with the shuttle 14 (e.g., when in a partially or fully advanced position), the shuttle stop 520 can prevent or inhibit the shuttle 14 from being moved (e.g., pulled, pushed) out of the jaws in direction 526. When the shuttle stop 520 is engaged with the shuttle 14 (e.g., when in a partially advanced position), the shuttle stop 520 can allow the shuttle 14 to be moved (e.g., pulled, pushed) further into the jaws in direction 524, for example, until the fully advanced position is reached. For example, when the shuttle 14 is engaged with the shuttle stop 520, shuttle movement in the outward direction 526 toward the other jaw is prevented or inhibited. FIGS. 47I and 47J illustrate the shuttle 14 trying to be moved out of the and into the other jaw (e.g., from the first to second jaw) in direction 526 but the shuttle 14 is inhibited or prevented from moving in or moving further in direction 526 until the shuttle stop 520 is disengaged from the shuttle 14 (e.g., via the shuttle stop engage 538), and/or until the threshold release force is reached between the shuttle 14 and the shuttle stop 520.

To engage the shuttle 14 with the shuttle stop 520, the shuttle 14 can move a shuttle capture distance of about 0.25 mm to about 2.00 mm along the shuttle track in direction 526, including every 0.05 mm and 0.25 mm increment within this range, for example, from the fully advanced position to a partially advanced position, or from a first partially advanced position to a second partially advanced position where the first partially advanced position is closer to the fully advanced position than the second partially advanced position. The shuttle capture distance can be the distance that the shuttle 14 can move in direction 526 until the shuttle stop 520 fully inhibits or prevents further movement along direction 526. The shuttle capture distance can be the activation distance that the shuttle 14 can move in the shuttle track (e.g., in direction 526) before the movement of the shuttle 14 fully engages with the shuttle stop 520, thereby inhibiting or preventing further movement along direction 526 until the shuttle stop 520 is disengaged from the shuttle 14.

FIG. 47I further illustrates that when the shuttle stop 520 and the shuttle 14 engaged with one another, the shuttle stop 520 can have shuttle stop first deflected configuration, where the shuttle stop first longitudinal end 521a (e.g., the shuttle stop first longitudinal end terminal end 521aTE) has been deflected in the deflection second direction (e.g., rotation 530b, translation 531b, or both rotation 530b and translation 531b). The force of the shuttle 14 against the shuttle stop 520 when shuttle 14 is moved in direction 526 to activate or otherwise engage shuttle stop 520 can cause the shuttle stop first longitudinal end 521a (e.g., the shuttle stop first longitudinal end terminal end 521aTE) to deflect in the deflection second direction (e.g., rotation 530b, translation 531b, or both rotation 530b and translation 531b), for example, from the shuttle stop neutral configuration (e.g., shown in FIGS. 47F-47H) to the shuttle stop first deflected configuration, or from a shuttle stop second deflected configuration to the shuttle stop first deflected configuration. The second deflected configuration can be the configuration of the shuttle stop 520 when the shuttle stop first longitudinal end 521a (e.g., the shuttle stop first longitudinal end terminal end 521a$_{TE}$) has been deflected in the deflection first direction (e.g., rotation 530a, translation 531a, or both rotation 530a and translation 531a), which can occur, for example, when the shuttle 14 is moved over the shuttle stop 520 in direction 524 during advancement of the shuttle 14 into the jaw, and/or when the shuttle 14 is in a static position over the shuttle stop 520 after having been partially or fully advanced into the jaw.

FIG. 47J further illustrates that the shuttle stop engager 538 can extend across a width of the shuttle stop 520.

FIGS. 47I and 47J further illustrate the shuttle stop 520 and the shuttle engager 538 in a disengaged configuration.

FIGS. 47I and 47J further illustrate that half of the jaw (e.g., a transverse half on one side of the device longitudinal axis 476) is shown transparent.

FIGS. 47I and 47J illustrate the pushers as transparent and/or in a retracted position.

The jaw shown in FIGS. 47I and 47J can be the upper jaw. The jaw shown in FIGS. 47I and 47J can be the lower jaw.

Figure 47K:
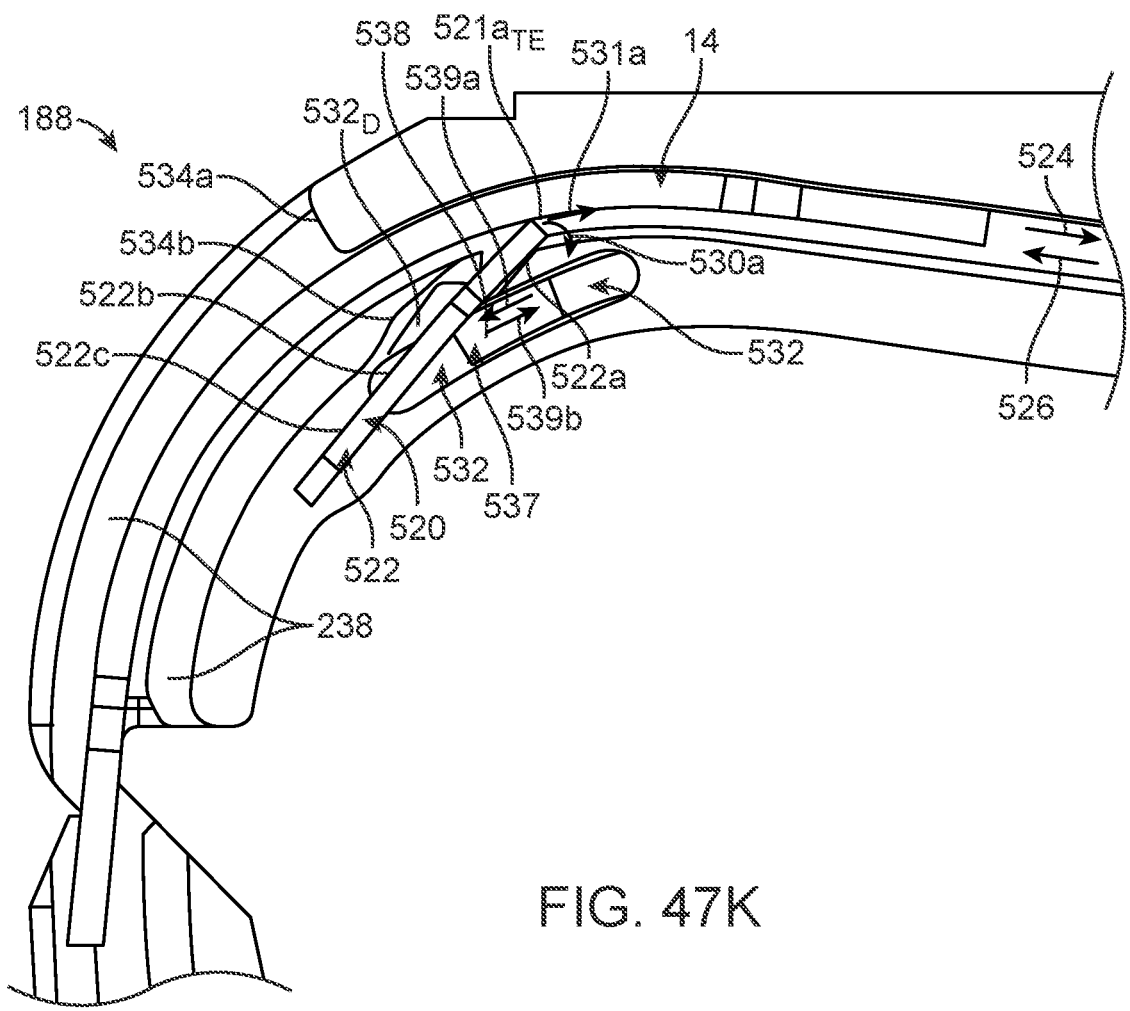
FIG. 47K illustrates a variation of the upper and/or lower jaw with various components in the upper and/or lower jaw with half of the upper and/or lower jaw shown transparent.
Figure 47L:
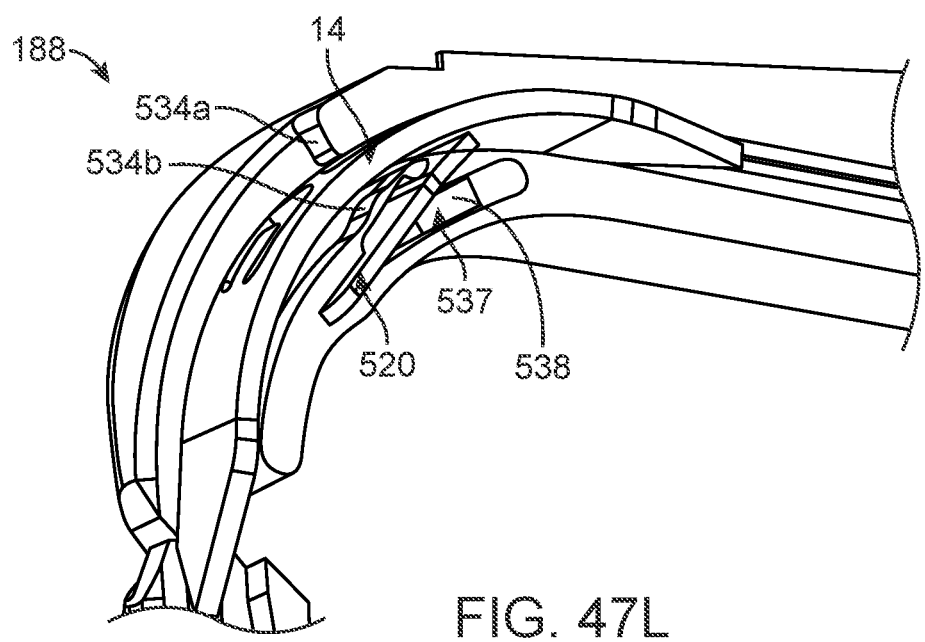
FIG. 47L illustrates a variation of the upper and/or lower jaw with various components in the upper and/or lower jaw with half of the upper and/or lower jaw shown transparent.

FIGS. 47K and 47L illustrate the shuttle stop 520 and the shuttle stop engager 538 engaged with one another. When the shuttle stop 520 and the shuttle stop engager 538 are engaged with one another, the shuttle stop first longitudinal end 521a (e.g., the shuttle stop first longitudinal end terminal end 521aTE) may or may not be in contact with the shuttle 14. For example, FIGS. 47I and 47J illustrate that when the shuttle stop 520 and the shuttle stop engager 538 are engaged with one another, a portion of the shuttle stop first longitudinal end 521a (e.g., the shuttle stop first longitudinal end terminal end 521aTE) can be in contact with the shuttle 14. To engage the shuttle stop engager 538 with the shuttle stop 520, the shuttle stop engager 538 can be moved in the chamber 532 toward the shuttle stop 520 (e.g., in direction 539a). When the shuttle stop engager 538 engages (e.g., pushes against) the shuttle stop 520, the shuttle stop engager 538 can deflect (e.g., flex, bend, buckle) the shuttle stop 520, allowing the shuttle 14 to release. For example, the shuttle stop engager 538 can flex or bend a middle portion of the shuttle stop 520 such that the shuttle stop first longitudinal end 521a can deflect away from the shuttle 14, for example, in the deflection first direction (e.g., rotation 530a, translation 531a, or both rotation 530a and translation 531a). The shuttle stop engager 538 can deflect the shuttle stop 520 from the shuttle stop first deflected configuration to the shuttle stop neutral configuration. As another example, the shuttle stop engager 538 can deflect the shuttle stop 520 from the shuttle stop first deflected configuration to the shuttle stop second deflected configuration. As yet another example, the shuttle stop engager 538 can deflect the shuttle stop 520 from the shuttle stop first deflected configuration to any deflected position resulting from deflection in the deflection first direction (e.g., rotation 530a, translation 531a, or both rotation 530a and translation 531a), for example, deflected configurations between the shuttle stop first deflected configuration and the shuttle stop neutral configuration, and deflected configurations between the shuttle stop neutral configuration and the shuttle stop second deflected configuration. FIGS. 47K and 47L further illustrate that the chamber 532 can have a deflection space 532D for the middle portion of the shuttle stop 520 to deflect into when the shuttle stop 520 is disengaged from the shuttle 14 via engagement with the shuttle stop engager 538. To disengage the shuttle stop engager 538 from the shuttle stop 520, the shuttle stop engager 538 can be moved in the chamber 532 away from the shuttle stop 520 (e.g., in direction 539b).

FIG. 47L illustrates that the shuttle stop engager 538 can extend across a width of the shuttle stop 520.

FIGS. 47K and 47L further illustrate that half of the jaw (e.g., a transverse half on one side of the device longitudinal axis 476) is shown transparent.

FIGS. 47K and 47L illustrate the pushers as transparent and/or in a retracted position.

The jaw shown in FIGS. 47K and 47L can be the upper jaw. The jaw shown in FIGS. 47K and 47L can be the lower jaw.

Figure 47M:
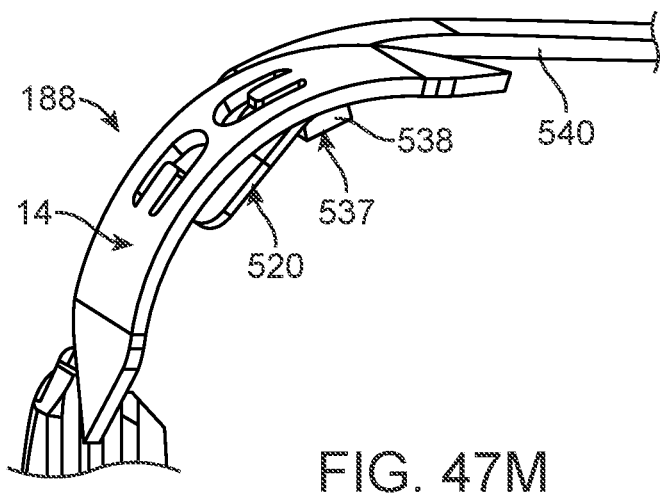
FIG. 47M illustrates a variation of a shuttle and a shuttle stop controller.

FIG. 47M illustrates that the shuttle stop controller 537 can have a control arm 540. The shuttle stop engager 538 can be attached to or integrated with the control arm 540. The shuttle control arm can be flexible or rigid. The control arm can be, for example, a rod or a cable, for example, a release rod or a release cable. The shuttle stop controller 537 can be a shuttle stop tape. The control arm 540 can engage and disengage the shuttle stop engager 538 with the shuttle stop 520, for example, by moving the shuttle stop engager 538 toward (e.g., direction 539a) the shuttle stop 520 and by moving the shuttle stop engager 538 away from (e.g., direction 539b) the shuttle stop 520, respectively. The shuttle stop controller 537 can be actuated and/or de-actuated by the jaw control extension 40 (also referred to as the jaw separator) or by a mechanism in the handle of the device. For example, the shuttle stop controller 537 can be controlled with one or multiple of the controls in or on the handle of the device, for example, by pushing, pulling, or rotating the controls into a shuttle stop controller articulation position. The shuttle stop controller 537 can be controlled, for example, by being engageable and dis-engageable with the jaw control extension 40 (also referred to as the jaw separator) or by a mechanism in the handle of the device. For example, the jaw control extension 40 or one or multiple of the controls on the handle of the device can be releasably engageable with the shuttle stop controller 537 (e.g., with the control arm 540) to control movement of the shuttle stop controller 537. The shuttle stop controller 537 (and thereby the shuttle stop engager 538) can be actuated by the jaw control extension 40 (also referred to as the jaw separator) or by a mechanism in the handle of the device. The jaw separator 40 can control the opening of the jaws, the closing of the jaws, or both the opening of the jaws and the closing of the jaws.

The shuttle stop controller 537 can be straight or curved. For example, FIG. 47M illustrates that the shuttle stop controller 537 can have an L-shape, with the shuttle stop engager 538 as the short leg of the L-shape and the control arm 540 as the long leg of the L-shape.

FIG. 47M further illustrates that the lower or upper jaw is shown transparent and half of the other jaw (e.g., the upper or lower jaw, respectively) is shown transparent so that the shuttle and shuttle stop controller 537 can be seen.

FIG. 47M further illustrates the pushers as transparent and/or in a retracted position.

The shuttle 14 and the shuttle stop controller 537 (e.g., shuttle stop engager 538, shuttle stop controller control arm 540) can be in the upper jaw, the lower jaw, or both jaws. The jaw shown in FIG. 47M can be the lower jaw. The jaw shown in FIG. 47M can be the upper jaw.

Figure 47N:
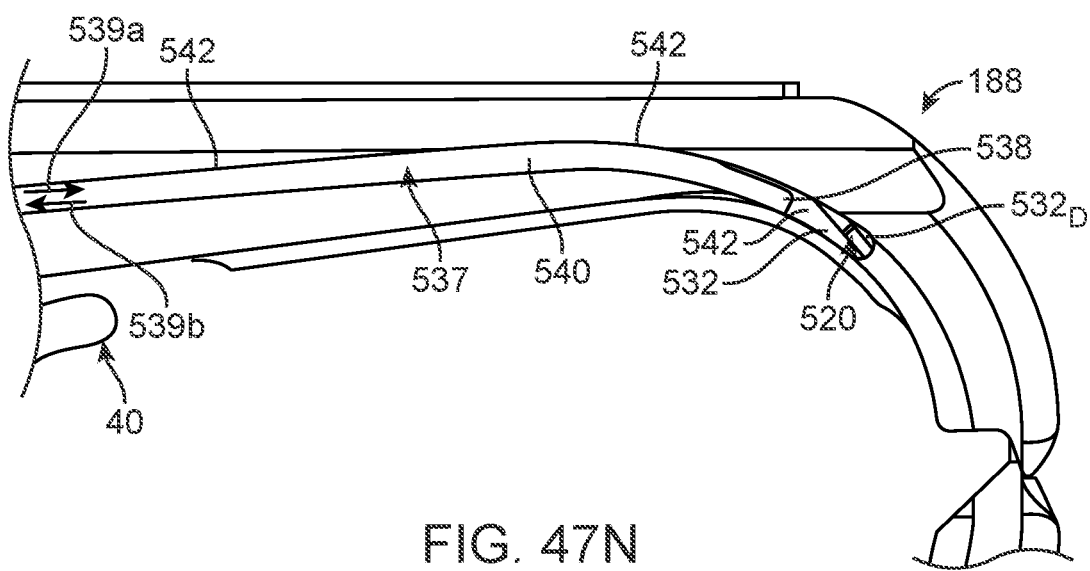
FIG. 47N illustrates a variation of the upper and/or lower jaw with various components in the upper and/or lower jaw.

FIG. 47N illustrates that the shuttle stop controller 337 (also referred to as shuttle stop tape) can be in a track 542 in the jaw (also referred to as a shuttle stop controller track or controller track). The shuttle stop engager 538, or a portion thereof, can be in the controller track 542. The control arm 540, or a portion thereof, can be in the controller track 542. The track 542 can be a groove. The track 542 can be a channel. The controller 537 can be advanceable in the track 542 (e.g., in direction 539a) and retractable in the track 542 (e.g., in direction 539b). For example, the controller 537 can be advanced and retracted in the track 542 to engage with and disengage with shuttle stop 520, or vice versa. The controller 337 (e.g., shuttle stop engager 538, control arm 540, or both) can be moveable (e.g., slideable, translatable) in the controller track 542. When the user wants to release the shuttle stop 520, the control arm 540 can be slid (e.g., translated) forward in the controller track 542 to press the shuttle stop engager 538 against the shuttle stop 520, flexing the shuttle stop 520, for example, from the shuttle stop first deflected configuration to the shuttle stop neutral configuration, from the shuttle stop first deflected configuration to the shuttle stop second deflected configuration. The shuttle stop controller 537 can be actuated by the jaw separator 40 or by a mechanism in the handle of the device 188. When the shuttle stop controller 537 is activated, the shuttle stop controller 537 can be in an advanced position. When the user wants to capture the shuttle 14 with the shuttle stop 520, the shuttle 14 can be slid (e.g., translated) forward over the shuttle stop 520, for example, while the shuttle stop engager 538 is disengaged from the shuttle stop 520. When the shuttle stop engager 538 is disengaged from the shuttle stop 520, the shuttle stop controller 537 can be in a retracted position. The shuttle stop controller advanced position can be the neutral position of the shuttle stop controller 537. The shuttle stop controller retracted position can be the neutral position of the shuttle stop controller 537. A position between the advanced and retracted positions of the shuttle stop controller can be the neutral position of the shuttle stop controller 537.

The shuttle stop controller 537 may or may not have the short leg of the L-shape. For example, FIG. 47N illustrates the shuttle stop controller 537 with the short leg of the L-shape, such as the shape shown in FIG. 47M. As another example, FIG. 47N illustrates the shuttle stop controller 537 without the short leg of the L-shape (e.g., an l-shape), where the distal terminal end of the control arm 540 can be the shuttle stop engager 538. The portion of the shuttle stop controller 537 configured to contact the shuttle stop 520 can be the shuttle stop engager 538. Any portion of the shuttle stop controller 537 configured to contact the shuttle stop 520 can be the shuttle stop engager 538.

FIG. 47N further illustrates that the chamber 532 can separate from or part of the controller track 542.

FIG. 47N further illustrates the shuttle stop 520 and the shuttle 14 engaged with one another.

FIG. 47N further illustrates the shuttle stop 520 and the shuttle stop engager 538 not engaged with one another.

FIG. 47N further illustrates the shuttle stop controller 537 in a disengaged position such that the shuttle stop 520 is not deflected by the shuttle stop engager 538. When the shuttle stop controller 537 is in a disengaged position, the shuttle stop controller 537 can be in a retracted position. The retracted position can be the default position of the shuttle stop controller 537.

FIG. 47N further illustrates that the shuttle stop controller 537 can move in direction 539a (e.g., toward the shuttle stop 520) to interface with or engage the shuttle stop 520, and that the shuttle stop controller 537 can be moved in direction 539b (e.g., away from the shuttle stop 520) to disengage with the shuttle stop 520.

FIG. 47N further illustrates that half of the jaw (e.g., a transverse half on one side of the device longitudinal axis 476) is shown transparent. As another example, FIG. 47N further illustrates a removable cover on the side of the jaw removed. The removable cover can advantageously improve access to the internal components in the jaws, for example, for repair, replacement, for cleaning, or any combination thereof. As yet another example, FIG. 47N can be a side view of the device 188 such that the controller 537 and the controller track 542 can be visible without taking a cross-section of the device 188.

The jaw shown in FIG. 47N can be the upper jaw. The jaw shown in FIG. 47N can be the lower jaw.

Figure 47O:
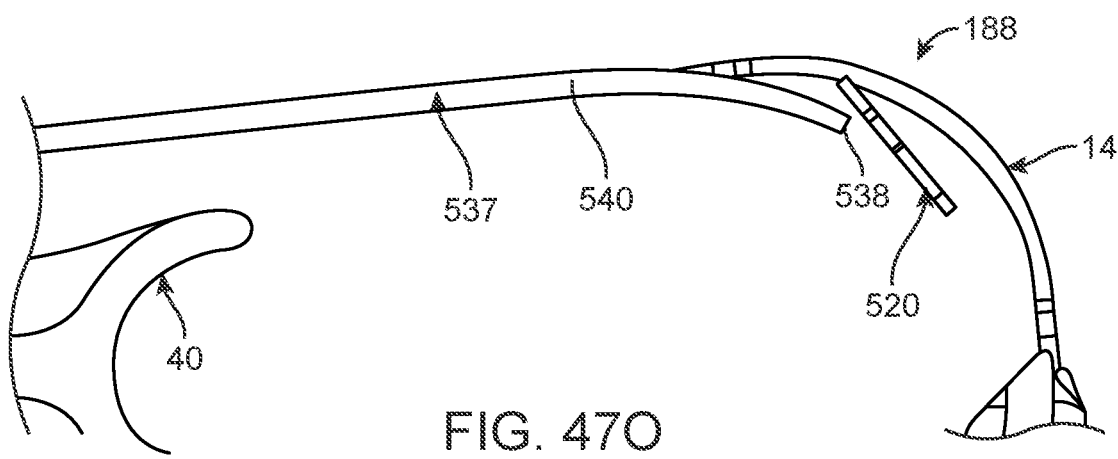
FIG. 47O illustrates a variation of the upper and/or lower jaw with various components in the upper and/or lower jaw with the upper and/or lower jaw shown transparent.

FIG. 47O illustrates the jaw transparent so that the shuttle 14, the shuttle stop 520, and the shuttle stop controller 537 can be seen relative to one another when the shuttle stop 520 and the shuttle 14 engaged with one another, and when the shuttle stop 520 and the shuttle stop engager 538 are not engaged with one another.

Figure 47P:
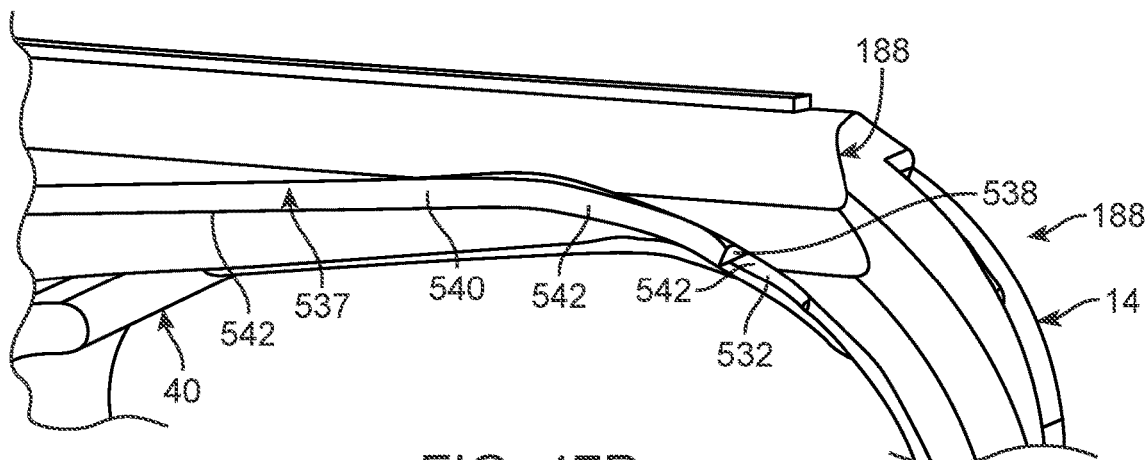
FIG. 47P is a perspective view of FIG. 47N.

FIG. 47P illustrates a perspective view of FIG. 47N with half the jaw (e.g., a transverse half on one side of the device longitudinal axis 476) shown transparent so that the shuttle 14 can be seen. FIG. 47P further illustrates that the distal terminal end of the control arm 540 can be the shuttle stop engager 538.

Figure 47Q:
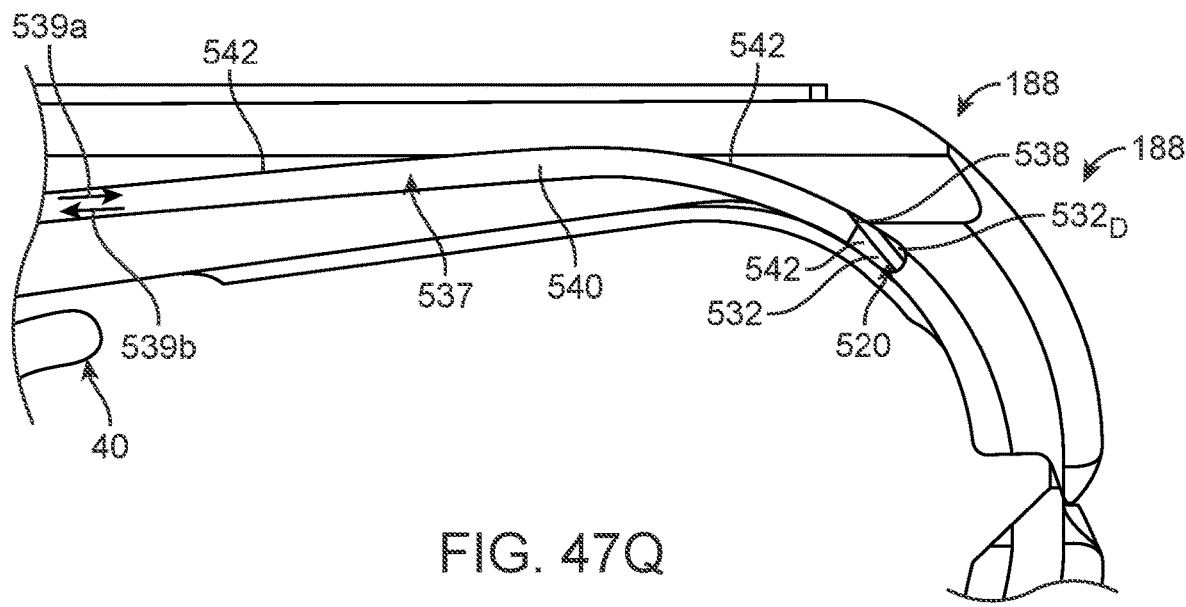
FIG. 47Q illustrates a variation of the upper and/or lower jaw with various components in the upper and/or lower jaw.

FIG. 47Q further illustrates the shuttle stop 520 and the shuttle 14 in contact with one another. As another example, FIG. 47Q further illustrates the shuttle stop 520 and the shuttle 14 not in contact with one another.

FIG. 47Q further illustrates the shuttle stop 520 and the shuttle stop engager 538 engaged with one another. When the user wants to engage the shuttle stop engager 538 with the shuttle stop 520 to release the shuttle 14 from the shuttle stop 520, the control arm 540 can be slid (e.g., translated) forward in the controller track 542 to press the shuttle stop engager 538 against the shuttle stop 520 to deflect the shuttle stop 520, for example, from the shuttle stop first deflected configuration to the shuttle stop neutral configuration, from the shuttle stop first deflected configuration to the shuttle stop second deflected configuration.

Figure 47R:
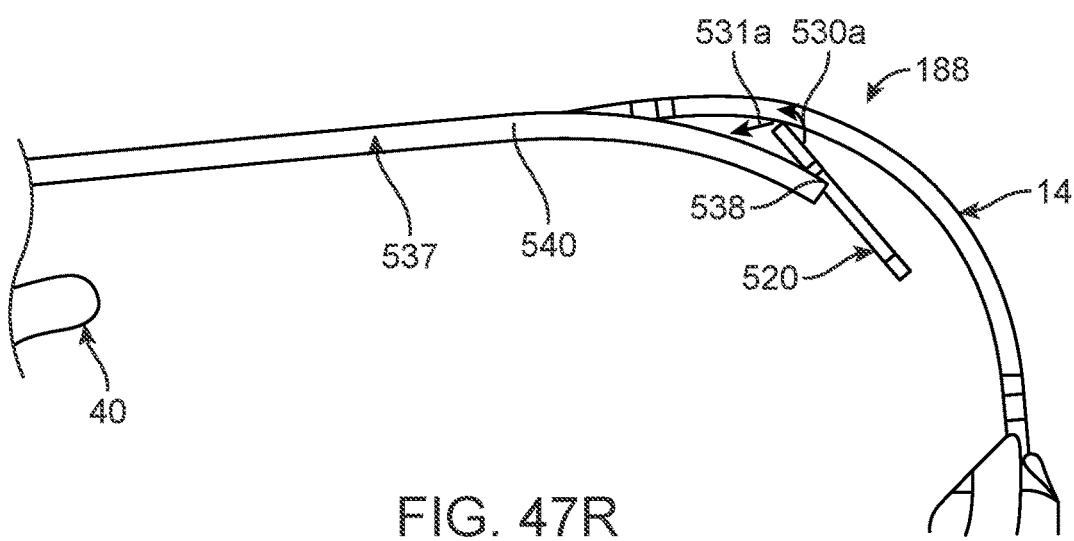
FIG. 47R illustrates a variation of the upper and/or lower jaw with various components in the upper and/or lower jaw with the upper and/or lower jaw shown transparent.

FIG. 47R illustrates the jaw transparent so that the shuttle 14, the shuttle stop 520, and the shuttle stop controller 537 can be seen relative to one another when the shuttle stop 520 and the shuttle stop engager 538 are engaged with one another.

Figure 47S:
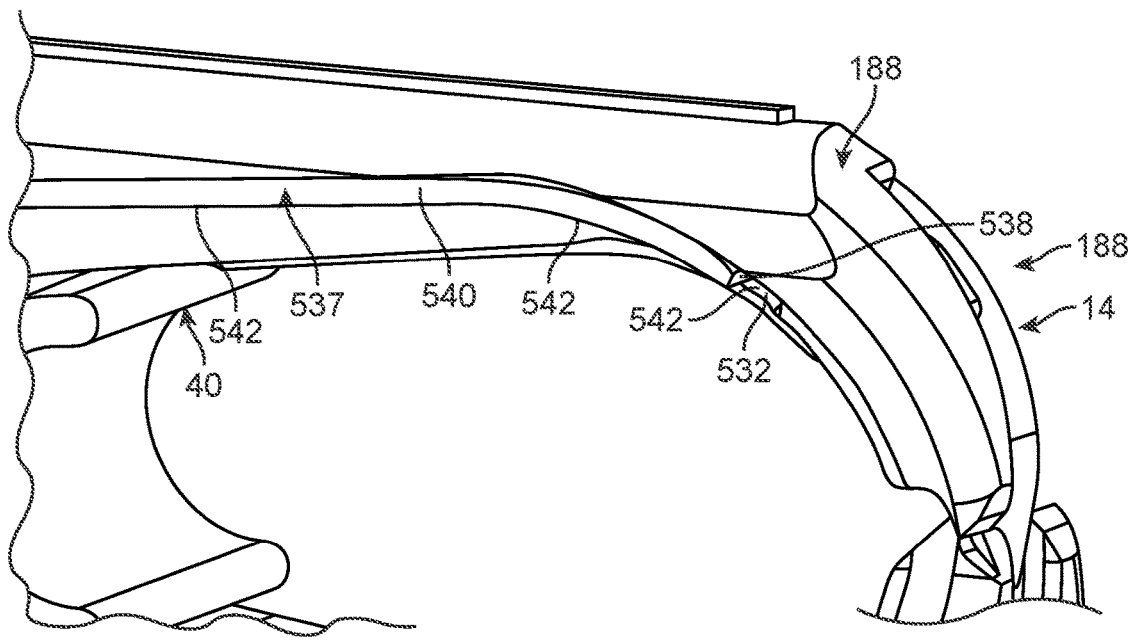
FIG. 47S is a perspective view of FIG. 47Q.

FIG. 47S illustrates a perspective view of FIG. 47Q with half the jaw (e.g., a transverse half on one side of the device longitudinal axis 476) shown transparent so that the shuttle 14 can be seen. FIG. 47S further illustrates that when a first portion of the shuttle stop engager 538 engages with the shuttle stop 538, a second portion of the shuttle stop engager may or may not engage with the shuttle stop 520. For example, FIG. 47S illustrates a second portion of the engager 538 (the portion labeled as 538 in FIG. 47S) does not contact the shuttle stop 520 when the first portion of the shuttle stop engager 538 (the portion obscured by the jaw in FIG. 47S) is in contact with the shuttle stop 520.

Figure 47T:
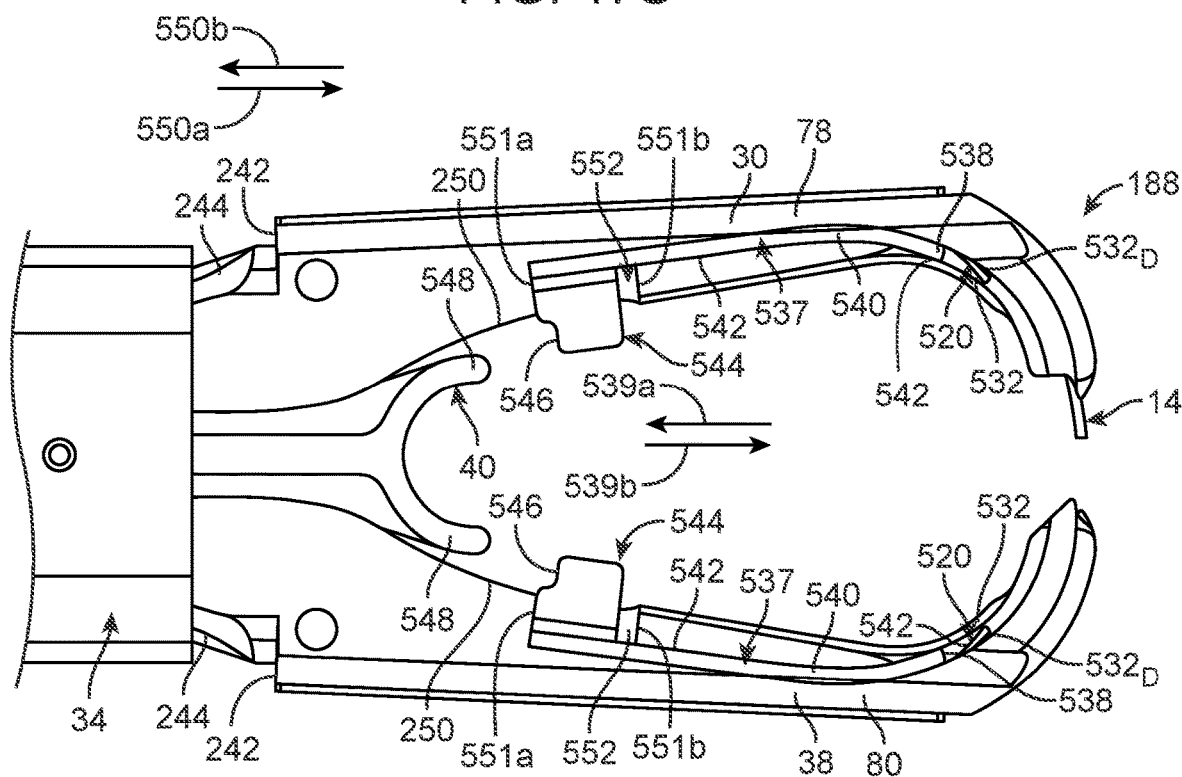
FIG. 47T is a side view of a variation of the device.

FIG. 47T illustrates that the shuttle stop controller 337 can have a proximal engager 544 (also referred to as the shuttle stop controller proximal engager). The proximal engager 544 can be attached to or integrated with the control arm 540. The proximal engager 544 can be on a proximal end of the controller 337. The proximal engager 544 can be on a proximal terminal end of the controller 337. The proximal engager 544 be a protrusion, for example, an arm or a leg, that extends away from the control arm 540 and toward the device longitudinal axis 476. For example, the proximal engager 544 can be a leg with a notch. The jaw control extension 40 or a mechanism in the handle of the device can activate the shuttle stop controller 537 by engaging with the proximal engager 544. The jaw control extension 40 or a mechanism in the handle of the device can deactivate the shuttle stop controller 537 by disengaging from the proximal engager 544. For example, FIG. 47T illustrates that the proximal engager can have a surface 546 that the jaw control extension can engage with. The jaw control extension 40 can have jaw control extension arms 548. The jaw control extension arms 548 can engage with the proximal engager 544, for example, with the surface 546. The surface 546 can be part of the notch of the proximal engager 544. The notch in the proximal engager can be a catch for the jaw control extension 40.

FIG. 47T further illustrates that when the jaws are open, the shuttle stop controller 537 is not engaged with the shuttle stop 520. When the jaws are open, the shuttle stop controller 537 may or may not be in contact with the shuttle stop 520. For example, FIG. 47T illustrates when the jaws are open, the shuttle stop controller 537 is not in contact with the shuttle stop 520.

FIG. 47T further illustrates that when the jaws are open, the jaw control extension 40 is not engaged with the shuttle stop controller 537 (e.g., not engaged with the proximal engager 544 and/or not engaged with the control arm 540). When the jaws are open, the jaw control extension 40 may or may not be in contact with the shuttle stop controller 537 (e.g., not engaged with the proximal engager 544 and/or not engaged with the control arm 540). For example, FIG. 47T illustrates that when the jaws are open, the jaw control extension 40 is not in n contact with the shuttle stop controller 537.

FIG. 47T further illustrates that when the jaws are open, the shuttle stop control 537 can be in a retracted position in the track 542. When the shuttle stop control 537 is in the retracted position in the track 542, a first end of the shuttle stop controller 537 (e.g., a first end of the proximal engager 544) can contact and/or rest against a jaw first surface 551a. When the shuttle stop controller 537 is in the retracted position in the track 542, there can be space 552 (also referred to as a gap) between the proximal engager 544 and a jaw second surface 551b. When the shuttle stop control 537 is in the advanced in the track 542 from the retracted position shown in FIG. 47T, the proximal engager 544 can be advanced through the space 552 until the second end of the proximal engager 544 contacts the jaw second surface 551b. The jaw first surface 551a can limit movement of the shuttle stop controller 537 in direction 539b. For example, when the first end of the shuttle stop controller 537 (e.g., a first end of the proximal engager 544) is in contact with the jaw first surface 551a, the shuttle stop controller 537 can be in a fully retracted position. The jaw second surface 551b can limit movement of the shuttle stop controller 537 in direction 539a. For example, when the second end of the proximal engager 544 is in contact with the jaw second surface 551b, the shuttle stop controller 537 can be in a fully advanced position. The jaw second surface 551b can, for example, prevent the shuttle stop controller 537 from over-deflecting the shuttle stop 520 to release the shuttle stop 520 from its engagement with the shuttle 14.

FIG. 47T further illustrates that the jaws can be advanceable in direction 550a and retractable in direction 550b. The jaws can be moveable in directions 550a and 550b, for example, translatable or slideable in these directions. The jaws can be moveable relative to the compression cover 34 and the jaw control extension 40. When the jaws are moved in directions 550a and 550b, the compression cover 34 and the jaw control extension 40 can be in a fixed position. For example, when the jaws are advanced and retracted in directions 550a and 550b, respectively, the compression cover 34 and the jaw control extension 40 can remain fixed such that the jaws can be advanced and retracted relative to the compression cover 34 and the jaw control extension 40. As another example, when the jaws are moved in directions 550a and 550b, the jaws, the compression cover 34, the jaw control extension 40, or any combination thereof can be moveable in direction 550a and/or in direction 550b. For example, when the jaws are advanced and retracted in directions 550a and 550b, respectively, the compression cover 34 and the jaw control extension 40 can be moveable in directions 550a and/or 550b before, after, or at the same time that the jaws are advanced or retracted.

FIG. 47T further illustrates the jaws in an open configuration, for example, a partially open configuration or a fully open configuration. When the jaws are in a partially open configuration, the jaws can be partially advanced out of the compression cover 34 and over the jaw control extension 40 as shown in FIG. 47T. When the jaws are in a fully open configuration, the jaws can be in a fully advanced position as shown in FIG. 47T. When the jaws are in a partially open configuration or a fully open configuration, the first end of the shuttle stop controller 537 (e.g., a first end of the proximal engager 544) can contact and/or rest against a jaw first surface 551a.

FIG. 47T further illustrates that the shuttle stop controller 537 can ride in the track 542, and that the track 542 can be in the jaws. The track 542 can be on the exterior side of the jaws (e.g., as shown in FIG. 47T) or on the interior of the jaws.

Figure 47U:
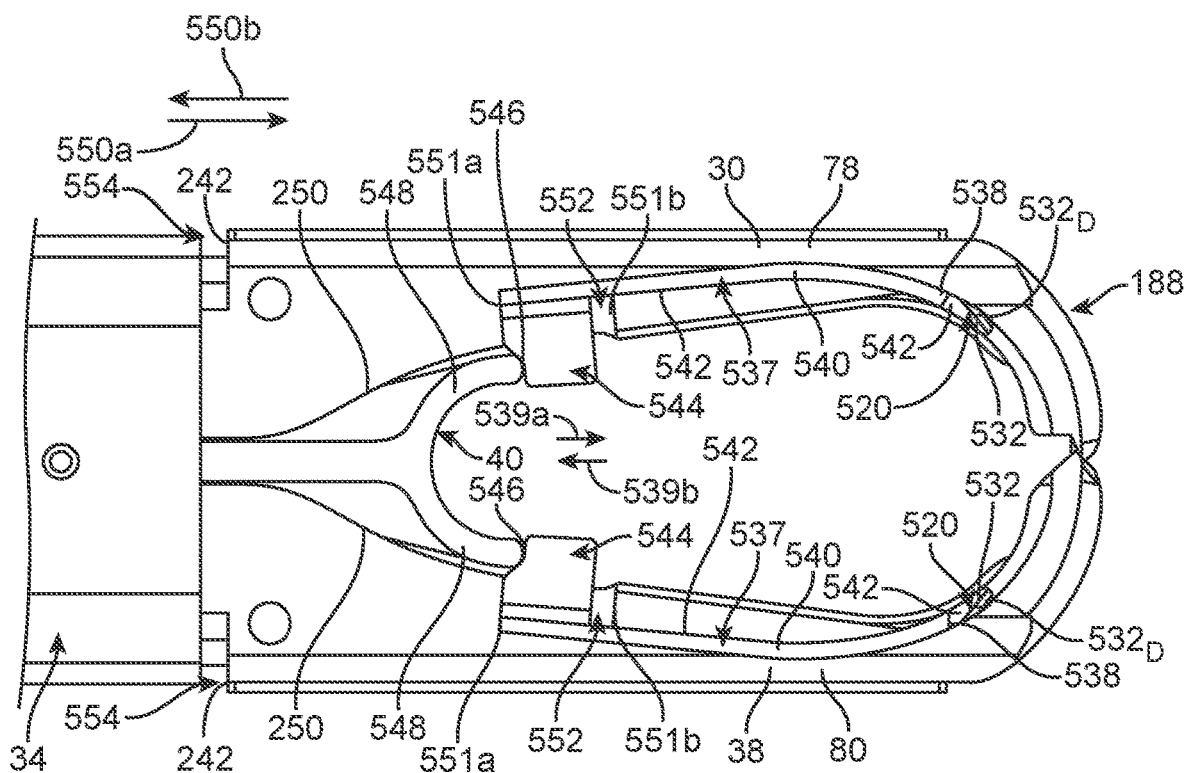
FIG. 47U is a side view of a variation of the device.

FIG. 47U illustrates that as the jaws are closed (e.g., are retracted into the compression cover 34), the jaw control extension 40 can be driven into the proximal engager 544 in the lower and upper jaws. For example, as the jaws are closed, the jaw control extension 40 can passively make contact with and push against the proximal engager 544 in the upper and lower jaws. The retraction of the jaws can thereby drive the shuttle controller 537 into the jaw control extension 40. As another example, FIG. 47U illustrates that as the jaws close (e.g., are retracted into the compression cover 34), the jaw control extension 40 can be driven forward into the proximal engager 540 in the lower and upper jaws. The advancement of the jaw control extension 40 can thereby be driven into the shuttle controller 537. For example, as the jaws close, or after the jaws are closed, the jaw control extension 40 can be advanced out of the compression cover 34 to make contact with and push against the proximal engager 544 in the upper and lower jaws.

FIG. 47U further illustrates that when the jaws are fully closed and in a partially retracted position, there can be a space 554 (also referred to as a gap) between the distal end of the compression cover 40 and the jaw stops 242. When the jaws are fully closed and in a partially retracted position, the jaw control extension 40 can begin to contact the proximal engager 544 (e.g., the surface 546 of the proximal engager 544) that extends from the shuttle stop controller 537. The space 554 can have a longitudinal length (e.g., as measure along the device longitudinal axis 476) of about 0.01 inches to about 0.10 inches, including every 0.01 inch increment within this range (e.g., 0.02 inches).

Figure 47V:
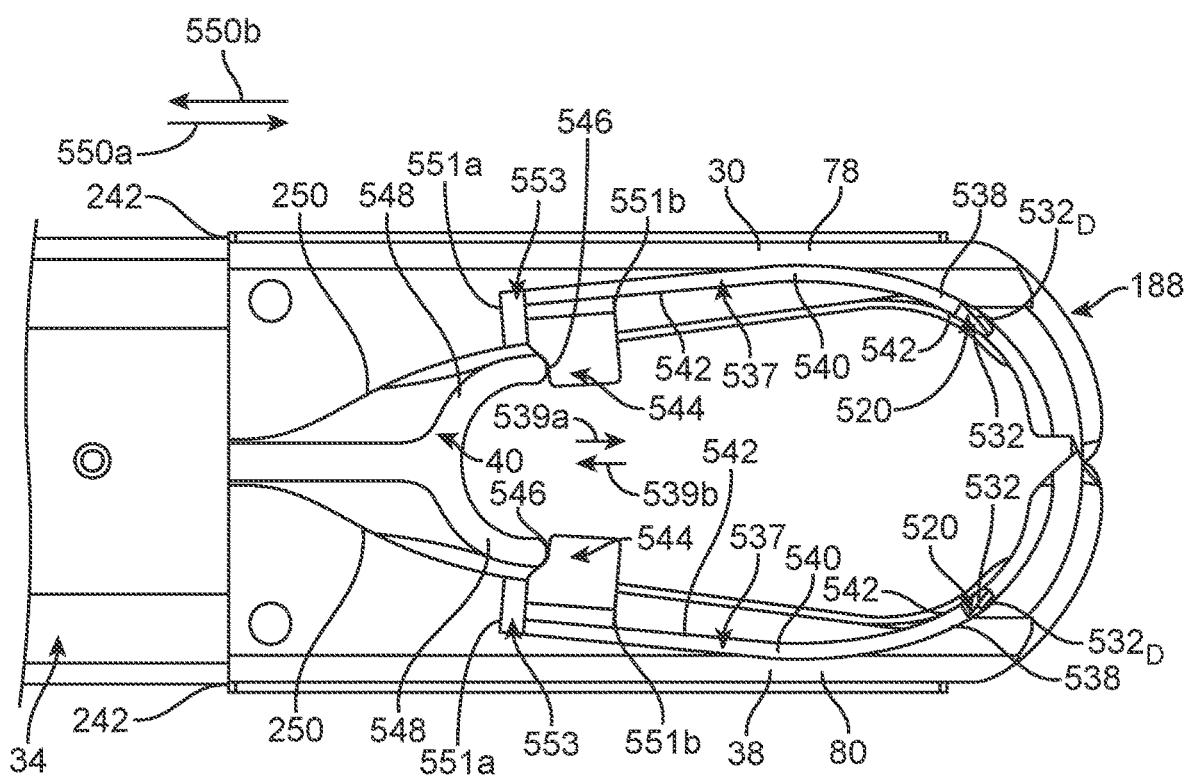
FIG. 47V is a side view of a variation of the device.

FIG. 47V illustrates that when the jaws are fully retracted into the compression cover 34, the jaw stops 242 can contact the distal end of the compression cover 40. As the jaws are fully retracted into the compression cover 34, for example, from the partially retracted position shown in FIG. 47U, the jaws can move in direction 550b (e.g., can move 0.01 inches to 0.10 inches in direction 550b) to close the space 554. As the jaws are retracted into the compression cover 34 the final distance to close the space 554, the jaws can move the shuttle stop controller 537 into the jaw control extension 40 by the same amount. As the jaws are retracted into the compression cover 34 the final distance to close the space 554, the jaw control extension 40 can be driven forward by the same amount (e.g., as caused by relative movement between the jaws and the jaw control extension 40 when the jaw control extension 40 is in a fixed position, or as caused by relative movement between the jaws and the jaw control extension 40 when the jaws are in a fixed position, or as caused by movement of both the jaws and the jaw control extension 40). The tips of the jaw control extension arms 548 can thereby drive the shuttle stop controller 537 forward, flexing and disengaging the shuttle stop 520 from the shuttle 14. This design advantageously allows the shuttle 14 to be automatically disengaged from the shuttle stop 520 once but not before the jaws are fully clamped, where the jaws can be considered fully clamped when the jaws are fully retracted into the compression cover 34 as shown in FIG. 47V.

As another example, once the jaws are partially retracted into the compression cover 34 as shown in FIG. 47U, the compression cover 34 can be moved in direction 550a (e.g., can move 0.01 inches to 0.10 inches in direction 550b) to close the space 554 and fully retract the jaws into the compression cover 34. As the jaws are retracted into the compression cover 34 the final distance to close the space 554, the jaws can move the shuttle stop controller 537 into the jaw control extension 40 by the same amount.

FIG. 47V further illustrates that when the shuttle stop controller 537 is in the advanced position in the track 542, there can be space 553 (also referred to as a gap) between the proximal engager 544 and the jaw first surface 551a. When the shuttle stop control 537 is retracted in the track 542 from the advanced position shown in FIG. 47V, the proximal engager 544 can be retracted through the space 553 until the first end of the proximal engager 544 contacts the jaw first surface 551a. The shuttle stop control 537 can be retracted when the jaws are opened, for example, when the jaws are advanced out of the compression cover 34 and over the jaw control extension 40. When the jaws are opened from a closed configuration, the shuttle stop control 537 can passively retract and return to its retracted position, for example, by sliding in direction 539b in the track 542. As another example, when the jaws are opened from a closed configuration, the jaw control extension 40 or a mechanism in the handle of the device can retract the shuttle stop controller 537 by engaging with the proximal engager 544. For example, the proximal engager 44 and the tip of the jaw control extension arms 548 can be magnetically attracted to one another such that when the jaws are advanced out of the compression cover 34, the jaw control extension 40 can remain attached to the shuttle stop controller 537 as the jaws are advanced. In this way, the jaw control extension 40, while not being retracted itself, can pull the shuttle stop controller 537 back to the retracted position when the jaws are advanced. Other released attachments configurations such as friction fit and snap fit arrangements in addition to or in lieu of the magnets can be used. Such releasable engagements between the jaw control extension and the shuttle stop controller 537 can be overcome when the proximal engager 544 contacts the jaw first surface 551a and the jaws continue to be advanced, for example, to fully open the jaws.

Figure 47W:
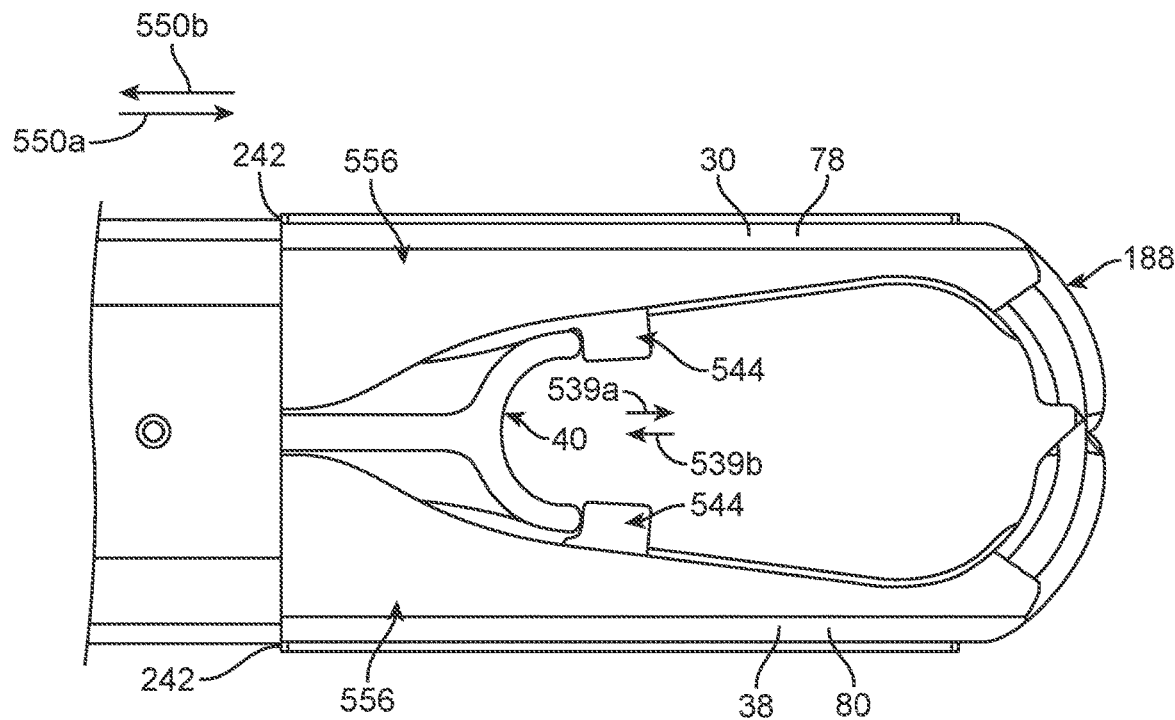
FIG. 47W is a side view of a variation of the device.

FIG. 47W illustrates that a cover 556 can be placed on the external surface of the jaws to contain, shield, and/or protect the shuttle stop controller 537. FIG. 47W illustrates a portion of the proximal engager 544 can be left exposed when the cover 556 is on the jaws.

Figure 48A:
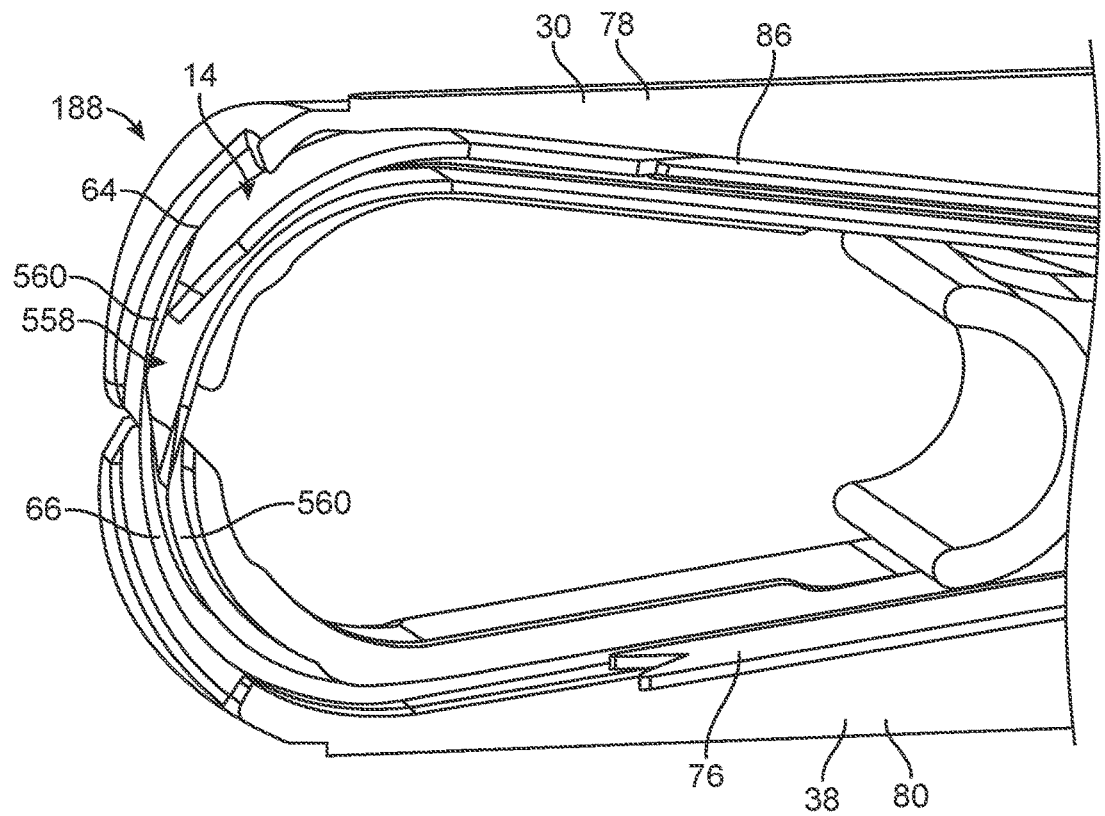
FIG. 48A illustrates a variation of the device having a piercer.

FIG. 48A illustrates that the device 188 can have a piercer 558. The piercer 558 can have a sharp tip. The piercer 558 can have a sharp point. Each jaw can house a sharp nitinol or other flexible tape with a sharp point (also referred to as the piercer 558). The piercer 558 can be, for example, a piercer tape. Each jaw can have a piercer track 560 that the piercer 558 can be moveable in. For example, the piercer 558 can be translatable or slideable in the piercer track 560. The piercer 558 can be advanceable and retractable in the piercer track 560. The first jaw can have a piercer track 560. The second jaw can have a piercer track 560.

The piercer 558 can pre-pierce tissue, for example, to provide a pathway for the shuttle 14 to pass through. When shuttle 14 is retracted and jaws are closed, the piercer 558 can be driven forward, piercing the tissue. The piercer 558 can then be retracted and the shuttle 14 can be passed between the jaws.

The device 188 can have one piercer 558. The piercer 558 can be in the first jaw or the second jaw. For example, FIG. 48A illustrates that the device 188 can have one piercer 558. The piercer 558 can be in the lower or upper jaw. For example, FIG. 48A illustrates that the piercer 558 can be in the upper jaw.

The device 188 can have two piercers 558, for example, a first piercer and a second piercer. For example, FIG. 48A illustrates that the upper jaw (e.g., jaw 30, 78) can have the piercer 558. The piercer 558 can be extended into the lower jaw (e.g., 38, 80) to pierce the tissue, and then retracted back into the upper jaw to allow room for the shuttle 14 space to pass into the lower jaw.

FIG. 48A further illustrates that the shuttle 14 can be radially outside of the piercer 558. As another example, the piercer 558 can be radially outside of the piercer 558.

Figure 48B:
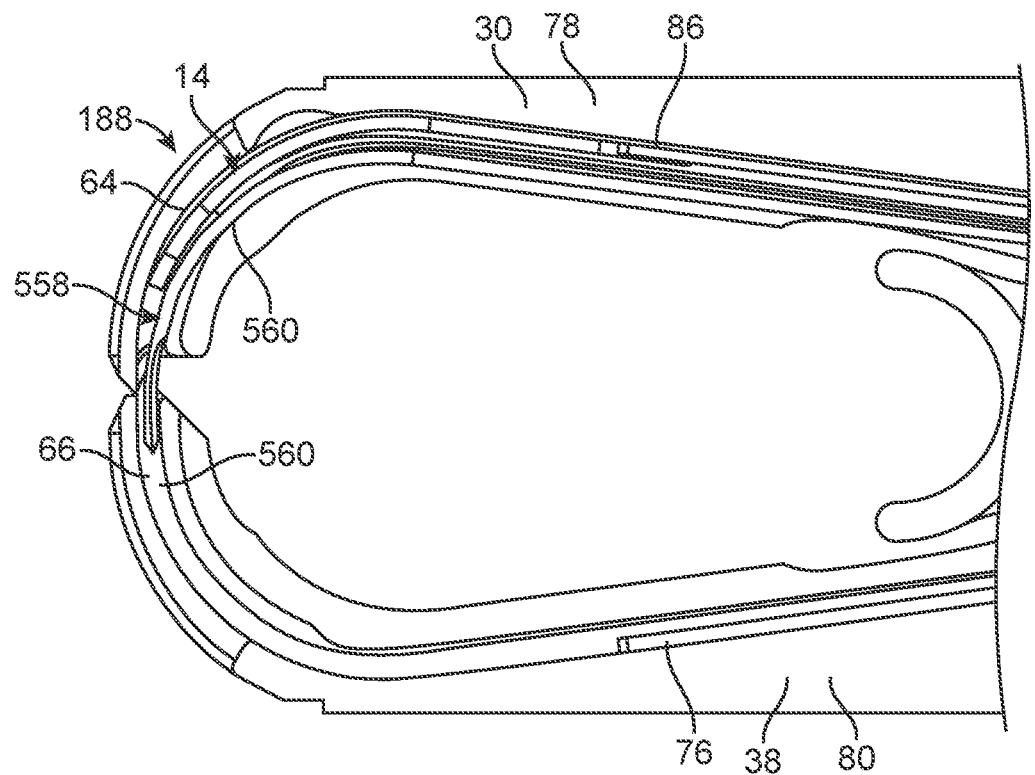
FIG. 48B illustrates a variation of the device having a piercer.

FIG. 48B illustrates the piercer 558 in a partially advanced position.

Figure 48C:
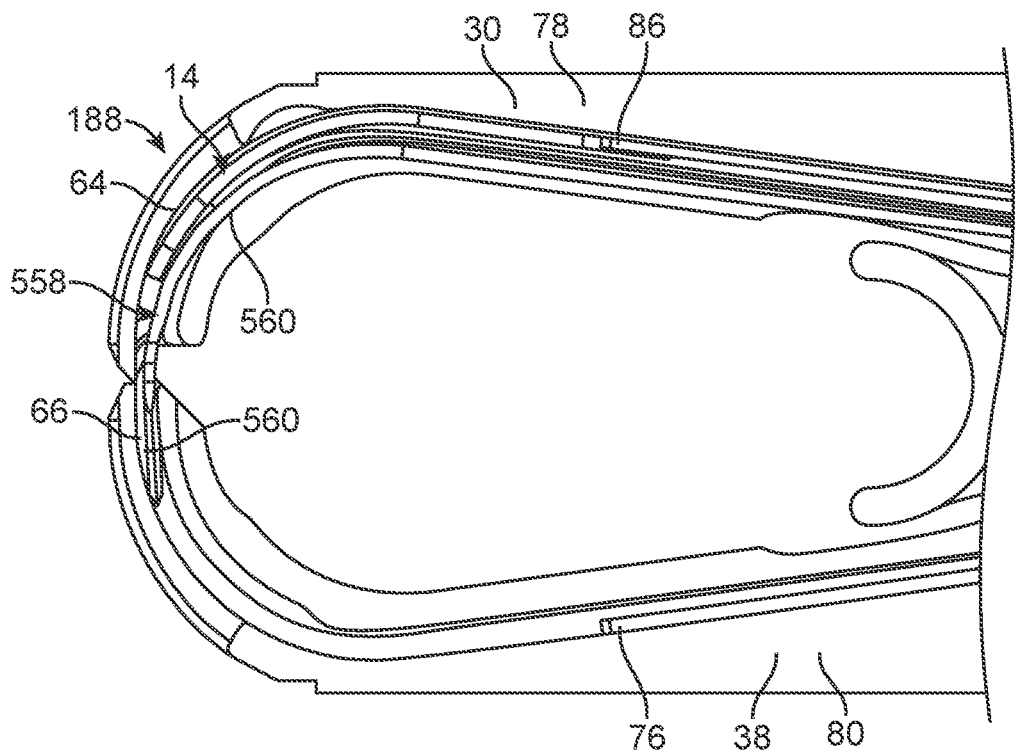
FIG. 48C illustrates a variation of the device having a piercer.

FIG. 48C illustrates the piercer 558 in a fully advanced position.

Figure 48D:
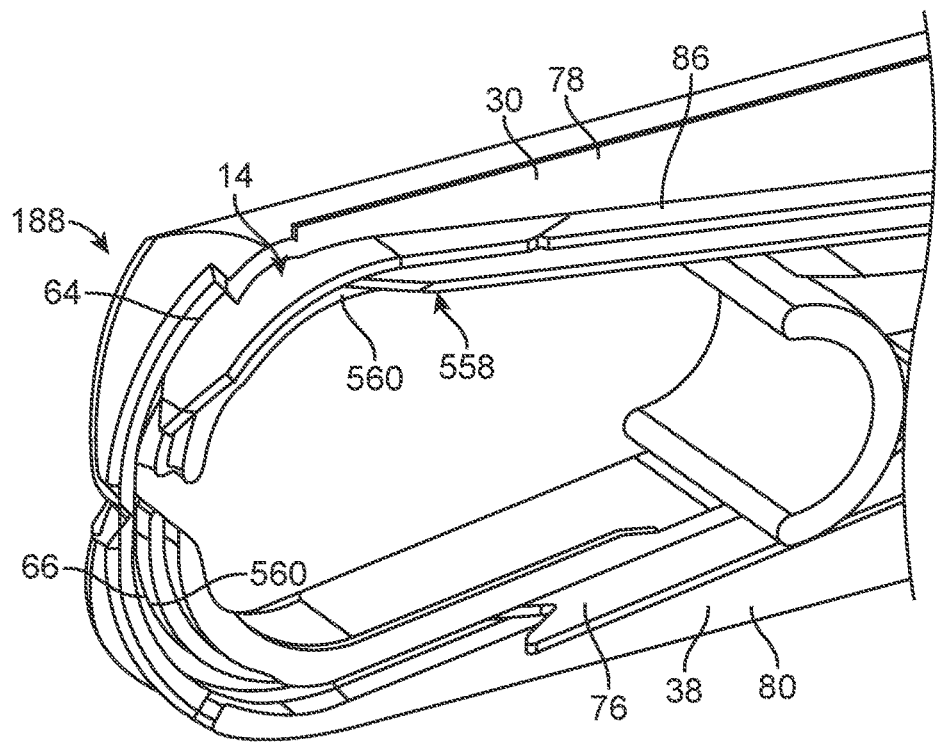
FIG. 48D illustrates a variation of the device having a piercer.
Figure 48E:
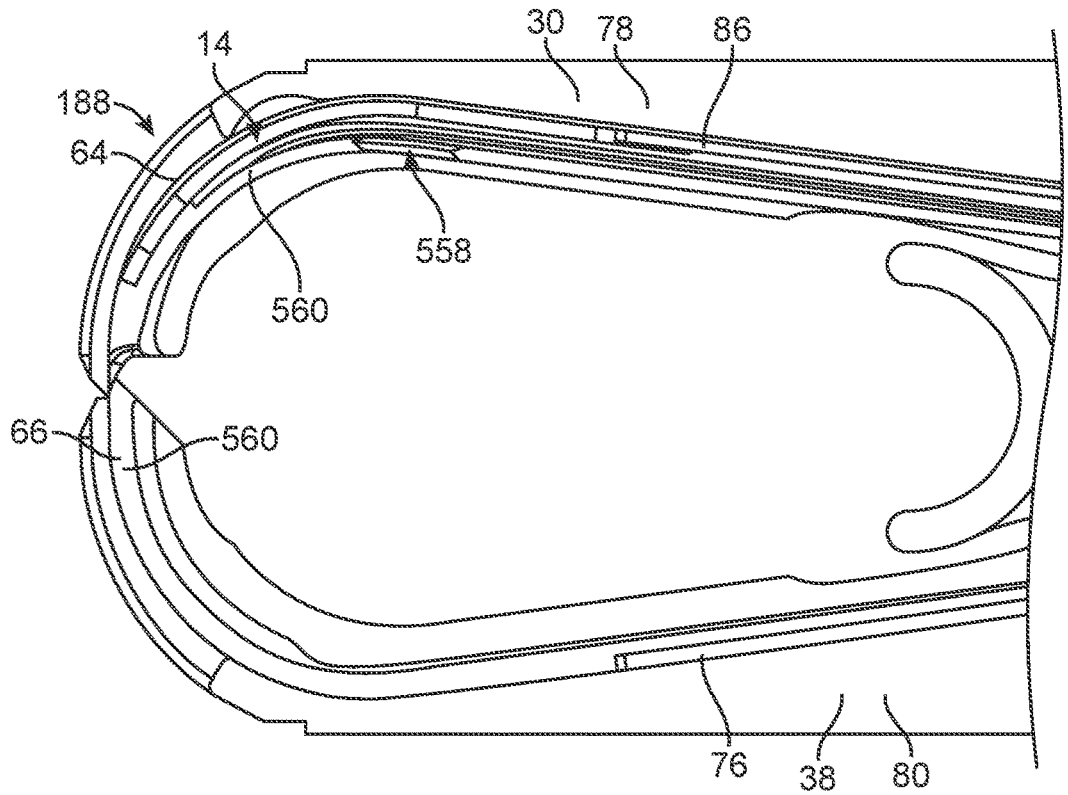
FIG. 48E illustrates a variation of the device having a piercer.

FIGS. 48D and 48E illustrates the piercer in a fully retracted position.

Figure 48F:
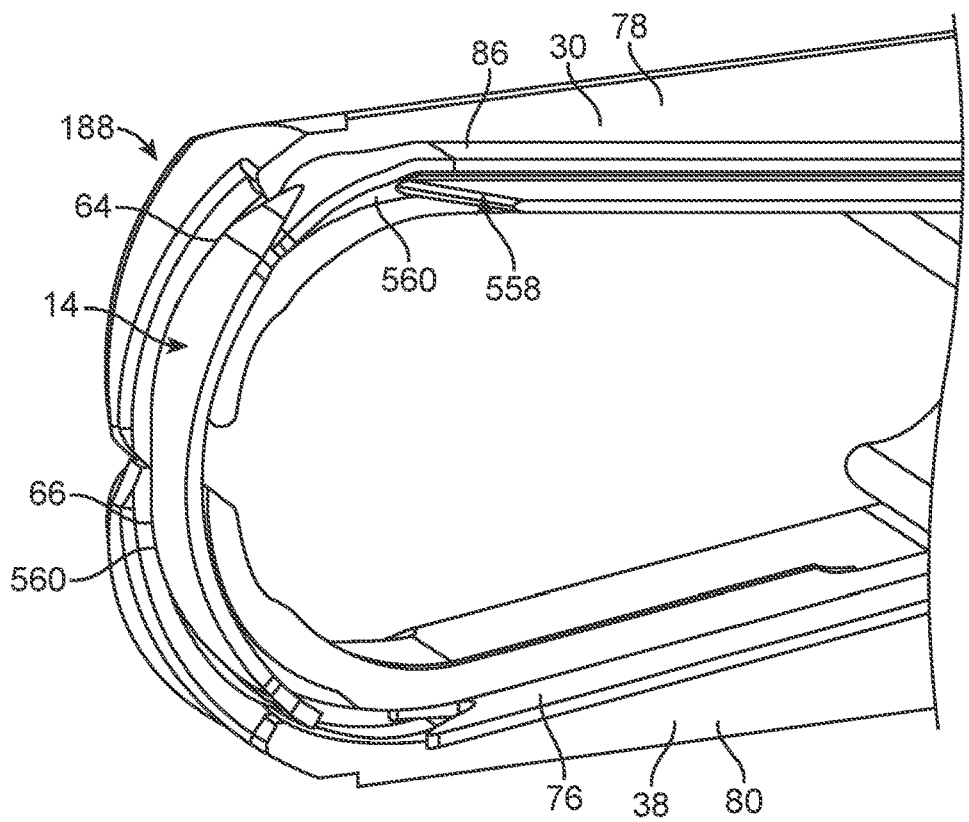
FIG. 48F illustrates a variation of the device having a piercer.
Figure 48G:
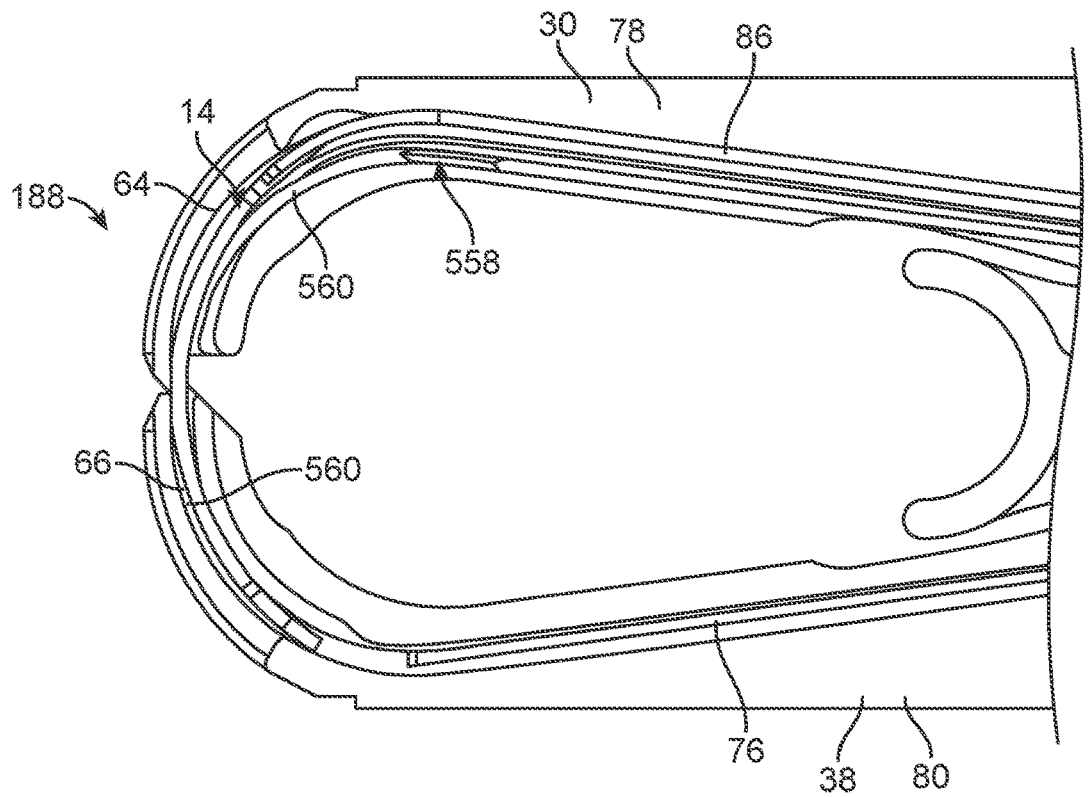
FIG. 48G illustrates a variation of the device having a piercer.

FIGS. 48F and 48G illustrate the shuttle 14 being passed from one jaw to the other after the piercer 558 is advanced to pierce the tissue and then retracted (e.g., fully retracted) to allow the shuttle 14 to be passed between the jaws.

Figure 48H:
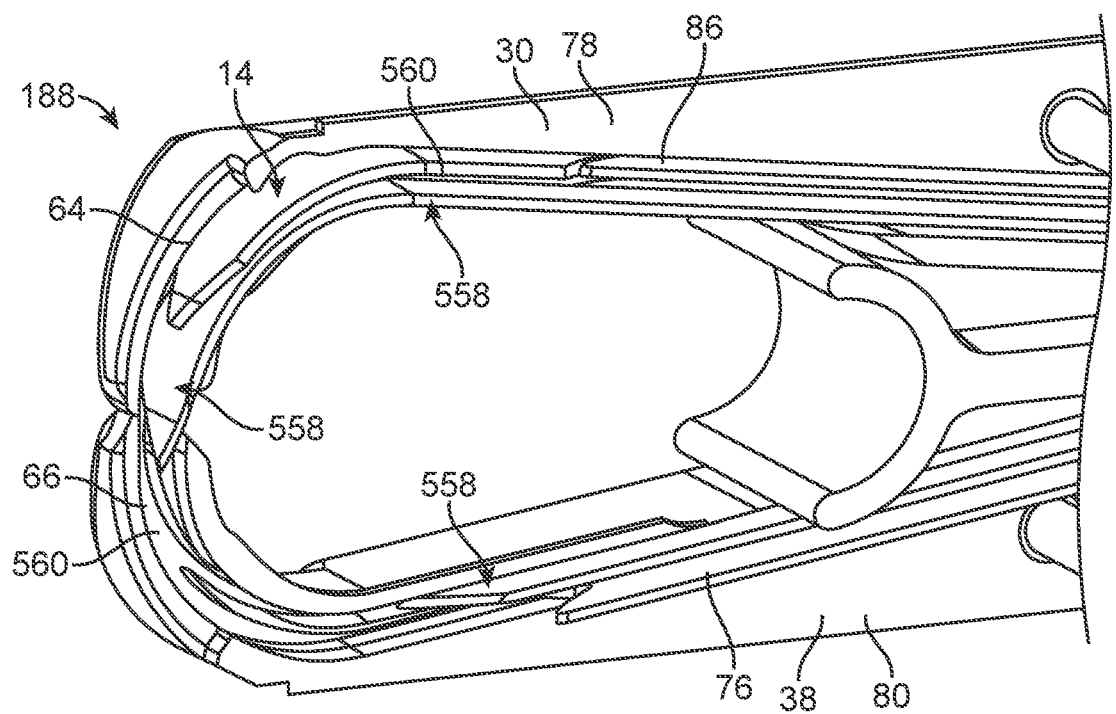
FIG. 48H illustrates a variation of the device having two piercers.
Figure 48I:
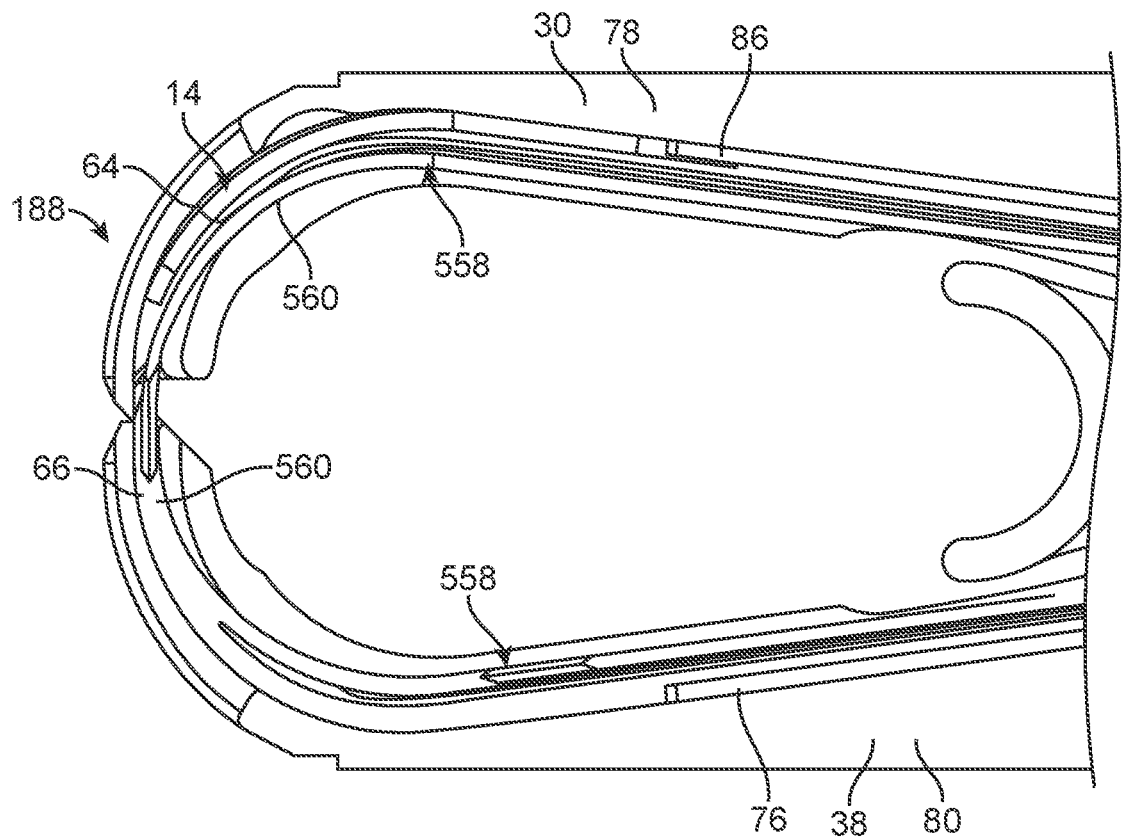
FIG. 48I illustrates a variation of the device having two piercers.

FIGS. 48H and 48I illustrate that the device 188 can have a first piercer 558 in the upper jaw and a second piercer 558 in the second jaw.

FIGS. 48A-48I further illustrate that the piercer track 560 can merge with the shuttle track in the lower and upper jaws, for example, so that the shuttle 14 can go through the same hole in the tissue that the piercer 558 created. As another example, the piercer track 560 and the shuttle track in the lower and upper jaws may not merge in the jaws, where the exit angles from the jaw(s) of the piercer 558 and the exit angles from the jaws of the shuttle 14 can cross such that there is less tissue for the shuttle 14 to pierce through after the piercer 558 pre-pierces the tissue. In such cases, the path of the shuttle 14 and the path of the piercer 558 can cross within space between the jaws.

FIG. 49A illustrates that the male stops 412 can have a male stop first longitudinal end $412_{FE}$ and a male stop second longitudinal end $412_{SE}$, and that the male stop first and second longitudinal ends $412_{FE}$, $412_{SE}$ can have different sizes and/or shapes as each other. All or a portion of the male stop first longitudinal end $412_{FE}$ can be, for example, smaller or larger than a portion of the male stop second longitudinal end $412_{SE}$ along one or multiple dimensions of the male stops 412. For example, FIG. 49A illustrates that a portion of the male stop second longitudinal end $412_{SE}$ can be larger (e.g., wider, thicker) than a portion of the male stop first longitudinal end $412_{FE}$ along one or multiple dimensions (e.g., width, thickness) of the male stops 412. FIG. 49A illustrates, for example, that the male stops 412 can have a hammerhead shape (also referred to as a T-shape) that has a proximal end (also referred to as the male stop first longitudinal end $412_{FE}$) that is smaller (e.g., narrower) than the distal end (also referred to as the male stop second longitudinal end $412_{SE}$).

The male stop first longitudinal end $412_{FE}$ and the male stop second longitudinal end $412_{SE}$ can be first and second longitudinal halves of the male stops 412. The male stop first and second longitudinal ends $412_{FE}$, $412_{SE}$ can have the same longitudinal length. For example, FIG. 49A illustrates that the male stop first longitudinal end $412_{FE}$ can include a first portion of the narrow section of the hammerhead shape and that the male stop second longitudinal end $412_{SE}$ can include a second portion of the narrow section of the hammerhead shape and the wide section of the hammer head shape. The male stop first and second longitudinal ends $412_{FE}$, $412_{SE}$ can thereby form the T-shape, with the male stop first longitudinal end $412_{FE}$ forming the base of the T-shape and with the male stop second longitudinal end $412_{SE}$ forming the top of the T-shape.

FIG. 49A further illustrates that the male stops 412 can have multiple sections $412_S$ (also referred to as male stop sections $412_S$) having different sizes and/or shapes as each other, including for example, 2-10 or more sections $412_S$, including every 1 section increment within this range (e.g., 2 sections, 3 sections, 10 sections). For example, FIG. 49A illustrates that the male stops 412 can have a male stop first section $412_{S1}$ and a male stop second section $412_{S2}$. The male stop first section $412_{S1}$ can have a different size and/or shape as the male stop second section $412_{S2}$. For example, FIG. 49A illustrates that the male stop first section $412_{S1}$ can be the base of the T-shape and the male top second section $412_{S2}$ can be the top of the T-shape. The male stop first and second sections $412_{S1}$, $412_{S2}$ can have one or multiple different dimensions as each other. For example, the male stop first section $412_{S1}$ can be longer, wider, and/or thicker than the male stop second section $412_{S2}$, or vice versa. The male stop second section $412_{S2}$ can be longer, wider, and/or thicker than the male stop first section $412_{S1}$, or vice versa. For example, FIG. 49A illustrates that the male stop first section $412_{S1}$ can be narrower than the male stop second section $412_{S2}$. As another example, FIG. 49A illustrates that the male stop first section $412_{S1}$ can be longer and narrower than the male stop second section $412_{S2}$, whereby some of the male stop first section $412_{S1}$ is part of the male stop first longitudinal end $412_{FE}$, some of the male stop first section $412_{S1}$ is part of the male stop second longitudinal end $412_{SE}$, and all of the male stop second section $412_{S2}$ is part of the male stop second longitudinal end $412_{SE}$. The multiple sections $412_S$ can be attached to or integrated with each other. The sections $412_S$ can be, for example, monolithically formed with each other. The male stops 412 and the shuttle body 160 (also referred to as the shuttle spine 160) can be a monolithic structure.

Relative to male stops 412 that have a straight shape or a straight diving board design (e.g., as shown in FIGS. 33A-36C), male stops 412 that have a distal end that is larger (e.g., wider) than their proximal end (e.g., the hammerhead shape shown in FIG. 49A) can increase the retention force of the male stops 412 in the female stops 416 while keeping the bending force of the male stops 412 the same relative to a straight shape (e.g., the straight shape shown in FIGS. 33A-36C). The wider distal end can increase the surface area of the male stops 412 that engages with the female stops 416, and the narrower proximal end can keep the deflection force of the male stops 412 the same (e.g., relative to the straight male stops 412 in FIGS. 33A-36C that have male stops 412 with proximal and distal ends of equal width). As another example, the larger surface area of the wide distal end of the hammerhead shape can advantageously increase the tactile feedback to the user of the device 188 by increasing the drag force into and out of the female stop 416.

FIG. 49A further illustrates that the male stops 412 can have a male stop first terminal end $412_{TE1}$ and a male stop second terminal end $412_{TE2}$. The male stops 412 can be attached to, integrated with, or integrally formed with the shuttle 14 such that the male stop first terminal end $412_{TE1}$ can be flush with or coincident with the shuttle body 160. The male stops 412 can be, for example, extensions of the shuttle body 160 that extend away from and/or along the shuttle longitudinal axis $14_{A1}$. For example, FIG. 49A illustrates that the male stops 412 can be extensions of the shuttle body 160 that extend away from the shuttle longitudinal axis $14_{A1}$. The male stop second terminal end $412_{TE2}$ can be an edge, a surface, or both. The edge can be straight, curved, or both. The surface can be straight, curved, or both. For example, FIG. 49A illustrates that the male stop second terminal end $412_{TE2}$ can be a flat surface. FIG. 49A further illustrates that the male stop first section $412_{S1}$ can have a male stop first section first terminal end $412_{S1TE1}$ and a male stop first section second terminal end $412_{S1TE2}$, and that the male stop second section $412_{S2}$ can have a male stop second section first terminal end $412_{S2TE1}$ and a male stop second section second terminal end $412_{S2TE2}$. As shown in FIG. 49A, the male stop first section first terminal end $412_{S1TE1}$ can be the same as the male stop first terminal end $412_{TE1}$, and the male stop second section second terminal end $412_{S2TE2}$ can be the same as the male stop second terminal end $412_{TE2}$. As further shown in FIG. 49A, the male stop first section second terminal end $412_{S1TE2}$ can terminate where the male stop second section first terminal end $412_{S2TE1}$ begins (e.g., as designated by the dashed line labeled as the male stop first section second terminal end $412_{S1TE2}$ and the male stop second section first terminal end $412_{S2TE1}$ in FIG. 49A).

FIG. 49A further illustrates that the male stop second longitudinal end $412_{SE}$ can be closer to a longitudinal center of the shuttle 14 (e.g., the suture holder 18) than the male stop first longitudinal end $412_{FE}$. The male stop second longitudinal end $412_{SE}$ can be closer to the suture holder 18 than the male stop first longitudinal end $412_{FE}$. The male stop first longitudinal end $412_{FE}$ can be closer to the shuttle tip 164 than the male stop second longitudinal end $412_{SE}$. FIG. 49A further illustrates that the male stop second section $412_{S2}$ can be closer to the longitudinal center of the shuttle 14 than the male stop first section $412_{S1}$. The male stop second section $412_{S2}$ can be closer to the suture holder 18 than the male stop first section $412_{S1}$. The male stop first section $412_{S1}$ can be closer to the shuttle tip 164 than the male stop second section $412_{S2}$. FIG. 49A further illustrates that the male stop second terminal end $412_{TE2}$ can be closer to the longitudinal center of the shuttle 14 than the male stop first terminal end $412_{TE1}$. The male stop second terminal end $412_{TE2}$ can be closer to the suture holder 18 than the male stop first terminal end $412_{TE1}$. The male stop first terminal end $412_{TE1}$ can be closer to the shuttle tip 164 than the male stop second terminal end $412_{TE2}$.

One or multiple portions of the male stops 412 can be engageable with a female stop 416. For example, the male stop second terminal end $412_{TE2}$ can be engageable with a female stop 416, a surface between the male stop first terminal end $412_{TE1}$ and the male stop second terminal end $412_{TE2}$ (e.g., the male surface 414) can be engageable with a female stop 416, an edge between the male stop first terminal end $412_{TE1}$ and the male stop second terminal end $412_{TE2}$ can be engageable with a female stop 416, or any combination thereof can be engageable with a female stop 416. For example, FIG. 49A illustrates that the male surface 414 can be engageable with a female stop 416. The male stop first section $412_{S1}$ and/or the male stop second section $412_{S2}$ can be engageable with a female stop 416. For example, FIG. 49A illustrates that the male stop second section $412_{S2}$ can be engageable with a female stop 416.

The male stop first section $412_{S1}$ can be bendable or deflectable, for example, about the base of the male stops 412 at or near the male stop first terminal end 412mi and/or anywhere along the length of the male stop first section $412_{S1}$. For example, when the male stop second section $412_{S2}$ is moved into contact with a female stop 416, the male stop first section $412_{S1}$ can deflect to allow the male stop 412 to pass into the female stop 416. In this way, the female stop 416 can passively retain the shuttle 14 in a jaw of the device 188 by passively retaining the male stop 412. For example, the deflection of the male stop first section $412_{S1}$ can allow male stop 412 to pass into and out of a female stop 416, and can, for example, allow the male stop second section $412_{S2}$ to engage with and disengage with the female stop 416. In this way the male stops 412 can be a spring which can be deflectable from a neutral or a non-neutral configuration (e.g., the configuration shown in FIG. 49A) to a compressed configuration or tensed configuration.

FIG. 49A further illustrates that the shuttle 14 can have the shuttle longitudinal axis $14_{A1}$, a shuttle first transverse axis $14_{A2}$, and a shuttle second transverse axis $14_{A3}$.

The shuttle longitudinal axis $14_{A1}$ can be a center longitudinal axis of the shuttle 14 (e.g., as shown in FIG. 49) or can be offset from the center longitudinal axis of the shuttle 14. The length of the shuttle 14 (e.g., the length of the shuttle 14 as measured between the two terminal tips 165) can be measured along the shuttle longitudinal axis $14_{A1}$ or along an axis parallel to the shuttle longitudinal axis $14_{A1}$. For clarity with the other labels shown in FIG. 49A, only a portion of the shuttle longitudinal axis $14_{A1}$ is shown in FIG. 49A. The rest of the shuttle longitudinal axis $14_{A1}$ in FIG. 49A is shown transparent for illustrative purposes only. The shuttle longitudinal axis $14_{A1}$ can extend along the length of the shuttle 14, for example, as shown by the shuttle longitudinal axis 157 (also referred to as the shuttle longitudinal axis $14_{A1}$) in FIG. 12A or by the shuttle longitudinal axis $14_{A1}$ shown in FIG. 49D.

The shuttle first transverse axis $14_{A2}$ can be a center first transverse axis of the shuttle 14 or, as shown in FIG. 49A, can be offset from the center first transverse axis of the shuttle 14. The shuttle width 292 can be measured along the shuttle first transverse axis $14_{A2}$ or along an axis parallel to the shuttle first transverse axis $14_{A2}$. The shuttle first transverse axis $14_{A2}$ can be perpendicular to the shuttle longitudinal axis $14_{A1}$. The shuttle first transverse axis $14_{A2}$ can be straight or curved. For example, FIG. 49A illustrates that the shuttle first transverse axis $14_{A2}$ can be straight. When the shuttle first transverse axis $14_{A2}$ is curved, the shuttle 14 can have a first side (e.g., top side) that is convex and a second side (e.g., bottom side) of the shuttle 14 that is concave, or vice versa. A curved shuttle first transverse axis $14_{A2}$ can have a radius of curvature. Having a shuttle 14 that has a concave side and a convex side can advantageously inhibit or prevent lateral movement of the shuttle 14 as the shuttle 14 is advanced through tissue, and/or can promote longitudinal movement of the shuttle 14 as the shuttle 14 is advanced through tissue.

The shuttle second transverse axis $14_{A3}$ can be a center second transverse axis of the shuttle 14 or, as shown in FIG. 49A, can be offset from the center second transverse axis of the shuttle 14. A shuttle thickness $14_T$ can be measured along the shuttle second transverse axis $14_{A3}$ or along an axis parallel to the shuttle second transverse axis $14_{A3}$. The shuttle thickness $14_T$ can be the same as or different from the shuttle tip thickness 408. For example, the shuttle thickness $14_T$ can be equal to (e.g., as shown in FIG. 49A), greater than, or less than the shuttle tip thickness 408. The shuttle second transverse axis $14_{A3}$ can be perpendicular to the shuttle longitudinal axis $14_{A1}$. The shuttle second transverse axis $14_{A3}$ can be perpendicular to the shuttle first transverse axis $14_{A2}$. The shuttle second transverse axis $14_{A3}$ can be straight or curved. For example, 49A illustrates that the shuttle second transverse axis $14_{A3}$ can be straight.

FIG. 49A further illustrates that the male stops 412 can have a male stop longitudinal axis $412_{A1}$, a male stop first transverse axis $412_{A2}$, and a male stop second transverse axis $412_{A3}$.

The male stop longitudinal axis $412_{A1}$ can be straight and/or curved. For example, FIG. 49A illustrates that when the male stops 412 are in a neutral position, the male stop longitudinal axis $412_{A1}$ can be curved in the male stop first longitudinal end $412_{FE}$ and can be straight in the male stop second longitudinal end $412_{SE}$. The male stop longitudinal axis $412_{A1}$ can be a center longitudinal axis that extends down the middle of the male stops 412. The male stop longitudinal axis $412_{A1}$ can be in the same plane as the shuttle longitudinal axis $14_{A1}$. The male stops 412 can be symmetrical or asymmetrical about the male stop longitudinal axis $412_{A1}$. For example, FIG. 49A illustrates that the male stops 412 can be symmetrical about the male stop longitudinal axis $412_{A1}$. The length of the male stops 412 can be measured along the male stop longitudinal axis $412_{A1}$, for example, between the male stop first terminal end $412_{TE1}$ and the male stop second terminal end $412_{TE2}$. As further shown in FIG. 49A, the base of the male stop longitudinal axis $412_{A1}$ can extend onto and/or extend from the shuttle body 160. The portion of the male stop longitudinal axis $412_{A1}$ that extends onto the shuttle body 160 can be coincident or parallel to the shuttle longitudinal axis $14_{A1}$.

The male stop first transverse axis $412_{A2}$ can be straight and/or curved. The male stop first transverse axis $412_{A2}$ can be perpendicular to the male stop longitudinal axis $412_{A1}$. The male stop first transverse axis $412_{A2}$ can be perpendicular to the shuttle longitudinal axis (e.g., shuttle longitudinal axis $14_{A1}$). The male stops 412 can be symmetrical or asymmetrical about the male stop first transverse axis $412_{A2}$. For example, FIG. 49A illustrates that the male stops 412 can be asymmetrical about the male stop first transverse axis $412_{A2}$. The width of the male stops 412, for example, the width of the male stop first section $412_{S1}$ and the width of the male stop second section $412_{S2}$, can be measured along the male stop first transverse axis $412_{A2}$. The shuttle width 292 can be measured along the shuttle first transverse axis $14_{A2}$ or along an axis parallel to the shuttle first transverse axis $14_{A2}$. The male stop second terminal end $412_{TE2}$ can be, for example, parallel to the shuttle first transverse axis $14_{A2}$ (e.g., as shown in FIG. 49A). For example, the flat surface of the male stop second terminal end $412_{TE2}$ can be parallel to the shuttle first transverse axis $14_{A2}$.

The male stop second transverse axis $412_{A3}$ can be straight and/or curved. The male stop second transverse axis $412_{A3}$ can be perpendicular to the male stop longitudinal axis $412_{A1}$. The male stop second transverse axis $412_{A3}$ can be perpendicular to the male stop first transverse axis $412_{A2}$. The male stops 412 can be symmetrical or asymmetrical about the male stop second transverse axis $412_{A3}$. For example, FIG. 49A illustrates that the male stops 412 can be symmetrical about the male stop second transverse axis $412_{A3}$ (e.g., a first half of the T-shape can be on a first side of the male stop second transverse axis $412_{A3}$ and a second half of the T-shape can be on a second side of the male stop second transverse axis $412_{A3}$). The thickness of the male stops 412 can be measured along the male stop second transverse axis $412_{A3}$.

FIG. 49A further illustrates that the male stops 412 can extend from the shuttle body 160. For example, FIG. 49A illustrates that the male stops 412 can extend from the shuttle body 160 into and/or over a suture hole (e.g., suture holes 404a, 404b), for example, from the male stop first terminal end $412_{TE1}$ to the male stop second terminal end $411_{TE2}$.

FIG. 49A illustrates, for example, that the male stops 412 can extend away from the shuttle body 160 (e.g., extend away from shuttle longitudinal axis $14_{A1}$), for example, along the male stop longitudinal axis $412_{A1}$. The male stops 412 can extend radially and/or longitudinally away from the shuttle longitudinal axis $14_{A1}$ along the male stop longitudinal axis $14_{A1}$. As shown in FIG. 49A, the male stops 412 can be radial male stops that extend radially away from the shuttle longitudinal axis $14_{A1}$, for example, along the male stop longitudinal axis $412_{A1}$. As another example, FIG. 49A illustrates that the male stops 412 can be radial male stops that extend radially away from the shuttle longitudinal axis $14_{A1}$ and longitudinally along the male stop longitudinal axis $412_{A1}$. One or both of the male stop first and second longitudinal ends $412_{FE}$, $412_{SE}$ can extend away from the shuttle body 160 and/or away from the shuttle longitudinal axis $14_{A1}$. For example, FIG. 49A illustrates that both the male stop first and second longitudinal ends $412_{FE}$, $412_{SE}$ can extend radially away from the shuttle longitudinal axis $14_{A1}$, for example, along the male stop longitudinal axis $412_{A1}$. As another example, FIG. 49A illustrates that both the male stop first and second longitudinal ends $412_{FE}$, $412_{SE}$ can extend longitudinally away from the shuttle longitudinal axis $14_{A1}$, for example, along the male stop longitudinal axis $412_{A1}$. As yet another example, FIG. 49A illustrates that both the male stop first and second longitudinal ends $412_{FE}$, $412_{SE}$ can extend longitudinally away from the shuttle longitudinal axis $14_{A1}$, for example, along the male stop longitudinal axis $412_{A1}$, and can extend radially away from the shuttle longitudinal axis $14_{A1}$, for example, along the shuttle second transverse axis $14_{A2}$. One or both of the male stop first and second sections $412_{S1}$, $412_{S2}$ can extend away from the shuttle body 160 and/or away from the shuttle longitudinal axis $14_{A1}$. For example, FIG. 49A illustrates that both the male stop first and second sections $412_{S1}$, $412_{S2}$ can extend radially away from the shuttle longitudinal axis $14_{A1}$, for example, along the male stop longitudinal axis $412_{A1}$. As another example, FIG. 49A illustrates that both the male stop first and second sections $412_{S1}$, $412_{S2}$ can extend longitudinally away from the shuttle longitudinal axis $14_{A1}$, for example, along the male stop longitudinal axis $412_{A1}$. As yet another example, FIG. 49A illustrates that both the male stop first and second sections $412_{S1}$, $412_{S2}$ can extend longitudinally away from the shuttle longitudinal axis $14_{A1}$, for example, along the male stop longitudinal axis $412_{A1}$, and can extend radially away from the shuttle longitudinal axis $14_{A1}$, for example, along the shuttle second transverse axis $14_{A2}$.

As another example, the male stop first longitudinal end $412_{FE}$ can extend away from (e.g., radially away from) the shuttle longitudinal axis $14_{A1}$, and the male stop second longitudinal end $412_{SE}$ can extend toward (e.g., radially toward) the shuttle longitudinal axis $14_{A1}$. As yet another example, the male stop first longitudinal end $412_{FE}$ can extend away from the shuttle body 160 parallel to the shuttle longitudinal axis $14_{A1}$ such that the male stop first longitudinal end $412_{FE}$ does not radially extend away from the shuttle longitudinal axis $14_{A1}$, and the male stop second longitudinal end $412_{SE}$ can extend away (e.g., radially away) from the shuttle body 160 or the shuttle longitudinal axis $14_{A1}$. As yet still another example, the male stop first longitudinal end $412_{FE}$ can extend away (e.g., radially away) from the shuttle longitudinal axis $14_{A1}$, the male stop second longitudinal end $412_{SE}$ can extend parallel to the shuttle longitudinal axis $14_{A1}$ such that the male stop second longitudinal end $412_{SE}$ does not radially extend away from the shuttle longitudinal axis $14_{A1}$.

As another example, the male stop first section $412_{S1}$ can extend away from (e.g., radially away from) the shuttle longitudinal axis $14_{A1}$, and the male stop second section $412_{S2}$ can extend toward (e.g., radially toward) the shuttle longitudinal axis $14_{A1}$. As yet another example, the male stop first section $412_{S1}$ can extend away from the shuttle body 160 parallel to the shuttle longitudinal axis $14_{A1}$ such that the male stop first section $412_{S1}$ does not radially extend away from the shuttle longitudinal axis $14_{A1}$, and the male stop second section $412_{S2}$ can extend away (e.g., radially away) from the shuttle body 160 or the shuttle longitudinal axis $14_{A1}$. As yet still another example, the male stop first section $412_{S1}$ can extend away (e.g., radially away) from the shuttle longitudinal axis $14_{A1}$, the male stop second section $412_{S2}$ can extend parallel to the shuttle longitudinal axis $14_{A1}$ such that the male stop second section $412_{S2}$ does not radially extend away from the shuttle longitudinal axis $14_{A1}$.

FIG. 49A further illustrates that the male stops 412 can extend laterally away from and/or toward the shuttle longitudinal axis $14_{A1}$, for example, along the male stop first transverse axis $412_{A2}$. The male stops 412 can, for example, extend laterally toward a shuttle first lateral side $14_{L1}$ and/or away from a shuttle second lateral side $14_{L2}$, for example, along the male stop first transverse axis $412_{A2}$. FIG. 49A illustrates that the male stop second longitudinal end $412_{SE}$ can extend along the male stop first transverse axis $412_{A2}$ farther than the male stop first longitudinal end $412_{FE}$. A first side of the male stop second longitudinal end $412_{SE}$ can extend away from male stop first longitudinal end $412_{FE}$ toward the shuttle first lateral side $14_{L1}$ and away from the shuttle second lateral side $14_{L2}$. A second side of the male stop second longitudinal end $412_{SE}$ can extend away from male stop first longitudinal end $412_{FE}$ toward the shuttle second lateral side $14_{L2}$ and away from the shuttle first lateral side $14_{L1}$. In this way the male stops 412 can define the hammerhead shape shown in FIG. 49A. FIG. 49A illustrates that the male stop second section $412_{S2}$ can extend along the male stop first transverse axis $412_{A2}$ farther than the male stop first section $412_{S1}$. A first side of the male stop second section $412_{S2}$ (e.g., on a first side of the male stop longitudinal axis $412_{A1}$) can extend away from the male stop first section $412_{S1}$ toward the shuttle first lateral side $14_{L1}$ and away from the shuttle second lateral side $14_{L2}$. A second side of the male stop second section $412_{S2}$ (e.g., on a second side of the male stop longitudinal axis $412_{A1}$) can extend away from the male stop first section $412_{S1}$ toward the shuttle second lateral side $14_{L2}$ and away from the shuttle first lateral side $14_{L1}$. In this way the male stops 412 can define the hammerhead shape shown in FIG. 49A. FIG. 49A further illustrates that the shuttle longitudinal axis $14_{A1}$ can be a center longitudinal axis such that the shuttle first lateral side $14_{L1}$ is half of the shuttle 14 on a first side of the shuttle longitudinal axis $14_{A1}$ and the shuttle second lateral side $14_{L2}$ is half of the shuttle 14 on a second side of the shuttle longitudinal axis $14_{A1}$.

The shuttle first and second lateral sides $14_{L1}$, $14_{L2}$ can be the portions of the shuttle 14 that are on first and second sides of the shuttle longitudinal axis $14_{A1}$ such that the shuttle first lateral side $14_{L1}$ is a first lateral half of the shuttle 14 and the shuttle second lateral side $14_{L2}$ is a second lateral half of the shuttle 14. The shuttle first and second lateral sides $14_{L1}$, $14_{L2}$ can have shuttle lateral side terminal ends $14_{LTE}$. The shuttle lateral side terminal ends $14_{LTE}$ can be an edge and or a surface. For example, FIG. 49A illustrates that the shuttle lateral side terminal ends $14_{LTE}$ can be a flat surface which can be, for example, perpendicular to the top and bottom surfaces of the shuttle 14 (e.g., as shown in FIG. 49A) or can be beveled. As FIG. 49A shows, the surfaces 406 and the shuttle lateral side terminal ends $14_{LTE}$ can form a surface and/or an edge around the perimeter of the shuttle 14.

FIG. 49A further illustrates that the shuttle 14 can have a shuttle first longitudinal side $14_{S1}$ and a shuttle second longitudinal side $14_{S2}$. The shuttle first longitudinal side $14_{S1}$ can be a first longitudinal half of the shuttle 14 and the shuttle second longitudinal side $14_{S2}$ can be a second longitudinal half of the shuttle 14. For example, the shuttle first longitudinal side $14_{S1}$ can include half of the suture holder 18, and the shuttle second longitudinal side $14_{S2}$ can include the other half of the suture holder 18. The shuttle first longitudinal side $14_{S1}$ can have zero, one, or multiple male stops 412, and the shuttle second longitudinal side $14_{S2}$ can have zero, one, or multiple male stops 412. For example, FIG. 49A illustrates that the shuttle first longitudinal side $14_{S1}$ can have one male stop 412 (e.g., the first male stop 412a) and that the shuttle second longitudinal side $14_{S2}$ can have one male stop 412 (e.g., the second male stop 412b). FIG. 49A further illustrates that the shuttle 14 can have a shuttle first terminal end $14_{TE1}$ and a shuttle second terminal end $14_{TE2}$. The shuttle first longitudinal side $14_{S1}$ can have the shuttle first terminal end $14_{TE1}$ and the shuttle second longitudinal side $14_{S2}$ can have the shuttle second terminal end $14_{TE2}$. The shuttle first and second terminal ends $14_{TE1}$, $14_{TE2}$ can be the terminal tip 165 at each end of the shuttle 14 or any other point of the shuttle 14 or the shuttle tips 164 that is the farthest from the longitudinal center of the shuttle 14 (e.g., from the suture holder 18 as shown in FIG. 49A) as measured along any axis, including, for example, along the shuttle longitudinal axis $14_{A1}$. For example, FIG. 49A illustrates that the shuttle first terminal end $14_{TE1}$ can be, for example, the terminal tip 165 of the shuttle first tip 164a and that the shuttle second terminal end $14_{TE2}$ can be, for example, the terminal tip 165 of the shuttle second tip 164b.

FIG. 49A further illustrates that the male stops 412 can have a male stop transition region $412_{TR}$ between the male stop first and second terminal ends $412_{TE1}$, $412_{TE2}$. The male stop transition region $412_{TR}$ can be straight, curved, or both. The male stop transition region $412_{TR}$ can be where the male stop 412 changes from one male stop section $412_{S}$ to another male stop section $412_{S}$. For example, FIG. 49A illustrates that the male stop transition region $412_{TR}$ can be where the male stop 412 changes from the male stop first section $412_{S1}$ to the male stop second section $412_{S2}$. The male stop transition region $412_{TR}$ can include one or multiple steps. For example, FIG. 49A illustrates that the male stop transition region $412_{TR}$ can be a single step, such that the narrow proximal end transitions to the wide distal end with a single step as shown, for example, so that the male stops 412 have or resemble a hammerhead shape. As another example, the male stop transition region $412_{TR}$ can be tapered instead of having one or multiple steps, or can be tapered in addition to having one or multiple steps. The male stop transition region $412_{TR}$ can be anywhere along the length of the male stops 412, including, for example, closer to the male stop first terminal end $412_{TE1}$ than to the male stop second terminal end $412_{TE2}$, closer to the male stop second terminal end $412_{TE2}$ than to the male stop first terminal end $412_{TE1}$ (e.g., as shown in FIG. 49A), or halfway between the male stop first and second terminal ends $412_{TE1}$, $412_{TE2}$ (e.g., as measured between the male stop first and second terminal ends $412_{TE1}$, $412_{TE2}$ along the male stop longitudinal axis $412_{A1}$).

FIG. 49A further illustrates that the male surface 414 of the male stops 412 can be a surface of the male stop second longitudinal ends $412_{SE}$, and that the male surface 414 can laterally extend from a first side of the male stop second longitudinal end $412_{SE}$ (e.g., the side closer to the shuttle first lateral side $14_{L1}$) to a second side of the male stop second longitudinal end $412_{SE}$ (e.g., the side closer to the shuttle second lateral side $14_{L2}$). FIG. 49A further illustrates that the male surface 414 of the male stops 412 can be a surface of the male stop second section $412_{S2}$, and that the male surface 414 can laterally extend from a first side of the male stop second section $412_{S2}$ (e.g., the side closer to the shuttle first lateral side $14_{L1}$) to a second side of the male stop second section $412_{S2}$ (e.g., the side closer to the shuttle second lateral side $14_{L2}$).

The male stops 412 can have one or multiple bends 426 (e.g., one, two, three, four, or more bends 426) along the length of the male stops 412. The male stop first section $412_{S1}$ and/or the male stop second section $412_{S2}$ can each have zero, one, or multiple bends 426. For example, FIG. 49A illustrates that the base of the male stop 412 can have a bend 426. For example, FIG. 49A illustrates that the male stop first section $412_{S1}$ can have a bend 426. The bend 426 can be, for example, near the male stop first terminal end $412_{TE1}$. For example, FIG. 49A illustrates that the male stops 412 can have one bend 426, and that the one bend 426 can be at the base of the male stops 412 near the male stop first terminal end $412_{TE1}$. The bend 426 can become more bent or less bent when the male stops 412 enter a female stop 416, are in a female stop 416, exit a female stop 416, or any combination thereof. For example, the male stops 412 can have a first bend when the male stops 412 are in a neutral configuration and a second bend when the male stops 412 are in a deflected configuration, where the first bend can be greater than or less than than the second bend.

FIG. 49A further illustrates that the shuttle 14 can have the arrangement of the male stops 412 as shown, including, for example, the first and second male stops 412a, 412b. The first male stop 412a can have a T-shape and the second male stop 412b can have a T-shape. As another example, the first male stop 412a can have a different shape than the second male stop 412b, or vice versa.

FIG. 49A further illustrates that the first male stop 412a can have a first male stop first terminal end $412a_{TE1}$, a first male stop first longitudinal end $412a_{FE}$, a first male stop transition region $412a_{TR}$, a first male stop second longitudinal end $412a_{SE}$, and a first male stop second terminal end $412a_{TE2}$. The male stop first terminal end $412_{TE1}$ of the first male stop 412a can be the first male stop first terminal end $412a_{TE1}$. The male stop first longitudinal end $412_{FE}$ of the first male stop 412a can be the first male stop first longitudinal end $412a_{FE}$. The male stop transition region $412_{TR}$ of the first male stop 412a can be the first male stop transition region $412a_{TR}$. The male stop second longitudinal end $412_{SE}$ of the first male stop 412a can be the first male stop second longitudinal end $412a_{SE}$. The male stop second terminal end $412_{TE2}$ of the first male stop 412a can be the first male stop second terminal end $412a_{TE2}$.

FIG. 49A further illustrates that the second male stop 412b can have a second male stop first terminal end $412b_{TE1}$, a second male stop first longitudinal end $412b_{FE}$, a second male stop transition region $412b_{TR}$, a second male stop second longitudinal end $412b_{SE}$, and a second male stop second terminal end $412b_{TE2}$. The male stop first terminal end $412_{TE1}$ of the second male stop 412b can be the second male stop first terminal end $412b_{TE1}$. The male stop first longitudinal end $412_{FE}$ of the second male stop 412b can be the second male stop first longitudinal end $412b_{FE}$. The male stop transition region $412_{TR}$ of the second male stop 412b can be the second male stop transition region $412b_{TR}$. The male stop second longitudinal end $412_{SE}$ of the second male stop 412b can be the second male stop second longitudinal end $412b_{SE}$. The male stop second terminal end $412_{TE2}$ of the second male stop 412b can be the second male stop second terminal end $412b_{TE2}$.

Figure 49B:
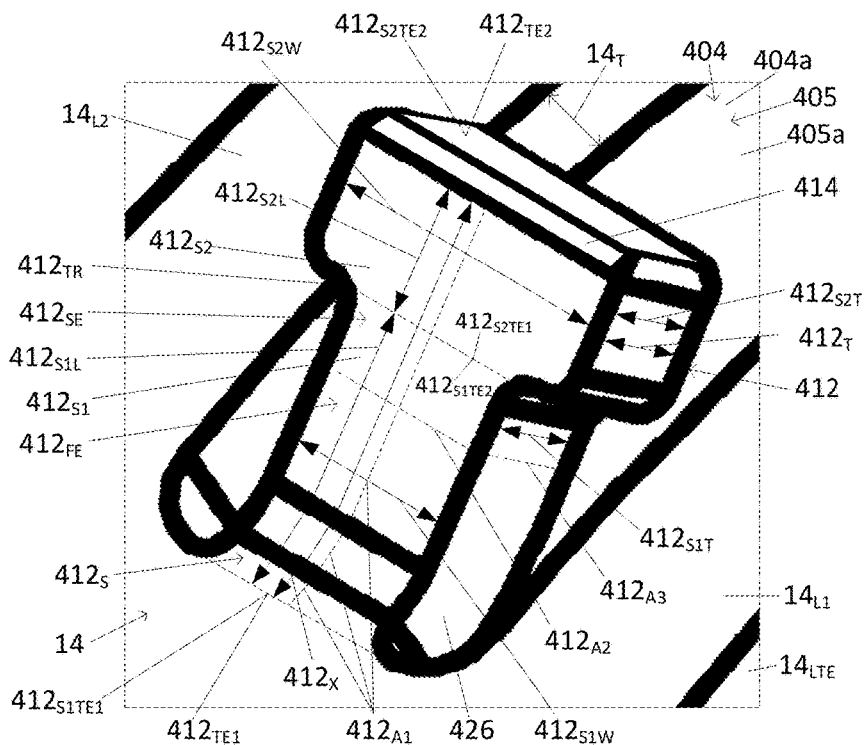
FIG. 49B is a magnified view of the shuttle of FIG. 49A at section 49B-49B (the square box in dashed lines).

FIG. 49B illustrates various dimensions that the male stops 412 (e.g., the first male stop 412a and/or the second male stop 412b) can have, including, for example, a male stop first section longitudinal length $412_{S1L}$, a male stop first section width $412_{S1W}$, a male stop first section thickness $412_{S1T}$, a male stop second section length $412_{S2L}$, a male stop second section width $412_{S2W}$, a male stop second section thickness $412_{S2T}$, a male stop length $412_X$, and a male stop thickness $412_T$.

The male stop first section length $412_{S1L}$ can be about 0.0050 in. to about 0.1250 in., including every 0.0001 in. increment within this range (e.g., 0.0050 in., 0.0225 in., 0.1250 in.). The male stop first section length $412_{S1L}$ can be measured along the male stop longitudinal axis $412_{A1}$. The male stop first section length $412_{S1L}$ can be measured, for example, from the male stop first section first terminal end $412_{S1TE1}$ to the male stop first section second terminal end $412_{S1TE2}$.

The male stop first section width $412_{S1W}$ can be about 0.0030 in. to about 0.0450 in., including every 0.0001 in. increment within this range (e.g., 0.0030 in., 0.0130 in., 0.0450 in.). The male stop first section width $412_{S1W}$ can be measured along the male stop first transverse axis $412_{A2}$, for example, from a first lateral side of the male stop first section $412_{S1}$ to a second lateral side of the male stop first section $412_{S1}$ as shown in FIG. 49A.

The male stop first section thickness $412_{S1T}$ can be from about 0.0080 in. to about 0.0090 in., or more broadly from about 0.0050 in. to about 0.0125 in., including every 0.0001 in. increment within these ranges (e.g., 0.0050 in., 0.0085 in., 0.0125 in.). The male stop first section thickness $412_{S1T}$ can be measured along the male stop second transverse axis $412_{A3}$. The male stop first section thickness $412_{S1T}$ can be equal to (e.g., as shown in FIG. 49A), greater than, or less than the shuttle thickness $14_T$. The male stop first section thickness $412_{S1T}$ can be equal to (e.g., as shown in FIG. 49A), greater than, or less than the shuttle tip thickness 408.

The male stop second section length $412_{S2L}$ can be about 0.0050 in. to about 0.1250 in., including every 0.0001 in. increment within this range (e.g., 0.0050 in., 0.0100 in., 0.1250 in.). The male stop second section length $412_{S2L}$ can be measured along the male stop longitudinal axis $412_{A1}$. The male stop second section length $412_{S2L}$ can be measured, for example, from the male stop second section first terminal end $412_{S2TE1}$ to the male stop second section second terminal end $412_{S2TE2}$. The male stop second section length $412_{S2L}$ can be less than (e.g., as shown in FIG. 49A), equal to, or greater than the male stop first section length $412_{S1L}$.

The male stop second section width $412_{S2W}$ can be about 0.0120 in. to about 0.0550 in., including every 0.0001 in. increment within this range (e.g., 0.0120 in., 0.0220 in., 0.0550 in.). The male stop second section width $412_{S2W}$ can be measured along the male stop first transverse axis $412_{A2}$, for example, from a first lateral side of the male stop second section $412_{S2}$ to a second lateral side of the male stop second section $412_{S2}$ as shown in FIG. 49A. The male stop second section width $412_{S2W}$ can be equal to, greater than (e.g., as shown in FIG. 49A), or less than the male stop first section width $412_{S1W}$.

The male stop second section thickness $412_{S2T}$ can from about 0.0080 in. to about 0.0090 in., or more broadly from about 0.0050 in. to about 0.0125 in., including every 0.0001 in. increment within these ranges (e.g., 0.0050 in., 0.0085 in., 0.0125 in.). The male stop second section thickness $412_{S2T}$ can be measured along the male stop second transverse axis $412_{A3}$. The male stop second section thickness $412_{S2T}$ can be equal to (e.g., as shown in FIG. 49A), greater than, or less than the shuttle thickness $14_T$. The male stop second section thickness $412_{S2T}$ can be equal to (e.g., as shown in FIG. 49A), greater than, or less than the male stop first section thickness $412_{S1T}$. The male stop second section thickness $412_{S2T}$ can be equal to (e.g., as shown in FIG. 49A), greater than, or less than the shuttle tip thickness 408.

The male stop length 412x can be about 0.0150 in. to about 0.2000 in., including every 0.0001 in. increment within this range (e.g., 0.0150 in. 0.0325 in., 0.2000 in.). The male stop length 412x can be measured along the male stop longitudinal axis $412_{A1}$, and can be, for example, the male stop first section length $412_{S1L}$ and the male stop second section length $412_{S2L}$ added together.

The male stop thickness $412_T$ can be from about 0.0080 in. to about 0.0090 in., or more broadly from about 0.0050 in. to about 0.0125 in., including every 0.0001 in. increment within these ranges (e.g., 0.0050 in., 0.0085 in., 0.0125 in.). The male stop thickness $412_T$ can be equal to (e.g., as shown in FIG. 49A), greater than, or less than the shuttle thickness $14_T$. As shown in FIG. 49B, the male stops 412 can have a constant or uniform male stop thickness $412_T$ (e.g., the male stop first section thickness $412_{S1T}$ and the male stop second section thickness $412_{S2T}$ can be equal to each other). As another example, the male stop first section thickness $412_{S1T}$ can be less than or greater than the male stop second section thickness $412_{S2T}$, for example, by about 0.0050 in. to about 0.0150 in., including every 0.0001 in. increment within this range (e.g., 0.0050 in., 0.0150 in.).

The first male stop 412a can have the dimensions and features shown in FIG. 49B.

The second male stop 412b can have the dimensions and features shown in FIG. 49B.

FIGS. 49A and 49B further illustrate that the male stops 412 (e.g., their length, width, and/or thickness) can be shorter than the length, width, and/or thickness of the shuttle 14, for example, as measured along the shuttle longitudinal axis $14_{A1}$ (e.g., for length), along the shuttle first transverse axis $14_{A2}$ (e.g., for width), and/or along the shuttle second transverse axis $14_{A3}$ (e.g., for thickness). The male stops 412 (e.g., their length, width, and/or thickness) can be shorter than the shuttle width (e.g., shuttle width 292).

Figure 49C:
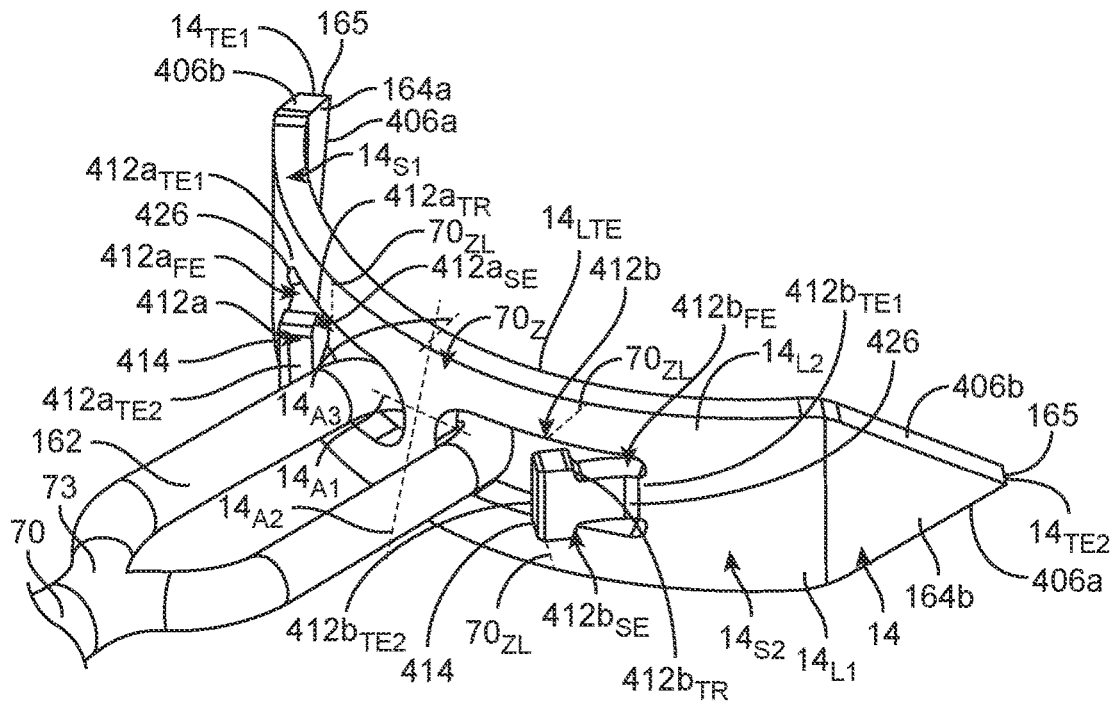
FIG. 49C illustrates a perspective view of the shuttle of FIG. 49A with suture attached.

FIG. 49C illustrates that the suture 70 can be attached to the shuttle 14, for example, to the suture holder 18 via the suture loop 162.

FIG. 49C further illustrates that the male stops 412 can be suture stops, whereby the male stops 412 can be engageable with the suture 70 and/or the suture loop 162. When the suture 70 or the suture loop 162 is engaged with a male stop 412, the suture 70 or the suture loop 162 can contact the male stop 412. When the suture 70 or suture loop 162 is in contact a male stop 412 (e.g., with the first male stop 412a or with the second male stop 412b), movement of the shuttle 14 into the jaw can be inhibited or prevented. When the suture 70 or suture loop 162 is in contact a male stop 412 (e.g., with the first male stop 412a or with the second male stop 412b), movement of the suture 70 or the suture loop 162 into the jaw can be inhibited or prevented. The male stops 412 can, for example, inhibit or prevent the suture 70 and/or the suture loop 162 from entering the shuttle track beyond the suture holder slot. In this way, the male stops 412 can advantageously prevent or inhibit the device 188 from getting jammed with the suture 70 or the suture loop 162 by inhibiting or preventing the suture 70 or the suture loop 162 from entering in the shuttle track beyond the suture holder slot. The male stops 412 can thereby be, for example, mono-functional and/or bi-functional male stops, restricting movement of the shuttle 14 when engaged with the jaws and/or restricting movement of the suture 70 and/or the suture loop 162.

FIG. 49A further illustrates that the male stops 412 can, for example, guide and/or limit where the suture 70 or the suture loop 162 can fold over the shuttle first and second lateral sides $14_{L1}$, $14_{L2}$. For example, FIG. 49A illustrates that the shuttle 14 can have a suture zone $70_Z$ defined within suture zone lines $70_{ZL}$ (e.g., four suture zone lines $70_{ZL}$, for example, the three shown and a fourth obstructed by the first male stop 412a, where the fourth suture zone line $70_{ZL}$ can be on the opposite lateral side of the shuttle 14 than the suture zone line $70_{ZL}$ that is illustrated next to the first male stop 412a). If or when the suture 70 or the suture loop 162 folds over shuttle first lateral side $14_{L1}$ or over the shuttle second lateral side $14_{L2}$, the male stops 412 (e.g., the first and second male stops 412a, 412b) can guide the suture 70 or the suture loop 162 to fold or bend onto or above the suture zone $70_Z$ and/or can inhibit or prevent the suture 70 or the suture loop 162 from folding or bending on or above the shuttle 14 outside of the suture zone $70_Z$.

The male stop second longitudinal end $412_{SE}$ can be engageable with the suture 70 and/or the suture loop 162 such that one or multiple portions of the male stop second longitudinal end $412_{SE}$ can be engageable with the suture 70 and/or the suture loop 162 (e.g., the male stop first and/or second sections $412_{S1}$, $412_{S2}$). For example, the suture 70 and/or the suture loop 162 can be engageable with the male surface 414, with the male stop second terminal end $412_{TE2}$, and/or with another surface of the male stops 412. For example, FIG. 49C illustrates that the first male stop 412a can be a shuttle first suture stop and that the second male stop 412b can be a shuttle second suture stop.

FIG. 49C further illustrates that the shuttle first transverse axis $14_{A2}$ can be a center axis that splits the shuttle 14 into two halves (e.g., into the shuttle first and second longitudinal sides $14_{S1}$, $14_{S2}$). Half of the suture holder 18 can be on a first side of the shuttle first transverse axis $14_{A2}$ and that half of the suture holder 18 can be on a second side of the shuttle first transverse axis $14_{A2}$. For example, FIG. 49C illustrates that the shuttle first longitudinal side $14_{S1}$ can include a first half of the suture holder 18 and that the shuttle second longitudinal side $14_{S2}$ can include a second half of the suture holder 18.

FIGS. 49A-49C further illustrate that a male stop 412 can be on each longitudinal side of the shuttle 14. For example, FIGS. 49A-49C illustrate that the first male stop 412a can be on the shuttle first longitudinal side $14_{S1}$ and the second male stop 412b can be on the shuttle second longitudinal side $14_{S2}$.

FIGS. 49A-49C further illustrate that a male stop 412 can be on each lateral side of the shuttle 14. The male stops 412 can be on the shuttle first and second lateral sides $14_{L1}$, $14_{L2}$. For example, FIGS. 49A-49C illustrate that a first half of the first male stop 412a (e.g., a first half of the first male stop first longitudinal end $412a_{FE}$ and a first half of the first male stop second longitudinal end $412a_{SE}$) can be on the shuttle first lateral side $14_{L1}$ and that a second half of the first male stop 412a (e.g., a second half of the first male stop first longitudinal end $412a_{FE}$ and a second half of the first male stop second longitudinal end $412a_{SE}$) can be on the shuttle second lateral side $14_{L2}$. FIGS. 49A-49C further illustrate that a first half of the second male stop 412b (e.g., a first half of the second male stop first longitudinal end $412b_{FE}$ and a first half of the second male stop second longitudinal end $412b_{SE}$) can be on the shuttle first lateral side $14_{L1}$ and that a second half of the second male stop 412b (e.g., a second half of the second male stop first longitudinal end $412b_{FE}$ and a second half of the second male stop second longitudinal end $412b_{SE}$) can be on the shuttle second lateral side $14_{L2}$.

FIGS. 49A-49C further illustrate that the shuttle 14 can have a hammerhead-shaped male stop 412 on each longitudinal side of the shuttle 14, for example, one on the shuttle first longitudinal side $14_{S1}$ and one on the shuttle second longitudinal side $14_{S2}$.

FIGS. 49A-49C further illustrate that the first male stop 412a can be closer to the shuttle first terminal end $14_{TE1}$ than to the shuttle second terminal end $14_{TE2}$. The first male stop 412a can be between a shuttle center (e.g., a shuttle longitudinal midpoint) and the shuttle first terminal end $14_{TE1}$.

The shuttle longitudinal midpoint can be halfway between the shuttle first and second terminal ends $14_{TE1}$, $14_{TE2}$. For example, FIGS. 49A and 49C illustrate that the shuttle longitudinal midpoint can be halfway across the suture holder 18, and FIG. 49C further illustrates that where the shuttle longitudinal axis $14_{A1}$ and the shuttle first transverse axis $14_{A2}$ are center axes, respectively, the shuttle longitudinal midpoint can be where the shuttle longitudinal axis $14_{A1}$ intersects the shuttle first transverse axis $14_{A2}$.

FIGS. 49A-49C further illustrate that the second male stop 412b can be closer to the shuttle second terminal end $14_{TE2}$ than to the shuttle first terminal end $14_{TE1}$. The second male stop 412b can be between the shuttle center (e.g., the shuttle longitudinal midpoint) and the shuttle second terminal end $14_{TE2}$.

FIGS. 49A-49C further illustrate that the first and second male stops 412a, 412b can each extend toward a midpoint (e.g., the longitudinal center) of the shuttle 14, for example, toward the suture holder 18. As another example, however, the first and second male stops 412a, 412b can extend away from the center of the shuttle 14. For example, the first and second male stops 412a, 412b can both extend from the suture holder 18, with the first and second male stops 412a, 412b each extending away from the suture holder 18. In this example, the first and second male stops 412a, 412b can be integrated with or integrally formed with the suture holder 18.

FIGS. 49A-49C further illustrate that the first male stop 412a can extend toward the second male stop 412b and that the second male stop 412b can extend toward the first male stop 412a. As another example, the first and second male stops 412a, 412b can extend away from each other. As another example, the first and second male stops 412a, 412b can extend away from each other and away from a longitudinal center of the shuttle (also referred to as the shuttle longitudinal midpoint).

Figure 49D:
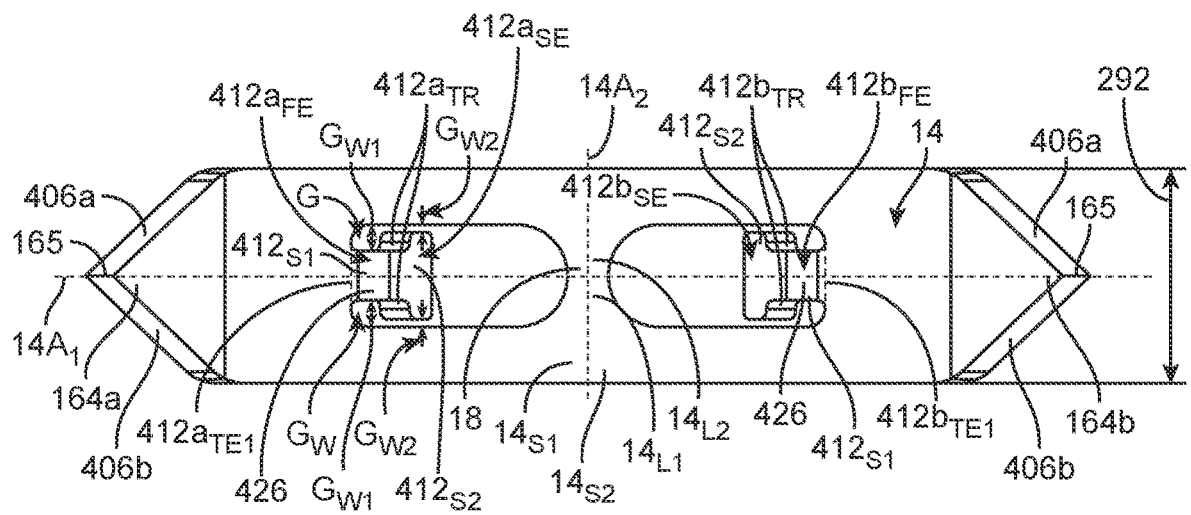
FIG. 49D illustrates a bottom view of the shuttle of FIG. 49A.

FIG. 49D illustrates that a gap G can be between the male stops 412 and the shuttle body 160. The width of the gaps G can be constant. The gaps G can have multiple widths. For example, FIG. 49D illustrates that the gaps G can have multiple gap widths $G_W$, including, for example, a first gap width $G_{W1}$ and a second gap width $G_{W2}$. The first gap width $G_{W1}$ can be between the male stop first section $412_{S1}$ and the shuttle body 160, for example, as measured along the shuttle first transverse axis $14_{A2}$ and/or along the male stop first transverse axis $412_{A2}$. The second gap width $G_{W2}$ can be between the male stop second section $412_{S2}$ and the shuttle body 160, for example, as measured along the shuttle first transverse axis $14_{A2}$ and/or along the male stop first transverse axis $412_{A2}$. The first gap width $G_{W1}$ can be greater than or less than the second gap width $G_{W2}$. For example, FIG. 49D illustrates that for a hammerhead shape, the second gap width $G_{W2}$ can be less than the first gap width $G_{W1}$. As another example, the first gap width $G_{W1}$ can be zero or very small such that the male stop first section $412_{S1}$ is flush with the shuttle body 160 (e.g., so that male stop first section $412_{S1}$ can deflect into and out of the holes 404 and/or 405) and the male stop second section $412_{S2}$ can extend over the shuttle first and/or second lateral sides $14_{L1}$, $14_{L2}$. Where the male stop second section $412_{S2}$ extends over the shuttle first and/or second lateral sides $14_{L1}$, $14_{L2}$, the male stop second section $412_{S2}$ can be engageable with the shuttle body 160, for example, to inhibit or prevent too much deflection of the male stops 412. The shuttle body 160 can thereby act as a stop for the male stops 412 and limit the range of motion of the male stops 412.

Figure 49E:
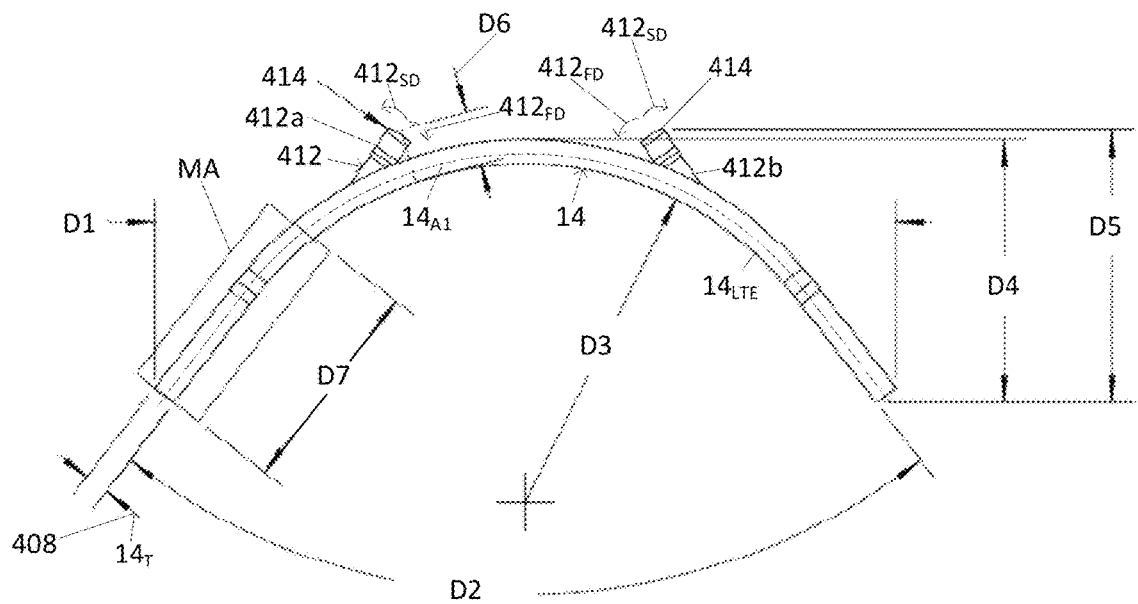
FIG. 49E illustrates a side view of the shuttle of FIG. 49A.

FIG. 49E illustrates that the male stops 412 can be moveable (e.g., deflectable), for example, toward the shuttle longitudinal axis $14_{A1}$ and/or away from the shuttle longitudinal axis $14_{A1}$. The male stops 412 can move (e.g., deflect), for example, by bending (e.g., linear bending), twisting, or both. For example, the male stops 412 can be moveable away from the shuttle longitudinal axis $14_{A1}$ in a male stop first direction $412_{FD}$ and/or can be moveable toward the shuttle longitudinal axis $14_{A1}$ in a male stop second direction $412_{SD}$. The male stop first direction $412_{FD}$ can be, for example, a rotation and/or a translation of the male stop 412 toward the shuttle longitudinal axis $14_{A1}$. The male stop second direction $412_{SD}$ can be, for example, a rotation and/or a translation of the male stop 412 away from the shuttle longitudinal axis $14_{A1}$. For example, FIG. 49E illustrates in the orientation shown that the male stop first direction $412_{FD}$ for the first male stop 412a can be a clockwise rotation, that the male stop first direction $412_{FD}$ for the second male stop 412b can be a counterclockwise rotation, that the male stop second direction $412_{SD}$ for the first male stop 412a can be a counterclockwise rotation, and that the male stop second direction $412_{SD}$ for the second male stop 412b can be a clockwise rotation.

When the male stops 412 move in the male stop first and/or second directions $412_{FD}$, $412_{SD}$, the male stops 412 can pivot about their base (e.g., about the male stop first terminal ends $412_{TE1}$), can bend along their length, or both. The male stop first terminal ends $412_{TE1}$ can be the fulcrum around which the male stops 412 rotate when the male stops 412 are moved (e.g., deflected) from a neutral configuration to a deflected configuration and vice versa. When the male stops 412 are deflected by a female stop 416, the male stops 412 can bend distal to the fulcrum (e.g., the bend 426) when the male stop 412 pivots about the fulcrum. When the male stops 412 are deflected by a female stop 416, the male stops 412 can be rigid and not bend distal to the fulcrum (e.g., the bend 426) when the male stop 412 pivots about the fulcrum.

FIG. 49E further illustrates that the male stops 412 (e.g., the first and second male stops 412a, 412b) can be moveable (e.g., deflectable) back and forth between a male stop first configuration and a male stop second configuration. The male stop first configuration can be the male stop neutral configuration (also referred to as the male stop non-deflected configuration). The male stop neutral configuration can be the configuration of the male stops 412 shown, for example, in FIGS. 49A-49E. The male stops 412 can have the male stop first configuration (e.g., neutral configuration), for example, when the male stop 412 is not engaged with a female stop 416, when the male stop 412 is fully engaged with a female stop 416, or both. The male stop second configuration can be a male stop deflected configuration in which the male stop 412 is in a configuration different from the male stop neutral configuration. For example, the male stop second configuration can be a deflected configuration in which the male stop 412 (e.g., the male stop first section $412_{S1}$ and/or the male stop second section $412_{S2}$) is closer to the shuttle longitudinal axis $14_{A1}$ than when the male stop 412 is in the male stop first configuration. As another example, the male stop second configuration can be a deflected configuration in which the male stop 412 (e.g., the male stop first section $412_{S1}$ and/or the male stop second section $412_{S2}$) is farther from the shuttle longitudinal axis $14_{A1}$ than when the male stop 412 is in the male stop first configuration. The male stops 412 can have the male stop second configuration (e.g., deflected configuration), for example, when the male stop 412 partially engaged with a female stop 416, when the male stop 412 is fully engaged with a female stop 416, or both.

FIG. 49E further illustrates the arrangement of features shown, for example, with exemplary dimensions $D_1$-$D_7$, the shuttle thickness $14_T$, and the shuttle tip thickness 408.

The dimension $D_1$ can be the distance between the terminal ends 165 of the first and second shuttle tips 164a, 164b. For example, the dimension $D_1$ can be the shortest distance between the terminal ends 165 of the first and second shuttle tips 164a, 164b (e.g., as measured along a straight line). The dimension $D_1$ can be, for example, 0.150 in. to about 0.500 in., including every 0.001 in. increment within this range (e.g., 0.257 in.).

The dimension $D_2$ can be the angle between the shuttle first and second tips 164a, 164b. The dimension $D_2$ can be, for example, 60 degrees to about 85 degrees, or more narrowly from about 70 degrees to about 80 degrees, including every 1 degree increment within these ranges (e.g., 70 degrees, 75 degrees, 80 degrees).

The dimension $D_3$ can be the radius of curvature of the shuttle 14. The dimension $D_3$ can be the radius of curvature of the shuttle body 160, the shuttle first tip 164a, and/or the shuttle second tip 164b. For example, FIG. 49E illustrates that the dimension $D_3$ can be the radius of curvature of the shuttle body 160 between the shuttle first and second tips 164a, 164b, and that the shuttle first and second tips 164a, 164b can be straight. The dimension $D_3$ can be, for example, 0.075 in. to about 0.300 in., including every 0.001 in. increment within this range (e.g., 0.118 in.). A shuttle 14 with two straight sections (e.g., the shuttle first and second tips 164a, 164b) and a curved section in between (e.g., the shuttle body 160 between the shuttle first and second tips 164a, 164b) can advantageously flex the shuttle 14 when the shuttle 14 is in the jaw tracks. This can advantageously keep the shuttle 14 engaged with the jaw tracks and inhibit or prevent the shuttle from floating in the jaw tracks. The straight sections (e.g., the shuttle tips 164) can cause the shuttle 14 to flex when in a jaw track such that the dimension $D_3$ is less when the shuttle 14 is in a jaw track than when the shuttle 14 is not in a jaw track. For example, the dimension $D_3$ can be about 0.010 in. to about 0.075 in. less when the shuttle 14 is in a jaw track, including every 0.001 in. increment within this range (e.g., 0.015 in.). In addition to or in lieu of the two straight sections, the radius of curvature of the jaw tracks can be less than the dimension $D_3$ when the shuttle 14 is in a neutral position outside of the jaws. The radius of curvature of the jaw tracks can be, for example, about 0.010 in. to about 0.075 in., including every 0.001 in. increment within this range (e.g., 0.015 in.). The shuttle 14 can thereby be a spring when in the jaw track, being biased to push the male stops 412 radially outward into the female stops 416 when the shuttle 14 is moved (e.g., translated) into them.

The dimension $D_4$ can be the height between the shuttle tips 164 and the apex of the shuttle body 160. The dimension $D_4$ can be, for example, 0.050 in. to about 1.350 in., including every 0.001 in. increment within this range (e.g., 0.092 in.).

The dimension $D_5$ can be the height between the shuttle tips 164 and the apex of the male stops 412. The dimension $D_5$ can be, for example, 0.050 in. to about 1.350 in., including every 0.001 in. increment within this range (e.g., 0.095 in.).

The dimension $D_6$ can be the height between the bottom of the shuttle 14 and the apex of the male stops 412. The dimension $D_6$ can be, for example, 0.0175 in. to about 0.0205 in., or more broadly from about 0.0100 in. to about 0.1250 in., including every 0.0001 in. increment within these ranges (e.g., 0.0190 in.).

The dimension $D_7$ can be the length of a masked area MA as measured, for example, from the terminal tips 165 of the shuttle tips 164 as shown. The dimension $D_7$ can be, for example, 0.055 in. to about 0.095 in., including every 0.001 in. increment within this range (e.g., 0.075 in.). A coating or a finish can be applied to the masked area, for example, around the perimeter of the shuttle 14 in the masked area MA.

FIG. 49E further illustrates that the shuttle tip thickness 408 and the shuttle thickness $14_T$ can be the same, for example, from about 0.0080 in. to about 0.0090 in., or more broadly from about 0.0050 in. to about 0.0125 in., including every 0.0001 in. increment within these ranges (e.g., 0.0050 in., 0.0085 in., 0.0125 in.).

Figure 49F:
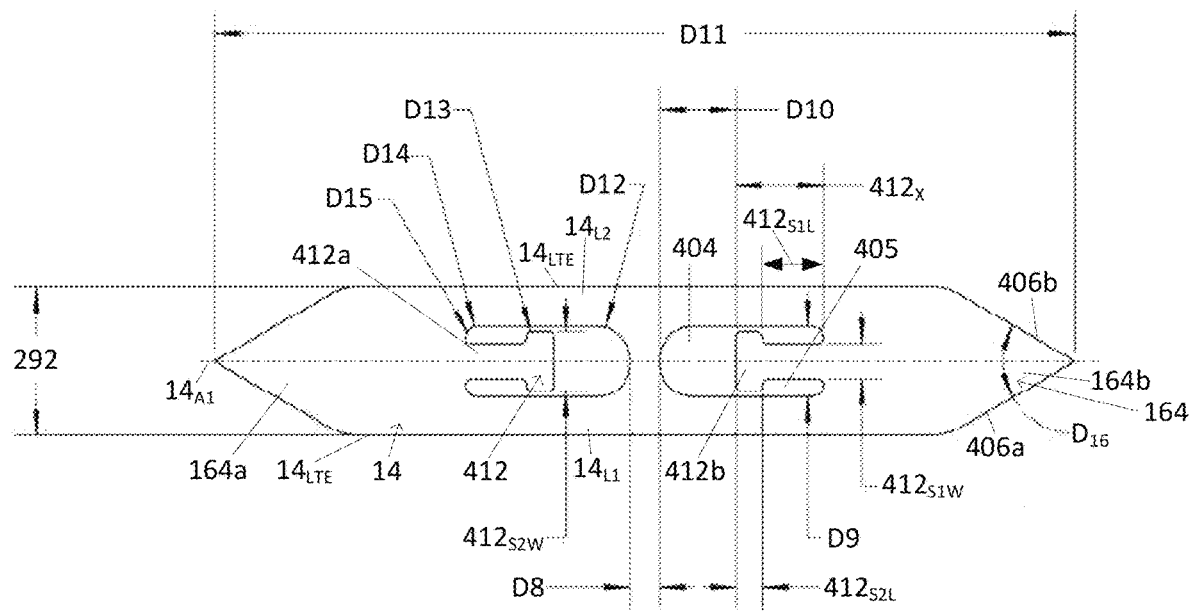
FIG. 49F illustrates a top view of the shuttle of FIG. 49A in a flat configuration.

FIG. 49F illustrates that the shuttle 14 can have a straight configuration (also referred to as a flat configuration). When the shuttle 14 is in the straight configuration, the shuttle longitudinal axis $14_{A1}$ can be straight. The straight configuration can be a non-shape set configuration or a pre-shape set configuration. A shuttle 14 in a flat configuration can be shape set to have a non-flat shape (e.g., a shape with a curve). For example, the shuttle 14 illustrated in FIG. 49F can be shape set to have the shape shown in FIGS. 49A-49E. FIGS. 49A-49F thereby illustrate that the shuttle 14 can have a flat configuration and a non-flat configuration, whereby the shuttle 14 can be shape set from the flat configuration to have the non-flat configuration.

FIG. 49F further illustrates the arrangement of features shown, for example, with exemplary dimensions $D_8$-$D_{16}$, the male stop first section length $412_{S1L}$, the male stop first section width $412_{S1W}$, the male stop second section length $412_{S2L}$, the male stop second section width $412_{S2W}$, the male stop length 412x, and the shuttle width 292.

The dimension $D_8$ can be the length of the suture holder 18 which can be, for example, from about 0.0050 in. to about 0.0200 in., including every 0.0001 in. increment within this range (e.g., 0.0050 in., 0.0110 in., 0.0200 in.).

The dimension $D_9$ can be the width of the holes 404 and/or 405 that the male stops 412 are in, extend over, and/or extend into, for example, from the shuttle body 160. The dimension $D_9$ can be, for example, from about 0.0110 in. to about 0.540 in., including every 0.0001 in. increment within this range (e.g., 0.0110 in., 0.0260 in., 0.0540 in.). The male stops 412 can extend into and/or over from the shuttle body 160 from any point around the holes 404 and/or 405. For example, FIG. 49F illustrates that the male stops 412 can extend toward the suture holder 18 from longitudinal ends of the holes 404 and/or 405.

The dimension $D_{10}$ can be the length of the holes 404 and/or 405 between the suture holder 18 and the male stops 412. The dimension $D_{10}$ can be, for example, from about 0.0150 in. to about 0.0410 in., including every 0.0001 in. increment within this range (e.g., 0.0150 in., 0.0280 in., 0.0410 in.).

The dimension $D_{11}$ can be the length of the shuttle 14 which can be, for example, from about 0.200 in. to about 0.400 in., including every 0.001 in. increment within this range (e.g., 0.200 in., 0.317 in., 0.400 in.).

The dimension $D_{12}$ can be the radius of curvature of the shuttle body 160 and of the holes 404 and/or 405 at the position shown, and can be, for example, from about 0.007 in. to about 0.019 in., including every 0.001 in. increment within this range (e.g., 0.007 in., 0.012 in., 0.019 in.).

The dimension $D_{13}$ can be the radius of curvature of the male stop transition region $412_{TR}$ at the position shown, and can be, for example, from about 0.001 in. to about 0.005 in., including every 0.001 in. increment within this range (e.g., 0.001 in., 0.002 in., 0.007 in.).

The dimension $D_{14}$ can be the radius of curvature of the shuttle body 160 and of the holes 404 and/or 405 at the position shown, and can be, for example, from about 0.002 in. to about 0.008 in., including every 0.001 in. increment within this range (e.g., 0.002 in., 0.005 in., 0.008 in.).

The dimension $D_{15}$ can be the radius of curvature of the shuttle body 160 and of the holes 404 and/or 405 at the position shown, and can be, for example, from about 0.001 in. to about 0.005 in., including every 0.001 in. increment within this range (e.g., 0.001 in., 0.002 in., 0.005 in.).

The dimension $D_{16}$ can be the angle of the shuttle tips 164 (e.g., the shuttle first and second tips 164a, 164b). The dimension $D_{16}$ can be, for example, the angle between the first and second tip surfaces 406a, 406b of the shuttle tips 164. The dimension $D_{16}$ can be, for example, 25 degrees to about 85 degrees, or more narrowly from about 45 degrees to about 75 degrees, including every 1 degree increment within these ranges (e.g., 25 degrees, 45 degrees, 60 degrees, 75 degrees, 85 degrees).

FIG. 49F further illustrates that the shuttle 14, the male stops 412, and the shuttle tips 164 can be a monolithic piece of material.

Figure 49G:
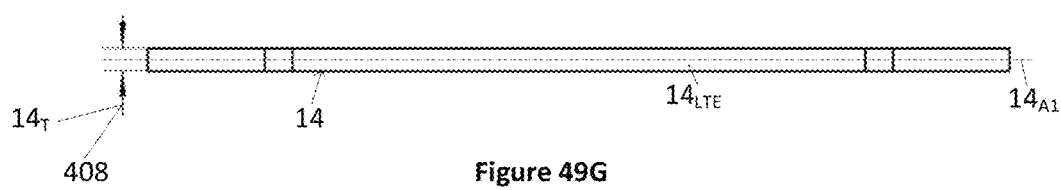
FIG. 49G illustrates a side view of the shuttle of FIG. 49F.

FIG. 49G illustrates that the shuttle longitudinal axis $14_{A1}$ can be straight when the shuttle is in a straight configuration.

FIGS. 49A-49G illustrate the features and dimensions shown, and that the shuttle 14 can have these features and dimensions, for example, in the configurations shown. As another example, the shuttle 14 can have the features and dimensions shown in FIGS. 49A-49G when the shuttle 14 is in a jaw track.

FIG. $49H_1$ illustrates that when the shuttle 14 is moved (e.g., translated, slid) in the upper jaw shuttle track 64 as shown by arrow 602, one or multiple male stops 412 can move (e.g., deflect) into a female stop 416, for example, by moving past (e.g., under) the lip 420. For example, FIG. $49H_1$ illustrates that when the shuttle 14 is moved into the upper jaw shuttle track 64, a male stop 412 (e.g., the second male stop 412b) can move into and/or engage with a female stop 416 (e.g., with the second female stop 416b), for example, by moving (e.g., deflecting) under the lip 420. FIG. $49H_1$ further illustrates that when the shuttle 14 is moved (e.g., translated, slid) out of the upper jaw shuttle track 64 as shown by arrow 604, one or multiple male stops 412 can move (e.g., deflect) out of a female stop 416, for example, by moving past (e.g., under) the lip 420. For example, FIG. $49H_1$ illustrates that when the shuttle 14 is moved out of the upper jaw shuttle track 64, a male stop 412 (e.g., the second male stop 412b) can move under the lip 420 and disengage with a female stop 416 (e.g., with the second female stop 416b). Half of the upper jaw is shown transparent in FIG. $49H_1$ so that the shuttle 14 can be more easily seen in the upper jaw 30, and so that the engagement between the male and female stops 412, 416 can be more easily seen.

When the second male stop 412b is between the lip 420 and the upper jaw pusher 86, the second male stop 412b can be engaged with the second female stop 416b. When the second male stop 412b is engaged with the second female stop 416b, the second male stop 412b can be in contact with the second female stop 416b. For example, when the second male stop 412b is engaged with the second female stop 416b, the male surface 414 can be in contact with the female surface 418. As another example, when the second male stop 412b is engaged with the second female stop 416b, the second male stop 412b may not be in contact with the second female stop 416b. For example, when the second male stop 412b is engaged with the second female stop 416b, the male surface 414 may not be in contact with the female surface 418 such that the second male stop 412b can float in the second female stop 416b. When the second male stop 412b is engaged with the second female stop 416b, the second male stop 412b can have a male stop first configuration or a male stop second configuration. The male stop first configuration can be a male stop neutral configuration (e.g., the configuration of the second male stop 412b shown in FIGS. 49A-49E). The male stop second configuration can be a male stop deflected configuration.

When the second male stop 412b is engaged with the lip 420, for example, as the shuttle 14 is moving into or out of the second female stop 416b, the second male stop 412b can have the male stop second configuration or a male stop third configuration. The male stop third configuration can be a male stop deflected configuration. When the second male stop 412b is in the male stop third configuration, the second male stop 412b can be more deflected than when in the male stop second configuration.

When the second male stop 412b is in the upper jaw 30 and before the second male stop 412b is in contact with the lip 420, the second male stop 412b can have the male stop first configuration.

When the second male stop 412b has the male stop first, second, or third configuration, the first male stop 412a can have the male stop first configuration. As another example, the male stop first configuration of the second male stop 412b can be a second male stop first configuration, the male stop second configuration of the second male stop 412b can be a second male stop second configuration, the male stop third configuration of the second male stop 412b can be a second male stop third configuration, the male stop first configuration of the first male stop 412a can be a first male stop first configuration, the male stop second configuration of the first male stop 412a can be a first male stop second configuration, and the male stop third configuration of the first male stop 412a can be a first male stop third configuration. The first male stop first configuration can be, for example, the same or different neutral configuration as the second male stop first configuration. The first male stop second configuration can be, for example, the same or different amount of deflection as the second male stop second configuration. The first male stop third configuration can be, for example, the same or different amount of deflection as the second male stop third configuration.

The female stops 416 can be flexible and/or rigid. For example, the female stops 416 can have the same configuration when the male stops 412 are in the male stop first, second, and/or third configurations. As another example, the female stops 416 can have a female stop first configuration (also referred to as a female stop neutral configuration or a female stop non-deflected configuration) when the male stops 412 are not engaged with the female stops 416, and can have a female stop second configuration (also referred to as a female stop deflected configuration) when the male stops 412 are engaged with the female stops 416.

The male stops 412 can be springs biased to have the male stop first configuration. For example, when the second male stop 412b is in the male stop second configuration, the second male stop 412b can be biased to return (e.g., passively return) to the male stop first configuration. For example, when the second male stop 412b is in the male stop second configuration, the second male stop 412b can be biased to rebound or spring back to the male stop first configuration. This can advantageously allow the second male stop 412*b* to passively engage with the second female stop 416*b* as the second male stop 412*b* is moved into the upper jaw 30, past the lip 420, and into the second female stop 416*b*.

FIG. 49H$_2$ illustrates that when the shuttle 14 is moved (e.g., translated, slid) in the lower jaw shuttle track 66 as shown by arrow 604, one or multiple male stops 412 can move (e.g., deflect) into a female stop 416, for example, by moving past (e.g., under) the lip 420. For example, FIG. 49H$_2$ illustrates that when the shuttle 14 is moved into the lower jaw shuttle track 66, a male stop 412 (e.g., the first male stop 412*a*) can move into and/or engage with a female stop 416 (e.g., with the first female stop 416*a*), for example, by moving (e.g., deflecting) under the lip 420. FIG. 49H$_2$ further illustrates that when the shuttle 14 is moved (e.g., translated, slid) out of the lower jaw shuttle track 66 as shown by arrow 602, one or multiple male stops 412 can move (e.g., deflect) out of a female stop 416, for example, by moving past (e.g., under) the lip 420. For example, FIG. 49H$_2$ illustrates that when the shuttle 14 is moved out of the lower jaw shuttle track 66, a male stop 412 (e.g., the first male stop 412*a*) can move under the lip 420 and disengage with a female stop 416 (e.g., with the first female stop 416*a*). Half of the lower jaw is shown transparent in FIG. 49H$_2$ so that the shuttle 14 can be more easily seen in the lower jaw 38, and so that the engagement between the male and female stops 412, 416 can be more easily seen.

When the first male stop 412*a* is between the lip 420 and the lower jaw pusher 76, the first male stop 412*a* can be engaged with the first female stop 416*a*. When the first male stop 412*a* is engaged with the first female stop 416*a*, the first male stop 412*a* can be in contact with the first female stop 416*a*. For example, when the first male stop 412*a* is engaged with the first female stop 416*a*, the male surface 414 can be in contact with the female surface 418. As another example, when the first male stop 412*a* is engaged with the first female stop 416*a*, the first male stop 412*a* may not be in contact with the first female stop 416*a*. For example, when the first male stop 412*a* is engaged with the first female stop 416*a*, the male surface 414 may not be in contact with the female surface 418 such that the first male stop 412*a* can float in the first female stop 416*a*. When the first male stop 412*a* is engaged with the first female stop 416*a*, the first male stop 412*a* can have a male stop first configuration or a male stop second configuration. The male stop first configuration can be a male stop neutral configuration (e.g., the configuration of the first male stop 412*a* shown in FIGS. 49A-49E). The male stop second configuration can be a male stop deflected configuration.

When the first male stop 412*a* is engaged with the lip 420, for example, as the shuttle 14 is moving into or out of the second female stop 416*b*, the first male stop 412*a* can have the male stop second configuration or a male stop third configuration. The male stop third configuration can be a male stop deflected configuration. When the first male stop 412*a* is in the male stop third configuration, the first male stop 412*a* can be more deflected than when in the male stop second configuration.

When the first male stop 412*a* is in the lower jaw 38 and before the first male stop 412*a* is in contact with the lip 420, the first male stop 412*a* can have the male stop first configuration.

The male stops 412 can be springs biased to have the male stop first configuration. For example, when the first male stop 412*a* is in the male stop second configuration, the first male stop 412*a* can be biased to return (e.g., passively return) to the male stop first configuration. For example, when the first male stop 412*a* is in the male stop second configuration, the first male stop 412*a* can be biased to rebound or spring back to the male stop first configuration. This can advantageously allow the first male stop 412*a* to passively engage with the first female stop 416*a* as the second male stop 412*b* is moved into the lower jaw 38, past the lip 420, and into the first female stop 416*a*.

FIG. 49H$_3$ illustrates that when the second male stop 412*b* is engaged with the second female stop 416*b*, the male surface 414 of the second male stop 412*b* can be in contact with the female surface 418. When the male surface 414 is in contact with the female surface 418 of the second female stop 416*b*, the second male stop 412*b* can have, for example, the second male stop first configuration (e.g., a non-deflected configuration) or the second male stop second configuration (e.g., a partially deflected configuration).

FIG. 49H$_3$ further illustrates that when the second male stop 412*b* is engaged with the second female stop 416*b*, the suture loop 162 can be engaged with the first suture stop 534*a*. FIG. 49H$_3$ further illustrates that that the outer surface 419 can be a surface of the first suture stop 534*a*.

FIG. 49H$_3$ further illustrates that when the second male stop 412*b* is engaged with the second female stop 416*b*, tissue can be moveable (e.g., pushable) by the second male stop 412*b* out of the second female stop 416*b*, away from the second female stop 416*b*, or out of and away from the second female stop 416*b*. The second male stop 412*b* can thereby be a tissue mover that can advantageously keep the second female stop 416*b* clear of tissue (or can minimize the amount of tissue in it) that could, for example, otherwise cause the shuttle 14 to get jammed in the upper jaw 30. The first suture stop 534*a*, the outer surface 419, and/or the lip 420 can be a tissue barrier, inhibiting or preventing tissue from entering the second female stop 416*b*. The deflection of the second male stop 412*b* toward the shuttle longitudinal axis $14_{A1}$ as the second male stop 412*b* passes by (e.g., under) the lip 420 can advantageously force tissue away from the second female stop 416*b*, for example, by squeezing tissue that may be in the holes 404 and/or 405 progressively toward the suture holder 18 as the second male stop 412*b* is progressively pinched closer to the shuttle longitudinal axis $14_{A1}$ by the lip 420 as the second male stop 412*b* is moved into the second female stop 416*b*. The second male stop 412*b* can clear tissue from the second female stop 416*b*, can inhibit or prevent tissue from entering the second female stop 416*b*, or can do any combination thereof.

FIG. 49H$_3$ further illustrates that the outer surface 419, the lip 420, and/or the first shuttle stop 534*a* can be engageable with the first male stop 412*a* to inhibit or prevent overextension of the shuttle 14 into the upper jaw 30. For example, the outer surface 419, the lip 420, and/or the first shuttle stop 534*a* can cause the first male stop 412*a* to move in the male stop second direction $412_{SD}$ when the first male stop 412*a* makes contact with the outer surface 419, the lip 420, and/or the first shuttle stop 534*a*. This can advantageously inhibit or prevent the first male stop 412*a* from moving past (e.g., under) the lip 420 in the upper jaw 30.

FIG. 49H$_4$ illustrates that when the first male stop 412*a* is engaged with the first female stop 416*a*, the male surface 414 of the first male stop 412*a* can be in contact with the female surface 418 of the first female stop 416*a*. When the male surface 414 is in contact with the female surface 418, the first male stop 412*a* can have, for example, the second male stop first configuration (e.g., a non-deflected configuration) or the second male stop second configuration (e.g., a partially deflected configuration).

FIG. 49H$_4$ further illustrates that when the first male stop 412a is engaged with the first female stop 416a, the suture loop 162 can be engaged with the first suture stop 534a. FIG. 49H$_4$ further illustrates that that the outer surface 419 can be a surface of the first suture stop 534a.

FIG. 49H$_4$ further illustrates that when the first male stop 412a is engaged with the first female stop 416a, tissue can be moveable (e.g., pushable) by the first male stop 412a out of the first female stop 416a, away from the first female stop 416a, or out of and away from the first female stop 416a. The first male stop 412a can thereby be a tissue mover that can advantageously keep the first female stop 416a clear of tissue (or can minimize the amount of tissue in it) that could, for example, otherwise cause the shuttle 14 to get jammed in the lower jaw 38. The first suture stop 534a, the outer surface 419, and/or the lip 420 can be a tissue barrier, inhibiting or preventing tissue from entering the first female stop 416a. The deflection of the first male stop 412a toward the shuttle longitudinal axis 14$_{A1}$ as the first male stop 412a passes by (e.g., under) the lip 420 can advantageously force tissue away from the first female stop 416a, for example, by squeezing tissue that may be in the holes 404 and/or 405 progressively toward the suture holder 18 as the first male stop 412a is progressively pinched closer to the shuttle longitudinal axis 14$_{A1}$ by the lip 420 as the first male stop 412a is moved into the first female stop 416a. The first male stop 412a can clear tissue from the first female stop 416a, can inhibit or prevent tissue from entering the first female stop 416a, or can do any combination thereof.

FIG. 49H$_4$ further illustrates that the outer surface 419, the lip 420, and/or the first shuttle stop 534a can be engageable with the first male stop 412a to inhibit or prevent overextension of the shuttle 14 into the lower jaw 38. For example, the outer surface 419, the lip 420, and/or the first shuttle stop 534a can cause the first male stop 412a to move in the male stop second direction 412$_{SD}$ when the first male stop 412a makes contact with the outer surface 419, the lip 420, and/or the first shuttle stop 534a. This can advantageously inhibit or prevent the first male stop 412a from moving past (e.g., under) the lip 420 in the lower jaw 38.

FIGS. 49H$_1$ and 49H$_3$ further illustrate that when the shuttle 14 is in the upper jaw 30, the first male stop 412a and the second male stop 412b can be in the upper jaw 30. For example, when the shuttle 14 is in the upper jaw 30, the first and second male stops 412a, 412b can be moveable (e.g., translatable, slideable) in the upper jaw shuttle track 64, in the upper jaw suture slot 238b, or in both. FIGS. 49H$_1$ and 49H$_3$ further illustrate that when the shuttle 14 is in the upper jaw 30 and the second male stop 412b is in the second female stop 416b, the first male stop 412a can be in the upper jaw shuttle track 64, in the upper jaw suture slot 238b, or in both. FIGS. 49H$_1$ and 49H$_3$ further illustrate that when the shuttle 14 is in the upper jaw 30, the second male stop 412b can be farther along the upper jaw track 64 than the first male stop 412a. FIGS. 49H$_1$ and 49H$_3$ further illustrate that when the second male stop 412b has the second male stop first, second, or third configuration, the first male stop 412a can have the first male stop first configuration. For example, FIGS. 49H$_1$ and 49H$_3$ illustrate that when the shuttle 14 is in the upper jaw 30 and the second male stop 412b is in a deflected configuration or in a non-deflected configuration, the first male stop 412a can be in a non-deflected configuration.

FIGS. 49H$_2$ and 49H$_4$ further illustrate that when the shuttle 14 is in the lower jaw 38, the first male stop 412a and the second male stop 412b can be in the lower jaw 38. For example, when the shuttle 14 is in the lower jaw 38, the first and second male stops 412a, 412b can be moveable (e.g., translatable, slideable) in the lower jaw shuttle track 66, in the lower jaw suture slot 238a, or in both. FIGS. 49H$_2$ and 49H$_4$ further illustrate that when the shuttle 14 is in the lower jaw 38 and the first male stop 412a is in the first female stop 416a, the second male stop 412b can be in the lower jaw shuttle track 66, in the lower jaw suture slot 238a, or in both. FIGS. 49H$_2$ and 49H$_4$ further illustrate that when the shuttle 14 is in the lower jaw 38, the first male stop 412a can be farther along the lower jaw track 66 than the second male stop 412b. FIGS. 49H$_2$ and 49H$_4$ further illustrate that when the first male stop 412a has the first male stop first, second, or third configuration, the second male stop 412b can have the second male stop first configuration. For example, FIGS. 49H$_2$ and 49H$_4$ illustrate that when the shuttle 14 is in the lower jaw 38 and the first male stop 412a is in a deflected configuration or in a non-deflected configuration, the second male stop 412b can be in a non-deflected configuration.

FIGS. 49H$_1$-49H$_4$ further illustrate that the distance between the first and second male stops 412a, 412b (also referred to as the inter-male stop distance) can be constant, for example, as measured along the shuttle longitudinal axis 14$_{A1}$. The inter-male stop distance can be measured, for example, between the male stop first terminal end 412$_{TE1}$ of the first male stop 412a and the male stop first terminal end 412$_{TE1}$ of the second male stop 412b, for example, along the shuttle longitudinal axis 14$_{A1}$. The inter-male stop distance can be the same when the shuttle 14 is in the upper jaw 30 and when the shuttle 14 is in the lower jaw 38. For example, the inter-male stop distance can be the same when the shuttle 14 is in the upper jaw 30 and the second male stop 412b is in the second female stop 416b as when the shuttle 14 is in the lower jaw 38 and the first male stop 412a is in the first female stop 416a.

As another example, the inter-male stop distance can be measured, for example, between the male stop second terminal end 412$_{TE2}$ of the first male stop 412a and the male stop second terminal end 412$_{TE2}$ of the second male stop 412b, for example, along an axis parallel to the shuttle longitudinal axis 14$_{A1}$ or along a straight measurement axis between the two male stop second terminal ends 412$_{TE2}$. For example, when the shuttle 14 is in the upper jaw 30 and the second male stop 412b is in a deflected configuration and the first male stop 412a is in a non-deflected configuration, the inter-male stop distance can be a first distance, and when the shuttle 14 is in the upper jaw 30 and the second male stop 412b is in a non-deflected configuration and the first male stop 412a is in a non-deflected configuration, the inter-male stop distance can be a second distance, where the first distance can be less than the second distance. As another example, the first distance can be the same as the second distance or greater than the second distance. When the shuttle 14 is in the lower jaw 38 and the first male stop 412a is in a deflected configuration and the second male stop 412b is in a non-deflected configuration, the inter-male stop distance can be the first distance, and when the shuttle 14 is in the lower jaw 38 and the first male stop 412a is in a non-deflected configuration and the second male stop 412b is in a non-deflected configuration, the inter-male stop distance can be the second distance, where the first distance can be less than the second distance. As another example, the first distance can be the same as the second distance or greater than the second distance.

FIGS. 49H$_1$-49H$_4$ illustrate that the male stops 412 can be passively retained in the female stops 416. FIGS. 49H$_1$-49H$_4$ illustrate that when the first male stop 412a is engaged with the first female stop 416a, the shuttle 14 can be passively retained in the lower jaw 38, and that when the second male stop 412b is engaged with the second female stop 416b, the shuttle 14 can be passively retained in the upper jaw 30. Movement of the shuttle 14, for example, via the lower and upper pushers 76, 86, can engage and disengage the male and female stops 412, 416 from each other. For example, for engagement, the lower jaw pusher 76 can move the second male stop 412b into the second female stop 416b to engage the second male stop 412b with the second female stop 416b, and the upper jaw pusher 86 can move the first male stop 412a into the first female stop 416a to engage the first male stop 412a with the first female stop 416a. As another example, for disengagement, the lower jaw pusher 76 can move the first male stop 412a out of the first female stop 416a to disengage the first male stop 412a with the first female stop 416a, and the upper jaw pusher 86 can move the second male stop 412b out of the second female stop 416b to disengage the second male stop 412b with the second female stop 416b. The male stops 412 and the female stops 416 can thereby be passive stops, where movement of the shuttle 14 cases the male stops 412 to engage and disengage with the female stops 416. In this way, the lower jaw pusher 76 can move the shuttle 14 (e.g., the second male stop 412b) into engagement with the second female stop 416b, the upper jaw pusher 86 can move the shuttle 14 (e.g., the second male stop 412b) out of engagement with the second female stop 416b, the upper jaw pusher 86 can move the shuttle 14 (e.g., the first male stop 412a) into engagement with the first female stop 416a, and the lower jaw pusher 76 can move the shuttle 14 (e.g., the first male stop 412a) out of engagement with the first female stop 416a.

When the lower jaw pusher 76 moves the shuttle 14 (e.g., the second male stop 412b) into engagement with the second female stop 416b, the second male stop 412b can be deflected from the male stop first configuration to the male stop second configuration, for example, by the lip 420, and the second male stop 412b can rebound from the male stop second configuration back to the male stop first or third configuration, for example, once the second male stop 412b is moved into the second female stop 416b.

When the upper jaw pusher 86 moves the shuttle 14 (e.g., the second male stop 412b) out of engagement with the second female stop 416b, the second male stop 412b can be deflected from the male stop first or third configuration to the male stop second configuration, for example, by the lip 420, and the second male stop 412b can rebound from the male stop second configuration back to the male stop first configuration, for example, once the second male stop 412b is moved out of the first female stop 416a and past the lip 420.

When the upper jaw pusher 86 moves the shuttle 14 (e.g., the first male stop 412a) into engagement with the first female stop 416a, the first male stop 412a can be deflected from the male stop first configuration to the male stop second configuration, for example, by the lip 420, and the first male stop 412a can rebound from the male stop second configuration back to the male stop first or third configuration, for example, once the first male stop 412a is moved into the first female stop 416a.

When the lower jaw pusher 76 moves the shuttle 14 (e.g., the first male stop 412a) out of engagement with the first female stop 416a, the first male stop 412a can be deflected from the male stop first or third configuration to the male stop second configuration, for example, by the lip 420, and the first male stop 412a can rebound from the male stop second configuration back to the male stop first configuration, for example, once the first male stop 412a is moved out of the first female stop 416a and past the lip 420.

When the male stops 412 are engaged with a female stop 416, one or both of the lower jaw pusher 76 and the upper jaw pusher 86 may or may not be in contact with the male stops 412. For example, FIGS. $49H_1$ and $49H_3$ illustrate that after the second male stop 412b is moved into engagement with the second female stop 416b, the lower jaw pusher 76 can be moved (e.g., retracted, withdrawn) into the lower jaw 38 and a gap can be between the second male stop 412b before the upper jaw pusher 86 is moved into engagement with the shuttle 14 to move the shuttle 14 from the upper jaw 30 into the lower jaw 38. As another example, FIGS. $49H_2$ and $49H_4$ illustrate that after the first male stop 412a is moved into engagement with the first female stop 416a, the upper jaw pusher 86 can be moved (e.g., retracted, withdrawn) into the upper jaw 30 and a gap can be between the first male stop 412a before the lower jaw pusher 76 is moved into engagement with the shuttle 14 to move the shuttle 14 from the lower jaw 38 into the upper jaw 30.

FIGS. $49H_1$-$49H_4$ further illustrate that the female stops 416 (e.g., the first female stop 416a and the second female stop 416b) can be radial female stops in which the female stop extends radially away from shuttle track (e.g., radially away from shuttle tracks 64 and 66).

FIG. 50A illustrates that the shuttle 14 can have one or multiple male stops 412 that extend laterally away from the shuttle longitudinal axis $14_{A1}$. The shuttle 14 can have 1-8 or more male stops 412 that extend laterally away from the shuttle longitudinal axis $14_{A1}$, including every one increment within this range (e.g., 1 male stop that extends laterally away from the shuttle longitudinal axis $14_{A1}$, 2 male stops that extend laterally away from the shuttle longitudinal axis $14_{A1}$, 8 male stops that extend laterally away from the shuttle longitudinal axis $14_{A1}$). For example, FIG. 50A illustrates that the shuttle 14 can have two male stops 412 that extend laterally away from the shuttle longitudinal axis $14_{A1}$, for example, as opposed to radially away from the shuttle longitudinal axis $14_{A1}$ like the hammerhead design in FIGS. 49A-$49H_4$ or like the straight design (also referred to as the diving board design) in FIGS. 33A-36C. The shuttle 14 can have lateral stops in addition to or in lieu of radial stops (e.g., the diving board design or the new hammerhead design). The shuttle 14 can thereby have a retention feature in one plane of the shuttle (e.g., in the radial or lateral plane of the shuttle 14), in two planes (e.g., in the radial and lateral planes of the shuttle 14), or in more planes, where the retention feature can be one or multiple male stops 412. The radial and lateral directions can be perpendicular to each other. The radial and lateral planes can be perpendicular to each other.

FIG. 50A shows, for example, that the shuttle 14 can have radial male stops $412_R$ and lateral male stops $412_L$. The shuttle 14 can have 0-8 radial male stops $412_R$, including every 1 radial male stop increment within this range (e.g., 0 radial male stops, 1 radial male stop, 2 radial male stops). The shuttle 14 can have 0-8 lateral male stops $412_L$, including every 1 lateral male stop increment within this range (e.g., 0 lateral male stops, 1 lateral male stop, 2 lateral male stops). For example, FIG. 50A illustrates that the shuttle 14 can have a first radial male stop $412_{R1}$, a second radial male stop $412_{R2}$, a first lateral male stop $412_{L1}$, and a second lateral male stop $412_{L2}$, or any combination thereof. The radial male stops $412_R$ (e.g., the first and second radial male stops $412_{R1}$, $412_{R2}$) are also referred to as the male stops 412 (e.g., the first and second male stops 412a, 412b) in FIGS. 33A-$49H_4$, where the male stops 412 in FIGS. 33A-$49H_4$ can also be referred to as radial male stops. The lateral male stops $412_L$ can have the same features and functions as the radial male stops $412_R$ (e.g., shown in FIGS. 33A-49H$_4$) but can be positioned differently on the shuttle 14 (e.g., laterally as opposed to radially), for example, as shown in FIG. 50A.

The lateral male stops $412_L$ can be anywhere along the length of the shuttle 14. For example, FIG. 50A illustrates that the shuttle first longitudinal end $14_{S1}$ can have a lateral male stop (e.g., the first lateral male stop $412_{L1}$) and that the shuttle second longitudinal end $14_{S2}$ can have a lateral male stop (e.g., the second lateral male stop $412_{L2}$) in the arrangement shown.

The lateral male stops $412_L$, can be, for example, springs moveable (e.g., deflectable) toward and away from the shuttle longitudinal axis $14_{A1}$ as shown by arrows 605 and 607 when engaging and/or disengaging with a female stop 416. As shown in FIG. 50A, for example, the first lateral male stop $412_{L1}$ can be moveable toward (e.g., arrow 605) the shuttle longitudinal axis $14_{A1}$ when exiting a female stop 416 and can be moveable away from (e.g., arrow 607) the shuttle longitudinal axis $14_{A1}$ when entering a female stop 416. The first lateral male stop $412_{L1}$ can be moveable toward (e.g., arrow 605) the shuttle second lateral side $14_{L2}$ when exiting a female stop 416 and can be moveable away from (e.g., arrow 607) the shuttle first lateral side $14_{L1}$ when entering a female stop 416. For example, the first lateral male stop $412_{L1}$ can be moveable toward (e.g., arrow 605) the shuttle lateral side terminal end $14_{LTE}$ of the shuttle second lateral side $14_{L2}$ when exiting a female stop 416 and can be moveable away from (e.g., arrow 607) the shuttle lateral side terminal end $14_{LTE}$ of the shuttle first lateral side $14_{L1}$ when entering a female stop 416. As further shown in FIG. 50A, the second lateral male stop $412_{L2}$ can be moveable toward (e.g., arrow 605) the shuttle longitudinal axis $14_{A1}$ when exiting a female stop 416 and can be moveable away from (e.g., arrow 607) the shuttle longitudinal axis $14_{A1}$ when entering a female stop 416. The second lateral male stop $412_{L2}$ can be moveable toward (e.g., arrow 605) the shuttle first lateral side $14_{L1}$ when exiting a female stop 416 and can be moveable away from (e.g., arrow 607) the shuttle second lateral side $14_{L2}$ when entering a female stop 416. For example, the second lateral male stop $412_{L2}$ can be moveable toward (e.g., arrow 605) the shuttle lateral side terminal end $14_{LTE}$ of the shuttle first lateral side $14_{L1}$ when exiting a female stop 416 and can be moveable away from (e.g., arrow 607) the shuttle lateral side terminal end $14_{LTE}$ of the shuttle second lateral side $14_{L2}$ when entering a female stop 416.

The lateral male stops $412_L$ can have wider distal ends than proximal ends. For example, FIG. 50A illustrates that the male stop second longitudinal end $412_{SE}$ of the first lateral male stop $412_{L1}$ can be wider than the male stop first longitudinal end $412_{FE}$ of the first lateral male stop $412_{L1}$. FIG. 50A further illustrates that the male stop second section $412_{S2}$ of the first lateral male stop $412_{L1}$ can be wider than the male stop first section $412_{S1}$ of the first lateral male stop $412_{L1}$. FIG. 50A further illustrates that the male stop second longitudinal end $412_{SE}$ of the second lateral male stop $412_{L2}$ can be wider than the male stop first longitudinal end $412_{FE}$ of the second lateral male stop $412_{L2}$. FIG. 50A further illustrates that the male stop second section $412_{S2}$ of the second lateral male stop $412_{L2}$ can be wider than the male stop first section $412_{S1}$ of the second lateral male stop $412_{L2}$.

FIG. 50A further illustrates that the lateral male stops $412_L$ can form part of the shuttle tips 164 (e.g., first and second tips 164a, 164b) and/or can form part of the shuttle body 160.

The lateral male stops $412_L$ can be moveable (e.g., deflectable) between multiple configurations. For example, FIG. 50A illustrates that the lateral male stops $412_L$ (e.g., the first and second lateral male stops $412_{L1}$, $412_{L2}$) can be moveable (e.g., deflectable) back and forth between the male stop first configuration and the male stop second configuration. The male stop first configuration for the lateral male stops $412_L$ can be the male stop neutral configuration (also referred to as the male stop non-deflected configuration). The male stop neutral configuration can be the configuration of the lateral male stops $412_L$ shown, for example, in FIG. 50A. The lateral male stops $412_L$ can have the male stop first configuration (e.g., neutral configuration), for example, when the lateral male stop $412_L$ is partially engaged with a female stop 416, when the male stop 412 is fully engaged with a female stop 416, or both. FIG. 50A illustrates, for example, that when the lateral male stops $412_L$ are in the male stop first configuration, the shuttle tips 164 can be wider than a center portion of the shuttle body 160. For example, FIG. 50A illustrates that when the first lateral male stop $412_{L1}$ is in the male stop first configuration, the shuttle first tip 164a can be wider than a center portion of the shuttle body 160, can be wider than the shuttle width 292, or both, and that when the second lateral male stop $412_{L2}$ is in the male stop first configuration, the shuttle first tip 164b can be wider than a center portion of the shuttle body 160, can be wider than the shuttle width 292, or both. FIG. 50A further illustrates that the shuttle 14 can have a space 608 when the lateral male stops $412_L$ are in the male stop first configuration. The space 608 can be, for example, between the lateral male stops $412_L$ and the shuttle body 160. FIG. 50A illustrates that the space 608 can have multiple arms such that the space 608 can have an L-shape (e.g., a long arm and a short arm, where the arms can be straight, curved or irregular in shape). For example, FIG. 50A illustrates that the space 608 can have an irregular shaped long arm that terminates in the shuttle tips 164 and a straight short arm that terminates at or next to a shuttle lateral terminal end $14_{LTE}$.

The male stop second configuration for the lateral male stops $412_L$ can be a male stop deflected configuration in which the lateral male stop $412_L$ is in a configuration different from the male stop neutral configuration. For example, the male stop second configuration of the lateral male stops $412_L$ can be a deflected configuration in which the lateral male stop $412_L$ (e.g., the male stop first section $412_{S1}$ of the lateral male stop $412_L$ and/or the male stop second section $412_{S2}$ of the lateral male stop $412_L$) is closer to the shuttle longitudinal axis $14_{A1}$, is closer to a shuttle lateral side (e.g., the shuttle first or second lateral side $14_{L1}$, $14_{L2}$), and/or is closer to a shuttle lateral side terminal end $14_{LTE}$ (e.g., the shuttle lateral side terminal end $14_{LTE}$ of the shuttle first lateral side $14_{L1}$ or of the shuttle lateral side terminal end $14_{LTE}$ of the shuttle second lateral side $14_{L2}$) than when the lateral male stop $412_L$ is in the male stop first configuration. As another example, the male stop second configuration of the lateral male stops $412_L$ can be a deflected configuration in which the lateral male stop $412_L$ (e.g., the male stop first section $412_{S1}$ of the lateral male stop $412_L$ and/or the male stop second section $412_{S2}$ of the lateral male stop $412_L$) is farther from the shuttle longitudinal axis $14_{A1}$, is farther from a shuttle lateral side (e.g., the shuttle first or second lateral side $14_{L1}$, $14_{L2}$), and/or is farther from a shuttle lateral side terminal end $14_{LTE}$ (e.g., the shuttle lateral side terminal end $14_{LTE}$ of the shuttle first lateral side $14_{L1}$ or of the shuttle lateral side terminal end $14_{LTE}$ of the shuttle second lateral side $14_{L2}$) than when the lateral male stop $412_L$ is in the male stop first configuration. The lateral male stops $412_L$ can have the male stop second configuration (e.g., deflected configuration), for example, when the lateral male stop 412 is in a shuttle track (e.g., shuttle tracks 64 and/or 66), when the lateral male stop 16 is partially engaged with a female stop 416, when the lateral male stop 412 is not in a female stop 416, or any combination thereof. The space 608 can be smaller when the lateral male stops $412_L$ are in the male stop second configuration than when in the male stop first configuration. For example, the space 608 can be partially or completely closed when the lateral male stops $412_L$ are in the male stop second configuration than when in the male stop first configuration. When the lateral male stops $412_L$ are moved from the male stop first configuration to the male stop second configuration, the lateral male stops $412_L$ can move into the space 608. When the lateral male stops $412_L$ move into the space 608, the lateral male stops $412_L$ can pivot about the shuttle tips 164 (e.g., about shuttle first and second tips 164a, 164b).

FIG. 50A illustrates the shuttle 14 and the male stops 412 (e.g., the radial and lateral male stops $412_R$, $412_L$) in a flat configuration before being shape-set into a curved configuration.

FIG. 50A further illustrates the arrangement of features shown, for example, with exemplary dimensions $D_8$-$D_{11}$, $D_{17}$-$D_{20}$, and the shuttle width 292.

FIG. 50A illustrates that the dimension $D_8$ can be, for example, from about 0.10 mm to about 0.60 mm, including every 0.01 mm increment within this range (e.g., 0.10 mm, 0.28 mm, 0.60 mm).

FIG. 50A illustrates that the dimension $D_9$ can be, for example, from about 0.30 mm to about 1.00 mm, including every 0.01 mm increment within this range (e.g., 0.30 mm, 0.66 mm, 1.00 mm).

FIG. 50A illustrates that the dimension $D_{10}$ can be, for example, from about 0.30 mm to about 1.25 mm, including every 0.01 mm increment within this range (e.g., 0.30 mm, 0.74 mm, 1.25 mm).

FIG. 50A illustrates that the dimension $D_{11}$ can be, for example, from about 6.00 mm to about 10.00 mm, including every 0.01 mm increment within this range (e.g., 6.00 mm, 8.05 mm, 10.00 mm).

FIG. 50A illustrates that the male stop length $412_X$ of the radial male stops $412_R$ can be, for example, from about 0.30 mm to about 1.15 mm, including every 0.01 mm increment within this range (e.g., 0.30 mm, 0.64 mm, 1.15 mm).

The radial male stop width $412_{RW}$ can be about 0.15 mm to about 0.65 mm, including every 0.01 mm increment within this range (e.g., 0.15 mm 0.36 mm, 0.65 mm). As another example, the radial male stop width $412_{RW}$ can be the same dimension as the male stop first section width $412_{S1W}$.

The dimension $D_{17}$ can be the length shown, which can be from about 1.40 mm to about 4.50 mm, including every 0.01 mm increment within this range (e.g., 1.40 mm, 2.93 mm, 4.50 mm).

The dimension $D_{18}$ can be the angle shown, which can be from about 80 degrees to about 145 degrees, including every 1 degree increment within this range (e.g., 80 degrees, 100 degrees, 145 degrees).

The dimension $D_{19}$ can be the radius of curvature of the shuttle body 160 at the position shown, and can be, for example, from about 0.20 mm to about 0.50 mm, including every 0.01 mm increment within this range (e.g., 0.20 mm, 0.30 mm, 0.50 mm).

The dimension $D_{20}$ can be the radius of curvature of the shuttle body 160 at the position shown, and can be, for example, from about 0.05 mm to about 0.25 mm, including every 0.01 mm increment within this range (e.g., 0.05 mm, 0.15 mm, 0.25 mm).

FIG. 50B illustrates the shuttle 14 of FIG. 50A in a shape-set configuration, and that the dimension $D_1$ can be, for example, from about 4.10 mm to about 8.10 mm, including every 0.01 mm increment within this range (e.g., 4.10 mm, 6.10 mm, 8.10 mm) and that the dimension $D_4$ can be from about 1.30 mm to about 3.20 mm, including every 0.01 mm increment within this range (e.g., 1.30 mm, 2.31 mm, 3.20 mm).

FIG. 50B further illustrates that the shuttle body 160 and the shuttle tips 164 can have the same radius of curvature (e.g., dimension $D_3$).

FIG. 50C illustrates that the first and second tip surfaces 406a, 406b of the shuttle tips 164 (e.g., shuttle first and second tips 164a, 164b) can be beveled, and that the shuttle width 292 can be, for example, from about 0.40 mm to about 2.00 mm, including every 0.01 mm increment within this range (e.g., 0.40 mm, 1.40 mm, 2.00 mm).

FIGS. 50D and 50E illustrate that the lateral male stops $412_L$ and the jaw pushers (e.g., lower and upper jaw pushers 76, 86) can have the dimensions and features shown. FIG. 50D illustrates that the first lateral male stop $412_{L1}$ and the lower jaw pusher 76 can have the dimensions and features shown. FIG. 50E illustrates that the second lateral male stop $412_{L2}$ and the upper jaw pusher 86 can have the dimensions and features shown. The dimensions shown are in millimeters and are exemplary only and can be increased or decreased, for example, by plus or minus 10% to 50% as desired. The upper and lower jaws 30, 38 and the female stop 416 in FIGS. 50D and 50E are shown transparent for illustrative purposes so that the features of the shuttle 14, the lower jaw pusher 76, and the upper jaw pusher 86 can be more easily seen.

FIG. 50D illustrates two configurations of the lower jaw pusher 76 and the first lateral male stop $412_{L1}$, for example, a first configuration in which the lower jaw pusher 76 is not engaged with the first lateral male stop 412L$_1$, and a second configuration in which the lower jaw pusher 76 is engaged with the first lateral male stop $412_{L1}$. When the lower jaw pusher 76 is not engaged with the first lateral male stop $412_{L1}$, the shuttle 14 (e.g., the first lateral male stop $412_{L1}$) can have the features and arrangement shown by the solid lines in FIG. 50D (e.g., as shown by arrow 610a) and the lower jaw pusher 76 can have the features and arrangement shown by the solid lines in FIG. 50D (e.g., as shown by arrow 611). When the lower jaw pusher 76 is engaged with the first lateral male stop $412_{L1}$, the shuttle 14 (e.g., the first lateral male stop $412_{L1}$) can have the features and arrangement shown by the dashed lines in FIG. 50D (as shown by arrow 612a) and the lower jaw pusher 76 can have the features and arrangement shown by the dashed lines in FIG. 50D (as shown by arrow 613). The configuration of the first lateral male stop $412_{L1}$ shown by arrow 610a is also referred to as the configuration 610a, where the configuration 610a can be, for example, the male stop first configuration of the first lateral male stop $412_{L1}$. The configuration of the first lateral male stop $412_{L1}$ shown by arrow 612a is also referred to as the configuration 612a, where the configuration 612a can be, for example, the male stop second configuration of the first lateral male stop $412_{L1}$. The configuration 612a can be a fully deflected configuration of the first lateral male stop $412_{L1}$.

FIG. 50D illustrates that when the lower jaw pusher 76 is moved into contact with the second lateral stop $412_{L2}$, the second lateral stop $412_{L2}$ can be moved from the first configuration as shown by arrow 610a to the second configuration as shown by arrow 612a. The arrow 610a shows, for example, the male stop first configuration of the second lateral stop $412_{L2}$, and the arrow 612a shows, for example, the male stop second configuration of the second lateral stop $412_{L2}$. FIG. 50D further illustrates that the lower jaw pusher 76 can have a lateral stop engager 615. When the lower jaw pusher 76 is moved into contact with the second lateral stop $412_{L2}$, the lateral stop engager 615 can move the second lateral stop $412_{L2}$ from the male stop first configuration (e.g., the configuration shown by arrow 610a) to the male stop second configuration (e.g., the configuration shown by arrow 612a). The lateral stop engager 615 can advantageously inhibit or prevent the shuttle 14 and the lower jaw pusher 76 from becoming stuck together by creating a space 618 between the shuttle first tip 164a and the lower jaw pusher 76 when the shuttle first tip 164a is in the shuttle seat 274 of the lower jaw pusher 76. FIG. 50D further illustrates that the lower jaw pusher 76 can have a tip space 620 that inhibits or prevents the terminal tip 165 of the shuttle first tip 164a from contacting the lower jaw pusher 76 to inhibit or prevent the lower jaw pusher 76 from dulling or chipping the shuttle first tip 164a (e.g., the terminal tip 165).

FIG. 50E illustrates two configurations of the upper jaw pusher 86 and the second lateral male stop $412_{L2}$, for example, a first configuration in which the upper jaw pusher 86 is not engaged with the second lateral male stop $412L_2$, and a second configuration in which the upper jaw pusher 86 is engaged with the second lateral male stop $412_{L2}$. When the upper jaw pusher 86 is not engaged with the second lateral male stop $412_{L2}$, the shuttle 14 (e.g., the second lateral male stop $412_{L2}$) can have the features and arrangement shown by the solid lines in FIG. 50E (e.g., as shown by arrow 610b) and the upper jaw pusher 86 can have the features and arrangement shown by the solid lines in FIG. 50E (e.g., as shown by arrow 611). When the upper jaw pusher 86 is engaged with the second lateral male stop $412_{L2}$, the shuttle 14 (e.g., the second lateral male stop $412_{L2}$) can have the features and arrangement shown by the dashed lines in FIG. 50E (as shown by arrow 612b) and the upper jaw pusher 86 can have the features and arrangement shown by the dashed lines in FIG. 50E (as shown by arrow 613). The configuration of the second lateral male stop $412_{L2}$ shown by arrow 610b is also referred to as the configuration 610b, where the configuration 610b can be, for example, the male stop first configuration of the second lateral male stop $412_{L2}$. The configuration of the second lateral male stop $412_{L2}$ shown by arrow 612b is also referred to as the configuration 612b, where the configuration 612b can be, for example, the male stop second configuration of the second lateral male stop $412_{L2}$. The configuration 612b can be a fully deflected configuration of the second lateral male stop $412_{L2}$.

FIG. 50E illustrates that when the upper jaw pusher 86 is moved into contact with the first lateral stop $412_{L1}$, the first lateral stop $412_{L1}$ can be moved from the first configuration as shown by arrow 610b to the second configuration as shown by arrow 612b. The arrow 610b shows, for example, the male stop first configuration of the first lateral stop $412_{L1}$, and the arrow 612b shows, for example, the male stop second configuration of the first lateral stop $412_{L1}$. FIG. 50E further illustrates that the upper jaw pusher 86 can have a lateral stop engager 615. When the upper jaw pusher 86 is moved into contact with the first lateral stop $412_{L1}$, the lateral stop engager 615 can move the first lateral stop $412_{L1}$ from the male stop first configuration (e.g., the configuration shown by arrow 610b) to the male stop second configuration (e.g., the configuration shown by arrow 612b). The lateral stop engager 615 can advantageously inhibit or prevent the shuttle 14 and the upper jaw pusher 86 from becoming stuck together by creating a space 618 between the shuttle second tip 164b and the upper jaw pusher 86 when the shuttle second tip 164b is in the shuttle seat 274 of the upper jaw pusher 86. FIG. 50E further illustrates that the upper jaw pusher 86 can have a tip space 620 that inhibits or prevents the terminal tip 165 of the shuttle second tip 164b from contacting the upper jaw pusher 86 to inhibit or prevent the upper jaw pusher 86 from dulling or chipping the shuttle second tip 164b (e.g., the terminal tip 165).

FIGS. 50F and 50G illustrate that upper and lower jaws 30, 38 can each have one or multiple lateral female stops $416_L$ that can, for example, extend laterally away from the shuttle tracks (e.g., from the upper and lower jaw shuttle tracks 64, 66). The shuttle tracks 64 and 66 are shown in 50F and 50G with the rest of the upper and lower jaws 30, 38 shown transparent for illustrative purposes. The lower jaw 38 can have, for example, 0-8 lateral female stops $416_L$, including every 1 lateral female stop increment within this range (e.g., 0 lateral female stops, 1 lateral female stop, 2 lateral female stops). The upper jaw 30 can have, for example, 0-8 lateral female stops $416_L$, including every 1 lateral female stop increment within this range (e.g., 0 lateral female stops, 1 lateral female stop, 2 lateral female stops). For example, FIGS. 50F and 50G illustrate that the lower jaw 38 can have a first lateral female stop $416_{L1}$ and that the upper jaw 30 can have a second lateral female stop $416_{L2}$. FIG. 50F illustrates that the first lateral female stop $416_{L1}$ can extend laterally away from the lower jaw shuttle track 66 and FIG. 50G illustrates that the second lateral female stop $416_{L2}$ can extend laterally away from the upper jaw shuttle track 64. For example, the first lateral female stop $416_{L1}$ can extend laterally away from the longitudinal axis (e.g., a center longitudinal axis $66_{LA}$) of the lower jaw shuttle track 66, and the second lateral female stop $416_{L2}$ can extend laterally away from the longitudinal axis (e.g., a center longitudinal axis $64_{LA}$) of the upper jaw shuttle track 64, for example, as opposed to radially away from the longitudinal axis of the upper jaw shuttle tracks 66, 64 like the female stops 416 in FIGS. 33A-35 and $49H_1$-$49H_4$.

The upper and lower jaws 30, 38 can have lateral female stops $416_L$ in addition to or in lieu of radial female stops (e.g., the female stops 416 in FIGS. 33A-35 and $49H_1$-$49H_4$). The upper and lower jaws 30, 38 can thereby have a retention feature in one plane of the jaws (e.g., in the radial or lateral plane of the upper and/or lower jaws 30, 38), in two planes (e.g., in the radial and lateral planes of the upper and/or lower jaws 30, 38), or in more planes, where the retention feature can be one or multiple female stops 416. The female stops 416 in FIGS. 33A-35 and $49H_1$-$49H_4$ are also referred to as radial female stops 4168 (e.g., the first female stop 416a and the second female stop 416b). The lateral female stops $416_L$ can have the same features and functions as the radial female stops 4168 (e.g., shown in FIGS. 33A-35 and $49H_1$-$49H_4$) but can be positioned differently on in the jaws (e.g., they can extend laterally as opposed to radially), for example, as shown in FIGS. 50F and 50G.

FIG. 50F further illustrates that when the first lateral male stop $412_{L1}$ is engaged with the first lateral female stop $416_{L1}$, the first lateral male stop $412_{L1}$ can have the male stop first configuration (e.g., a partially deflected configuration or a neutral configuration such as, for example, the configuration 610a). FIG. 50F further illustrates that when the first lateral male stop $412_{L1}$ is engaged with the first lateral female stop $416_{L1}$, the second lateral male stop $412_{L2}$ can have the male stop first configuration (e.g., a partially deflected configuration or a neutral configuration such as, for example, the configuration 610b). When the first lateral male stop $412_{L1}$ is engaged with the first lateral female stop $416_{L1}$, the male stop first configuration of the second lateral male stop $412_{L2}$ can be the same male stop first configuration of the first lateral male stop $412_{L1}$ (e.g., as shown in FIG. 50F). The configuration 610a can be, for example, the same as the configuration 610b. As another example, when the first lateral male stop $412_{L1}$ is engaged with the first lateral female stop $416_{L1}$, the male stop first configuration of the second lateral male stop $412_{L2}$ can be different from the male stop first configuration of the first lateral male stop $412_{L1}$. For example, when the first lateral male stop $412_{L1}$ is engaged with the first lateral female stop $416_{L1}$, the second lateral male stop $412_{L2}$ can have the male stop second configuration (e.g., the configuration 612b or a partially deflected configuration somewhere between the configurations 610b and 612b). FIG. 50F further illustrates that the longitudinal axis $76_{LA}$ of the lower jaw pusher 76, the longitudinal axis $66_{LA}$ of the lower jaw shuttle track 66, and the shuttle longitudinal axis $14_{A1}$ can be coincident with each other when the shuttle 14 is in the lower jaw 38. The shuttle 14, the lower jaw shuttle track 66, and the lower jaw pusher 76 are shown flat in FIG. 50F for illustrative purposes to more easily see the relationship between the features shown.

FIG. 50G further illustrates that when the second lateral male stop $412_{L2}$ is engaged with the second lateral female stop $416_{L2}$, the second lateral male stop $412_{L2}$ can have the male stop first configuration (e.g., a partially deflected configuration or a neutral configuration such as, for example, the configuration 610b). FIG. 50G further illustrates that when the second lateral male stop $412_{L2}$ is engaged with the second lateral female stop $416_{L2}$, the first lateral male stop $412_{L1}$ can have the male stop first configuration (e.g., a partially deflected configuration or a neutral configuration such as, for example, the configuration 610a). When the second lateral male stop $412_{L2}$ is engaged with the second lateral female stop $416_{L2}$, the male stop first configuration of the first lateral male stop $412_{L1}$ can be the same male stop first configuration of the second lateral male stop $412_{L2}$ (e.g., as shown in FIG. 50G). As another example, when the second lateral male stop $412_{L2}$ is engaged with the second lateral female stop $416_{L2}$, the male stop first configuration of the first lateral male stop $412_{L1}$ can be different from the male stop first configuration of the second lateral male stop $412_{L2}$. For example, when the second lateral male stop $412_{L2}$ is engaged with the second lateral female stop $416_{L2}$, the first lateral male stop $412_{L1}$ can have the male stop second configuration (e.g., the configuration 612a or a partially deflected configuration somewhere between the configurations 610a and 612a). FIG. 50G further illustrates that the longitudinal axis $86_{LA}$ of the upper jaw pusher 86, the longitudinal axis $64_{LA}$ of the upper jaw shuttle track 64, and the shuttle longitudinal axis $14_{A1}$ can be coincident with each other when the shuttle 14 is in the upper jaw 30. The shuttle 14, the upper jaw shuttle track 64, and the upper jaw pusher 86 are shown flat in FIG. 50G for illustrative purposes to more easily see the relationship between the features shown.

FIGS. 50F and 50G illustrate that the lateral male stops $412_L$ can be springs biased to have the male stop first configuration. For example, when the lateral male stops $412_L$ (e.g., the first and second lateral male stops $412_{L1}$, $412_{L2}$) are in the male stop second configuration, the lateral male stops $412_L$ can be biased to return (e.g., passively return) to the male stop first configuration. For example, when the lateral male stops $412_L$ are in the male stop second configuration, the lateral male stops $412_L$ can be biased to rebound or spring back to the male stop first configuration. This can advantageously allow the lateral male stops $412_L$ (e.g., the first and second lateral male stops $412_{L1}$, $412_{L2}$) to passively engage with the lateral female stops $416_L$ (e.g., the first and second lateral female stops $416_{L1}$, $416_{L2}$) as lateral male stops $412_L$ are moved into the lateral female stops $416_L$.

FIG. $50H_1$ illustrates the lower jaw shuttle track 66 of FIG. 50F having a curve in the lower jaw 38, with half of the lower jaw 38 shown transparent for illustrative purposes.

FIG. $50H_1$ further illustrates that the first lateral female stop $416_{L1}$ can be straight. As another example, the first lateral female stop $416_{L1}$ can have a curve having a radius of curvature that is the same as, for example, the radius of curvature of the shuttle 14.

FIG. $50H_1$ further illustrates that the lower jaw 38 can have a radial female stop 4168, a lateral female stop $416_L$, or both. For example, the lower jaw 38 can have a first radial female stop $416_{R1}$ and the first lateral female stop $416_{L1}$.

FIG. $50H_2$ illustrates the shuttle 14 in the lower jaw 38 of FIG. $50H_1$ with half of the lower jaw 38 shown transparent for illustrative purposes. FIG. $50H_2$ illustrates the first lateral male stop $412_{L1}$ engaged with the first lateral female stop $416_{L1}$, and the first radial male stop $412_{R1}$ engaged with the first radial female stop $416_{R1}$.

FIG. $50H_3$ illustrates the upper jaw shuttle track 64 of FIG. 50G having a curve in the upper jaw 30, with half of the upper jaw 30 shown transparent for illustrative purposes.

FIG. $50H_3$ further illustrates that the second lateral female stop $416_{L2}$ can be straight. As another example, the second lateral female stop $416_{L2}$ can have a curve having a radius of curvature that is the same as, for example, the radius of curvature of the shuttle 14.

FIG. $50H_3$ further illustrates that the upper jaw 30 can have a radial female stop 4168, a lateral female stop $416_L$, or both. For example, the upper jaw 30 can have a second radial female stop $416_{R2}$ and the second lateral female stop $416_{L2}$.

FIG. $50H_4$ illustrates the shuttle 14 in the upper jaw 30 of FIG. $50H_3$ with half of the upper jaw 30 shown transparent for illustrative purposes. FIG. $50H_4$ illustrates the second lateral male stop $412_{L2}$ engaged with the second lateral female stop $416_{L2}$, and the second radial male stop $412_{R2}$ engaged with the second radial female stop $416_{R2}$.

FIGS. $50H_2$ $50H_4$ further illustrate that the first radial male stop $412_{R1}$ can have a hammer head shape (e.g., the same hammer head shape as the first male stop 412a in FIGS. 49A-$49H_4$) and that the second radial male stop $412_{R2}$ can have a hammer head shape (e.g., the same hammer head shape as the second male stop 412b in FIGS. 49A-$49H_4$)

The radial shuttle female stops 4168 (e.g., the first and second radial shuttle female stops $416_{R1}$, $416_{R2}$) are also referred to as the female stops 416 (e.g., the first and second female stops 416a, 416b) in FIGS. 33A-35 and $49H_1$-$49H_4$.

FIGS. $50H_1$-$50H_4$ together illustrate, for example, the shuttle 14 with four male stops 412 and the upper and lower jaws 30, 38 each with two female stops 416. The male stops 412 can deflect toward the shuttle longitudinal axis $14_{A1}$ when the shuttle 14 is moved away from the female stops 416 the shuttle 14 is engaged with.

FIGS. 51A-51L illustrate the male stops 412 can have the shapes and features shown, and that the shuttle 14 can have any combination of the male stops 412 shown. The male stops 412 in FIGS. 51A-51L can be, for example, radial male stops $412_R$. As another example, the male stops 412 in FIGS. 51A-51L can be lateral male stops $412_L$. As yet another example, the male stops 412 in FIGS. 51A-51L can be radial and/or lateral male stops, whereby they can have a radial component and/or a lateral component. The shuttles 14 in FIGS. 51A-51L are shown in a flat configuration before being shape-set into a curved configuration. When the shuttles 14 in FIGS. 51A-51L are in a shape set configuration, the shuttles 14 can have the same radius of curvature of the other shape set shuttles 14 described and/or contemplated herein. For example, the shuttle 14 in FIGS. 33A-36C, 38A-38C, 49A-50G, $50H_2$, and $50H_4$ can have any combination of the male stops 412 shown in FIGS. 33A-36C, 38A-38C, 49A-50G, $50H_2$, $50H_4$, and 51A-51L. For example, one or both of the male stops 412 in FIGS. 33A-36C, 49A-50G, $50H_2$, and $50H_4$, can any of the male stops 412 shown in FIGS. 51A-51L.

FIGS. 51A-51L that the male stops 412 can have a proximal end (e.g., the male stop first longitudinal end $412_{FE}$) wider than a distal end (e.g., the male stop second longitudinal end $412_{SE}$), can have a distal end (e.g., the male stop second longitudinal end $412_{SE}$) wider than a proximal end (e.g., the male stop first longitudinal end $412_{FE}$), can have a symmetric shape (e.g., about the shuttle longitudinal axis $14_{A1}$), can have an asymmetric shape (e.g., about the shuttle longitudinal axis $14_{A1}$), can have a hooked shape, can have multiple arms with or without support between the multiple arms, can have relief cuts (e.g., along the perimeter of the male stops, on the sides of the male stops, on the distal terminal end of the male stops), any other feature and/or shape shown in FIGS. 51A-51L, or any combination thereof.

The various shapes of the male stops 412 in FIGS. 33A-36C, 49A-50G, $50H_2$, $50H_4$, and 51A-51L are exemplary ways to tune the catch force and the release force independently, for example, through the geometry of the male stops 412 and the mating catch geometry with the female stops 416. These exemplary shapes can advantageously pierce and transit through tissue when the shuttle 14 is moved from one jaw to the other. The ability to tune different portions of the male stops 412 as shown in these figures is important. For example, some of the shapes and geometries in FIGS. 51A-51L are similar to the hammerhead shape, but vary along the bending length to tune the bending resistance. Others can interface with different catch designs of the female stops 416. For example, the male stops 412 with a hook shape (e.g., FIG. 51A, 51D, 51E, 51H, 51K) can provide catch forces that are lower than the release forces. The male stops 412 that have a hook shape can, for example, interface with a hook receiver (e.g., a hole or cross-pin) on the jaw that can catch the hook. The asymmetric designs (e.g., FIG. 51A, 51E, 51H, 51K, 51L) can require a torque or a rotation from the pusher (e.g., the lower jaw pusher 76 or the upper jaw pusher 86) to make the male stops 412 to catch the female stop 416 and/or release from the female stop 416, which can be different from the hammerhead shape that can catch and release from the female stops 416 with linear bending. The tapered or angled designs (e.g., 51A, 51B, 51C, 51F, 51G, 51J) can have a catch force different from the release force and/or the catch and release forces can be tuned, for example, by replacing surface on surface contact between the male and female stops 412, 416 with line or point on surface contact between the male and female stops 412, 416. The designs with splits along the length or width (e.g., FIGS. 51I, 51L) can combine the bendable (e.g., linearly bendably) male stops (e.g., FIGS. 33A-33C and 49A-49H$_4$) with a lateral catcher (e.g., the lateral male stops $412_L$).

The female stops 416 in the upper and lower jaws 30, 38 can have a shape to mate with the male stops 412 illustrated in FIGS. 51A-51L.

FIG. 52A illustrates that the male stop 412 can have the features shown. The male stop 412 can have a locker 702 and one or multiple male stop arms 704. The male stop arms 704 can have or can be springs $704_S$. The springs $704_S$ can be, for example, one or multiple bends in the male stop arms $704_S$. The male stop 412 can have a channel 703. The shuttle 14 can be moveable through the channel 703 when the locker 702 is in an unlocked position. The shuttle 14 can be prevented from moving through the channel 703 when the locker 702 is in a locked position. For example, FIG. 52B illustrates the locker 702 in an unlocked position and FIG. 52C illustrates the locker 702 in a locked position.

FIGS. 52B and 52C illustrate that the male stop 412 can be moveable in a channel 707 in the jaws. The male stop 412 can be moveable in the channel 707, for example, by the jaw control extension 40, by the springs $704_S$, or by both. The jaw control extension arms 548 can engage and disengage with the male stop arms 704, for example, as the jaws are opened and closed by the jaw control extension 40. FIG. 52B illustrates that the jaw control extension 40 can be moved in direction 708 relative to the jaws and/or the male stop 412 to engage with the male stop 412, and FIG. 52C illustrates that the jaw control extension 40 can be moved in direction 710 relative to the jaws and/or the male stop 412 to disengage from the male stop 412.

FIG. 52B illustrates that when the jaws are in a closed configuration, the male stop 412 can be in an advanced position (e.g., having been actively pushed forward by the jaw control extension 40) out of the way of the shuttle 14 and/or out of the way of a male stop on the shuttle 14, so that the shuttle 14 can be moveable through channel 703. In FIG. 52B, the male stop 412 is shown pressed forward by the jaw control extension 40, allowing the shuttle 14 to be released from the male stop 412. FIG. 52B illustrates that when the locker 702 is pushed fully forward, the locker 702 can be moved out of the path of the shuttle and/or out of the path of a male stop 412 on the shuttle 14. FIG. 52B shows, for example, the active retention when the locker 702 is in a disengaged position (e.g., when the jaws are closed), allowing free motion of the shuttle 14.

FIG. 52C illustrates that when the jaws are in an open configuration, the male stop 412 can be in a retracted position (e.g., having been sprung backward into the channel 707 via the springs $704_S$), forming a catch for the shuttle 14 and/or for a male stop 412 on the shuttle 14 to inhibit or prevent the shuttle 14 from moving out of the jaw, for example, through the channel 703. For example, FIG. 52C illustrates that when the jaws are in an open configuration, the locker 702 can form a catch for the shuttle 14 by pressing against the shuttle body 160 and/or can form a catch for a male stop 412 on the shuttle 14 to inhibit or prevent the shuttle 14 from moving through the channel 703. FIG. 52C illustrates that when the male stop 412 is in a retracted position, the locker 702 can be moved into the path of the shuttle 14 and/or into the path of a male stop 412 on the shuttle 14, blocking motion of the shuttle 14. FIG. 52C shows, for example, the active retention when the locker 702 is in an engaged position (e.g., when the jaws are open), restricting motion of the shuttle 14.

FIGS. 52B and 52C together illustrate, for example, that the jaw control extension 40 can push the male stop 40 forward in the channel 707 so the locker 702 is clear of (e.g., forward of, distal of) the shuttle 14 and/or of a male stop 412 on the shuttle 14, and that the springs $704_S$ can retract the male stop 412 into the channel 707 so that the locker 702 can inhibit or block movement of the shuttle 14 and/or of a male stop 412 on the shuttle. For example, FIG. 52C illustrates that when the jaw control extension 40 is retracted or the jaws are advanced over the jaw control extension 40, that the springs $704_S$ can rebound back to a neutral configuration (e.g., the configuration shown in FIG. 52A). The springs $704_S$ returning to their neutral configuration can retract the male stop 412 into the channel 707 to lock the shuttle 14 in position.

FIG. 52B further illustrates that when the jaw control extension 40 is in a fully advanced configuration, the male stop arms 704 can be pressed against a surface 711 defining an arm space 712. FIG. 52C further illustrates that when the jaw control extension 40 is in a retracted configuration (e.g., a fully retracted configuration), the male stop arms 704 can be in less contact with the surface 711 than when the jaw control extension 40 is in an advanced configuration (e.g., the fully advanced configuration shown in FIG. 52B). For example, as the springs $704_S$ return to a neutral configuration as the jaw control extension 40 is retracted, the male stop arms 704 can press against the surface 711 and create the gap between the male stop arms 704 and the surface 711 shown in FIG. 52C.

FIGS. 52B and 52C further illustrate that male stop channel 707 can have a first section on a first side of the shuttle track and a second section on a second side of the shuttle track.

FIGS. 52B and 52C further illustrate that the device 188 may or may not have passive male stops 412 in addition to the male stop 412 that can be actively engaged with the shuttle 14 and/or can be positionable to block movement of a passive male stop extending from the shuttle 14. The passive male stops 412 can be any of the male stops described, illustrated, and/or contemplated herein. For example, FIGS. 52B and 52C illustrate that the passive male stops 412 can be radial male stops $412_R$. FIGS. 52B and 52C further illustrate that the device 188 can have passive female stops 416 for the passive male stops 412. The passive female stops 412 can be any of the female stops described, illustrated, and/or contemplated herein. For example, FIGS. 52B and 52C illustrate that the passive female stops 416 can be radial female stops 4168.

Half of the upper jaw 30 and the features therein are shown transparent in FIGS. 52B and 52C for illustrative purposes.

FIG. 52D illustrates a close-up view of the male shuttle channel 707 intersecting with the upper jaw shuttle track 64.

FIG. 52E illustrates a close-up view showing that when the male stop 412 is in a disengaged position (e.g., jaws closed), the locker 702 can be pushed away from the shuttle 14 so that the male stop on the shuttle 14 can pass beneath it. In the engaged scenario (e.g., as shown in FIG. 52C) the locker 702 can be moved down (e.g., from its built in springs 704 and $704_S$) to block the forward path of the male stop 412 on the shuttle 14.

FIGS. 52A-52E illustrate that male stops 412 can be engageable and disengageable with one another. For example, a first male stop 412 can be engageable and disengageable with a second male stop 412. The second male stop 412 can be, for example, on the shuttle 14 and/or can extend from the shuttle 14.

Any male stop 412 can be replaced with a female stop 416 and vice versa. For example, any of the male and female stops 412, 416 in FIGS. 49A-50H$_4$ can be swapped with each other such that the shuttle 14 has the female stops 416 and the upper and lower jaws have the male stops 412.

The upper and lower jaws referred to throughout the application can be any of the upper and lower jaws disclosed, illustrated, and/or contemplated herein. For example, the upper and lower jaws 30, 48 can be the upper and lower jaws 78, 80, respectively. As another example, the upper jaw 30 can be interchangeable with the upper jaw 78, and the lower jaw 38 can be interchangeable with the upper jaw 80. As yet another example, the upper jaw 30 can also be referred to as the upper jaw 78, and the lower jaw 38 can also be referred to as the lower jaw 80. The lower jaw can be a first jaw and the upper jaw can be a second jaw. The lower jaw can be a second jaw and the upper jaw can be a first jaw.

The features in FIGS. 1a-52D, the features described herein, and/or the features contemplated herein can be combined with each other in any combination. For example, the shuttle 14 in any of the figures can be any of the shuttles 14 illustrated, described, and/or contemplated herein. For example, FIGS. 49H$_1$-49H$_4$ illustrate that the shuttle 14 moveable by the device 188 can have male stops 412 that have a hammerhead shape.

For example, a suture manipulating device is disclosed that can have a first jaw. The first jaw can have a first jaw channel (e.g., upper jaw track 64 or lower jaw track 66) and a first jaw first stop (e.g., a male stop 412 or a female stop 416). The suture manipulating device can have a shuttle. The shuttle can have a shuttle longitudinal axis and a shuttle first stop (e.g., a male stop 412 or a female stop 416). The shuttle can be slideable in the first jaw channel. The shuttle first stop can extend away from the shuttle longitudinal axis. The shuttle first stop can have a shuttle first stop proximal end (e.g., male stop first longitudinal end $412_{FE}$) and a shuttle first stop distal end (e.g., male stop second longitudinal end $412_{SE}$). The shuttle first stop proximal end can be narrower than the shuttle first stop distal end. The shuttle first stop distal end can be deflectable into the first jaw first stop. The shuttle first stop can be engageable with the first jaw first stop. When the shuttle first stop is engaged with the first jaw first stop, the shuttle first stop distal end can be in contact with the first jaw first stop. When the shuttle first stop distal end is in contact with the first jaw first stop, the shuttle can be passively retained in the first jaw.

The suture manipulating device can have a second jaw. The second jaw can have a second jaw channel (e.g., upper jaw track 64 or lower jaw track 66) and a second jaw first stop (e.g., a male stop 412 or a female stop 416). The shuttle can be slideable in the second jaw channel.

The shuttle can have a shuttle second stop (e.g., a male stop 412 or a female stop 416). The shuttle first stop can be slideable into and out of the first jaw first stop. The shuttle second stop can be slideable into and out of the second jaw first stop.

The shuttle second stop can extend away from the shuttle longitudinal axis. The shuttle second stop can have a shuttle second stop proximal end (e.g., male stop first longitudinal end $412_{FE}$) and a shuttle second stop distal end (e.g., male stop second longitudinal end $412_{SE}$). The shuttle second stop proximal end can be narrower than the shuttle second stop distal end. The shuttle second stop distal end can be deflectable into the second jaw first stop. The shuttle second stop can be engageable with the second jaw first stop. When the shuttle second stop is engaged with the second jaw first stop, the shuttle second stop distal end can be in contact with the second jaw first stop. When the shuttle second stop distal end is in contact with the second jaw first stop, the shuttle can be passively retained in the second jaw.

The shuttle first stop distal end can be closer to a center of the shuttle than the shuttle first stop proximal end. The shuttle second stop distal end can be closer to the center of the shuttle than the shuttle second stop proximal end.

At least one of the shuttle first stop and the shuttle second stop can be a male stop.

At least one of the shuttle first stop and the shuttle second stop can have a hammerhead shape.

The shuttle first stop can extend radially away from the shuttle longitudinal axis, and the shuttle second stop can extend radially away from the shuttle longitudinal axis.

The shuttle first stop can extend radially away from the shuttle longitudinal axis, and the shuttle second stop can extend laterally away from the shuttle longitudinal axis.

The shuttle first stop can extend laterally away from the shuttle longitudinal axis, and the shuttle second stop can extend laterally away from the shuttle longitudinal axis.

When the shuttle first stop is engaged with the first jaw first stop, tissue can be moveable away from the first jaw first stop via the shuttle first stop.

The shuttle can have a shuttle first section, a shuttle second section, and a shuttle third section. The shuttle first section can be straight, the shuttle second section can be curved, and the shuttle third section can be straight.

Before the shuttle is loaded into the first jaw channel, the shuttle can have a first radius of curvature. After the shuttle is loaded into the first jaw channel, the shuttle can have a second radius of curvature. The second radius of curvature can be less than the first radius of curvature. The shuttle can be biased to have the first radius of curvature.

The first jaw can have a first jaw second stop (e.g., a male stop 412 or a female stop 416). The shuttle can have a shuttle third stop (e.g., a male stop 412 or a female stop 416). The shuttle third stop can extend away from the shuttle longitudinal axis. The shuttle third stop can have a shuttle third stop proximal end (e.g., male stop first longitudinal end $412_{FE}$) and a shuttle third stop distal end (e.g., male stop second longitudinal end $412_{SE}$). The shuttle third stop proximal end can be narrower than the shuttle third stop distal end. The shuttle third stop distal end can be deflectable into the first jaw second stop. The shuttle third stop can be engageable with the first jaw second stop. When the shuttle third stop is engaged with the first jaw second stop, the shuttle third stop distal end can be in contact with the first jaw second stop. When the shuttle third stop distal end is in contact with the first jaw third stop, the shuttle can be passively retained in the first jaw. The shuttle third stop can be slideable into and out of the first jaw second stop.

The second jaw can have a second jaw second stop (e.g., a male stop 412 or a female stop 416). The shuttle can have a shuttle fourth stop (e.g., a male stop 412 or a female stop 416). The shuttle fourth stop can be slideable into and out of the second jaw second stop. The shuttle fourth stop can extend away from the shuttle longitudinal axis. The shuttle fourth stop can have a shuttle fourth stop proximal end (e.g., male stop first longitudinal end $412_{FE}$) and a shuttle fourth stop distal end (e.g., male stop second longitudinal end $412_{SE}$). The shuttle fourth stop proximal end can be narrower than the shuttle fourth stop distal end. The shuttle fourth stop distal end can be deflectable into the second jaw second stop. The shuttle fourth stop can be engageable with the second jaw second stop. When the shuttle fourth stop is engaged with the second jaw second stop, the shuttle fourth stop distal end can be in contact with the second jaw second stop. When the shuttle fourth stop distal end is in contact with the second jaw second stop, the shuttle can be passively retained in the second jaw.

The shuttle first stop can be a radial male stop (e.g., $412_R$) or a lateral male stop (e.g., $412_L$). The shuttle first stop can be a radial female stop (e.g., $416_R$) or a lateral female stop (e.g., $416_L$).

The shuttle second stop can be a radial male stop (e.g., $412_R$) or a lateral male stop (e.g., $412_L$). The shuttle second stop can be a radial female stop (e.g., $416_R$) or a lateral female stop (e.g., $416_L$).

The shuttle third stop can be a radial male stop (e.g., $412_R$) or a lateral male stop (e.g., $412_L$). The shuttle third stop can be a radial female stop (e.g., $416_R$) or a lateral female stop (e.g., $416_L$).

The shuttle fourth stop can be a radial male stop (e.g., $412_R$) or a lateral male stop (e.g., $412_L$). The shuttle fourth stop can be a radial female stop (e.g., $416_R$) or a lateral female stop (e.g., $416_L$).

The first jaw first stop can be a radial male stop (e.g., $412_R$) or a lateral male stop (e.g., $412_L$). The first jaw first stop can be a radial female stop (e.g., $416_R$) or a lateral female stop (e.g., $416_L$).

The second jaw first stop can be a radial male stop (e.g., $412_R$) or a lateral male stop (e.g., $412_L$). The second jaw first stop can be a radial female stop (e.g., $416_R$) or a lateral female stop (e.g., $416_L$).

The first jaw second stop can be a radial male stop (e.g., $412_R$) or a lateral male stop (e.g., $412_L$). The first jaw second stop can be a radial female stop (e.g., $416_R$) or a lateral female stop (e.g., $416_L$).

The second jaw second stop can be a radial male stop (e.g., $412_R$) or a lateral male stop (e.g., $412_L$). The second jaw second stop can be a radial female stop (e.g., $416_R$) or a lateral female stop (e.g., $416_L$).

As another example, a suture manipulating device is disclosed that can have a jaw structure (e.g., jaw structure 28). The jaw structure can have a shuttle channel (e.g., upper jaw track 64 and/or the lower jaw track 66, where when the jaw structure is in a closed configuration, the jaw structure can form a continuous track defined, for example, by the upper and lower jaw tracks 64, 66) having a shuttle channel first stop (e.g., a male stop 412 or a female stop 416). The suture manipulating device can have a shuttle. The shuttle can have a shuttle longitudinal axis and a shuttle first stop (e.g., a male stop 412 or a female stop 416). The shuttle can be slideable in the shuttle channel. The shuttle first stop can extend away from the shuttle longitudinal axis. The shuttle first stop can have a shuttle first stop proximal end (e.g., male stop first longitudinal end $412_{FE}$) and a shuttle first stop distal end (e.g., male stop second longitudinal end $412_{SE}$). The shuttle first stop proximal end can be narrower than the shuttle first stop distal end. The shuttle first stop can be moveable into the shuttle channel first stop. The shuttle first stop can be engageable with the shuttle channel first stop. When the shuttle first stop is not engaged with the shuttle channel first stop, the shuttle first stop can have a shuttle first stop non-deflected shape. When the shuttle first stop is engaged with the shuttle channel first stop, the shuttle first stop can have a shuttle first stop deflected shape.

The shuttle channel can have a shuttle channel second stop (e.g., a male stop 412 or a female stop 416).

The shuttle can have a shuttle second stop (e.g., a male stop 412 or a female stop 416).

The shuttle second stop can extend away from the shuttle longitudinal axis. The shuttle second stop can have a shuttle second stop proximal end (e.g., male stop first longitudinal end $412_{FE}$) and a shuttle second stop distal end (e.g., male stop second longitudinal end $412_{SE}$). The shuttle second stop proximal end can be narrower than the shuttle second stop distal end. The shuttle second stop can be moveable into the shuttle channel second stop. The shuttle second stop can be engageable with the shuttle channel second stop. When the shuttle second stop is not engaged with the shuttle channel second stop, the shuttle second stop can have a shuttle second stop non-deflected shape. When the shuttle second stop is engaged with the shuttle channel second stop, the shuttle second stop can have a shuttle second stop deflected shape.

The shuttle first stop distal end can be closer to a center of the shuttle than the shuttle first stop proximal end. The shuttle second stop distal end can be closer to the center of the shuttle than the shuttle second stop proximal end. When the shuttle first stop is engaged with the shuttle channel first stop, movement of the shuttle in the shuttle channel can be restricted. When the shuttle second stop is engaged with the shuttle channel second stop, movement of the shuttle in the shuttle channel can be restricted.

At least one of the shuttle first stop and the shuttle second stop can be a male stop.

At least one of the shuttle first stop and the shuttle second stop can have a hammerhead shape.

The shuttle first stop can extend radially away or laterally away from the shuttle longitudinal axis, and the shuttle second stop can extend radially away or laterally away from the shuttle longitudinal axis.

The shuttle channel first stop and the shuttle channel second stop can be in a first jaw of the suture manipulating device.

The shuttle channel first stop can be in a first jaw of the suture manipulating device, and the shuttle channel second stop can be in a second jaw of the suture manipulating device.

As another example, a suture manipulating device is disclosed that can have a jaw. The jaw can have a shuttle channel (e.g., upper jaw track 64 and/or the lower jaw track 66) having a female stop (e.g., female stop 416). The suture manipulating device can have a shuttle. The shuttle can have a shuttle longitudinal axis and a male stop (e.g., male stop 412). The shuttle can be translatable in the shuttle channel. The male stop can be engageable with the female stop. The male stop can extend away from the shuttle longitudinal axis. The male stop can have a male stop proximal end (e.g., male stop first longitudinal end $412_{FE}$) and a male stop distal end (e.g., male stop second longitudinal end $412_{SE}$). The male stop distal end can be wider than the male stop proximal end. The male stop can be translatable into and out of the female stop. The male stop can be deflectable into and out of the female stop.

The first male stop can extend radially away or laterally away from the shuttle longitudinal axis.

When the male stop is in the female stop, movement of the shuttle in the shuttle channel can be inhibited.

The male stop distal end can be closer to a center of the shuttle than the male stop proximal end.

The male stop can have a hammerhead shape.

The upper jaw 30 can be any jaw disclosed, illustrated, and/or contemplated herein.

The lower jaw 38 can be any jaw disclosed, illustrated, and/or contemplated herein.

It is apparent to one skilled in the art that various changes and modifications can be made to this disclosure, and equivalents employed, without departing from the spirit and scope of the invention. Elements shown with any variation are exemplary for the specific variation and can be used on other variations within this disclosure. Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination. Any phrase involving an "A and/or B" construction or similar construction can mean (1) A alone, (2) B alone, (3) A and B together. Any range disclosed can include any subrange of the range disclosed, for example, a range of 1-10 units can include 2-10 units, 8-10 units, or any other subrange.

We claim:

1. A suture manipulating device comprising:
a first jaw having a first jaw channel and a first jaw first stop; and
a shuttle having a shuttle longitudinal axis and a shuttle first stop, wherein the shuttle is slideable in the first jaw channel,
wherein the shuttle first stop extends away from the shuttle longitudinal axis, wherein the shuttle first stop has a shuttle first stop proximal end and a shuttle first stop distal end, wherein the shuttle first stop proximal end is narrower than the shuttle first stop distal end, wherein the shuttle first stop distal end is deflectable into the first jaw first stop, wherein the shuttle first stop is engageable with the first jaw first stop, wherein when the shuttle first stop is engaged with the first jaw first stop, the shuttle first stop distal end is in contact with the first jaw first stop, and wherein when the shuttle first stop distal end is in contact with the first jaw first stop, the shuttle is passively retained in the first jaw.

2. The suture manipulating device of claim 1, further comprising:
a second jaw having a second jaw channel and a second jaw first stop, wherein the shuttle is slideable in the second jaw channel,
wherein the shuttle further comprises a shuttle second stop, wherein the shuttle first stop is slideable into and out of the first jaw first stop, wherein the shuttle second stop is slideable into and out of the second jaw first stop,
wherein the shuttle second stop extends away from the shuttle longitudinal axis, wherein the shuttle second stop has a shuttle second stop proximal end and a shuttle second stop distal end, wherein the shuttle second stop proximal end is narrower than the shuttle second stop distal end, wherein the shuttle second stop distal end is deflectable into the second jaw first stop, wherein the shuttle second stop is engageable with the second jaw first stop, wherein when the shuttle second stop is engaged with the second jaw first stop, the shuttle second stop distal end is in contact with the second jaw first stop, wherein when the shuttle second stop distal end is in contact with the second jaw first stop, the shuttle is passively retained in the second jaw, and
wherein the shuttle first stop distal end is closer to a center of the shuttle than the shuttle first stop proximal end, and wherein the shuttle second stop distal end is closer to the center of the shuttle than the shuttle second stop proximal end.

3. The suture manipulating device of claim 2, wherein at least one of the shuttle first stop and the shuttle second stop has a hammerhead shape.

4. The suture manipulating device of claim 2, wherein the shuttle first stop extends radially away from the shuttle longitudinal axis, and wherein the shuttle second stop extends radially away from the shuttle longitudinal axis.

5. The suture manipulating device of claim 2, wherein the shuttle first stop extends radially away from the shuttle longitudinal axis, and wherein the shuttle second stop extends laterally away from the shuttle longitudinal axis.

6. The suture manipulating device of claim 2, wherein the shuttle first stop extends laterally away from the shuttle longitudinal axis, and wherein the shuttle second stop extends laterally away from the shuttle longitudinal axis.

7. The suture manipulating device of claim 1, wherein when the shuttle first stop is engaged with the first jaw first stop, tissue is moveable away from the first jaw first stop via the shuttle first stop.

8. The suture manipulating device of claim 1, wherein the shuttle has a shuttle first section, a shuttle second section, and a shuttle third section, wherein the shuttle first section is straight, the shuttle second section is curved, and the shuttle third section is straight.

9. The suture manipulating device of claim 1, wherein before the shuttle is loaded into the first jaw channel, the shuttle has a first radius of curvature, wherein after the shuttle is loaded into the first jaw channel, the shuttle has a second radius of curvature, wherein the second radius of curvature is less than the first radius of curvature, and wherein the shuttle is biased to have the first radius of curvature.

10. A suture manipulating device comprising:
a jaw structure having a shuttle channel having a shuttle channel first stop; and
a shuttle having a shuttle longitudinal axis and a shuttle first stop, wherein the shuttle is slideable in the shuttle channel,
wherein the shuttle first stop extends away from the shuttle longitudinal axis, wherein the shuttle first stop has a shuttle first stop proximal end and a shuttle first stop distal end, wherein the shuttle first stop proximal end is narrower than the shuttle first stop distal end, wherein the shuttle first stop is moveable into the shuttle channel first stop, wherein the shuttle first stop is engageable with the shuttle channel first stop, wherein when the shuttle first stop is not engaged with the shuttle channel first stop, the shuttle first stop has a shuttle first stop non-deflected shape, wherein when the shuttle first stop is engaged with the shuttle channel first stop, the shuttle first stop has a shuttle first stop deflected shape.

11. The suture manipulating device of claim 10, further comprising:
wherein the shuttle channel has a shuttle channel second stop,
wherein the shuttle has a shuttle second stop,
wherein the shuttle second stop extends away from the shuttle longitudinal axis, wherein the shuttle second stop has a shuttle second stop proximal end and a shuttle second stop distal end, wherein the shuttle second stop proximal end is narrower than the shuttle second stop distal end, wherein the shuttle second stop is moveable into the shuttle channel second stop, wherein the shuttle second stop is engageable with the shuttle channel second stop, wherein when the shuttle second stop is not engaged with the shuttle channel second stop, the shuttle second stop has a shuttle second stop non-deflected shape, wherein when the shuttle second stop is engaged with the shuttle channel second stop, the shuttle second stop has a shuttle second stop deflected shape.

12. The suture manipulating device of claim 11, wherein the shuttle first stop distal end is closer to a center of the shuttle than the shuttle first stop proximal end, wherein the shuttle second stop distal end is closer to the center of the shuttle than the shuttle second stop proximal end, wherein when the shuttle first stop is engaged with the shuttle channel first stop, movement of the shuttle in the shuttle channel is restricted, wherein when the shuttle second stop is engaged with the shuttle channel second stop, movement of the shuttle in the shuttle channel is restricted.

13. The suture manipulating device of claim 11, wherein at least one of the shuttle first stop and the shuttle second stop has a hammerhead shape.

14. The suture manipulating device of claim 11, wherein the shuttle first stop extends radially away or laterally away from the shuttle longitudinal axis, and wherein the shuttle second stop extends radially away or laterally away from the shuttle longitudinal axis.

15. The suture manipulating device of claim 11, wherein the shuttle channel first stop and the shuttle channel second stop are in a first jaw of the jaw structure of the suture manipulating device.

16. The suture manipulating device of claim 11, wherein the shuttle channel first stop is in a first jaw of the jaw structure of the suture manipulating device, and wherein the shuttle channel second stop is in a second jaw of the jaw structure of the suture manipulating device.

17. A suture manipulating device comprising:
a jaw having a shuttle channel having a female stop; and
a shuttle having a shuttle longitudinal axis and a male stop, wherein the shuttle is translatable in the shuttle channel, wherein the male stop is engageable with the female stop,
wherein the male stop extends away from the shuttle longitudinal axis, wherein the male stop has a male stop proximal end and a male stop distal end, wherein the male stop distal end is wider than the male stop proximal end, wherein the male stop is translatable into and out of the female stop, and wherein the male stop is deflectable into and out of the female stop.

18. The suture manipulating device of claim 17, wherein the male stop extends radially away or laterally away from the shuttle longitudinal axis, and wherein when the male stop is in the female stop, movement of the shuttle in the shuttle channel is inhibited.

19. The suture manipulating device of claim 18, wherein the male stop distal end is closer to a center of the shuttle than the male stop proximal end.

20. The suture manipulating device of claim 19, wherein the male stop has a hammerhead shape.

* * * * *